US007989595B2

(12) United States Patent
Dennis et al.

(10) Patent No.: US 7,989,595 B2
(45) Date of Patent: Aug. 2, 2011

(54) COMPOSITIONS AND METHODS FOR THE DIAGNOSIS AND TREATMENT OF TUMOR

(75) Inventors: Mark S. Dennis, San Carlos, CA (US); William Mallet, Redwood City, CA (US); Paul Polakis, Mill Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 929 days.

(21) Appl. No.: 11/452,990

(22) Filed: Jun. 14, 2006

(65) Prior Publication Data

US 2009/0041749 A1 Feb. 12, 2009

Related U.S. Application Data

(60) Provisional application No. 60/793,951, filed on Apr. 21, 2006, provisional application No. 60/692,092, filed on Jun. 20, 2005.

(51) Int. Cl.

| | |
|---|---|
| *C12P 21/08* | (2006.01) |
| *C07K 16/00* | (2006.01) |
| *C07K 17/00* | (2006.01) |
| *C07K 17/14* | (2006.01) |
| *A61K 39/395* | (2006.01) |
| *C12N 5/00* | (2006.01) |
| *C12N 5/02* | (2006.01) |

(52) U.S. Cl. ............... 530/388.1; 530/391.1; 424/130.1; 424/141.1; 435/325

(58) Field of Classification Search ........................ None
See application file for complete search history.

(56) References Cited

U.S. PATENT DOCUMENTS 6,037,454 A * 3/2000 Jardieu et al. .............. 530/387.3
2005/0106644 A1* 5/2005 Cairns et al. ................. 435/7.23

FOREIGN PATENT DOCUMENTS

| | | | |
|---|---|---|---|
| WO | 96/16990 | | 6/1996 |
| WO | WO98/45331 | * | 10/1998 |
| WO | 02/06317 | A | 1/2002 |
| WO | WO02/092836 | A2 | 11/2002 |
| WO | 2004/005470 | | 1/2004 |
| WO | WO2004/035537 | A2 | 4/2004 |
| WO | 2004/072286 | A1 | 8/2004 |
| WO | WO2005/005638 | A2 | 1/2005 |
| WO | 2005/080432 | A2 | 9/2005 |
| WO | WO2005/081711 | A2 | 9/2005 |
| WO | 2006/106912 | A1 | 10/2006 |

OTHER PUBLICATIONS

Fundamental Immunology, William E. Paul, M.D., ed. 3rd ed. 1993. pp. 292-295.*
Rudikoff, Giusti, Cook, and Scharff. Single amino acid substitution altering antigen-binding specificity. Proceedings of the National Academy of Sciences, 1982. vol. 79 p. 1979.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity-determining regions containing specificity determining residues for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoloncal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Yin, B. W., et al., "Molecular cloning of the CA125 ovarian cancer antigen" *Journal of Biological Chemistry, American Society of Biolochemical Biologists*, Birmingham, US 276 (29) :27371-27375 (Jul. 20, 2001).
Kobayashi et al., "A human/mouse chimeric monoclonal antibody against CA125 for radioimmunoimaging of ovarian cancer" *Cancer Immunology Immunotherapy* 37 (3) :143-149 (1993).
Sweet et al., "Daunorubicin conjugated to a monoclonal anti-CA125 antibody selectively kills human ovarian cancer cells" *Gynecologic Oncology* 34 (3) :305-311 (Sep. 1989).
Sanderson, R. J. et al., "In Vivo drug-linker stability of an anti-CD30 dipeptide-linked auristatin immunoconjugate" *Clin. Cancer Res.* 11:843-852 (2005).

* cited by examiner

*Primary Examiner* — Anne M. Gussow
(74) *Attorney, Agent, or Firm* — Alex Andrus; Genentech, Inc.

(57) ABSTRACT

The present invention is directed to compositions of matter useful for the diagnosis and treatment of tumor in mammals and to methods of using those compositions of matter for the same.

30 Claims, 45 Drawing Sheets

FIGURE 1A

CCTGTGACTTCTCTTCTCACCCCTGGCCTGGTGATAACCACAGACAGGATGGGCATAAGCAGAGAACCTGGAACCAG
TTCCACTTCAAATTTGAGCAGCACCTCCCATGAGAGACTGACCACTTTGGAAGACACTGTAGATACAGAAGCCATGC
AGCCTTCCACACACACAGCAGTGACCAACGTGAGGACCTCCATTTCTGGACATGAATCACAATCTTCTGTCCTATCT
GACTCAGAGACACCCAAAGCCACATCTCCAATGGGTACCACCTACACCATGGGGGAAACGAGTGTTTCCATATCCAC
TTCTGACTTCTTTGAGACCAGCAGAATTCAGATAGAACCAACATCCTCCCTGACTTCTGGATTGAGGGAGACCAGCA
GCTCTGAGAGGATCAGCTCAGCCACAGAGGGAAGCACTGTCCTTTCTGAAGTGCCCAGTGGTGCTACCACTGAGGTC
TCCAGGACAGAAGTGATATCCTCTAGGGGAACATCCATGTCAGGGCCTGATCAGTTCACCATATCACCAGACATCTC
TACTGAAGCGATCACCAGGCTTTCTACTTCCCCCATTATGACAGAATCAGCAGAAAGTGCCATCACTATTGAGACAG
GTTCTCCTGGGGCTACATCAGAGGGTACCCTCACCTTGGACACCTCAACAACAACCTTTTGGTCAGGGACCCACTCA
ACTGCATCTCCAGGATTTTCACACTCAGAGATGACCACTCTTATGAGTAGAACTCCTGGAGATGTGCCATGGCCGAG
CCTTCCCTCTGTGGAAGAAGCCAGCTCTGTCTCTTCCTCACTGTCTTCACCTGCCATGACCTCAACTTCTTTTTTCT
CCACATTACCAGAGAGCATCTCCTCCTCTCCTCATCCTGTGACTGCACTTCTCACCCTTGGCCCAGTGAAGACCACA
GACATGTTGCGCACAAGCTCAGAACCTGAAACCAGTTCACCTCCAAATTTGAGCAGCACCTCAGCTGAAATATTAGC
CACGTCTGAAGTCACCAAAGATAGAGAGAAAATTCATCCCTCCTCAAACACACCTGTAGTCAATGTAGGGACTGTGA
TTTATAAACATCTATCCCCTTCCTCTGTTTTGGCTGACTTAGTGACAACAAAACCCACATCTCCAATGGCTACCACC
TCCACTCTGGGGAATACAAGTGTTTCCACATCAACTCCTGCCTTCCCAGAAACTATGATGACACAGCCAACTTCCTC
CCTGACTTCTGGATTAAGGGAGATCAGTACCTCTCAAGAGACCAGCTCAGCAACAGAGAGAAGTGCTTCTCTTTCTG
GAATGCCCACTGGTGCTACTACTAAGGTCTCCAGAACAGAAGCCCTCTCCTTAGGCAGAACATCCACCCCAGGTCCT
GCTCAATCCACAATATCACCAGAAATCTCCACGGAAACCATCACTAGAATTTCTACTCCCCTCACCACGACAGGATC
AGCAGAAATGACCATCACCCCCAAAACAGGTCATTCTGGGGCATCCTCACAAGGTACCTTTACCTTGGACACATCAA
GCAGAGCCTCCTGGCCAGGAACTCACTCAGCTGCAACTCACAGATCTCCACACTCAGGGATGACCACTCCTATGAGC
AGAGGTCCTGAGGATGTGTCATGGCCAAGCCGCCCATCAGTGGAAAAAACTAGCCCTCCATCTTCCCTGGTGTCTTT
ATCTGCAGTAACCTCACCTTCGCCACTTTATTCCACACCATCTGAGAGTAGCCACTCGTCTCCTCTCCGGGTGACTT
CTCTTTTCACCCCTGTCATGATGAAGACCACAGACATGTTGGACACAAGCTTGGAACCTGTGACCACTTCACCTCCC
AGTATGAATATCACCTCAGATGAGAGTCTGGCCACTTCTAAAGCCACCATGGAGACAGAGGCAATTCAGCTTTCAGA
AAACACAGCTGTGACTCAGATGGGCACCATCAGTGCTAGACAAGAATTCTATTCCTCTTATCCAGGCCTCCCAGAGC
CATCCAAAGTGACATCTCCAGTGGTCACCTCTTCCACCATAAAAGACATTGTTTCTACAACCATACCTGCTTCCTCT
GAGATAACAAGAATTGAGATGGAGTCAACATCCACCCTGACCCCCACACCAAGGGAGACCAGCACCTCCCAGGAGAT
CCACTCAGCCACAAAGCCAAGCACTGTTCCTTACAAGGCACTCACTAGTGCCACGATTGAGGACTCCATGACACAAG
TCATGTCCTCTAGCAGAGGACCTAGCCCTGATCAGTCCACAATGTCACAAGACATATCCACTGAAGTGATCACCAGG
CTCTCTACCTCCCCCATCAAGACAGAATCTACAGAAATGACCATTACCACCCAAACAGGTTCTCCTGGGGCTACATC
AAGGGGTACCCTTACCTTGGACACTTCAACAACTTTTATGTCAGGGACCCATTCAACTGCATCTCAAGGATTTTCAC
ACTCACAGATGACCGCTCTTATGAGTAGAACTCCTGGAGAGGTGCCATGGCTAAGCCATCCCTCTGTGGAAGAAGCC
AGCTCTGCCTCTTTCTCACTGTCTTCACCTGTCATGACCTCATCTTCTCCCGTTTCTTCCACATTACCAGACAGCAT
CCACTCTTCTTCGCTTCCTGTGACATCACTTCTCACCTCAGGGCTGGTGAAGACCACAGAGCTGTTGGGCACAAGCT
CAGAACCTGAAACCAGTTCACCCCCAAATTTGAGCAGCACCTCAGCTGAAATACTGGCCACCACTGAAGTCACTACA
GATACAGAGAAACTGGAGATGACCAATGTGGTAACCTCAGGTTATACACATGAATCTCCTTCCTCTGTCCTAGCTGA
CTCAGTGACAACAAAGGCCACATCTTCAATGGGTATCACCTACCCCACAGGAGATACAAATGTTCTCACATCAACCC
CTGCCTTCTCTGACACCAGTAGGATTCAAACAAAGTCAAAGCTCTCACTGACTCCTGGGTTGATGGAGACCAGCATC
TCTGAAGAGACCAGCTCTGCCACAGAAAAAAGCACTGTCCTTTCTAGTGTGCCCACTGGTGCTACTACTGAGGTCTC
CAGGACAGAAGCCATCTCTTCTAGCAGAACATCCATCCCAGGCCCTGCTCAATCCACAATGTCATCAGACACCTCCA
TGGAAACCATCACTAGAATTTCTACCCCCCTCACAAGGAAAGAATCAACAGACATGGCCATCACCCCCAAAACAGGT
CCTTCTGGGGCTACCTCGCAGGGTACCTTTACCTTGGACTCATCAAGCACAGCCTCCTGGCCAGGAACTCACTCAGC
TACAACTCAGAGATTTCCACGGTCAGTGGTGACAACTCCTATGAGCAGAGGTCCTGAGGATGTGTCATGGCCAAGCC
CGCTGTCTGTGGAAAAAAACAGCCCTCCATCTTCCCTGGTATCTTCATCTTCAGTAACCTCACCTTCGCCACTTTAT
TCCACACCATCTGGGAGTAGCCACTCCTCTCCTGTCCCTGTCACTTCTCTTTTCACCTCTATCATGATGAAGGCCAC
AGACATGTTGGATGCAAGTTTGGAACCTGAGACCACTTCAGCTCCCAATATGAATATCACCTCAGATGAGAGTCTGG
CCGCTTCTAAAGCCACCACGGAGACAGAGGCAATTCACGTTTTTGAAAATACAGCAGCGTCCCATGTGGAAACCACC
AGTGCTACAGAGGAACTCTATTCCTCTTCCCCAGGCTTCTCAGAGCCAACAAAAGTGATATCTCCAGTGGTCACCTC
TTCCTCTATAAGAGACAACATGGTTTCCACAACAATGCCTGGCTCCTCTGGCATTACAAGGATTGAGATAGAGTCAA
TGTCATCTCTGACCCCTGGACTGAGGGAGACCAGAACCTCCCAGGACATCACCTCATCCACAGAGACAAGCACTGTC
CTTTACAAGATGCCCTCTGGTGCCACTCCTGAGGTCTCCAGGACAGAAGTTATGCCCTCTAGCAGAACATCCATTCC
TGGCCCTGCTCAGTCCACAATGTCACTAGACATCTCCGATGAAGTTGTCACCAGGCTGTCTACCTCTCCCATCATGA
CAGAATCTGCAGAAATAACCATCACCACCCAAACAGGTTATTCTCTGGCTACATCCCAGGTTACCCTTCCCTTGGGC
ACCTCAATGACCTTTTTGTCAGGGACCCACTCAACTATGTCTCAAGGACTTTCACACTCAGAGATGACCAATCTTAT
GAGCAGGGGTCCTGAAAGTCTGTCATGGACGAGCCCTCGCTTTGTGGAAACAACTAGATCTTCCTCTTCTCTGACAT
CATTACCTCTCACGACCTCACTTTCTCCTGTGTCCTCCACATTACTAGACAGTAGCCCCTCCTCTCCTCTTCCTGTG
ACTTCACTTATCCTCCCAGGCCTGGTGAAGACTACAGAAGTGTTGGATACAAGCTCAGAGCCTAAAACCAGTTCATC
TCCAAATTTGAGCAGCACCTCAGTTGAAATACCGGCCACCTCTGAAATCATGACAGATACAGAGAAAATTCATCCTT
CCTCAAACACAGCGGTGGCCAAAGTGAGGACCTCCAGTTCTGTTCATGAATCTCATTCCTCTGTCCTAGCTGACTCA
GAAACAACCATAACCATACCTTCAATGGGTATCACCTCCGCTGTGGAGGATACCACTGTTTTCACATCAAATCCTGC
CTTCTCTGAGACTAGGAGGATTCCGACAGAGCCAACATTCTCATTGACTCCTGGATTCAGGGAGACTAGCACCTCTG
AAGAGACCACCTCAATCACAGAAACAAGTGCAGTCCTTTTTGGAGTGCCCACTAGTGCTACTACTGAAGTCTCCATG

FIGURE 1B

ACAGAAATAATGTCCTCTAATAGAACACACATCCCTGACTCTGATCAGTCCACGATGTCTCCAGACATCATCACTGA
AGTGATCACCAGGCTCTCTTCCTCATCCATGATGTCAGAATCAACACAAATGACCATCACCACCCAAAAAGTTCTC
CTGGGGCTACAGCACAGAGTACTCTTACCTTGGCCACAACAACAGCCCCCTTGGCAAGGACCCACTCAACTGTTCCT
CCTAGATTTTACACTCAGAGATGACAACTCTTATGAGTAGGAGTCCTGAAAATCCATCATGGAAGAGCTCTCCCTT
TGTGGAAAAAACTAGCTCTTCATCTTCTCTGTTGTCCTTACCTGTCACGACCTCACCTTCTGTTTCTTCCACATTAC
CGCAGAGTATCCCTTCCTCCTCTTTTTCTGTGACTTCACTCCTCACCCCAGGCATGGTGAAGACTACAGACACAAGC
ACAGAACCTGGAACCAGTTTATCTCCAAATCTGAGTGGCACCTCAGTTGAAATACTGGCTGCCTCTGAAGTCACCAC
AGATACAGAGAAAATTCATCCTTCTTCAAGCATGGCAGTGACCAATGTGGGAACCACCAGTTCTGGACATGAACTAT
ATTCCTCTGTTTCAATCCACTCGGAGCCATCCAAGGCTACATACCCAGTGGGTACTCCCTCTTCCATGGCTGAAACC
TCTATTTCCACATCAATGCCTGCTAATTTTGAGACCACAGGATTTGAGGCTGAGCCATTTTCTCATTTGACTTCTGG
ACTTAGGAAGACCAACATGTCCCTGGACACCAGCTCAGTCACACCAACAAATACACCTTCTTCTCCTGGGTCCACTC
ACCTTTTACAGAGTTCCAAGACTGATTTCACCTCTTCTGCAAAAACATCATCCCCAGACTGGCCTCCAGCCTCACAG
TATACTGAAATTCCAGTGGACATAATCACCCCCTTTAATGCTTCTCCATCTATTACGGAGTCCACTGGGATAACCTC
CTTCCCAGAATCCAGGTTTACTATGTCTGTAACAGAAAGTACTCATCATCTGAGTACAGATTTGCTGCCTTCAGCTG
AGACTATTTCCACTGGCACAGTGATGCCTTCTCTATCAGAGGCCATGACTTCATTTGCCACCACTGGAGTTCCACGA
GCCATCTCAGGTTCAGGTAGTCCATTCTCTAGGACAGAGTCAGGCCCTGGGGATGCTACTCTGTCCACCATTGCAGA
GAGCCTGCCTTCATCCACTCCTGTGCCATTCTCCTCTTCAACCTTCACTACCACTGATTCTTCAACCATCCCAGCCC
TCCATGAGATAACTTCCTCTTCAGCTACCCCATATAGAGTGGACACCAGTCTTGGGACAGAGAGCAGCACTACTGAA
GGACGCTTGGTTATGGTCAGTACTTTGGACACTTCAAGCCAACCAGGCAGGACATCTTCATCACCCATTTTGGATAC
CAGAATGACAGAGAGCGTTGAGCTGGGAACAGTGACAAGTGCTTATCAAGTTCCTTCACTCTCAACACGGTTGACAA
GAACTGATGGCATTATGGAACACATCACAAAAATACCCAATGAAGCAGCACACAGAGGTACCATAAGACCAGTCAAA
GGCCCTCAGACATCCACTTCGCCTGCCAGTCCTAAAGGACTACACACAGGAGGGACAAAAAGAATGGAGACCACCAC
CACAGCTCTGAAGACCACCACCACAGCTCTGAAGACCACTTCCAGAGCCACCTTGACCACCAGTGTCTATACTCCCA
CTTTGGGAACACTGACTCCCCTCAATGCATCAATGCAAATGGCCAGCACAATCCCCACAGAAATGATGATCACAACC
CCATATGTTTTCCCTGATGTTCCAGAAACGACATCCTCATTGGCTACCAGCCTGGGAGCAGAAACCAGCACAGCTCT
TCCCAGGACAACCCCATCTGTTTTCAATAGAGAATCAGAGACCACAGCCTCACTGGTCTCTCGTTCTGGGGCAGAGA
GAAGTCCGGTTATTCAAACTCTAGATGTTTCTTCTAGTGAGCCAGATACAACAGCTTCATGGGTTATCCATCCTGCA
GAGACCATCCCAACTGTTTCCAAGACAACCCCCAATTTTTTCCACAGTGAATTAGACACTGTATCTTCCACAGCCAC
CAGTCATGGGGCAGACGTCAGCTCAGCCATTCCAACAAATATCTCACCTAGTGAACTAGATGCACTGACCCCACTGG
TCACTATTTCGGGGACAGATACTAGTACAACATTCCCAACACTGACTAAGTCCCCACATGAAACAGAGACAAGAACC
ACATGGCTCACTCATCCTGCAGAGACCAGCTCAACTATTCCCAGAACAATCCCCAATTTTTCTCATCATGAATCAGA
TGCCACACCTTCAATAGCCACCAGTCCTGGGGCAGAAACCAGTTCAGCTATTCCAATTATGACTGTCTCACCTGGTG
CAGAAGATCTGGTGACCTCACAGGTCACTAGTTCTGGCACAGACAGAAATATGACTATTCCAACTTTGACTCTTTCT
CCTGGTGAACCAAAGACCATAGCCTCATTAGTCACCCATCCTGAAGCACAGACAAGTTCGGCCATTCCAACTTCAAC
TATCTCGCCTGCTGTATCACGGTTGGTGACCTCAATGGTCACCAGTTTGGCGGCAAAGACAAGTACAACTAATCGAG
CTCTGACAAACTCCCCTGGTGAACCAGCTACAACAGTTTCATTGGTCACGCATTCTGCACAGACCAGCCCAACAGTT
CCCTGGACAACTTCCATTTTTTTCCATAGTAAATCAGACACCACACCTTCAATGACCACCAGTCATGGGGCAGAATC
CAGTTCAGCTGTTCCAACTCCAACTGTTTCAACTGAGGTACCAGGAGTAGTGACCCCTTTGGTCACCAGTTCTAGGG
CAGTGATCAGTACAACTATTCCAATTCTGACTCTTTCTCCTGGTGAACCAGAGACCACACCTTCAATGGCCACCAGT
CATGGGGAAGAAGCCAGTTCTGCTATTCCAACTCCAACTGTTTCACCTGGGGTACCAGGAGTGGTGACCTCTCTGGT
CACTAGTTCTAGGGCAGTGACTAGTACAACTATTCCAATTCTGACTTTTTCTCTTGGTGAACCAGAGACCACACCTT
CAATGGCCACCAGTCATGGGACAGAAGCTGGCTCAGCTGTTCCAACTGTTTTACCTGAGGTACCAGGAATGGTGACC
TCTCTGGTTGCTAGTTCTAGGGCAGTAACCAGTACAACTCTTCCAACTCTGACTCTTTCTCCTGGTGAACCAGAGAC
CACACCTTCAATGGCCACCAGTCATGGGGCAGAAGCCAGCTCAACTGTTCCAACTGTTTCACCTGAGGTACCAGGAG
TGGTGACCTCTCTGGTCACTAGTTCTAGTGGAGTAAACAGTACAAGTATTCCAACTCTGATTCTTTCTCCTGGTGAA
CTAGAAACCACACCTTCAATGGCCACCAGTCATGGGGCAGAAGCCAGCTCAGCTGTTCCAACTCCAACTGTTTCACC
TGGGGTATCAGGAGTGGTGACCCCTCTGGTCACTAGTTCCAGGGCAGTGACCAGTACAACTATTCCAATTCTAACTC
TTTCTTCTAGTGAGCCAGAGACCACACCTTCAATGGCCACCAGTCATGGGGTAGAAGCCAGCTCAGCTGTTCTAACT
GTTTCACCTGAGGTACCAGGAATGGTGACCTTTCTGGTCACTAGTTCTAGAGCAGTAACCAGTACAACTATTCCAAC
TCTGACTATTTCTTCTGATGAACCAGAGACCACAACTTCATTGGTCACCCATTCTGAGGCAAAGATGATTTCAGCCA
TTCCAACTTTAGGTGTCTCCCCTACTGTACAAGGGCTGGTGACTTCACTGGTCACTAGTTCTGGGTCAGAGACCAGT
GCGTTTTCAAATCTAACTGTTGCCTCAAGTCAACCAGAGACCATAGACTCATGGGTCGCTCATCCTGGGACAGAAGC
AAGTTCTGTTGTTCCAACTTTGACTGTCTCCACTGGTGAGCCGTTTACAAATATCTCATTGGTCACCCATCCTGCAG
AGAGTAGCTCAACTCTTCCCAGGACAACCTCAAGGTTTTCCCACAGTGAATTAGACACTATGCCTTCTACAGTCACC
AGTCCTGAGGCAGAATCCAGCTCAGCCATTTCAACAACTATTTCACCTGGTATACCAGGTGTGCTGACATCACTGGT
CACTAGCTCTGGGAGAGACATCAGTGCAACTTTTCCAACAGTGCCTGAGTCCCCACATGAATCAGAGGCAACAGCCT
CATGGGTTACTCATCCTGCAGTCACCAGCACAACAGTTCCCAGGACAACCCCTAATTATTCTCATAGTGAACCAGAC
ACCACACCATCAATAGCCACCAGTCCTGGGGCAGAAGCCACTTCAGATTTTCCAACAATAACTGTCTCACCTGATGT
ACCAGATATGGTAACCTCACAGGTCACTAGTTCTGGGACAGACACCAGTATAACTATTCCAACTCTGACTCTTTCTT
CTGGTGAGCCAGAGACCACAACCTCATTTATCACCTATTCTGAGACACATACAAGTTCAGCCATTCCAACTCTCCCT
GTCTCCCCTGATGCATCAAAGATGCTGACCTCACTGGTCATCAGTTCTGGGACAGACAGCACTACAACTTTCCCAAC
ACTGACGGAGACCCCATATGAACCAGAGACAACAGCCATACAGCTCATTCATCCTGCAGAGACCAACACAATGGTTC
CCAGGACAACTCCCAAGTTTTCCCATAGTAAGTCAGACACCACACTCCCAGTAGCCATCACCAGTCCTGGGCCAGAA

FIGURE 1C

GCCAGTTCAGCTGTTTCAACGACAACTATCTCACCTGATATGTCAGATCTGGTGACCTCACTGGTCCCTAGTTCTGG
GACAGACACCAGTACAACCTTCCCAACATTGAGTGAGACCCCATATGAACCAGAGACTACAGCCACGTGGCTCACTC
ATCCTGCAGAAACCAGCACAACGGTTTCTGGGACAATTCCCAACTTTTCCCATAGGGGATCAGACACTGCACCCTCA
ATGGTCACCAGTCCTGGAGTAGACACGAGGTCAGGTGTTCCAACTACAACCATCCCACCCAGTATACCAGGGGTAGT
GACCTCACAGGTCACTAGTTCTGCAACAGACACTAGTACAGCTATTCCAACTTTGACTCCTTCTCCTGGTGAACCAG
AGACCACAGCCTCATCAGCTACCCATCCTGGGACACAGACTGGCTTCACTGTTCCAATTCGGACTGTTCCCTCTAGT
GAGCCAGATACAATGGCTTCCTGGGTCACTCATCCTCCACAGACCAGCACACCTGTTTCCAGAACAACCTCCAGTTT
TTCCCATAGTAGTCCAGATGCCACACCTGTAATGGCCACCAGTCCTAGGACAGAAGCCAGTTCAGCTGTACTGACAA
CAATCTCACCTGGTGCACCAGAGATGGTGACTTCACAGATCACTAGTTCTGGGGCAGCAACCAGTACAACTGTTCCA
ACTTTGACTCATTCTCCTGGTATGCCAGAGACCACAGCCTTATTGAGCACCCATCCCAGAACAGAGACAAGTAAAAC
ATTTCCTGCTTCAACTGTGTTTCCTCAAGTATCAGAGACCACAGCCTCACTCACCATTAGACCTGGTGCAGAGACTA
GCACAGCTCTCCCAACTCAGACAACATCCTCTCTCTTCACCCTACTTGTAACTGGAACCAGCAGAGTTGATCTAAGT
CCAACTGCTTCACCTGGTGTTTCTGCAAAAACAGCCCCACTTTCCACCCATCCAGGGACAGAAACCAGCACAATGAT
TCCAACTTCAACTCTTTCCCTTGGTTTACTAGAGACTACAGGCTTACTGGCCACCAGCTCTTCAGCAGAGACCAGCA
CGAGTACTCTAACTCTGACTGTTTCCCCTGCTGTCTCTGGGCTTTCCAGTGCCTCTATAACAACTGATAAGCCCCAA
ACTGTGACCTCCTGGAACACAGAAACCTCACCATCTGTAACTTCAGTTGGACCCCCAGAATTTTCCAGGACTGTCAC
AGGCACCACTATGACCTTGATACCATCAGAGATGCCAACACCACCTAAAACCAGTCATGGAGAAGGAGTGAGTCCAA
CCACTATCTTGAGAACTACAATGGTTGAAGCCACTAATTTAGCTACCACAGGTTCCAGTCCCACTGTGGCCAAGACA
ACAACCACCTTCAATACACTGGCTGGAAGCCTCTTTACTCCTCTGACCACACCTGGGATGTCCACCTTGGCCTCTGA
GAGTGTGACCTCAAGAACAAGTTATAACCATCGGTCCTGGATCTCCACCACCAGCAGTTATAACCGTCGGTACTGGA
CCCCTGCCACCAGCACTCCAGTGACTTCTACATTCTCCCCAGGGATTTCCACATCCTCCATCCCCAGCTCCACAGCA
GCCACAGTCCCATTCATGGTGCCATTCACCCTCAACTTCACCATCACCAACCTGCAGTACGAGGAGGACATGCGGCA
CCCTGGTTCAAGGAAGTTCAACGCCACAGAGAGAGAACTGCAGGGTCTGCTCAAACCCTTGTTCAGGAATAGCAGTC
TGGAATACCTCTATTCAGGCTGCAGACTAGCCTCACTCAGGCCAGAGAAGGATAGCTCAGCCACGGCAGTGGATGCC
ATCTGCACACATCGCCCTGACCCTGAAGACCTCGGACTGGACAGAGAGCGACTGTACTGGGAGCTGAGCAATCTGAC
AAATGGCATCCAGGAGCTGGGCCCCTTACACCCTGGACCGGAACAGTCTCTATGTCAATGGTTTCACCCATCGAAGCT
CTATGCCCACCACCAGCACTCCTGGGACCTCCACAGTGGATGTGGGAACCTCAGGGACTCCATCCTCCAGCCCCAGC
CCCACGACTGCTGGCCCTCTCCTGATGCCGTTCACCCTCAACTTCACCATCACCAACCTGCAGTACGAGGAGGACAT
GCGTCGCACTGGCTCCAGGAAGTTCAACACCATGGAGAGTGTCCTGCAGGGTCTGCTCAAGCCATTGTTCAAGAACA
CCAGTGTTGGCCCTTTGTACTCTGGCTGCAGATTGACCTTGCTCAGGCCCGAGAAAGATGGGGCAGCCACTGGAGTG
GATGCCATCTGCACCCACCGCCTTGACCCCAAAAGCCCTGGACTCAACAGGGAGCAGCTGTACTGGGAGCTAAGCAA
ACTGACCAATGACATTGAAGAGCTGGGCCCCTACACCCTGGACAGGAACAGTCTCTATGTCAATGGTTTCACCCATC
AGAGCTCTGTGTCCACCACCAGCACTCCTGGGACCTCCACAGTGGATCTCAGAACCTCAGGGACTCCATCCTCCCTC
TCCAGCCCCACAATTATGGCTGCTGGCCCTCTCCTGGTACCATTCACCCTCAACTTCACCATCACCAACCTGCAGTA
TGGGGAGGACATGGGTCACCCTGGCTCCAGGAAGTTCAACACCACAGAGAGGGTCCTGCAGGGTCTGCTTGGTCCCA
TATTCAAGAACACCAGTGTTGGCCCTCTGTACTCTGGCTGCAGACTGACCTCTCTCAGGTCCGAGAAGGATGGAGCA
GCCACTGGAGTGGATGCCATCTGCATCCATCATCTTGACCCCAAAAGCCCTGGACTCAACAGAGAGCGGCTGTACTG
GGAGCTGAGCCAACTGACCAATGGCATCAAAGAGCTGGGCCCCTACACCCTGGACAGGAACAGTCTCTATGTCAATG
GTTTCACCCATCGGACCTCTGTGCCCACCACCAGCACTCCTGGGACCTCCACAGTGGACCTTGGAACCTCAGGGACT
CCATTCTCCCTCCCAAGCCCCGCAACTGCTGGCCCTCTCCTGGTGCTGTTCACCCTCAACTTCACCATCACCAACCT
GAAGTATGAGGAGGACATGCATCGCCCTGGCTCCAGGAAGTTCAACACCACTGAGAGGGTCCTGCAGACCCTGGTTG
GTCCTATGTTCAAGAACACCAGTGTTGGCCTTCTGTACTCTGGCTGCAGACTGACCTTGCTCAGGTCCGAGAAGGAT
GGAGCAGCCACTGGAGTGGATGCCATCTGCACCCACCGTCTTGACCCCAAAAGCCCTGGAGTGGACAGGGAGCAGCT
ATACTGGGAGCTGAGCCAACTGACCAATGGCATCAAAGAGCTGGGCCCCTACACCCTGGACAGGAACAGTCTCTATG
TCAATGGTTTCACCCATTGGATCCCTGTGCCCACCAGCAGCACCCCTGGGACCTCCACAGTGGACCTTGGGTCAGGG
ACTCCATCCTCCCTCCCCAGCCCCACAAGTGCTACTGCTGGCCCTCTCCTGGTGCCGTTCACCCTCAACTTCACCAT
CACCAACCTGAAGTACGAGGAGGACATGCATTGCCCTGGCTCCAGGAAGTTCAACACCACAGAGAGAGTCCTGCAGA
GTCTGCTTGGTCCCATGTTCAAGAACACCAGTGTTGGCCCTCTGTACTCTGGCTGCAGACTGACCTTGCTCAGGTCC
GAGAAGGATGGAGCAGCCACTGGAGTGGATGCCATCTGCACCCACCGTCTTGACCCCAAAAGCCCTGGAGTGGACAG
GGAGCAGCTATACTGGGAGCTGAGCCAGCTGACCAATGGCATCAAAGAGCTGGGTCCCTACACCCTGGACAGAAACA
GTCTCTATGTCAATGGTTTCACCCATCAGACCTCTGCGCCCAACACCAGCACTCCTGGGACCTCCACAGTGGACCTT
GGGACCTCAGGGACTCCATCCTCCCTCCCCAGCCCTACATCTGCTGGCCCTCTCCTGGTGCCATTCACCCTCAACTT
CACCATCACCAACCTGCAGTACGAGGAGGACATGCATCACCCAGGCTCCAGGAAGTTCAACACCACGGAGCGGGTCC
TGCAGGGTCTGCTTGGTCCCATGTTCAAGAACACCAGTGTCGGCCTTCTGTACTCTGGCTGCAGACTGACCTTGCTC
AGGCCTGAGAAGAATGGGGCAGCCACTGGAATGGATGCCATCTGCAGCCACCGTCTTGACCCCAAAAGCCCTGGACT
CAACAGAGAGCAGCTGTACTGGGAGCTGAGCCAGCTGACCCATGGCATCAAAGAGCTGGGCCCCTACACCCTGGACA
GGAACAGTCTCTATGTCAATGGTTTCACCCATCGGAGCTCTGTGGCCCCCACCAGCACTCCTGGGACCTCCACAGTG
GACCTTGGGACCTCAGGGACTCCATCCTCCCTCCCCAGCCCCACAACAGCTGTTCCTCTCCTGGTGCCGTTCACCCT
CAACTTTACCATCACCAATCTGCAGTATGGGGAGGACATGCGTCACCCTGGCTCCAGGAAGTTCAACACCACAGAGA
GGGTCCTGCAGGGTCTGCTTGGTCCCTTGTTCAAGAACTCCAGTGTCGGCCCTCTGTACTCTGGCTGCAGACTGATC
TCTCTCAGGTCTGAGAAGGATGGGGCAGCCACTGGAGTGGATGCCATCTGCACCCACCACCTTAACCCTCAAAGCCC
TGGACTGGACAGGGAGCAGCTGTACTGGCAGCTGAGCCAGATGACCAATGGCATCAAAGAGCTGGGCCCCTACACCC
TGGACCGGAACAGTCTCTACGTCAATGGTTTCACCCATCGGAGCTCTGGGCTCACCACCAGCACTCCTTGGACTTCC
ACAGTTGACCTTGGAACCTCAGGGACTCCATCCCCCGTCCCCAGCCCCACAACTGCTGGCCCTCTCCTGGTGCCATT

FIGURE 1D

CACCCTAAACTTCACCATCACCAACCTGCAGTATGAGGAGGACATGCATCGCCCTGGATCTAGGAAGTTCAACGCCA
CAGAGAGGGTCCTGCAGGGTCTGCTTAGTCCCATATTCAAGAACTCCAGTGTTGGCCCTCTGTACTCTGGCTGCAGA
CTGACCTCTCTCAGGCCCGAGAAGGATGGGGCAGCAACTGGAATGGATGCTGTCTGCCTCTACCACCCTAATCCCAA
AAGACCTGGGCTGGACAGAGAGCAGCTGTACTGGGAGCTAAGCCAGCTGACCCACAACATCACTGAGCTGGGCCCCT
ACAGCCTGGACAGGGACAGTCTCTATGTCAATGGTTTCACCCATCAGAACTCTGTGCCCACCACCAGTACTCCTGGG
ACCTCCACAGTGTACTGGGCAACCACTGGGACTCCATCCTCCTTCCCCGGCCACACAGAGCCTGGCCCTCTCCTGAT
ACCATTCACTTTCAACTTTACCATCACCAACCTGCATTATGAGGAAAACATGCAACACCCTGGTTCCAGGAAGTTCA
ACACCACGGAGAGGGTTCTGCAGGGTCTGCTCAAGCCCTTGTTCAAGAACACCAGTGTTGGCCCTCTGTACTCTGGC
TGCAGACTGACCTTGCTCAGACCTGAGAAGCAGGAGGCAGCCACTGGAGTGGACACCATCTGTACCCACCGCGTTGA
TCCCATCGGACCTGGACTGGACAGAGAGCGGCTATACTGGGAGCTGAGCCAGCTGACCAACAGCATCACAGAGCTGG
GACCCTACACCCTGGATAGGGACAGTCTCTATGTCAATGGCTTCAACCCTTGGAGCTCTGTGCCAACCACCAGCACT
CCTGGGACCTCCACAGTGCACCTGGCAACCTCTGGGACTCCATCCTCCCTGCCTGGCCACACAGCCCCTGTCCCTCT
CTTGATACCATTCACCCTCAACTTTACCATCACCAACCTGCATTATGAAGAAAACATGCAACACCCTGGTTCCAGGA
AGTTCAACACCACGGAGAGGGTTCTGCAGGGTCTGCTCAAGCCCTTGTTCAAGAGCACCAGCGTTGGCCCTCTGTAC
TCTGGCTGCAGACTGACCTTGCTCAGACCTGAGAAACATGGGGCAGCCACTGGAGTGGACGCCATCTGCACCCTCCG
CCTTGATCCCACTGGTCCTGGACTGGACAGAGAGCGGCTATACTGGGAGCTGAGCCAGCTGACCAACAGCGTTACAG
AGCTGGGCCCCTACACCCTGGACAGGGACAGTCTCTATGTCAATGGCTTCACCCATCGGAGCTCTGTGCCAACCACC
AGTATTCCTGGGACCTCTGCAGTGCACCTGGAAACCTCTGGGACTCCAGCCTCCCTCCCTGGCCACACAGCCCCTGG
CCCTCTCCTGGTGCCATTCACCCTCAACTTCACTATCACCAACCTGCAGTATGAGGAGGACATGCGTCACCCTGGTT
CCAGGAAGTTCAACACCACGGAGAGAGTCCTGCAGGGTCTGCTCAAGCCCTTGTTCAAGAGCACCAGTGTTGGCCCT
CTGTACTCTGGCTGCAGACTGACCTTGCTCAGGCCTGAAAAACGTGGGGCAGCCACCGGCGTGGACACCATCTGCAC
TCACCGCCTTGACCCTCTAAACCCTGGACTGGACAGAGAGCAGCTATACTGGGAGCTGAGCAAACTGACCCGTGGCA
TCATCGAGCTGGGCCCCTACCTCCTGGACAGAGGCAGTCTCTATGTCAATGGTTTCACCCATCGGAACTTTGTGCCC
ATCACCAGCACTCCTGGGACCTCCACAGTACACCTAGGAACCTCTGAAACTCCATCCTCCCTACCTAGACCCATAGT
GCCTGGCCCTCTCCTGGTGCCATTCACCCTCAACTTCACCATCACCAACTTGCAGTATGAGGAGGCCATGCGACACC
CTGGCTCCAGGAAGTTCAATACCACGGAGAGGGTCCTACAGGGTCTGCTCAGGCCCTTGTTCAAGAATACCAGTATC
GGCCCTCTGTACTCCAGCTGCAGACTGACCTTGCTCAGGCCAGAGAAGGACAAGGCAGCCACCAGAGTGGATGCCAT
CTGTACCCACCACCCTGACCCTCAAAGCCCTGGACTGAACAGAGAGCAGCTGTACTGGGAGCTGAGCCAGCTGACCC
ACGGCATCACTGAGCTGGGCCCCTACACCCTGGACAGGGACAGTCTCTATGTCGATGGTTTCACTCATTGGAGCCCC
ATACCAACCACCAGCACTCCTGGGACCTCCATAGTGAACCTGGGAACCTCTGGGATCCCACCTTCCCTCCCTGAAAC
TACAGCCACCGGCCCTCTCCTGGTGCCATTCACACTCAACTTCACCATCACTAACCTACAGTATGAGGAGAACATGG
GTCACCCTGGCTCCAGGAAGTTCAACATCACGGAGAGTGTTCTGCAGGGTCTGCTCAAGCCCTTGTTCAAGAGCACC
AGTGTTGGCCCTCTGTATTCTGGCTGCAGACTGACCTTGCTCAGGCCTGAGAAGGACGGAGTAGCCACCAGAGTGGA
CGCCATCTGCACCCACCGCCCTGACCCCAAAATCCCTGGGCTAGACAGACAGCAGCTATACTGGGAGCTGAGCCAGC
TGACCCACAGCATCACTGAGCTGGGACCCTACACCCTGGATAGGGACAGTCTCTATGTCAATGGTTTCACCCAGCGG
AGCTCTGTGCCCACCACCAGCACTCCTGGGACTTTCACAGTACAGCCGGAAACCTCTGAGACTCCATCATCCCTCCC
TGGCCCCACAGCCACTGGCCCTGTCCTGCTGCCATTCACCCTCAATTTTACCATCATTAACCTGCAGTATGAGGAGG
ACATGCATCGCCCTGGCTCCAGGAAGTTCAACACCACGGAGAGGGTCCTTCAGGGTCTGCTTATGCCCTTGTTCAAG
AACACCAGTGTCAGCTCTCTGTACTCTGGTTGCAGACTGACCTTGCTCAGGCCTGAGAAGGATGGGGCAGCCACCAG
AGTGGATGCTGTCTGCACCCATCGTCCTGACCCCAAAAGCCCTGGACTGGACAGAGAGCGGCTGTACTGGAAGCTGA
GCCAGCTGACCCACGGCATCACTGAGCTGGGCCCCTACACCCTGGACAGGCACAGTCTCTATGTCAATGGTTTCACC
CATCAGAGCTCTATGACGACCACCAGAACTCCTGATACCTCCACAATGCACCTGGCAACCTCGAGAACTCCAGCCTC
CCTGTCTGGACCTACGACCGCCAGCCCTCTCCTGGTGCTATTCACAATTAACTTCACCATCACTAACCTGCGGTATG
AGGAGAACATGCATCACCCTGGCTCTAGAAAGTTTAACACCACGGAGAGAGTCCTTCAGGGTCTGCTCAGGCCTGTG
TTCAAGAACACCAGTGTTGGCCCTCTGTACTCTGGCTGCAGACTGACCTTGCTCAGGCCCAAGAAGGATGGGGCAGC
CACCAAAGTGGATGCCATCTGCACCTACCGCCCTGATCCCAAAAGCCCTGGACTGGACAGAGAGCAGCTATACTGGG
AGCTGAGCCAGCTAACCCACAGCATCACTGAGCTGGGCCCCTACACCCTGGACAGGGACAGTCTCTATGTCAATGGT
TTCACACAGCGGAGCTCTGTGCCCACCACTAGCATTCCTGGGACCCCCACAGTGGACCTGGGAACATCTGGGACTCC
AGTTTCTAAACCTGGTCCCTCGGCTGCCAGCCCTCTCCTGGTGCTATTCACTCTCAACTTCACCATCACCAACCTGC
GGTATGAGGAGAACATGCAGCACCCTGGCTCCAGGAAGTTCAACACCACGGAGAGGGTCCTTCAGGGCCTGCTCAGG
TCCCTGTTCAAGAGCACCAGTGTTGGCCCTCTGTACTCTGGCTGCAGACTGACTTTGCTCAGGCCTGAAAAGGATGG
GACAGCCACTGGAGTGGATGCCATCTGCACCCACCACCCTGACCCCAAAAGCCCTAGGCTGGACAGAGAGCAGCTGT
ATTGGGAGCTGAGCCAGCTGACCCACAATATCACTGAGCTGGGCCCCTATGCCCTGGACAACGACAGCCTCTTTGTC
AATGGTTTCACTCATCGGAGCTCTGTGTCCACCACCAGCACTCCTGGGACCCCCACAGTGTATCTGGGAGCATCTAA
GACTCCAGCCTCGATATTTGGCCCTTCAGCTGCCAGCCATCTCCTGATACTATTCACCCTCAACTTCACCATCACTA
ACCTGCGGTATGAGGAGAACATGTGGCCTGGCTCCAGGAAGTTCAACACTACAGAGAGGGTCCTTCAGGGCCTGCTA
AGGCCCTTGTTCAAGAACACCAGTGTTGGCCCTCTGTACTCTGGCTGCAGGCTGACCTTGCTCAGGCCAGAGAAAGA
TGGGGAAGCCACCGGAGTGGATGCCATCTGCACCCACCGCCCTGACCCCACAGGCCCTGGGCTGGACAGAGAGCAGC
TGTATTTGGAGCTGAGCCAGCTGACCCACAGCATCACTGAGCTGGGCCCCTACACACTGGACAGGGACAGTCTCTAT
GTCAATGGTTTCACCCATCGGAGCTCTGTACCCACCACCAGCACCGGGGTGGTCAGCGAGGAGCCATTCACACTGAA
CTTCACCATCAACAACCTGCGCTACATGGCGGACATGGGCCAACCCGGCTCCCTCAAGTTCAACATCACAGACAACG
TCATGCAGCACCTGCTCAGTCCTTTGTTCCAGAGGAGCAGCCTGGGTGCACGGTACACAGGCTGCAGGGTCATCGCA
CTAAGGTCTGTGAAGAACGGTGCTGAGACACGGGTGGACCTCCTCTGCACCTACCTGCAGCCCCTCAGCGGCCCAGG
TCTGCCTATCAAGCAGGTGTTCCATGAGCTGAGCCAGCAGACCCATGGCATCACCCGGCTGGGCCCCTACTCTCTGG

FIGURE 1E

ACAAAGACAGCCTCTACCTTAACGGTTACAATGAACCTGGTCCAGATGAGCCTCCTACAACTCCCAAGCCAGCCACC
ACATTCCTGCCTCCTCTGTCAGAAGCCACAACAGCCATGGGGTACCACCTGAAGACCCTCACACTCAACTTCACCAT
CTCCAATCTCCAGTATTCACCAGATATGGGCAAGGGCTCAGCTACATTCAACTCCACCGAGGGGGTCCTTCAGCACC
TGCTCAGACCCTTGTTCCAGAAGAGCAGCATGGGCCCCTTCTACTTGGGTTGCCAACTGATCTCCCTCAGGCCTGAG
AAGGATGGGGCAGCCACTGGTGTGGACACCACCTGCACCTACCACCCTGACCCTGTGGGCCCCGGGCTGGACATACA
GCAGCTTTACTGGGAGCTGAGTCAGCTGACCCATGGTGTCACCCAACTGGGCTTCTATGTCCTGGACAGGGATAGCC
TCTTCATCAATGGCTATGCACCCCAGAATTTATCAATCCGGGGCGAGTACCAGATAAATTTCCACATTGTCAACTGG
AACCTCAGTAATCCAGACCCCACATCCTCAGAGTACATCACCCTGCTGAGGGACATCCAGGACAAGGTCACCACACT
CTACAAAGGCAGTCAACTACATGACACATTCCGCTTCTGCCTGGTCACCAACTTGACGATGGACTCCGTGTTGGTCA
CTGTCAAGGCATTGTTCTCCTCCAATTTGGACCCCAGCCTGGTGGAGCAAGTCTTTCTAGATAAGACCCTGAATGCC
TCATTCCATTGGCTGGGCTCCACCTACCAGTTGGTGGACATCCATGTGACAGAAATGGAGTCATCAGTTTATCAACC
AACAAGCAGCTCCAGCACCCAGCACTTCTACCTGAATTTCACCATCACCAACCTACCATATTCCCAGGACAAAGCCC
AGCCAGGCACCACCAATTACCAGAGGAACAAAAGGAATATTGAGGATGCGCTCAACCAACTCTTCCGAAACAGCAGC
ATCAAGAGTTATTTTTCTGACTGTCAAGTTTCAACATTCAGGTCTGTCCCCAACAGGCACCACACCGGGGTGGACTC
CCTGTGTAACTTCTCGCCACTGGCTCGGAGAGTAGACAGAGTTGCCATCTATGAGGAATTTCTGCGGATGACCCGGA
ATGGTACCCAGCTGCAGAACTTCACCCTGGACAGGAGCAGTGTCCTTGTGGATGGGTATTCTCCCAACAGAAATGAG
CCCTTAACTGGGAATTCTGACCTTCCCTTCTGGGCTGTCATCCTCATCGGCTTGGCAGGACTCCTGGGACTCATCAC
ATGCCTGATCTGCGGTGTCCTGGTGACCACCCGCCGGCGGAAGAAGGAAGGAGAATACAACGTCCAGCAACAGTGCC
CAGGCTACTACCAGTCACACCTAGACCTGGAGGATCTGCAATGACTGGAACTTGCCGGTGCCTGGGGTGCCTTTCCC
CCAGCCAGGGTCCAAAGAAGCTTGGCTGGGGCAGAAATAAACCATATTGGTCGGAAAAAAAAAAAAAAAAAAAAAAA
AAAAAAAAAAAAAA

FIGURE 2A

PVTSLLTPGLVITTDRMGISREPGTSSTSNLSSTSHERLTTLEDTVDTEAMQPSTHTAVTNVRTSISGHESQSSVLS
DSETPKATSPMGTTYTMGETSVSISTSDFFETSRIQIEPTSSLTSGLRETSSSERISSATEGSTVLSEVPSGATTEV
SRTEVISSRGTSMSGPDQFTISPDISTEAITRLSTSPIMTESAESAITIETGSPGATSEGTLTLDTSTTTFWSGTHS
TASPGFSHSEMTTLMSRTPGDVPWPSLPSVEEASSVSSSLSSPAMTSTSFFSTLPESISSSPHPVTALLTLGPVKTT
DMLRTSSEPETSSPPNLSSTSAEILATSEVTKDREKIHPSSNTPVVNVGTVIYKHLSPSSVLADLVTTKPTSPMATT
STLGNTSVSTSTPAFPETMMTQPTSSLTSGLREISTSQETSSATERSASLSGMPTGATTKVSRTEALSLGRTSTPGP
AQSTISPEISTETITRISTPLTTTGSAEMTITPKTGHSGASSQGTFTLDTSSRASWPGTHSAATHRSPHSGMTTPMS
RGPEDVSWPSRPSVEKTSPPSSLVSLSAVTSPSPLYSTPSESSHSSPLRVTSLFTPVMMKTTDMLDTSLEPVTTSPP
SMNITSDESLATSKATMETEAIQLSENTAVTQMGTISARQEFYSSYPGLPEPSKVTSPVVTSSTIKDIVSTTIPASS
EITRIEMESTSTLTPTPRETSTSQEIHSATKPSTVPYKALTSATIEDSMTQVMSSSRGPSPDQSTMSQDISTEVITR
LSTSPIKTESTEMTITTQTGSPGATSRGTLTLDTSTTFMSGTHSTASQGFSHSQMTALMSRTPGEVPWLSHPSVEEA
SSASFSLSSPVMTSSSPVSSTLPDSIHSSSLPVTSLLTSGLVKTTELLGTSSEPETSSPPNLSSTSAEILATTEVTT
DTEKLEMTNVVTSGYTHESPSSVLADSVTTKATSSMGITYPTGDTNVLTSTPAFSDTSRIQTKSKLSLTPGLMETSI
SEETSSATEKSTVLSSVPTGATTEVSRTEAISSSRTSIPGPAQSTMSSDTSMETITRISTPLTRKESTDMAITPKTG
PSGATSQGTFTLDSSSTASWPGTHSATTQRFPRSVVTTPMSRGPEDVSWPSPLSVEKNSPPSSLVSSSSVTSPSPLY
STPSGSSHSSPVPVTSLFTSIMMKATDMLDASLEPETTSAPNMNITSDESLAASKATTETEAIHVFENTAASHVETT
SATEELYSSSPGFSEPTKVISPVVTSSSIRDNMVSTTMPGSSGITRIEIESMSSLTPGLRETRTSQDITSSTETSTV
LYKMPSGATPEVSRTEVMPSSRTSIPGPAQSTMSLDISDEVVTRLSTSPIMTESAEITITTQTGYSLATSQVTLPLG
TSMTFLSGTHSTMSQGLSHSEMTNLMSRGPESLSWTSPRFVETTRSSSSLTSLPLTTSLSPVSSTLLDSSPSSPLPV
TSLILPGLVKTTEVLDTSSEPKTSSSPNLSSTSVEIPATSEIMTDTEKIHPSSNTAVAKVRTSSSVHESHSSVLADS
ETTITIPSMGITSAVEDTTVFTSNPAFSETRRIPTEPTFSLTPGFRETSTSEETTSITETSAVLFGVPTSATTEVSM
TEIMSSNRTHIPDSDQSTMSPDIITEVITRLSSSSMMSESTQMTITTQKSSPGATAQSTLTLATTTAPLARTHSTVP
PRFLHSEMTTLMSRSPENPSWKSSPFVEKTSSSSSLLSLPVTTSPSVSSTLPQSIPSSSFSVTSLLTPGMVKTTDTS
TEPGTSLSPNLSGTSVEILAASEVTTDTEKIHPSSSMAVTNVGTTSSGHELYSSVSIHSEPSKATYPVGTPSSMAET
SISTSMPANFETTGFEAEPFSHLTSGLRKTNMSLDTSSVTPTNTPSSPGSTHLLQSSKTDFTSSAKTSSPDWPPASQ
YTEIPVDIITPFNASPSITESTGITSFPESRFTMSVTESTHHLSTDLLPSAETISTGTVMPSLSEAMTSFATTGVPR
AISGSGSPFSRTESGPGDATLSTIAESLPSSTPVPFSSSTFTTTDSSTIPALHEITSSSATPYRVDTSLGTESSTTE
GRLVMVSTLDTSSQPGRTSSSPILDTRMTESVELGTVTSAYQVPSLSTRLTRTDGIMEHITKIPNEAAHRGTIRPVK
GPQTSTSPASPKGLHTGGTKRMETTTTALKTTTTALKTTSRATLTTSVYTPTLGTLTPLNASMQMASTIPTEMMITT
PYVFPDVPETTSSLATSLGAETSTALPRTTPSVFNRESETTASLVSRSGAERSPVIQTLDVSSSEPDTTASWVIHPA
ETIPTVSKTTPNFFHSELDTVSSTATSHGADVSSAIPTNISPSELDALTPLVTISGTDTSTTFPTLTKSPHETETRT
TWLTHPAETSSTIPRTIPNFSHHESDATPSIATSPGAETSSAIPIMTVSPGAEDLVTSQVTSSGTDRNMTIPTLTLS
PGEPKTIASLVTHPEAQTSSAIPTSTISPAVSRLVTSMVTSLAAKTSTTNRALTNSPGEPATTVSLVTHSAQTSPTV
PWTTSIFFHSKSDTTPSMTTSHGAESSSAVPTPTVSTEVPGVVTPLVTSSRAVISTTIPILTLSPGEPETTPSMATS
HGEEASSAIPTPTVSPGVPGVVTSLVTSSRAVTSTTIPILTFSLGEPETTPSMATSHGTEAGSAVPTVLPEVPGMVT
SLVASSRAVTSTTLPTLTLSPGEPETTPSMATSHGAEASSTVPTVSPEVPGVVTSLVTSSSGVNSTSIPTLILSPGE
LETTPSMATSHGAEASSAVPTPTVSPGVSGVVTPLVTSSRAVTSTTIPILTLSSSEPETTPSMATSHGVEASSAVLT
VSPEVPGMVTFLVTSSRAVTSTTIPTLTISSDEPETTTSLVTHSEAKMISAIPTLGVSPTVQGLVTSLVTSSGSETS
AFSNLTVASSQPETIDSWVAHPGTEASSVVPTLTVSTGEPFTNISLVTHPAESSSTLPRTTSRFSHSELDTMPSTVT
SPEAESSSAISTTISPGIPGVLTSLVTSSGRDISATFPTVPESPHESEATASWVTHPAVTSTTVPRTTPNYSHSEPD
TTPSIATSPGAEATSDFPTITVSPDVPDMVTSQVTSSGTDTSITIPTLTLSSGEPETTTSFITYSETHTSSAIPTLP
VSPDASKMLTSLVISSGTDSTTTFPTLTETPYEPETTAIQLIHPAETNTMVPRTTPKFSHSKSDTTLPVAITSPGPE
ASSAVSTTTISPDMSDLVTSLVPSSGTDTSTTFPTLSETPYEPETTATWLTHPAETSTTVSGTIPNFSHRGSDTAPS
MVTSPGVDTRSGVPTTTIPPSIPGVVTSQVTSSATDTSTAIPTLTPSPGEPETTASSATHPGTQTGFTVPIRTVPSS
EPDTMASWVTHPPQTSTPVSRTTSSFSHSSPDATPVMATSPRTEASSAVLTTISPGAPEMVTSQITSSGAATSTTVP
TLTHSPGMPETTALLSTHPRTETSKTFPASTVFPQVSETTASLTIRPGAETSTALPTQTTSSLFTLLVTGTSRVDLS
PTASPGVSAKTAPLSTHPGTETSTMIPTSTLSLGLLETTGLLATSSSAETSTSTLTLTVSPAVSGLSSASITTDKPQ
TVTSWNTETSPSVTSVGPPEFSRTVTGTTMTLIPSEMPTPPKTSHGEGVSPTTILRTTMVEATNLATTGSSPTVAKT
TTTFNTLAGSLFTPLTTPGMSTLASESVTSRTSYNHRSWISTTSSYNRRYWTPATSTPVTSTFSPGISTSSIPSSTA
ATVPFMVPFTLNFTITNLQYEEDMRHPGSRKFNATERELQGLLKPLFRNSSLEYLYSGCRLASLRPEKDSSATAVDA
ICTHRPDPEDLGLDRERLYWELSNLTNGIQELGPYTLDRNSLYVNGFTHRSSMPTTSTPGTSTVDVGTSGTPSSSPS
PTTAGPLLMPFTLNFTITNLQYEEDMRRTGSRKFNTMESVLQGLLKPLFKNTSVGPLYSGCRLTLLRPEKDGAATGV
DAICTHRLDPKSPGLNREQLYWELSKLTNDIEELGPYTLDRNSLYVNGFTHQSSVSTTSTPGTSTVDLRTSGTPSSL
SSPTIMAAGPLLVPFTLNFTITNLQYGEDMGHPGSRKFNTTERVLQGLLGPIFKNTSVGPLYSGCRLTSLRSEKDGA
ATGVDAICIHHLDPKSPGLNRERLYWELSQLTNGIKELGPYTLDRNSLYVNGFTHRTSVPTTSTPGTSTVDLGTSGT
PFSLPSPATAGPLLVLFTLNFTITNLKYEEDMHRPGSRKFNTTERVLQTLVGPMFKNTSVGLLYSGCRLTLLRSEKD
GAATGVDAICTHRLDPKSPGVDREQLYWELSQLTNGIKELGPYTLDRNSLYVNGFTHWIPVPTSSTPGTSTVDLGSG
TPSSLPSPTSATAGPLLVPFTLNFTITNLKYEEDMHCPGSRKFNTTERVLQSLLGPMFKNTSVGPLYSGCRLTLLRS
EKDGAATGVDAICTHRLDPKSPGVDREQLYWELSQLTNGIKELGPYTLDRNSLYVNGFTHQTSAPNTSTPGTSTVDL
GTSGTPSSLPSPTSAGPLLVPFTLNFTITNLQYEEDMHHPGSRKFNTTERVLQGLLGPMFKNTSVGLLYSGCRLTLL
RPEKNGAATGMDAICSHRLDPKSPGLNREQLYWELSQLTHGIKELGPYTLDRNSLYVNGFTHRSSVAPTSTPGTSTV
DLGTSGTPSSLPSPTTAVPLLVPFTLNFTITNLQYGEDMRHPGSRKFNTTERVLQGLLGPLFKNSSVGPLYSGCRLI
SLRSEKDGAATGVDAICTHHLNPQSPGLDREQLYWQLSQMTNGIKELGPYTLDRNSLYVNGFTHRSSGLTTSTPWTS

FIGURE 2B

TVDLGTSGTPSPVPSPTTAGPLLVPFTLNFTITNLQYEEDMHRPGSRKFNATERVLQGLLSPIFKNSSVGPLYSGCR
LTSLRPEKDGAATGMDAVCLYHPNPKRPGLDREQLYWELSQLTHNITELGPYSLDRDSLYVNGFTHQNSVPTTSTPG
TSTVYWATTGTPSSFPGHTEPGPLLIPFTFNFTITNLHYEENMQHPGSRKFNTTERVLQGLLKPLFKNTSVGPLYSG
CRLTLLRPEKQEAATGVDTICTHRVDPIGPGLDRERLYWELSQLTNSITELGPYTLDRDSLYVNGFNPWSSVPTTST
PGTSTVHLATSGTPSSLPGHTAPVPLLIPFTLNFTITNLHYEENMQHPGSRKFNTTERVLQGLLKPLFKSTSVGPLY
SGCRLTLLRPEKHGAATGVDAICTLRLDPTGPGLDRERLYWELSQLTNSVTELGPYTLDRDSLYVNGFTHRSSVPTT
SIPGTSAVHLETSGTPASLPGHTAPGPLLVPFTLNFTITNLQYEEDMRHPGSRKFNTTERVLQGLLKPLFKSTSVGP
LYSGCRLTLLRPEKRGAATGVDTICTHRLDPLNPGLDREQLYWELSKLTRGIIELGPYLLDRGSLYVNGFTHRNFVP
ITSTPGTSTVHLGTSETPSSLPRPIVPGPLLVPFTLNFTITNLQYEEAMRHPGSRKFNTTERVLQGLLRPLFKNTSI
GPLYSSCRLTLLRPEKDKAATRVDAICTHHPDPQSPGLNREQLYWELSQLTHGITELGPYTLDRDSLYVDGFTHWSP
IPTTSTPGTSIVNLGTSGIPPSLPETTATGPLLVPFTLNFTITNLQYEENMGHPGSRKFNITESVLQGLLKPLFKST
SVGPLYSGCRLTLLRPEKDGVATRVDAICTHRPDPKIPGLDRQQLYWELSQLTHSITELGPYTLDRDSLYVNGFTQR
SSVPTTSTPGTFTVQPETSETPSSLPGPTATGPVLLPFTLNFTIINLQYEEDMHRPGSRKFNTTERVLQGLLMPLFK
NTSVSSLYSGCRLTLLRPEKDGAATRVDAVCTHRPDPKSPGLDRERLYWKLSQLTHGITELGPYTLDRHSLYVNGFT
HQSSMTTTRTPDTSTMHLATSRTPASLSGPTTASPLLVLFTINFTITNLRYEENMHHPGSRKFNTTERVLQGLLRPV
FKNTSVGPLYSGCRLTLLRPKKDGAATKVDAICTYRPDPKSPGLDREQLYWELSQLTHSITELGPYTLDRDSLYVNG
FTQRSSVPTTSIPGTPTVDLGTSGTPVSKPGPSAASPLLVLFTLNFTITNLRYEENMQHPGSRKFNTTERVLQGLLR
SLFKSTSVGPLYSGCRLTLLRPEKDGTATGVDAICTHHPDPKSPRLDREQLYWELSQLTHNITELGPYALDNDSLFV
NGFTHRSSVSTTSTPGTPTVYLGASKTPASIFGPSAASHLLILFTLNFTITNLRYEENMWPGSRKFNTTERVLQGLL
RPLFKNTSVGPLYSGCRLTLLRPEKDGEATGVDAICTHRPDPTGPGLDREQLYLELSQLTHSITELGPYTLDRDSLY
VNGFTHRSSVPTTSTGVVSEEPFTLNFTINNLRYMADMGQPGSLKFNITDNVMQHLLSPLFQRSSLGARYTGCRVIA
LRSVKNGAETRVDLLCTYLQPLSGPGLPIKQVFHELSQQTHGITRLGPYSLDKDSLYLNGYNEPGPDEPPTTPKPAT
TFLPPLSEATTAMGYHLKTLTLNFTISNLQYSPDMGKGSATFNSTEGVLQHLLRPLFQKSSMGPFYLGCQLISLRPE
KDGAATGVDTTCTYHPDPVGPGLDIQQLYWELSQLTHGVTQLGFYVLDRDSLFINGYAPQNLSIRGEYQINFHIVNW
NLSNPDPTSSEYITLLRDIQDKVTTLYKGSQLHDTFRFCLVTNLTMDSVLVTVKALFSSNLDPSLVEQVFLDKTLNA
SFHWLGSTYQLVDIHVTEMESSVYQPTSSSSTQHFYLNFTITNLPYSQDKAQPGTTNYQRNKRNIEDALNQLFRNSS
IKSYFSDCQVSTFRSVPNRHHTGVDSLCNFSPLARRVDRVAIYEEFLRMTRNGTQLQNFTLDRSSVLVDGYSPNRNE
PLTGNSDLPFWAVILIGLAGLLGLITCLICGVLVTTRRRKKEGEYNVQQQCPGYYQSHLDLEDLQ

Mucin repeat sequences:
amino acids 3765-6397

FIGURE 3

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| huKI | D | I | Q | M | T | Q | S | P | S | S | L | S | A | S | V | G | D | R | V | T | I | T | C |
| mu11D10-L | D | I | V | L | T | Q | S | P | A | I | M | S | A | S | L | G | E | R | V | T | M | T | C |
| 11D10-graft | D | I | Q | M | T | Q | S | P | S | S | L | S | A | S | V | G | D | R | V | T | I | T | C |

| Kabat# | **24** | **25** | **26** | **27** | **A** | **B** | **C** | **D** | **E** | **F** | **28** | **29** | **30** | **31** | **32** | **33** | **34** | 35 | 36 | 37 | 38 | 39 | 40 |
|---|---|---|---|---|---|---|---|---|---|---|---|---|---|---|---|---|---|---|---|---|---|---|---|
| huKI | **R** | **A** | **S** | **Q** | | | | | | | **S** | **I** | **S** | **N** | **Y** | **L** | **A** | W | Y | Q | Q | K | P |
| mu11D10-L | **T** | **A** | **S** | **S** | **S** | | | | | | **V** | **S** | **S** | **S** | **Y** | **L** | **H** | W | Y | Q | Q | K | P |
| 11D10-graft | **T** | **A** | **S** | **S** | **S** | | | | | | **V** | **S** | **S** | **S** | **Y** | **L** | **H** | W | Y | Q | Q | K | P |

| Kabat# | 41 | 42 | 43 | 44 | 45 | 46 | 47 | 48 | **49** | **50** | **51** | **52** | **53** | **54** | **55** | **56** | 57 | 58 | 59 | 60 | 61 | 62 | 63 |
|---|---|---|---|---|---|---|---|---|---|---|---|---|---|---|---|---|---|---|---|---|---|---|---|
| huKI | G | K | A | P | K | L | L | I | **Y** | **A** | **A** | **S** | **S** | **L** | **E** | **S** | G | V | P | S | R | F | S |
| mu11D10-L | G | S | S | P | K | L | W | I | **Y** | **S** | **T** | **S** | **N** | **L** | **A** | **S** | G | V | P | G | R | F | S |
| 11D10-graft | G | K | A | P | K | L | L | I | **Y** | **S** | **T** | **S** | **N** | **L** | **A** | **S** | G | V | P | S | R | F | S |

| Kabat# | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 |
|---|---|---|---|---|---|---|---|---|---|---|---|---|---|---|---|---|---|---|---|---|---|---|---|
| huKI | G | S | G | S | G | T | D | F | T | L | T | I | S | S | L | Q | P | E | D | F | A | T | Y |
| mu11D10-L | G | S | G | S | G | T | S | Y | S | L | T | I | S | S | M | E | A | E | D | A | A | T | Y |
| 11D10-graft | G | S | G | S | G | T | D | F | T | L | T | I | S | S | L | Q | P | E | D | F | A | T | Y |

| Kabat# | 87 | 88 | **89** | **90** | **91** | **92** | **93** | **94** | **95** | **96** | **97** | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|
| huKI | Y | C | **Q** | **Q** | **Y** | **N** | **S** | **L** | **P** | **W** | **T** | F | G | Q | G | T | K | V | E | I | K | R | (SEQ ID NO:3) |
| mu11D10-L | Y | C | **H** | **Q** | **Y** | **H** | **R** | **S** | **P** | **Y** | **T** | F | G | G | G | T | K | V | E | I | K | R | (SEQ ID NO:4) |
| 11D10-graft | Y | C | **H** | **Q** | **Y** | **H** | **R** | **S** | **P** | **Y** | **T** | F | G | Q | G | T | K | V | E | I | K | R | (SEQ ID NO:5) |

FIGURE 4

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| hum III | E | V | Q | L | V | E | S | G | G | G | L | V | Q | P | G | G | S | L | R | L | S | C | A | A | S |
| mu11D10-H | E | V | Q | L | Q | Q | S | G | A | E | L | V | K | P | G | A | S | V | K | L | S | C | T | A | S |
| 11D10-graft | E | V | Q | L | V | E | S | G | G | G | L | V | Q | P | G | G | S | L | R | L | S | C | A | A | S |

| Kabat# | **26** | **27** | **28** | **29** | **30** | **31** | **32** | **33** | **34** | **35** | **A** | 36 | 37 | 38 | 39 | 40 | 41 | 42 | 43 | 44 | 45 | 46 | 47 | 48 | **49** |
|---|---|---|---|---|---|---|---|---|---|---|---|---|---|---|---|---|---|---|---|---|---|---|---|---|---|
| hum III | **G** | **F** | **T** | **F** | **S** | **S** | **Y** | **A** | **M** | **S** | | W | V | R | Q | A | P | G | K | G | L | E | W | V | **S** |
| mu11D10-H | **G** | **F** | **N** | **I** | **K** | **D** | **T** | **Y** | **M** | **H** | | W | V | K | Q | R | P | E | Q | G | L | E | W | I | **G** |
| 11D10-graft | **G** | **F** | **N** | **I** | **K** | **D** | **T** | **Y** | **M** | **H** | | W | V | R | Q | A | P | G | K | G | L | E | W | V | **G** |

| Kabat# | **50** | **51** | **52** | **A** | **B** | **C** | **53** | **54** | **55** | **56** | **57** | **58** | **59** | **60** | **61** | **62** | **63** | **64** | **65** | 66 | 67 | 68 | 69 | 70 | 71 |
|---|---|---|---|---|---|---|---|---|---|---|---|---|---|---|---|---|---|---|---|---|---|---|---|---|---|
| hum III | **V** | **I** | **S** | **G** | | | **D** | **G** | **G** | **S** | **T** | **Y** | **Y** | **A** | **D** | **S** | **V** | **K** | **G** | R | F | T | I | S | R |
| mu11D10-H | **R** | **V** | **D** | **P** | | | **A** | **N** | **G** | **N** | **T** | **K** | **Y** | **D** | **P** | **K** | **F** | **Q** | **G** | K | A | T | L | T | A |
| 11D10-graft | **R** | **V** | **D** | **P** | | | **A** | **N** | **G** | **N** | **T** | **K** | **Y** | **D** | **P** | **K** | **F** | **Q** | **G** | R | F | T | I | S | A |

| Kabat# | 72 | 73 | 74 | 75 | 76 | 77 | 78 | 79 | 80 | 81 | 82 | A | B | C | 83 | 84 | 85 | 86 | 87 | 88 | 89 | 90 | 91 | 92 | **93** |
|---|---|---|---|---|---|---|---|---|---|---|---|---|---|---|---|---|---|---|---|---|---|---|---|---|---|
| hum III | D | N | S | K | N | T | L | Y | L | Q | M | N | S | L | R | A | E | D | T | A | V | Y | Y | C | **A** |
| mu11D10-H | D | T | S | S | N | T | A | Y | L | Q | L | S | S | L | T | S | E | D | T | A | V | Y | F | C | **V** |
| 11D10-graft | D | T | S | K | N | T | A | Y | L | Q | M | N | S | L | R | A | E | D | T | A | V | Y | Y | C | **V** |

| Kabat# | **94** | **95** | **96** | **97** | **98** | **99** | **100** | **A** | **B** | **C** | **D** | **E** | **101** | **102** | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|
| hum III | **R** | **G** | | | | | | | | | | **F** | **D** | **Y** | W | G | Q | G | T | L | V | T | V | S | S (SEQ ID NO:6) |
| mu11D10-H | **R** | **D** | **Y** | **Y** | **G** | **H** | **T** | **Y** | **G** | | | **F** | **A** | **F** | C | D | Q | G | T | T | L | T | V | S | A (SEQ ID NO:7) |
| 11D10-graft | **R** | **D** | **Y** | **Y** | **G** | **H** | **T** | **Y** | **G** | | | **F** | **A** | **F** | W | G | Q | G | T | L | V | T | V | S | S (SEQ ID NO:8) |

FIGURE 5

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| huKI | D | I | Q | M | T | Q | S | P | S | S | L | S | A | S | V | G | D | R | V | T | I | T | C |
| mu3A5-L | D | I | Q | M | T | Q | S | S | S | F | L | S | V | S | L | G | G | R | V | T | I | T | C |
| 3A5-graft | D | I | Q | M | T | Q | S | P | S | S | L | S | A | S | V | G | D | R | V | T | I | T | C |

| Kabat# | 24 | 25 | 26 | 27 | A | B | C | D | E | F | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|
| huKI | R | A | S | Q | | | | | | | S | I | S | N | Y | L | A | W | Y | Q | Q | K | P |
| mu3A5-L | K | A | S | D | L | | | | | | | I | H | N | W | L | A | W | Y | Q | Q | K | P |
| 3A5-graft | K | A | S | D | L | | | | | | | I | H | N | W | L | A | W | Y | Q | Q | K | P |

| Kabat# | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|---|---|---|---|---|---|
| huKI | G | K | A | P | K | L | L | I | Y | A | A | S | S | L | E | S | G | V | P | S | R | F | S |
| mu3A5-L | G | N | A | P | R | L | L | I | S | G | A | T | S | L | E | T | G | V | P | S | R | F | S |
| 3A5-graft | G | K | A | P | K | L | L | I | S | G | A | T | S | L | E | T | G | V | P | S | R | F | S |

| Kabat# | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 |
|---|---|---|---|---|---|---|---|---|---|---|---|---|---|---|---|---|---|---|---|---|---|---|---|
| huKI | G | S | G | S | G | T | D | F | T | L | T | I | S | S | L | Q | P | E | D | F | A | T | Y |
| mu3A5-L | G | S | G | S | G | N | D | Y | T | L | S | I | A | S | L | Q | T | E | D | A | A | T | Y |
| 3A5-graft | G | S | G | S | G | T | D | F | T | L | T | I | S | S | L | Q | P | E | D | F | A | T | Y |

| Kabat# | 87 | 88 | 89 | 90 | 91 | 92 | 93 | 94 | 95 | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|
| huKI | Y | C | Q | Q | Y | N | S | L | P | W | T | F | G | Q | G | T | K | V | E | I | K | R | (SEQ ID NO:3) |
| mu3A5-L | Y | C | Q | Q | Y | W | T | T | P | F | T | F | G | S | G | T | K | L | E | I | K | | (SEQ ID NO:9) |
| 3A5-graft | Y | C | Q | Q | Y | W | T | T | P | F | T | F | G | Q | G | T | K | V | E | I | K | R | (SEQ ID NO:10) |

FIGURE 6A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| hum III | E | V | Q | L | V | E | S | G | G | G | L | V | Q | P | G | G | S | L | R | L | S | C | A | A | S |
| mu3A5-H | D | V | Q | L | Q | E | S | G | P | G | L | V | N | P | S | Q | S | L | S | L | T | C | T | V | T |
| 3A5.L-graft | E | V | Q | L | V | E | S | G | G | G | L | V | Q | P | G | G | S | L | R | L | S | C | A | A | S |
| 3A5.F-graft | E | V | Q | L | V | E | S | G | G | G | L | V | Q | P | G | G | S | L | R | L | S | C | A | A | S |

| Kabat# | **26** | **27** | **28** | **29** | **30** | **31** | **32** | **33** | **34** | **35** | **A** | 36 | 37 | 38 | 39 | 40 | 41 | 42 | 43 | 44 | 45 | 46 | 47 | 48 | **49** |
|---|---|---|---|---|---|---|---|---|---|---|---|---|---|---|---|---|---|---|---|---|---|---|---|---|---|
| hum III | **G** | **F** | **T** | **F** | **S** | **S** | **Y** | **A** | **M** | **S** | | W | V | R | Q | A | P | G | K | G | L | E | W | V | **S** |
| mu3A5-H | **G** | **Y** | **S** | **I** | **T** | **N** | **D** | **Y** | **A** | **W** | **N** | W | I | R | Q | F | P | G | N | K | L | E | W | M | **G** |
| 3A5.L-graft | **G** | **Y** | **S** | **I** | **T** | **N** | **D** | **Y** | **A** | **W** | **N** | W | V | R | Q | A | P | G | K | G | L | E | W | V | **G** |
| 3A5.F-graft | **G** | **Y** | **S** | **I** | **T** | **N** | **D** | **Y** | **A** | **W** | **N** | W | V | R | Q | A | P | G | K | G | L | E | W | V | **G** |

| Kabat# | **50** | **51** | **52** | **A** | **B** | **C** | **53** | **54** | **55** | **56** | **57** | **58** | **59** | **60** | **61** | **62** | **63** | **64** | **65** | 66 | 67 | 68 | 69 | 70 | 71 |
|---|---|---|---|---|---|---|---|---|---|---|---|---|---|---|---|---|---|---|---|---|---|---|---|---|---|
| hum III | **V** | **I** | **S** | **G** | | | **D** | **G** | **G** | **S** | **T** | **Y** | **Y** | **A** | **D** | **S** | **V** | **K** | **G** | R | F | T | I | S | R |
| mu3A5-H | **Y** | **I** | **N** | **Y** | | | | **S** | **G** | **Y** | **T** | **T** | **Y** | **N** | **P** | **S** | **L** | **K** | **S** | R | I | S | I | T | R |
| 3A5.L-graft | **Y** | **I** | **N** | **Y** | | | | **S** | **G** | **Y** | **T** | **T** | **Y** | **N** | **P** | **S** | **L** | **K** | **S** | R | F | T | I | S | R |
| 3A5.F-graft | **Y** | **I** | **N** | **Y** | | | | **S** | **G** | **Y** | **T** | **T** | **Y** | **N** | **P** | **S** | **L** | **K** | **S** | R | F | T | I | S | R |

| Kabat# | 72 | 73 | 74 | 75 | 76 | 77 | 78 | 79 | 80 | 81 | 82 | A | B | C | 83 | 84 | 85 | 86 | 87 | 88 | 89 | 90 | 91 | 92 | **93** |
|---|---|---|---|---|---|---|---|---|---|---|---|---|---|---|---|---|---|---|---|---|---|---|---|---|---|
| hum III | D | N | S | K | N | T | L | Y | L | Q | M | N | S | L | R | A | E | D | T | A | V | Y | Y | C | **A** |
| mu3A5-H | D | T | S | K | N | Q | F | F | L | H | L | N | S | V | T | T | E | D | T | A | T | Y | Y | C | **A** |
| 3A5.L-graft | D | N | S | K | N | T | L | Y | L | Q | M | N | S | L | R | A | E | D | T | A | V | Y | Y | C | **A** |
| 3A5.F-graft | D | N | S | K | N | T | F | Y | L | Q | M | N | S | L | R | A | E | D | T | A | V | Y | Y | C | **A** |

FIGURE 6B

| Kabat# | 94 | 95 | 96 | 97 | 98 | 99 | 100 | A | B | C | D | E | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|
| hum III | R | G | | | | | | | | | | F | D | Y | W | G | Q | G | T | L | V | T | V | S | S | (SEQ ID NO:6) |
| mu3A5-H | R | W | D | G | G | | | | | | | L | T | Y | W | G | Q | G | T | L | V | T | V | S | A | (SEQ ID NO:11) |
| 3A5.L-graft | R | W | D | G | G | | | | | | | L | T | Y | W | G | Q | G | T | L | V | T | V | S | S | (SEQ ID NO:12) |
| 3A5.F-graft | R | W | D | G | G | | | | | | | L | T | Y | W | G | Q | G | T | L | V | T | V | S | S | (SEQ ID NO:13) |

FIGURE 7

| Kabat# | 24 | 25 | 26 | 27 | A | 28 | 29 | 30 | 31 | 32 | 33 | 34 | |
|---|---|---|---|---|---|---|---|---|---|---|---|---|---|
| | T | A | S | S | S | V | S | S | S | Y | L | H | (SEQ ID NO:14) |
| | T | Q | R | T | S | V | K | R | S | Y | I | S | (SEQ ID NO:15) |
| | T | P | R | G | R | V | R | S | S | Y | L | S | (SEQ ID NO:16) |
| | P | E | C | X | S | L | G | T | I | Y | L | H | (SEQ ID NO:17) |
| | S | A | S | S | S | V | N | S | T | Y | L | H | (SEQ ID NO:18) |
| | T | A | S | T | A | V | G | S | S | Y | L | H | (SEQ ID NO:19) |
| | N | | S | R | S | V | S | T | R | Y | L | H | (SEQ ID NO:20) |
| | N | T | T | R | S | V | S | T | G | Y | L | H | (SEQ ID NO:21) |
| | T | A | S | S | R | V | T | S | T | Y | L | H | (SEQ ID NO:22) |
| | N | T | P | T | G | V | N | P | V | Y | L | H | (SEQ ID NO:23) |
| | A | A | S | S | D | V | I | G | S | Y | V | H | (SEQ ID NO:24) |
| | G | L | S | T | S | V | N | S | S | Y | M | H | (SEQ ID NO:25) |
| | N | A | K | S | G | V | R | S | S | X | V | H | (SEQ ID NO:26) |
| | N | S | N | G | S | V | S | S | K | Y | I | H | (SEQ ID NO:27) |
| | T | P | S | R | I | V | S | G | S | Y | L | S | (SEQ ID NO:28) |
| | N | P | S | R | R | V | T | G | H | Y | V | S | (SEQ ID NO:29) |
| | T | S | S | S | A | V | S | G | S | Y | V | S | (SEQ ID NO:30) |
| | T | S | T | T | I | V | R | G | R | Y | V | S | (SEQ ID NO:31) |
| | T | A | S | S | T | L | S | S | N | Y | L | T | (SEQ ID NO:32) |
| | T | P | T | G | S | I | S | R | R | Y | L | S | (SEQ ID NO:33) |
| | T | A | G | S | K | A | N | S | S | Y | I | H | (SEQ ID NO:34) |

FIGURE 8

| Kabat# | 49 | 50 | 51 | 52 | 53 | 54 | 55 | 56 | |
|---|---|---|---|---|---|---|---|---|---|
| | Y | S | T | S | N | L | A | S | (SEQ ID NO:35) |
| | Y | S | T | S | H | F | A | S | (SEQ ID NO:36) |
| | Y | S | A | S | N | V | P | S | (SEQ ID NO:37) |
| | Y | S | T | I | N | L | A | T | (SEQ ID NO:38) |
| | Y | S | T | S | K | V | A | N | (SEQ ID NO:39) |
| | Y | S | T | T | N | L | A | S | (SEQ ID NO:40) |
| | Y | S | T | N | H | L | A | S | (SEQ ID NO:41) |
| | Y | S | T | N | N | L | A | S | (SEQ ID NO:42) |
| | Y | S | T | I | H | P | A | S | (SEQ ID NO:43) |
| | Y | S | T | S | H | L | S | Y | (SEQ ID NO:44) |
| | Y | S | T | R | T | M | A | S | (SEQ ID NO:45) |
| | Y | S | T | S | X | L | F | S | (SEQ ID NO:46) |
| | Y | N | T | S | N | R | A | S | (SEQ ID NO:47) |
| | Y | G | T | S | H | L | A | S | (SEQ ID NO:48) |
| | Y | G | T | G | S | P | A | S | (SEQ ID NO:49) |
| | Y | S | T | N | K | L | A | R | (SEQ ID NO:50) |
| | Y | S | T | S | Q | L | G | R | (SEQ ID NO:51) |
| | Y | S | T | S | N | V | P | Q | (SEQ ID NO:52) |
| | Y | G | T | Y | N | L | P | I | (SEQ ID NO:53) |
| | Y | G | S | N | N | R | A | Y | (SEQ ID NO:54) |
| | Y | S | S | S | N | T | X | S | (SEQ ID NO:55) |
| | Y | S | A | N | K | L | A | S | (SEQ ID NO:56) |
| | Y | S | A | T | R | R | A | S | (SEQ ID NO:57) |
| | Y | S | A | S | N | R | A | R | (SEQ ID NO:58) |

FIGURE 9

| Kabat# | 89 | 90 | 91 | 92 | 93 | 94 | 95 | 96 | 97 | |
|---|---|---|---|---|---|---|---|---|---|---|
| | H | Q | Y | H | R | S | P | Y | T | (SEQ ID NO:59) |
| | H | Q | Y | H | R | S | P | Y | K | (SEQ ID NO:60) |
| | H | Q | Y | H | R | T | P | Y | K | (SEQ ID NO:61) |
| | H | Q | Y | H | R | S | P | Y | G | (SEQ ID NO:62) |
| | H | Q | Y | H | R | S | P | Y | N | (SEQ ID NO:63) |
| | H | Q | Y | H | R | S | P | Y | S | (SEQ ID NO:64) |
| | H | Q | Y | Y | R | S | P | Y | T | (SEQ ID NO:65) |
| | H | Q | Y | Y | R | T | P | Y | S | (SEQ ID NO:66) |
| | H | Q | Y | Q | R | S | P | Y | T | (SEQ ID NO:67) |
| | H | Q | Y | Q | R | S | P | Y | R | (SEQ ID NO:68) |
| | H | Q | Y | N | R | S | P | Y | A | (SEQ ID NO:69) |
| | H | Q | Y | H | R | T | P | Y | T | (SEQ ID NO:70) |
| | H | Q | Y | H | R | S | P | Y | I | (SEQ ID NO:71) |
| | H | Q | Y | H | R | R | P | Y | R | (SEQ ID NO:72) |
| | H | Q | Y | H | R | N | P | Y | I | (SEQ ID NO:73) |

FIGURE 10

| Kabat# | 26 | 27 | 28 | 29 | 30 | 31 | 32 | 33 | 34 | 35 | A | |
|---|---|---|---|---|---|---|---|---|---|---|---|---|
| | G | F | N | I | K | D | T | Y | M | H | | (SEQ ID NO:74) |
| | A | F | N | I | A | D | T | Y | I | H | | (SEQ ID NO:75) |
| | R | F | R | I | K | D | T | Y | V | H | | (SEQ ID NO:76) |
| | R | F | N | I | K | D | T | Y | I | H | | (SEQ ID NO:77) |
| | S | F | Q | I | N | D | T | Y | I | H | | (SEQ ID NO:78) |
| | S | F | Q | M | S | D | T | Y | V | H | | (SEQ ID NO:79) |
| | D | F | N | I | K | D | T | Y | I | H | | (SEQ ID NO:80) |
| | G | F | N | I | I | D | T | Y | I | H | | (SEQ ID NO:81) |
| | G | L | Q | I | V | D | T | Y | I | H | | (SEQ ID NO:82) |
| | G | F | N | I | K | D | T | Y | L | H | | (SEQ ID NO:83) |
| | G | F | N | I | Q | D | L | Y | L | H | | (SEQ ID NO:84) |
| | G | F | N | I | I | D | T | Y | M | H | | (SEQ ID NO:85) |
| | G | W | K | M | T | D | T | Y | M | H | | (SEQ ID NO:86) |
| | E | F | K | I | K | D | T | Y | V | H | | (SEQ ID NO:87) |
| | G | F | N | I | K | D | T | Y | V | H | | (SEQ ID NO:88) |
| | G | F | Y | I | S | N | T | Y | I | H | | (SEQ ID NO:89) |
| | G | F | N | I | K | N | T | Y | L | H | | (SEQ ID NO:90) |
| | G | F | S | I | E | N | T | Y | M | H | | (SEQ ID NO:91) |
| | G | F | N | I | K | N | T | Y | M | H | | (SEQ ID NO:92) |
| | D | F | K | I | E | N | T | Y | V | H | | (SEQ ID NO:93) |

FIGURE 11

| Kabat# | 49 | 50 | 51 | 52 | A | B | C | 53 | 54 | 55 | 56 | 57 | 58 | 59 | 60 | 61 | 62 | 63 | 64 | 65 | |
|---|---|---|---|---|---|---|---|---|---|---|---|---|---|---|---|---|---|---|---|---|---|
| | G | R | V | D | P | | | A | N | G | N | T | K | Y | D | P | K | F | Q | G | (SEQ ID NO:94) |
| | G | R | V | D | P | | | A | N | G | N | T | K | S | D | P | K | V | R | G | (SEQ ID NO:95) |
| | G | R | V | D | P | | | A | N | G | L | T | K | Y | D | P | K | F | Q | G | (SEQ ID NO:96) |
| | G | R | V | D | P | | | A | N | G | E | I | K | S | H | P | I | F | Q | G | (SEQ ID NO:97) |
| | G | R | V | D | P | | | A | N | G | N | T | K | E | D | R | Q | F | Q | G | (SEQ ID NO:98) |
| | G | R | V | D | P | | | E | Y | G | N | T | K | Y | D | P | K | F | Q | G | (SEQ ID NO:99) |
| | G | R | L | D | P | | | A | N | G | N | T | K | Y | D | P | K | F | Q | G | (SEQ ID NO:100) |
| | G | R | V | D | P | | | A | N | G | D | T | K | Y | D | P | K | F | Q | G | (SEQ ID NO:101) |
| | G | R | V | D | P | | | A | N | G | K | T | K | Y | D | P | K | F | Q | G | (SEQ ID NO:102) |
| | G | R | V | D | P | | | A | N | G | L | T | K | Y | N | P | K | F | Q | G | (SEQ ID NO:103) |
| | G | R | V | D | P | | | A | N | G | Y | T | K | Y | N | P | K | F | Q | G | (SEQ ID NO:104) |
| | G | R | V | D | P | | | A | N | G | Y | T | K | Y | D | P | K | F | Q | G | (SEQ ID NO:105) |
| | G | R | V | D | P | | | A | N | G | N | Y | K | Y | D | P | K | F | Q | G | (SEQ ID NO:106) |
| | G | R | V | D | P | | | A | N | G | N | S | K | Y | D | P | K | F | Q | G | (SEQ ID NO:107) |
| | G | R | V | D | P | | | A | N | G | N | T | K | Y | D | H | R | F | Q | G | (SEQ ID NO:108) |
| | G | R | V | D | P | | | A | N | G | N | T | K | Y | D | P | K | F | R | G | (SEQ ID NO:109) |
| | G | R | V | D | P | | | S | N | G | N | T | K | S | D | G | K | F | N | G | (SEQ ID NO:110) |
| | G | R | V | D | P | | | V | D | G | K | T | K | Y | N | P | Q | I | Q | G | (SEQ ID NO:111) |
| | G | R | V | D | P | | | A | H | G | N | I | K | Y | D | P | Q | I | M | G | (SEQ ID NO:112) |

FIGURE 12

| Kabat# | 93 | 94 | 95 | 96 | 97 | 98 | 99 | 100 | A | B | C | D | E | 101 | 102 |
|---|---|---|---|---|---|---|---|---|---|---|---|---|---|---|---|
| (SEQ ID NO:113) | V | R | D | Y | Y | G | H | T | Y | G | | | F | A | F |
| (SEQ ID NO:114) | V | R | D | Y | Y | G | H | T | Y | G | | | F | Q | P |
| (SEQ ID NO:115) | A | R | D | N | Y | G | H | T | Y | G | | | F | G | F |
| (SEQ ID NO:116) | V | R | D | T | Y | G | H | T | Y | G | | | F | A | Y |
| (SEQ ID NO:117) | V | R | D | Y | Y | G | H | T | Y | G | | | F | G | Y |
| (SEQ ID NO:118) | V | R | D | Y | Y | G | H | T | Y | G | | | F | G | V |

FIGURE 13

| | | | | | | | | | | | | | |
|---|---|---|---|---|---|---|---|---|---|---|---|---|---|
| Kabat# | 24 | 25 | 26 | 27 | A | 28 | 29 | 30 | 31 | 32 | 33 | 34 | |
| | K | A | S | D | L | | I | H | N | W | L | A | (SEQ ID NO:119) |

FIGURE 14

| Kabat# | 49 | 50 | 51 | 52 | 53 | 54 | 55 | 56 | |
|---|---|---|---|---|---|---|---|---|---|
| | S | G | A | T | S | L | E | T | (SEQ ID NO:120) |
| | Y | G | A | T | S | L | E | T | (SEQ ID NO:121) |

FIGURE 15

| Kabat# | 89 | 90 | 91 | 92 | 93 | 94 | 95 | 96 | 97 | |
|---|---|---|---|---|---|---|---|---|---|---|
| | Q | Q | Y | W | T | T | P | F | T | (SEQ ID NO:122) |

FIGURE 16

| Kabat# | 26 | 27 | 28 | 29 | 30 | 31 | 32 | 33 | 34 | 35 | A | |
|---|---|---|---|---|---|---|---|---|---|---|---|---|
| | G | Y | S | I | T | N | D | Y | A | W | N | (SEQ ID NO:123) |

FIGURE 17

| Kabat# | 49 | 50 | 51 | 52 | A | B | C | 53 | 54 | 55 | 56 | 57 | 58 | 59 | 60 | 61 | 62 | 63 | 64 | 65 | |
|---|---|---|---|---|---|---|---|---|---|---|---|---|---|---|---|---|---|---|---|---|---|
| | G | Y | I | N | Y | | | | S | G | Y | T | T | Y | N | P | S | L | K | S | (SEQ ID NO:124) |
| | G | Y | I | S | Y | | | | S | G | Y | T | T | Y | N | P | S | L | K | S | (SEQ ID NO:125) |
| | G | Y | I | N | Y | | | | A | G | Y | T | T | Y | N | P | S | L | K | S | (SEQ ID NO:126) |
| | G | Y | I | S | Y | | | | A | G | Y | T | T | Y | N | P | S | L | K | S | (SEQ ID NO:127) |

FIGURE 18A

| Kabat# | 93 | 94 | 95 | 96 | 97 | 98 | 99 | 100 A | B | C | D | E | 101 | 102 | |
|---|---|---|---|---|---|---|---|---|---|---|---|---|---|---|---|
| | A | R | W | D | G | G | | | | | | L | T | Y | (SEQ ID NO:128) |
| | A | R | W | A | A | G | | | | | | L | T | N | (SEQ ID NO:129) |
| | A | R | W | D | A | G | | | | | | L | S | Y | (SEQ ID NO:130) |
| | A | R | W | D | A | G | | | | | | L | T | Y | (SEQ ID NO:131) |
| | A | R | W | E | A | G | | | | | | L | N | H | (SEQ ID NO:132) |
| | A | R | W | E | A | G | | | | | | L | N | Y | (SEQ ID NO:133) |
| | A | R | W | M | A | G | | | | | | L | S | D | (SEQ ID NO:134) |
| | A | R | W | S | A | G | | | | | | L | D | H | (SEQ ID NO:135) |
| | A | R | W | T | A | G | | | | | | L | D | Y | (SEQ ID NO:136) |
| | A | R | W | T | A | G | | | | | | L | T | H | (SEQ ID NO:137) |
| | A | R | W | V | A | G | | | | | | L | T | N | (SEQ ID NO:138) |
| | A | R | W | A | G | G | | | | | | L | E | N | (SEQ ID NO:139) |
| | A | R | W | D | G | G | | | | | | L | S | Y | (SEQ ID NO:140) |
| | A | R | W | D | R | G | | | | | | L | T | Y | (SEQ ID NO:141) |
| | A | R | W | A | S | G | | | | | | L | S | H | (SEQ ID NO:142) |
| | A | R | W | A | S | G | | | | | | L | S | N | (SEQ ID NO:143) |
| | A | R | W | A | S | G | | | | | | L | S | Y | (SEQ ID NO:144) |
| | A | R | W | A | S | G | | | | | | L | T | H | (SEQ ID NO:145) |
| | A | R | W | A | S | G | | | | | | L | T | N | (SEQ ID NO:146) |
| | A | R | W | D | S | G | | | | | | L | K | Y | (SEQ ID NO:147) |
| | A | R | W | D | S | G | | | | | | L | N | Y | (SEQ ID NO:148) |
| | A | R | W | D | S | G | | | | | | L | S | S | (SEQ ID NO:149) |
| | A | R | W | D | S | G | | | | | | L | S | V | (SEQ ID NO:150) |
| | A | R | W | D | S | G | | | | | | L | S | Y | (SEQ ID NO:151) |
| | A | R | W | D | S | G | | | | | | L | T | Y | (SEQ ID NO:152) |
| | A | R | W | E | S | G | | | | | | L | S | H | (SEQ ID NO:153) |
| | A | R | W | E | S | G | | | | | | L | S | V | (SEQ ID NO:154) |
| | A | R | W | K | S | G | | | | | | L | D | S | (SEQ ID NO:155) |

FIGURE 18B

| Kabat# | 93 | 94 | 95 | 96 | 97 | 98 | 99 | 100 A | B | C | D | E | 101 | 102 | |
|---|---|---|---|---|---|---|---|---|---|---|---|---|---|---|---|
| | A | R | W | K | S | G | | | | | | L | E | Y | (SEQ ID NO:156) |
| | A | R | W | L | S | G | | | | | | L | D | F | (SEQ ID NO:157) |
| | A | R | W | L | S | G | | | | | | L | D | S | (SEQ ID NO:158) |
| | A | R | W | L | S | G | | | | | | L | E | S | (SEQ ID NO:159) |
| | A | R | W | L | S | G | | | | | | L | S | D | (SEQ ID NO:160) |
| | A | R | W | R | S | G | | | | | | L | E | H | (SEQ ID NO:161) |
| | A | R | W | S | S | G | | | | | | L | N | Y | (SEQ ID NO:162) |
| | A | R | W | S | S | G | | | | | | L | T | Y | (SEQ ID NO:163) |
| | A | R | W | T | S | G | | | | | | M | D | S | (SEQ ID NO:164) |
| | A | R | W | T | S | G | | | | | | L | T | Y | (SEQ ID NO:165) |
| | A | R | W | D | T | G | | | | | | L | T | Y | (SEQ ID NO:166) |
| | A | R | W | A | A | G | | | | | | L | D | H | (SEQ ID NO:167) |
| | A | R | W | A | A | G | | | | | | L | D | S | (SEQ ID NO:168) |
| | A | R | W | L | A | G | | | | | | L | S | N | (SEQ ID NO:169) |
| | A | R | W | T | A | G | | | | | | L | D | Q | (SEQ ID NO:170) |
| | A | R | W | A | S | G | | | | | | L | D | H | (SEQ ID NO:171) |
| | A | R | W | A | S | G | | | | | | L | D | N | (SEQ ID NO:172) |
| | A | R | W | A | S | G | | | | | | L | D | S | (SEQ ID NO:173) |
| | A | R | W | A | S | G | | | | | | L | D | Y | (SEQ ID NO:174) |
| | A | R | W | K | S | G | | | | | | L | D | T | (SEQ ID NO:175) |
| | A | R | W | K | S | G | | | | | | L | G | P | (SEQ ID NO:176) |
| | A | R | W | M | S | G | | | | | | L | D | S | (SEQ ID NO:177) |
| | A | R | W | R | S | G | | | | | | L | E | S | (SEQ ID NO:178) |
| | A | R | W | R | S | G | | | | | | L | E | Y | (SEQ ID NO:179) |
| | A | R | W | T | S | G | | | | | | L | D | S | (SEQ ID NO:180) |
| | A | R | W | T | S | G | | | | | | L | D | T | (SEQ ID NO:181) |
| | A | R | W | T | S | G | | | | | | L | D | V | (SEQ ID NO:182) |
| | A | R | W | T | S | G | | | | | | L | D | Y | (SEQ ID NO:183) |

FIGURE 19

Q V Q L V Q S G A E V K K P G A S V K V S C K A S G Y T F T [-H1-] W V R Q A P G Q G L E W M G [-H2-] R V T I T A D T S T S T A Y M E L S S L R S E D T A V Y Y C A R [-H3-] W G Q G T L V T V S S (SEQ ID NO:184)

Q V Q L V Q S G A E V K K P G A S V K V S C K A S [-H1-] W V R Q A P G Q G L E W M [-H2-] R V T I T A D T S T S T A Y M E L S S L R S E D T A V Y Y C A R [-H3-] W G Q G T L V T V S S (SEQ ID NO:185)

Q V Q L V Q S G A E V K K P G A S V K V S C K A S [-H1-] W V R Q A P G Q G L E W M [-H2-] R V T I T A D T S T S T A Y M E L S S L R S E D T A V Y Y C A [-H3-] W G Q G T L V T V S S (SEQ ID NO:186)

Q V Q L V Q S G A E V K K P G A S V K V S C K A S [-H1-] W V R Q A P G Q G L E W M [-H2-] R V T I T A D T S T S T A Y M E L S S L R S E D T A V Y Y C [-H3-] W G Q G T L V T V S S (SEQ ID NO:187)

Q V Q L Q E S G P G L V K P S Q T L S L T C T V S G G S V S [-H1-] W I R Q P P G K G L E W I G [-H2-] R V T I S V D T S K N Q F S L K L S S V T A A D T A V Y Y C A R [-H3-] W G Q G T L V T V S S (SEQ ID NO:188)

Q V Q L Q E S G P G L V K P S Q T L S L T C T V S [-H1-] W I R Q P P G K G L E W I [-H2-] R V T I S V D T S K N Q F S L K L S S V T A A D T A V Y Y C A R [-H3-] W G Q G T L V T V S S (SEQ ID NO:189)

Q V Q L Q E S G P G L V K P S Q T L S L T C T V S [-H1-] W I R Q P P G K G L E W I [-H2-] R V T I S V D T S K N Q F S L K L S S V T A A D T A V Y Y C A [-H3-] W G Q G T L V T V S S (SEQ ID NO:190)

Q V Q L Q E S G P G L V K P S Q T L S L T C T V S [-H1-] W I R Q P P G K G L E W I [-H2-] R V T I S V D T S K N Q F S L K L S S V T A A D T A V Y Y C [-H3-] W G Q G T L V T V S S (SEQ ID NO:191)

E V Q L V E S G G G L V Q P G G S L R L S C A A S [-H1-] W V R Q A P G K G L E W V [-H2-] R F T I S R D N S K N T L Y L Q M N S L R A E D T A V Y Y C [-H3-] W G Q G T L V T V S S (SEQ ID NO:192)

E V Q L V E S G G G L V Q P G G S L R L S C A A S [-H1-] W V R Q A P G K G L E W V [-H2-] R F T I S R D N S K N T F Y L Q M N S L R A E D T A V Y Y C [-H3-] W G Q G T L V T V S S (SEQ ID NO:193)

FIGURE 20

D I Q M T Q S P S S L S A S V G D R V T I T C [-L1-] W Y Q Q K P
G K A P K L L I [-L2-] G V P S R F S G S G S G T D F T L T I S S
L Q P E D F A T Y Y C [-L3-] F G Q G T K V E I K R (SEQ ID
NO:194)

D I V M T Q S P L S L P V T P G E P A S I S C [-L1-] W Y L Q K P
G Q S P Q L L I Y [-L2-] G V P D R F S G S G S G T D F T L K I S
R V E A E D V G V Y Y C [-L3-] F G Q G T K V E I K (SEQ ID
NO:195)

E I V L T Q S P G T L S L S P G E R A T L S C [-L1-] W Y Q Q K P
G Q A P R L L I Y [-L2-] G I P D R F S G S G S G T D F T L T I S
R L E P E D F A V Y Y C [-L3-] F G Q G T K V E I K (SEQ ID
NO:196)

D I V M T Q S P D S L A V S L G E R A T I N C [-L1-] W Y Q Q K P
G Q P P K L L I Y [-L2-] G V P D R F S G S G S G T D F T L T I S
S L Q A E D V A V Y Y C [-L3-] F G Q G T K V E I K (SEQ ID
NO:197)

FIGURE 21A

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T L Y L Q M N S L R A E D T A V Y Y C
A R W A S G L D Y W G Q G T L V T V S S (SEQ ID NO:198)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T F Y L Q M N S L R A E D T A V Y Y C
A R W A S G L S H W G Q G T L V T V S S (SEQ ID NO:199)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T F Y L Q M N S L R A E D T A V Y Y C
A R W A S G L S Y W G Q G T L V T V S S (SEQ ID NO:200)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T L Y L Q M N S L R A E D T A V Y Y C
A R W T S G L D Y W G Q G T L V T V S S (SEQ ID NO:201)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T F Y L Q M N S L R A E D T A V Y Y C
A R W D A G L T Y W G Q G T L V T V S S (SEQ ID NO:202)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T F Y L Q M N S L R A E D T A V Y Y C
A R W D S G L T Y W G Q G T L V T V S S (SEQ ID NO:203)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T L Y L Q M N S L R A E D T A V Y Y C
A R W K S G L D S W G Q G T L V T V S S (SEQ ID NO:204)

E V Q L V E S G G G L V Q P G G S L R L S C A A S G Y S I T N D
Y A W N W V R Q A P G K G L E W V G Y I N Y S G Y T T Y N P S L
K S R F T I S R D T S K N T L Y L Q M N S L R A E D T A V Y Y C
A R W T S G L D S W G Q G T L V T V S S (SEQ ID NO:205)

E V Q L V E S G G G L V Q P G G S L R L S C A A S G Y S I T N D
Y A W N W V R Q A P G K G L E W V G Y I S Y S G Y T T Y N P S L
K S R F T I S R D T S K N T L Y L Q M N S L R A E D T A V Y Y C
A R W A S G L D Y W G Q G T L V T V S S (SEQ ID NO:206)

E V Q L V E S G G G L V Q P G G S L R L S C A A S G Y S I T N D
Y A W N W V R Q A P G K G L E W V G Y I N Y A G Y T T Y N P S L
K S R F T I S R D T S K N T L Y L Q M N S L R A E D T A V Y Y C
A R W A S G L D Y W G Q G T L V T V S S (SEQ ID NO:207)

FIGURE 21B

E V Q L V E S G G G L V Q P G G S L R L S C A A S G Y S I T N D
Y A W N W V R Q A P G K G L E W V G Y I S Y S G Y T T Y N P S L
K S R F T I S R D T S K N T L Y L Q M N S L R A E D T A V Y Y C
A R W T S G L D Y W G Q G T L V T V S S (SEQ ID NO:208)

E V Q L V E S G G G L V Q P G G S L R L S C A A S G Y S I T N D
Y A W N W V R Q A P G K G L E W V G Y I N Y A G Y T T Y N P S L
K S R F T I S R D T S K N T L Y L Q M N S L R A E D T A V Y Y C
A R W T S G L D Y W G Q G T L V T V S S (SEQ ID NO:209)

FIGURE 22

D I Q M T Q S P S S L S A S V G D R V T I T C K A S D L I H N W
L A W Y Q Q K P G K A P K L L I S G A T S L E T G V P S R F S G
S G S G T D F T L T I S S L Q P E D F A T Y Y C Q Q Y W T T P F
T F G Q G T K V E I K R (SEQ ID NO:210)

D I Q M T Q S P S S L S A S V G D R V T I T C K A S D L I H N W
L A W Y Q Q K P G K A P K L L I Y G A T S L E T G V P S R F S G
S G S G T D F T L T I S S L Q P E D F A T Y Y C Q Q Y W T T P F
T F G Q G T K V E I K R (SEQ ID NO:211)

| | TI | PR | CR | mg/kg | ug/m² | Drugs/Ab | CNJ# |
|---|---|---|---|---|---|---|---|
| Vehicle | 7/7 | 0 | 0 | --- | --- | --- | --- |
| anti-gP120-MC-vc-PAB-MMAE | 2/2 | 0 | 0 | 3.96 | 267 | 4.7 | 643 |
| anti-gP120-MC-MMAF | 7/7 | 0 | 0 | 24 | 1088 | 3.1 | 887 |
| 3A5-MC-vc-PAB-MMAE | 4/4 | 0 | 0 | 1 | 45 | 3.1 | 802 |
| 3A5-MC-vc-PAB-MMAE | 5/6 | 1 | 1 | 3 | 134 | 3.1 | 802 |
| 3A5-MC-vc-PAB-MMAE | 2/10 | 2 | 8 | 6 | 267 | 3.1 | 802 |
| 3A5-MC-MMAF | 5/5 | 0 | 0 | 6 | 272 | 3.1 | 803 |
| 3A5-MC-MMAF | 7/7 | 0 | 0 | 12 | 544 | 3.1 | 803 |
| 3A5-MC-MMAF | 7/7 | 2 | 0 | 24 | 1088 | 3.1 | 803 |

| TI | PR | CR | mg/kg | ug/m$^2$ | Lot # | Drugs/Ab |
|---|---|---|---|---|---|---|
| 4/4 | 0 | 0 | --- | --- | 1218605 | --- |
| 4/4 | 0 | 0 | 1.74 | 118 | 540.064A | 4.70 |
| 7/7 | 0 | 0 | 5.61 | 386 | 540.064CR | 4.70 |
| 6/10 | 3 | 7 | 2 | 118 | 546.098 | 4.10 |
| 2/10 | 0 | 10 | 6 | 386 | 546.100 | 4.40 |

| TI | PR | CR | mg/kg | ug/m² | Lot # | Drugs/Ab |
|---|---|---|---|---|---|---|
| 7/7 | 0 | 0 | --- | --- | 1218605 | --- |
| 8/8 | 0 | 0 | 3.96 | 272 | 540.064CR | 4.7 |
| 6/6 | 0 | 0 | 7.86 | 433 | GNE | 3.74 |
| 10/10 | 6 | 0 | 6 | 272 | 546.121 | 3.10 |
| 10/10 | 4 | 0 | 6 | 433 | GNE | 4.90 |

SEQUENCE LISTING

```
<160> NUMBER OF SEQ ID NOS: 211

<210> SEQ ID NO 1
<211> LENGTH: 21112
<212> TYPE: DNA
<213> ORGANISM: Homo sapiens

<400> SEQUENCE: 1

cctgtgactt ctcttctcac ccctggcctg gtgataacca cagacaggat        50

gggcataagc agagaacctg gaaccagttc cacttcaaat ttgagcagca       100

cctcccatga gagactgacc actttggaag acactgtaga tacagaagcc       150

atgcagcctt ccacacacac agcagtgacc aacgtgagga cctccatttc       200

tggacatgaa tcacaatctt ctgtcctatc tgactcagag acacccaaag       250

ccacatctcc aatgggtacc acctacacca tgggggaaac gagtgtttcc       300

atatccactt ctgacttctt tgagaccagc agaattcaga tagaaccaac       350

atcctccctg acttctggat tgagggagac cagcagctct gagaggatca       400

gctcagccac agagggaagc actgtccttt ctgaagtgcc cagtggtgct       450

accactgagg tctccaggac agaagtgata tcctctaggg gaacatccat       500

gtcagggcct gatcagttca ccatatcacc agacatctct actgaagcga       550
```

```
tcaccaggct ttctacttcc cccattatga cagaatcagc agaaagtgcc        600
atcactattg agacaggttc tcctggggct acatcagagg gtaccctcac        650
cttggacacc tcaacaacaa ccttttggtc agggacccac tcaactgcat        700
ctccaggatt ttcacactca gagatgacca ctcttatgag tagaactcct        750
ggagatgtgc catggccgag ccttccctct gtggaagaag ccagctctgt        800
ctcttcctca ctgtcttcac ctgccatgac ctcaacttct tttttctcca        850
cattaccaga gagcatctcc tcctctcctc atcctgtgac tgcacttctc        900
acccttggcc cagtgaagac cacagacatg ttgcgcacaa gctcagaacc        950
tgaaaccagt tcacctccaa atttgagcag cacctcagct gaaatattag       1000
ccacgtctga agtcaccaaa gatagagaga aaattcatcc ctcctcaaac       1050
acacctgtag tcaatgtagg gactgtgatt tataaacatc tatccccttc       1100
ctctgttttg gctgacttag tgacaacaaa acccacatct ccaatggcta       1150
ccacctccac tctggggaat acaagtgttt ccacatcaac tcctgccttc       1200
ccagaaacta tgatgacaca gccaacttcc tccctgactt ctggattaag       1250
ggagatcagt acctctcaag agaccagctc agcaacagag agaagtgctt       1300
ctctttctgg aatgcccact ggtgctacta ctaaggtctc cagaacagaa       1350
gccctctcct taggcagaac atccacccca ggtcctgctc aatccacaat       1400
atcaccagaa atctccacgg aaaccatcac tagaatttct actcccctca       1450
ccacgacagg atcagcagaa atgaccatca cccccaaaac aggtcattct       1500
ggggcatcct cacaaggtac ctttaccttg gacacatcaa gcagagcctc       1550
ctggccagga actcactcag ctgcaactca cagatctcca cactcaggga       1600
tgaccactcc tatgagcaga ggtcctgagg atgtgtcatg gccaagccgc       1650
ccatcagtgg aaaaaactag ccctccatct tccctggtgt ctttatctgc       1700
agtaacctca ccttcgccac tttattccac accatctgag agtagccact       1750
cgtctcctct ccgggtgact tctcttttca cccctgtcat gatgaagacc       1800
acagacatgt tggacacaag cttggaacct gtgaccactt cacctcccag       1850
tatgaatatc acctcagatg agagtctggc cacttctaaa gccaccatgg       1900
agacagaggc aattcagctt tcagaaaaca cagctgtgac tcagatgggc       1950
accatcagtg ctagacaaga attctattcc tcttatccag gcctcccaga       2000
gccatccaaa gtgacatctc cagtggtcac ctcttccacc ataaaagaca       2050
ttgtttctac aaccatacct gcttcctctg agataacaag aattgagatg       2100
gagtcaacat ccaccctgac ccccacacca agggagacca gcacctccca       2150
ggagatccac tcagccacaa agccaagcac tgttccttac aaggcactca       2200
ctagtgccac gattgaggac tccatgacac aagtcatgtc ctctagcaga       2250
ggacctagcc ctgatcagtc cacaatgtca caagacatat ccactgaagt       2300
gatcaccagg ctctctacct cccccatcaa gacagaatct acagaaatga       2350
ccattaccac ccaaacaggt tctcctgggg ctacatcaag ggtaccctt        2400
accttggaca cttcaacaac ttttatgtca gggacccatt caactgcatc       2450
tcaaggattt tcacactcac agatgaccgc tcttatgagt agaactcctg       2500
gagaggtgcc atggctaagc catccctctg tggaagaagc cagctctgcc       2550
```

```
tctttctcac tgtcttcacc tgtcatgacc tcatcttctc ccgtttcttc      2600
cacattacca gacagcatcc actcttcttc gcttcctgtg acatcacttc      2650
tcacctcagg gctggtgaag accacagagc tgttgggcac aagctcagaa      2700
cctgaaacca gttcaccccc aaatttgagc agcacctcag ctgaaatact      2750
ggccaccact gaagtcacta cagatacaga gaaactggag atgaccaatg      2800
tggtaacctc aggttataca catgaatctc cttcctctgt cctagctgac      2850
tcagtgacaa caaaggccac atcttcaatg ggtatcacct accccacagg      2900
agatacaaat gttctcacat caacccctgc cttctctgac accagtagga      2950
ttcaaacaaa gtcaaagctc tcactgactc ctgggttgat ggagaccagc      3000
atctctgaag agaccagctc tgccacagaa aaaagcactg tcctttctag      3050
tgtgcccact ggtgctacta ctgaggtctc caggacagaa gccatctctt      3100
ctagcagaac atccatccca ggccctgctc aatccacaat gtcatcagac      3150
acctccatgg aaaccatcac tagaatttct acccccctca caaggaaaga      3200
atcaacagac atggccatca cccccaaaac aggtccttct ggggctacct      3250
cgcagggtac ctttaccttg gactcatcaa gcacagcctc ctggccagga      3300
actcactcag ctacaactca gagatttcca cggtcagtgg tgacaactcc      3350
tatgagcaga ggtcctgagg atgtgtcatg gccaagcccg ctgtctgtgg      3400
aaaaaaacag ccctccatct tccctggtat cttcatcttc agtaacctca      3450
ccttcgccac tttattccac accatctggg agtagccact cctctcctgt      3500
ccctgtcact tctcttttca cctctatcat gatgaaggcc acagacatgt      3550
tggatgcaag tttggaacct gagaccactt cagctcccaa tatgaatatc      3600
acctcagatg agagtctggc cgcttctaaa gccaccacgg agacagaggc      3650
aattcacgtt tttgaaaata cagcagcgtc ccatgtggaa accaccagtg      3700
ctacagagga actctattcc tcttccccag gcttctcaga gccaacaaaa      3750
gtgatatctc cagtggtcac ctcttcctct ataagagaca acatggtttc      3800
cacaacaatg cctggctcct ctggcattac aaggattgag atagagtcaa      3850
tgtcatctct gacccctgga ctgagggaga ccagaacctc ccaggacatc      3900
acctcatcca cagagacaag cactgtcctt tacaagatgc cctctggtgc      3950
cactcctgag gtctccagga cagaagttat gccctctagc agaacatcca      4000
ttcctggccc tgctcagtcc acaatgtcac tagacatctc cgatgaagtt      4050
gtcaccaggc tgtctacctc tcccatcatg acagaatctg cagaaataac      4100
catcaccacc caaacaggtt attctctggc tacatcccag gttacccttc      4150
ccttgggcac ctcaatgacc tttttgtcag ggacccactc aactatgtct      4200
caaggacttt cacactcaga gatgaccaat cttatgagca ggggtcctga      4250
aagtctgtca tggacgagcc ctcgctttgt ggaaacaact agatcttcct      4300
cttctctgac atcattacct ctcacgacct cactttctcc tgtgtcctcc      4350
acattactag acagtagccc ctcctctcct cttcctgtga cttcacttat      4400
cctcccaggc ctggtgaaga ctacagaagt gttggataca agctcagagc      4450
ctaaaaccag ttcatctcca aatttgagca gcacctcagt tgaaataccg      4500
gccacctctg aaatcatgac agatacagag aaaattcatc cttcctcaaa      4550
```

-continued

```
cacagcggtg gccaaagtga ggacctccag ttctgttcat gaatctcatt 4600
cctctgtcct agctgactca gaaacaacca taaccatacc ttcaatgggt 4650
atcacctccg ctgtggagga taccactgtt ttcacatcaa atcctgcctt 4700
ctctgagact aggaggattc cgacagagcc aacattctca ttgactcctg 4750
gattcaggga gactagcacc tctgaagaga ccacctcaat cacagaaaca 4800
agtgcagtcc tttttggagt gcccactagt gctactactg aagtctccat 4850
gacagaaata atgtcctcta atagaacaca catccctgac tctgatcagt 4900
ccacgatgtc tccagacatc atcactgaag tgatcaccag gctctcttcc 4950
tcatccatga tgtcagaatc aacacaaatg accatcacca cccaaaaaag 5000
ttctcctggg gctacagcac agagtactct taccttggcc acaacaacag 5050
ccccccttggc aaggacccac tcaactgttc ctcctagatt tttacactca 5100
gagatgacaa ctcttatgag taggagtcct gaaaatccat catggaagag 5150
ctctcccttt gtggaaaaaa ctagctcttc atcttctctg ttgtccttac 5200
ctgtcacgac ctcaccttct gtttcttcca cattaccgca gagtatccct 5250
tcctcctctt tttctgtgac ttcactcctc accccaggca tggtgaagac 5300
tacagacaca agcacagaac ctggaaccag tttatctcca aatctgagtg 5350
gcacctcagt tgaaatactg gctgcctctg aagtcaccac agatacagag 5400
aaaattcatc cttcttcaag catggcagtg accaatgtgg gaaccaccag 5450
ttctggacat gaactatatt cctctgtttc aatccactcg gagccatcca 5500
aggctacata cccagtgggt actccctctt ccatggctga aacctctatt 5550
tccacatcaa tgcctgctaa ttttgagacc acaggatttg aggctgagcc 5600
attttctcat ttgacttctg gacttaggaa gaccaacatg tccctggaca 5650
ccagctcagt cacaccaaca aatacacctt cttctcctgg gtccactcac 5700
cttttacaga gttccaagac tgatttcacc tcttctgcaa aaacatcatc 5750
cccagactgg cctccagcct cacagtatac tgaaattcca gtggacataa 5800
tcaccccctt taatgcttct ccatctatta cggagtccac tgggataacc 5850
tccttcccag aatccaggtt tactatgtct gtaacagaaa gtactcatca 5900
tctgagtaca gatttgctgc cttcagctga gactatttcc actggcacag 5950
tgatgccttc tctatcagag gccatgactt catttgccac cactggagtt 6000
ccacgagcca tctcaggttc aggtagtcca ttctctagga cagagtcagg 6050
ccctggggat gctactctgt ccaccattgc agagagcctg ccttcatcca 6100
ctcctgtgcc attctcctct tcaaccttca ctaccactga ttcttcaacc 6150
atcccagccc tccatgagat aacttcctct tcagctaccc catatagagt 6200
ggacaccagt cttgggacag agagcagcac tactgaagga cgcttggtta 6250
tggtcagtac tttggacact tcaagccaac caggcaggac atcttcatca 6300
cccattttgg ataccagaat gacagagagc gttgagctgg gaacagtgac 6350
aagtgcttat caagttcctt cactctcaac acggttgaca agaactgatg 6400
gcattatgga acacatcaca aaaataccca atgaagcagc acacagaggt 6450
accataagac cagtcaaagg ccctcagaca tccacttcgc ctgccagtcc 6500
taaaggacta cacacaggag ggacaaaaag aatggagacc accaccacag 6550
```

```
ctctgaagac caccaccaca gctctgaaga ccacttccag agccaccttg      6600

accaccagtg tctatactcc cactttggga acactgactc ccctcaatgc      6650

atcaatgcaa atggccagca caatccccac agaaatgatg atcacaaccc      6700

catatgtttt ccctgatgtt ccagaaacga catcctcatt ggctaccagc      6750

ctgggagcag aaaccagcac agctcttccc aggacaaccc catctgtttt      6800

caatagagaa tcagagacca cagcctcact ggtctctcgt tctggggcag      6850

agagaagtcc ggttattcaa actctagatg tttcttctag tgagccagat      6900

acaacagctt catgggttat ccatcctgca gagaccatcc caactgtttc      6950

caagacaacc cccaattttt tccacagtga attagacact gtatcttcca      7000

cagccaccag tcatggggca gacgtcagct cagccattcc aacaaatatc      7050

tcacctagtg aactagatgc actgacccca ctggtcacta tttcggggac      7100

agatactagt acaacattcc caacactgac taagtcccca catgaaacag      7150

agacaagaac cacatggctc actcatcctg cagagaccag ctcaactatt      7200

cccagaacaa tccccaattt ttctcatcat gaatcagatg ccacaccttc      7250

aatagccacc agtcctgggg cagaaaccag ttcagctatt ccaattatga      7300

ctgtctcacc tggtgcagaa gatctggtga cctcacaggt cactagttct      7350

ggcacagaca gaaatatgac tattccaact ttgactcttt ctcctggtga      7400

accaaagacc atagcctcat tagtcaccca tcctgaagca cagacaagtt      7450

cggccattcc aacttcaact atctcgcctg ctgtatcacg gttggtgacc      7500

tcaatggtca ccagtttggc ggcaaagaca agtacaacta atcgagctct      7550

gacaaactcc cctggtgaac cagctacaac agtttcattg gtcacgcatt      7600

ctgcacagac cagcccaaca gttccctgga caacttccat ttttttccat      7650

agtaaatcag acaccacacc ttcaatgacc accagtcatg gggcagaatc      7700

cagttcagct gttccaactc caactgtttc aactgaggta ccaggagtag      7750

tgaccccttt ggtcaccagt tctagggcag tgatcagtac aactattcca      7800

attctgactc tttctcctgg tgaaccagag accacacctt caatggccac      7850

cagtcatggg gaagaagcca gttctgctat tccaactcca actgtttcac      7900

ctggggtacc aggagtggtg acctctctgg tcactagttc tagggcagtg      7950

actagtacaa ctattccaat tctgactttt tctcttggtg aaccagagac      8000

cacaccttca atggccacca gtcatgggac agaagctggc tcagctgttc      8050

caactgtttt acctgaggta ccaggaatgg tgacctctct ggttgctagt      8100

tctagggcag taaccagtac aactcttcca actctgactc tttctcctgg      8150

tgaaccagag accacacctt caatggccac cagtcatggg gcagaagcca      8200

gctcaactgt tccaactgtt tcacctgagg taccaggagt ggtgacctct      8250

ctggtcacta gttctagtgg agtaaacagt acaagtattc caactctgat      8300

tctttctcct ggtgaactag aaaccacacc ttcaatggcc accagtcatg      8350

gggcagaagc cagctcagct gttccaactc caactgtttc acctggggta      8400

tcaggagtgg tgacccctct ggtcactagt tccagggcag tgaccagtac      8450

aactattcca attctaactc tttcttctag tgagccagag accacacctt      8500

caatggccac cagtcatggg gtagaagcca gctcagctgt tctaactgtt      8550
```

-continued

```
tcacctgagg taccaggaat ggtgaccttt ctggtcacta gttctagagc      8600
agtaaccagt acaactattc caactctgac tatttcttct gatgaaccag      8650
agaccacaac ttcattggtc acccattctg aggcaaagat gatttcagcc      8700
attccaactt taggtgtctc ccctactgta caagggctgg tgacttcact      8750
ggtcactagt tctgggtcag agaccagtgc gttttcaaat ctaactgttg      8800
cctcaagtca accagagacc atagactcat gggtcgctca tcctgggaca      8850
gaagcaagtt ctgttgttcc aactttgact gtctccactg gtgagccgtt      8900
tacaaatatc tcattggtca cccatcctgc agagagtagc tcaactcttc      8950
ccaggacaac ctcaaggttt tcccacagtg aattagacac tatgccttct      9000
acagtcacca gtcctgaggc agaatccagc tcagccattt caacaactat      9050
ttcacctggt ataccaggtg tgctgacatc actggtcact agctctggga      9100
gagacatcag tgcaactttt ccaacagtgc ctgagtcccc acatgaatca      9150
gaggcaacag cctcatgggt tactcatcct gcagtcacca gcacaacagt      9200
tcccaggaca acccctaatt attctcatag tgaaccagac accacaccat      9250
caatagccac cagtcctggg gcagaagcca cttcagattt tccaacaata      9300
actgtctcac ctgatgtacc agatatggta acctcacagg tcactagttc      9350
tgggacagac accagtataa ctattccaac tctgactctt tcttctggtg      9400
agccagagac cacaacctca tttatcacct attctgagac acatacaagt      9450
tcagccattc caactctccc tgtctcccct gatgcatcaa agatgctgac      9500
ctcactggtc atcagttctg ggacagacag cactacaact ttcccaacac      9550
tgacggagac cccatatgaa ccagagacaa cagccataca gctcattcat      9600
cctgcagaga ccaacacaat ggttcccagg acaactccca agttttccca      9650
tagtaagtca gacaccacac tcccagtagc catcaccagt cctgggccag      9700
aagccagttc agctgtttca acgacaacta tctcacctga tatgtcagat      9750
ctggtgacct cactggtccc tagttctggg acagacacca gtacaacctt      9800
cccaacattg agtgagaccc catatgaacc agagactaca gccacgtggc      9850
tcactcatcc tgcagaaacc agcacaacgg tttctgggac aattcccaac      9900
ttttcccata ggggatcaga cactgcaccc tcaatggtca ccagtcctgg      9950
agtagacacg aggtcaggtg ttccaactac aaccatccca cccagtatac     10000
caggggtagt gacctcacag gtcactagtt ctgcaacaga cactagtaca     10050
gctattccaa ctttgactcc ttctcctggt gaaccagaga ccacagcctc     10100
atcagctacc catcctggga cacagactgg cttcactgtt ccaattcgga     10150
ctgttccctc tagtgagcca gatacaatgg cttcctgggt cactcatcct     10200
ccacagacca gcacacctgt ttccagaaca acctccagtt tttcccatag     10250
tagtccagat gccacacctg taatggccac cagtcctagg acagaagcca     10300
gttcagctgt actgacaaca atctcacctg gtgcaccaga gatggtgact     10350
tcacagatca ctagttctgg ggcagcaacc agtacaactg ttccaacttt     10400
gactcattct cctggtatgc cagagaccac agccttattg agcacccatc     10450
ccagaacaga gacaagtaaa acatttcctg cttcaactgt gtttcctcaa     10500
gtatcagaga ccacagcctc actcaccatt agacctggtg cagagactag     10550
```

-continued

```
cacagctctc ccaactcaga caacatcctc tctcttcacc ctacttgtaa    10600
ctggaaccag cagagttgat ctaagtccaa ctgcttcacc tggtgtttct    10650
gcaaaaacag ccccactttc cacccatcca gggacagaaa ccagcacaat    10700
gattccaact tcaactcttt cccttggttt actagagact acaggcttac    10750
tggccaccag ctcttcagca gagaccagca cgagtactct aactctgact    10800
gtttcccctg ctgtctctgg gctttccagt gcctctataa caactgataa    10850
gccccaaact gtgacctcct ggaacacaga aacctcacca tctgtaactt    10900
cagttggacc cccagaattt tccaggactg tcacaggcac cactatgacc    10950
ttgataccat cagagatgcc aacaccacct aaaaccagtc atggagaagg    11000
agtgagtcca accactatct tgagaactac aatggttgaa gccactaatt    11050
tagctaccac aggttccagt cccactgtgg ccaagacaac aaccaccttc    11100
aatacactgg ctggaagcct ctttactcct ctgaccacac ctgggatgtc    11150
caccttggcc tctgagagtg tgacctcaag aacaagttat aaccatcggt    11200
cctggatctc caccaccagc agttataacc gtcggtactg gacccctgcc    11250
accagcactc cagtgacttc tacattctcc ccagggattt ccacatcctc    11300
catccccagc tccacagcag ccacagtccc attcatggtg ccattcaccc    11350
tcaacttcac catcaccaac ctgcagtacg aggaggacat gcggcaccct    11400
ggttcaagga agttcaacgc cacagagaga gaactgcagg gtctgctcaa    11450
acccttgttc aggaatagca gtctggaata cctctattca ggctgcagac    11500
tagcctcact caggccagag aaggatagct cagccacggc agtggatgcc    11550
atctgcacac atcgccctga ccctgaagac ctcggactgg acagagagcg    11600
actgtactgg gagctgagca atctgacaaa tggcatccag gagctgggcc    11650
cttacaccct ggaccggaac agtctctatg tcaatggttt cacccatcga    11700
agctctatgc ccaccaccag cactcctggg acctccacag tggatgtggg    11750
aacctcaggg actccatcct ccagccccag ccccacgact gctggccctc    11800
tcctgatgcc gttcaccctc aacttcacca tcaccaacct gcagtacgag    11850
gaggacatgc gtcgcactgg ctccaggaag ttcaacacca tggagagtgt    11900
cctgcagggt ctgctcaagc cattgttcaa gaacaccagt gttggccctt    11950
tgtactctgg ctgcagattg accttgctca ggcccgagaa agatggggca    12000
gccactggag tggatgccat ctgcacccac cgccttgacc ccaaaagccc    12050
tggactcaac agggagcagc tgtactggga gctaagcaaa ctgaccaatg    12100
acattgaaga gctgggcccc tacaccctgg acaggaacag tctctatgtc    12150
aatggtttca cccatcagag ctctgtgtcc accaccagca ctcctgggac    12200
ctccacagtg gatctcagaa cctcagggac tccatcctcc ctctccagcc    12250
ccacaattat ggctgctggc cctctcctgg taccattcac cctcaacttc    12300
accatcacca acctgcagta tggggaggac atgggtcacc ctggctccag    12350
gaagttcaac accacagaga gggtcctgca gggtctgctt ggtcccatat    12400
tcaagaacac cagtgttggc cctctgtact ctggctgcag actgacctct    12450
ctcaggtccg agaaggatgg agcagccact ggagtggatg ccatctgcat    12500
ccatcatctt gaccccaaaa gccctggact caacagagag cggctgtact    12550
```

-continued

```
gggagctgag ccaactgacc aatggcatca aagagctggg cccctacacc          12600
ctggacagga acagtctcta tgtcaatggt ttcacccatc ggacctctgt          12650
gcccaccacc agcactcctg ggacctccac agtggacctt ggaacctcag          12700
ggactccatt ctccctccca agccccgcaa ctgctggccc tctcctggtg          12750
ctgttcaccc tcaacttcac catcaccaac ctgaagtatg aggaggacat          12800
gcatcgccct ggctccagga agttcaacac cactgagagg gtcctgcaga          12850
ccctggttgg tcctatgttc aagaacacca gtgttggcct tctgtactct          12900
ggctgcagac tgaccttgct caggtccgag aaggatggag cagccactgg          12950
agtggatgcc atctgcaccc accgtcttga ccccaaaagc cctggagtgg          13000
acagggagca gctatactgg gagctgagcc aactgaccaa tggcatcaaa          13050
gagctgggcc cctacaccct ggacaggaac agtctctatg tcaatggttt          13100
cacccattgg atccctgtgc ccaccagcag cacccctggg acctccacag          13150
tggaccttgg gtcagggact ccatcctccc tccccagccc cacaagtgct          13200
actgctggcc ctctcctggt gccgttcacc ctcaacttca ccatcaccaa          13250
cctgaagtac gaggaggaca tgcattgccc tggctccagg aagttcaaca          13300
ccacagagag agtcctgcag agtctgcttg gtcccatgtt caagaacacc          13350
agtgttggcc ctctgtactc tggctgcaga ctgaccttgc tcaggtccga          13400
gaaggatgga gcagccactg gagtggatgc catctgcacc caccgtcttg          13450
accccaaaag ccctggagtg gacagggagc agctatactg ggagctgagc          13500
cagctgacca atggcatcaa agagctgggt ccctacaccc tggacagaaa          13550
cagtctctat gtcaatggtt tcacccatca gacctctgcg cccaacacca          13600
gcactcctgg gacctccaca gtggaccttg ggacctcagg gactccatcc          13650
tccctcccca gccctacatc tgctggccct ctcctggtgc cattcaccct          13700
caacttcacc atcaccaacc tgcagtacga ggaggacatg catcacccag          13750
gctccaggaa gttcaacacc acggagcggg tcctgcaggg tctgcttggt          13800
cccatgttca agaacaccag tgtcggcctt ctgtactctg gctgcagact          13850
gaccttgctc aggcctgaga agaatggggc agccactgga atggatgcca          13900
tctgcagcca ccgtcttgac cccaaaagcc ctggactcaa cagagagcag          13950
ctgtactggg agctgagcca gctgacccat ggcatcaaag agctgggccc          14000
ctacaccctg gacaggaaca gtctctatgt caatggtttc acccatcgga          14050
gctctgtggc ccccaccagc actcctggga cctccacagt ggaccttggg          14100
acctcaggga ctccatcctc cctccccagc cccacaacag ctgttcctct          14150
cctggtgccg ttcaccctca actttaccat caccaatctg cagtatgggg          14200
aggacatgcg tcaccctggc tccaggaagt tcaacaccac agagagggtc          14250
ctgcagggtc tgcttggtcc cttgttcaag aactccagtg tcggccctct          14300
gtactctggc tgcagactga tctctctcag gtctgagaag gatggggcag          14350
ccactggagt ggatgccatc tgcacccacc accttaaccc tcaaagccct          14400
ggactggaca gggagcagct gtactggcag ctgagccaga tgaccaatgg          14450
catcaaagag ctgggcccct acaccctgga ccggaacagt ctctacgtca          14500
atggtttcac ccatcggagc tctgggctca ccaccagcac tccttggact          14550
```

-continued

```
tccacagttg accttggaac ctcagggact ccatccccg tccccagccc 14600
cacaactgct ggccctctcc tggtgccatt caccctaaac ttcaccatca 14650
ccaacctgca gtatgaggag gacatgcatc gccctggatc taggaagttc 14700
aacgccacag agagggtcct gcagggtctg cttagtccca tattcaagaa 14750
ctccagtgtt ggccctctgt actctggctg cagactgacc tctctcaggc 14800
ccgagaagga tggggcagca actggaatgg atgctgtctg cctctaccac 14850
cctaatccca aaagacctgg gctggacaga gagcagctgt actgggagct 14900
aagccagctg acccacaaca tcactgagct gggcccctac agcctggaca 14950
gggacagtct ctatgtcaat ggtttcaccc atcagaactc tgtgcccacc 15000
accagtactc ctgggacctc cacagtgtac tgggcaacca ctgggactcc 15050
atcctccttc cccggccaca cagagcctgg ccctctcctg ataccattca 15100
ctttcaactt taccatcacc aacctgcatt atgaggaaaa catgcaacac 15150
cctggttcca ggaagttcaa caccacggag agggttctgc agggtctgct 15200
caagcccttg ttcaagaaca ccagtgttgg ccctctgtac tctggctgca 15250
gactgacctt gctcagacct gagaagcagg aggcagccac tggagtggac 15300
accatctgta cccaccgcgt tgatcccatc ggacctggac tggacagaga 15350
gcggctatac tgggagctga gccagctgac caacagcatc acagagctgg 15400
gaccctacac cctggatagg gacagtctct atgtcaatgg cttcaaccct 15450
tggagctctg tgccaaccac cagcactcct gggacctcca cagtgcacct 15500
ggcaacctct gggactccat cctccctgcc tggccacaca gcccctgtcc 15550
ctctcttgat accattcacc ctcaacttta ccatcaccaa cctgcattat 15600
gaagaaaaca tgcaacaccc tggttccagg aagttcaaca ccacggagag 15650
ggttctgcag ggtctgctca agcccttgtt caagagcacc agcgttggcc 15700
ctctgtactc tggctgcaga ctgaccttgc tcagacctga gaaacatggg 15750
gcagccactg gagtggacgc catctgcacc ctccgccttg atcccactgg 15800
tcctggactg gacagagagc ggctatactg ggagctgagc cagctgacca 15850
acagcgttac agagctgggc ccctacaccc tggacaggga cagtctctat 15900
gtcaatggct tcacccatcg gagctctgtg ccaaccacca gtattcctgg 15950
gacctctgca gtgcacctgg aaacctctgg gactccagcc tccctccctg 16000
gccacacagc ccctggccct ctcctggtgc cattcaccct caacttcact 16050
atcaccaacc tgcagtatga ggaggacatg cgtcaccctg gttccaggaa 16100
gttcaacacc acggagagag tcctgcaggg tctgctcaag cccttgttca 16150
agagcaccag tgttggccct ctgtactctg gctgcagact gaccttgctc 16200
aggcctgaaa aacgtggggc agccaccggc gtggacacca tctgcactca 16250
ccgccttgac cctctaaacc ctggactgga cagagagcag ctatactggg 16300
agctgagcaa actgacccgt ggcatcatcg agctgggccc ctacctcctg 16350
gacagaggca gtctctatgt caatggtttc acccatcgga actttgtgcc 16400
catcaccagc actcctggga cctccacagt acacctagga acctctgaaa 16450
ctccatcctc cctacctaga cccatagtgc ctggccctct cctggtgcca 16500
ttcaccctca acttcaccat caccaacttg cagtatgagg aggccatgcg 16550
```

acaccctggc tccaggaagt tcaataccac ggagagggtc ctacagggtc 16600
tgctcaggcc cttgttcaag aataccagta tcggccctct gtactccagc 16650
tgcagactga ccttgctcag gccagagaag gacaaggcag ccaccagagt 16700
ggatgccatc tgtacccacc accctgaccc tcaaagccct ggactgaaca 16750
gagagcagct gtactgggag ctgagccagc tgacccacgg catcactgag 16800
ctgggcccct acaccctgga cagggacagt ctctatgtcg atggtttcac 16850
tcattggagc cccataccaa ccaccagcac tcctgggacc tccatagtga 16900
acctgggaac ctctgggatc ccaccttccc tccctgaaac tacagccacc 16950
ggccctctcc tggtgccatt cacactcaac ttcaccatca ctaacctaca 17000
gtatgaggag aacatgggtc accctggctc caggaagttc aacatcacgg 17050
agagtgttct gcagggtctg ctcaagccct tgttcaagag caccagtgtt 17100
ggccctctgt attctggctg cagactgacc ttgctcaggc ctgagaagga 17150
cggagtagcc accagagtgg acgccatctg cacccaccgc cctgacccca 17200
aaatccctgg gctagacaga cagcagctat actgggagct gagccagctg 17250
acccacagca tcactgagct gggaccctac accctggata gggacagtct 17300
ctatgtcaat ggtttcaccc agcggagctc tgtgcccacc accagcactc 17350
ctgggacttt cacagtacag ccggaaacct ctgagactcc atcatccctc 17400
cctggcccca cagccactgg ccctgtcctg ctgccattca ccctcaattt 17450
taccatcatt aacctgcagt atgaggagga catgcatcgc cctggctcca 17500
ggaagttcaa caccacggag agggtccttc agggtctgct tatgcccttg 17550
ttcaagaaca ccagtgtcag ctctctgtac tctggttgca gactgacctt 17600
gctcaggcct gagaaggatg gggcagccac cagagtggat gctgtctgca 17650
cccatcgtcc tgaccccaaa agccctggac tggacagaga gcggctgtac 17700
tggaagctga gccagctgac ccacggcatc actgagctgg gcccctacac 17750
cctggacagg cacagtctct atgtcaatgg tttcacccat cagagctcta 17800
tgacgaccac cagaactcct gatacctcca caatgcacct ggcaacctcg 17850
agaactccag cctccctgtc tggacctacg accgccagcc ctctcctggt 17900
gctattcaca attaacttca ccatcactaa cctgcggtat gaggagaaca 17950
tgcatcaccc tggctctaga aagtttaaca ccacggagag agtccttcag 18000
ggtctgctca ggcctgtgtt caagaacacc agtgttggcc ctctgtactc 18050
tggctgcaga ctgaccttgc tcaggcccaa gaaggatggg gcagccacca 18100
aagtggatgc catctgcacc taccgccctg atcccaaaag ccctggactg 18150
gacagagagc agctatactg ggagctgagc cagctaaccc acagcatcac 18200
tgagctgggc ccctacaccc tggacaggga cagtctctat gtcaatggtt 18250
tcacacagcg gagctctgtg cccaccacta gcattcctgg gacccccaca 18300
gtggacctgg gaacatctgg gactccagtt tctaaacctg gtccctcggc 18350
tgccagccct ctcctggtgc tattcactct caacttcacc atcaccaacc 18400
tgcggtatga ggagaacatg cagcaccctg gctccaggaa gttcaacacc 18450
acggagaggg tccttcaggg cctgctcagg tccctgttca agagcaccag 18500
tgttggccct ctgtactctg gctgcagact gactttgctc aggcctgaaa 18550

-continued

```
aggatgggac agccactgga gtggatgcca tctgcaccca ccaccctgac 18600
cccaaaagcc ctaggctgga cagagagcag ctgtattggg agctgagcca 18650
gctgacccac aatatcactg agctgggccc ctatgccctg gacaacgaca 18700
gcctctttgt caatggtttc actcatcgga gctctgtgtc caccaccagc 18750
actcctggga cccccacagt gtatctggga gcatctaaga ctccagcctc 18800
gatatttggc ccttcagctg ccagccatct cctgatacta ttcaccctca 18850
acttcaccat cactaacctg cggtatgagg agaacatgtg gcctggctcc 18900
aggaagttca acactacaga gagggtcctt cagggcctgc taaggccctt 18950
gttcaagaac accagtgttg gccctctgta ctctggctgc aggctgacct 19000
tgctcaggcc agagaaagat ggggaagcca ccggagtgga tgccatctgc 19050
acccaccgcc ctgaccccac aggccctggg ctggacagag agcagctgta 19100
tttggagctg agccagctga cccacagcat cactgagctg ggcccctaca 19150
cactggacag ggacagtctc tatgtcaatg gtttcaccca tcggagctct 19200
gtacccacca ccagcaccgg ggtggtcagc gaggagccat tcacactgaa 19250
cttcaccatc aacaacctgc gctacatggc ggacatgggc caacccggct 19300
ccctcaagtt caacatcaca gacaacgtca tgcagcacct gctcagtcct 19350
ttgttccaga ggagcagcct gggtgcacgg tacacaggct gcagggtcat 19400
cgcactaagg tctgtgaaga acggtgctga gacacgggtg gacctcctct 19450
gcacctacct gcagcccctc agcggcccag gtctgcctat caagcaggtg 19500
ttccatgagc tgagccagca gacccatggc atcacccggc tgggccccta 19550
ctctctggac aaagacagcc tctaccttaa cggttacaat gaacctggtc 19600
cagatgagcc tcctacaact cccaagccag ccaccacatt cctgcctcct 19650
ctgtcagaag ccacaacagc catggggtac cacctgaaga ccctcacact 19700
caacttcacc atctccaatc tccagtattc accagatatg ggcaagggct 19750
cagctacatt caactccacc gagggggtcc ttcagcacct gctcagaccc 19800
ttgttccaga agagcagcat gggccccttc tacttgggtt gccaactgat 19850
ctccctcagg cctgagaagg atggggcagc cactggtgtg gacaccacct 19900
gcacctacca ccctgaccct gtgggccccg ggctggacat acagcagctt 19950
tactgggagc tgagtcagct gacccatggt gtcacccaac tgggcttcta 20000
tgtcctggac agggatagcc tcttcatcaa tggctatgca ccccagaatt 20050
tatcaatccg gggcgagtac cagataaatt tccacattgt caactggaac 20100
ctcagtaatc cagaccccac atcctcagag tacatcaccc tgctgaggga 20150
catccaggac aaggtcacca cactctacaa aggcagtcaa ctacatgaca 20200
cattccgctt ctgcctggtc accaacttga cgatggactc cgtgttggtc 20250
actgtcaagg cattgttctc ctccaatttg gaccccagcc tggtggagca 20300
agtctttcta gataagaccc tgaatgcctc attccattgg ctgggctcca 20350
cctaccagtt ggtggacatc catgtgacag aaatggagtc atcagtttat 20400
caaccaacaa gcagctccag cacccagcac ttctacctga atttcaccat 20450
caccaaccta ccatattccc aggacaaagc ccagccaggc accaccaatt 20500
accagaggaa caaaaggaat attgaggatg cgctcaacca actcttccga 20550
```

-continued aacagcagca tcaagagtta tttttctgac tgtcaagttt caacattcag 20600
gtctgtcccc aacaggcacc acaccggggt ggactccctg tgtaacttct 20650
cgccactggc tcggagagta gacagagttg ccatctatga ggaatttctg 20700
cggatgaccc ggaatggtac ccagctgcag aacttcaccc tggacaggag 20750
cagtgtcctt gtggatgggt attctcccaa cagaaatgag cccttaactg 20800
ggaattctga ccttcccttc tgggctgtca tcctcatcgg cttggcagga 20850
ctcctgggac tcatcacatg cctgatctgc ggtgtcctgg tgaccacccg 20900
ccggcggaag aaggaaggag aatacaacgt ccagcaacag tgcccaggct 20950
actaccagtc acacctagac ctggaggatc tgcaatgact ggaacttgcc 21000
ggtgcctggg gtgcctttcc cccagccagg gtccaaagaa gcttggctgg 21050
ggcagaaata aaccatattg gtcggaaaaa aaaaaaaaaa aaaaaaaaaa 21100
aaaaaaaaaa aa 21112

<210> SEQ ID NO 2
<211> LENGTH: 6995
<212> TYPE: PRT
<213> ORGANISM: Homo sapiens

<400> SEQUENCE: 2

Pro Val Thr Ser Leu Leu Thr Pro Gly Leu Val Ile Thr Thr Asp
1 5 10 15

Arg Met Gly Ile Ser Arg Glu Pro Gly Thr Ser Ser Thr Ser Asn
20 25 30

Leu Ser Ser Thr Ser His Glu Arg Leu Thr Thr Leu Glu Asp Thr
35 40 45

Val Asp Thr Glu Ala Met Gln Pro Ser Thr His Thr Ala Val Thr
50 55 60

Asn Val Arg Thr Ser Ile Ser Gly His Glu Ser Gln Ser Ser Val
65 70 75

Leu Ser Asp Ser Glu Thr Pro Lys Ala Thr Ser Pro Met Gly Thr
80 85 90

Thr Tyr Thr Met Gly Glu Thr Ser Val Ser Ile Ser Thr Ser Asp
95 100 105

Phe Phe Glu Thr Ser Arg Ile Gln Ile Glu Pro Thr Ser Ser Leu
110 115 120

Thr Ser Gly Leu Arg Glu Thr Ser Ser Ser Glu Arg Ile Ser Ser
125 130 135

Ala Thr Glu Gly Ser Thr Val Leu Ser Glu Val Pro Ser Gly Ala
140 145 150

Thr Thr Glu Val Ser Arg Thr Glu Val Ile Ser Ser Arg Gly Thr
155 160 165

Ser Met Ser Gly Pro Asp Gln Phe Thr Ile Ser Pro Asp Ile Ser
170 175 180

Thr Glu Ala Ile Thr Arg Leu Ser Thr Ser Pro Ile Met Thr Glu
185 190 195

Ser Ala Glu Ser Ala Ile Thr Ile Glu Thr Gly Ser Pro Gly Ala
200 205 210

Thr Ser Glu Gly Thr Leu Thr Leu Asp Thr Ser Thr Thr Thr Phe
215 220 225

Trp Ser Gly Thr His Ser Thr Ala Ser Pro Gly Phe Ser His Ser
230 235 240

Glu Met Thr Thr Leu Met Ser Arg Thr Pro Gly Asp Val Pro Trp
245 250 255

Pro Ser Leu Pro Ser Val Glu Glu Ala Ser Ser Val Ser Ser Ser
260 265 270

Leu Ser Ser Pro Ala Met Thr Ser Thr Ser Phe Phe Ser Thr Leu
275 280 285

Pro Glu Ser Ile Ser Ser Ser Pro His Pro Val Thr Ala Leu Leu
290 295 300

Thr Leu Gly Pro Val Lys Thr Thr Asp Met Leu Arg Thr Ser Ser
305 310 315

Glu Pro Glu Thr Ser Ser Pro Pro Asn Leu Ser Ser Thr Ser Ala
320 325 330

Glu Ile Leu Ala Thr Ser Glu Val Thr Lys Asp Arg Glu Lys Ile
335 340 345

His Pro Ser Ser Asn Thr Pro Val Val Asn Val Gly Thr Val Ile
350 355 360

Tyr Lys His Leu Ser Pro Ser Ser Val Leu Ala Asp Leu Val Thr
365 370 375

Thr Lys Pro Thr Ser Pro Met Ala Thr Thr Ser Thr Leu Gly Asn
380 385 390

Thr Ser Val Ser Thr Ser Thr Pro Ala Phe Pro Glu Thr Met Met
395 400 405

Thr Gln Pro Thr Ser Ser Leu Thr Ser Gly Leu Arg Glu Ile Ser
410 415 420

Thr Ser Gln Glu Thr Ser Ser Ala Thr Glu Arg Ser Ala Ser Leu
425 430 435

Ser Gly Met Pro Thr Gly Ala Thr Thr Lys Val Ser Arg Thr Glu
440 445 450

Ala Leu Ser Leu Gly Arg Thr Ser Thr Pro Gly Pro Ala Gln Ser
455 460 465

Thr Ile Ser Pro Glu Ile Ser Thr Glu Thr Ile Thr Arg Ile Ser
470 475 480

Thr Pro Leu Thr Thr Thr Gly Ser Ala Glu Met Thr Ile Thr Pro
485 490 495

Lys Thr Gly His Ser Gly Ala Ser Ser Gln Gly Thr Phe Thr Leu
500 505 510

Asp Thr Ser Ser Arg Ala Ser Trp Pro Gly Thr His Ser Ala Ala
515 520 525

Thr His Arg Ser Pro His Ser Gly Met Thr Thr Pro Met Ser Arg
530 535 540

Gly Pro Glu Asp Val Ser Trp Pro Ser Arg Pro Ser Val Glu Lys
545 550 555

Thr Ser Pro Pro Ser Ser Leu Val Ser Leu Ser Ala Val Thr Ser
560 565 570

Pro Ser Pro Leu Tyr Ser Thr Pro Ser Glu Ser Ser His Ser Ser
575 580 585

Pro Leu Arg Val Thr Ser Leu Phe Thr Pro Val Met Met Lys Thr
590 595 600

Thr Asp Met Leu Asp Thr Ser Leu Glu Pro Val Thr Thr Ser Pro
605 610 615

Pro Ser Met Asn Ile Thr Ser Asp Glu Ser Leu Ala Thr Ser Lys
620 625 630

Ala Thr Met Glu Thr Glu Ala Ile Gln Leu Ser Glu Asn Thr Ala

-continued

```
                635                 640                 645

Val Thr Gln Met Gly Thr Ile Ser Ala Arg Gln Glu Phe Tyr Ser
                650                 655                 660

Ser Tyr Pro Gly Leu Pro Glu Pro Ser Lys Val Thr Ser Pro Val
                665                 670                 675

Val Thr Ser Ser Thr Ile Lys Asp Ile Val Ser Thr Thr Ile Pro
                680                 685                 690

Ala Ser Ser Glu Ile Thr Arg Ile Glu Met Glu Ser Thr Ser Thr
                695                 700                 705

Leu Thr Pro Thr Pro Arg Glu Thr Ser Thr Ser Gln Glu Ile His
                710                 715                 720

Ser Ala Thr Lys Pro Ser Thr Val Pro Tyr Lys Ala Leu Thr Ser
                725                 730                 735

Ala Thr Ile Glu Asp Ser Met Thr Gln Val Met Ser Ser Ser Arg
                740                 745                 750

Gly Pro Ser Pro Asp Gln Ser Thr Met Ser Gln Asp Ile Ser Thr
                755                 760                 765

Glu Val Ile Thr Arg Leu Ser Thr Ser Pro Ile Lys Thr Glu Ser
                770                 775                 780

Thr Glu Met Thr Ile Thr Thr Gln Thr Gly Ser Pro Gly Ala Thr
                785                 790                 795

Ser Arg Gly Thr Leu Thr Leu Asp Thr Ser Thr Thr Phe Met Ser
                800                 805                 810

Gly Thr His Ser Thr Ala Ser Gln Gly Phe Ser His Ser Gln Met
                815                 820                 825

Thr Ala Leu Met Ser Arg Thr Pro Gly Glu Val Pro Trp Leu Ser
                830                 835                 840

His Pro Ser Val Glu Glu Ala Ser Ser Ala Ser Phe Ser Leu Ser
                845                 850                 855

Ser Pro Val Met Thr Ser Ser Ser Pro Val Ser Ser Thr Leu Pro
                860                 865                 870

Asp Ser Ile His Ser Ser Ser Leu Pro Val Thr Ser Leu Leu Thr
                875                 880                 885

Ser Gly Leu Val Lys Thr Thr Glu Leu Leu Gly Thr Ser Ser Glu
                890                 895                 900

Pro Glu Thr Ser Ser Pro Pro Asn Leu Ser Ser Thr Ser Ala Glu
                905                 910                 915

Ile Leu Ala Thr Thr Glu Val Thr Thr Asp Thr Glu Lys Leu Glu
                920                 925                 930

Met Thr Asn Val Val Thr Ser Gly Tyr Thr His Glu Ser Pro Ser
                935                 940                 945

Ser Val Leu Ala Asp Ser Val Thr Thr Lys Ala Thr Ser Ser Met
                950                 955                 960

Gly Ile Thr Tyr Pro Thr Gly Asp Thr Asn Val Leu Thr Ser Thr
                965                 970                 975

Pro Ala Phe Ser Asp Thr Ser Arg Ile Gln Thr Lys Ser Lys Leu
                980                 985                 990

Ser Leu Thr Pro Gly Leu Met Glu Thr Ser Ile Ser Glu Glu Thr
                995                1000                1005

Ser Ser Ala Thr Glu Lys Ser Thr Val Leu Ser Ser Val Pro Thr
               1010                1015                1020

Gly Ala Thr Thr Glu Val Ser Arg Thr Glu Ala Ile Ser Ser Ser
               1025                1030                1035
```

-continued

```
Arg Thr Ser Ile Pro Gly Pro Ala Gln Ser Thr Met Ser Ser Asp
                1040                1045                1050

Thr Ser Met Glu Thr Ile Thr Arg Ile Ser Thr Pro Leu Thr Arg
                1055                1060                1065

Lys Glu Ser Thr Asp Met Ala Ile Thr Pro Lys Thr Gly Pro Ser
                1070                1075                1080

Gly Ala Thr Ser Gln Gly Thr Phe Thr Leu Asp Ser Ser Ser Thr
                1085                1090                1095

Ala Ser Trp Pro Gly Thr His Ser Ala Thr Thr Gln Arg Phe Pro
                1100                1105                1110

Arg Ser Val Val Thr Thr Pro Met Ser Arg Gly Pro Glu Asp Val
                1115                1120                1125

Ser Trp Pro Ser Pro Leu Ser Val Glu Lys Asn Ser Pro Pro Ser
                1130                1135                1140

Ser Leu Val Ser Ser Ser Ser Val Thr Ser Pro Ser Pro Leu Tyr
                1145                1150                1155

Ser Thr Pro Ser Gly Ser Ser His Ser Ser Pro Val Pro Val Thr
                1160                1165                1170

Ser Leu Phe Thr Ser Ile Met Met Lys Ala Thr Asp Met Leu Asp
                1175                1180                1185

Ala Ser Leu Glu Pro Glu Thr Thr Ser Ala Pro Asn Met Asn Ile
                1190                1195                1200

Thr Ser Asp Glu Ser Leu Ala Ala Ser Lys Ala Thr Thr Glu Thr
                1205                1210                1215

Glu Ala Ile His Val Phe Glu Asn Thr Ala Ala Ser His Val Glu
                1220                1225                1230

Thr Thr Ser Ala Thr Glu Glu Leu Tyr Ser Ser Ser Pro Gly Phe
                1235                1240                1245

Ser Glu Pro Thr Lys Val Ile Ser Pro Val Val Thr Ser Ser Ser
                1250                1255                1260

Ile Arg Asp Asn Met Val Ser Thr Thr Met Pro Gly Ser Ser Gly
                1265                1270                1275

Ile Thr Arg Ile Glu Ile Glu Ser Met Ser Ser Leu Thr Pro Gly
                1280                1285                1290

Leu Arg Glu Thr Arg Thr Ser Gln Asp Ile Thr Ser Ser Thr Glu
                1295                1300                1305

Thr Ser Thr Val Leu Tyr Lys Met Pro Ser Gly Ala Thr Pro Glu
                1310                1315                1320

Val Ser Arg Thr Glu Val Met Pro Ser Ser Arg Thr Ser Ile Pro
                1325                1330                1335

Gly Pro Ala Gln Ser Thr Met Ser Leu Asp Ile Ser Asp Glu Val
                1340                1345                1350

Val Thr Arg Leu Ser Thr Ser Pro Ile Met Thr Glu Ser Ala Glu
                1355                1360                1365

Ile Thr Ile Thr Thr Gln Thr Gly Tyr Ser Leu Ala Thr Ser Gln
                1370                1375                1380

Val Thr Leu Pro Leu Gly Thr Ser Met Thr Phe Leu Ser Gly Thr
                1385                1390                1395

His Ser Thr Met Ser Gln Gly Leu Ser His Ser Glu Met Thr Asn
                1400                1405                1410

Leu Met Ser Arg Gly Pro Glu Ser Leu Ser Trp Thr Ser Pro Arg
                1415                1420                1425

Phe Val Glu Thr Thr Arg Ser Ser Ser Ser Leu Thr Ser Leu Pro
                1430                1435                1440
```

Leu Thr Thr Ser Leu Ser Pro Val Ser Ser Thr Leu Leu Asp Ser
1445 1450 1455

Ser Pro Ser Ser Pro Leu Pro Val Thr Ser Leu Ile Leu Pro Gly
1460 1465 1470

Leu Val Lys Thr Thr Glu Val Leu Asp Thr Ser Ser Glu Pro Lys
1475 1480 1485

Thr Ser Ser Ser Pro Asn Leu Ser Ser Thr Ser Val Glu Ile Pro
1490 1495 1500

Ala Thr Ser Glu Ile Met Thr Asp Thr Glu Lys Ile His Pro Ser
1505 1510 1515

Ser Asn Thr Ala Val Ala Lys Val Arg Thr Ser Ser Ser Val His
1520 1525 1530

Glu Ser His Ser Ser Val Leu Ala Asp Ser Glu Thr Thr Ile Thr
1535 1540 1545

Ile Pro Ser Met Gly Ile Thr Ser Ala Val Glu Asp Thr Thr Val
1550 1555 1560

Phe Thr Ser Asn Pro Ala Phe Ser Glu Thr Arg Arg Ile Pro Thr
1565 1570 1575

Glu Pro Thr Phe Ser Leu Thr Pro Gly Phe Arg Glu Thr Ser Thr
1580 1585 1590

Ser Glu Glu Thr Thr Ser Ile Thr Glu Thr Ser Ala Val Leu Phe
1595 1600 1605

Gly Val Pro Thr Ser Ala Thr Thr Glu Val Ser Met Thr Glu Ile
1610 1615 1620

Met Ser Ser Asn Arg Thr His Ile Pro Asp Ser Asp Gln Ser Thr
1625 1630 1635

Met Ser Pro Asp Ile Ile Thr Glu Val Ile Thr Arg Leu Ser Ser
1640 1645 1650

Ser Ser Met Met Ser Glu Ser Thr Gln Met Thr Ile Thr Thr Gln
1655 1660 1665

Lys Ser Ser Pro Gly Ala Thr Ala Gln Ser Thr Leu Thr Leu Ala
1670 1675 1680

Thr Thr Thr Ala Pro Leu Ala Arg Thr His Ser Thr Val Pro Pro
1685 1690 1695

Arg Phe Leu His Ser Glu Met Thr Thr Leu Met Ser Arg Ser Pro
1700 1705 1710

Glu Asn Pro Ser Trp Lys Ser Ser Pro Phe Val Glu Lys Thr Ser
1715 1720 1725

Ser Ser Ser Ser Leu Leu Ser Leu Pro Val Thr Thr Ser Pro Ser
1730 1735 1740

Val Ser Ser Thr Leu Pro Gln Ser Ile Pro Ser Ser Ser Phe Ser
1745 1750 1755

Val Thr Ser Leu Leu Thr Pro Gly Met Val Lys Thr Thr Asp Thr
1760 1765 1770

Ser Thr Glu Pro Gly Thr Ser Leu Ser Pro Asn Leu Ser Gly Thr
1775 1780 1785

Ser Val Glu Ile Leu Ala Ala Ser Glu Val Thr Thr Asp Thr Glu
1790 1795 1800

Lys Ile His Pro Ser Ser Ser Met Ala Val Thr Asn Val Gly Thr
1805 1810 1815

Thr Ser Ser Gly His Glu Leu Tyr Ser Ser Val Ser Ile His Ser
1820 1825 1830

Glu Pro Ser Lys Ala Thr Tyr Pro Val Gly Thr Pro Ser Ser Met

```
                1835                1840                1845

Ala Glu Thr Ser Ile Ser Thr Ser Met Pro Ala Asn Phe Glu Thr
                1850                1855                1860

Thr Gly Phe Glu Ala Glu Pro Phe Ser His Leu Thr Ser Gly Leu
                1865                1870                1875

Arg Lys Thr Asn Met Ser Leu Asp Thr Ser Ser Val Thr Pro Thr
                1880                1885                1890

Asn Thr Pro Ser Ser Pro Gly Ser Thr His Leu Leu Gln Ser Ser
                1895                1900                1905

Lys Thr Asp Phe Thr Ser Ser Ala Lys Thr Ser Ser Pro Asp Trp
                1910                1915                1920

Pro Pro Ala Ser Gln Tyr Thr Glu Ile Pro Val Asp Ile Ile Thr
                1925                1930                1935

Pro Phe Asn Ala Ser Pro Ser Ile Thr Glu Ser Thr Gly Ile Thr
                1940                1945                1950

Ser Phe Pro Glu Ser Arg Phe Thr Met Ser Val Thr Glu Ser Thr
                1955                1960                1965

His His Leu Ser Thr Asp Leu Leu Pro Ser Ala Glu Thr Ile Ser
                1970                1975                1980

Thr Gly Thr Val Met Pro Ser Leu Ser Glu Ala Met Thr Ser Phe
                1985                1990                1995

Ala Thr Thr Gly Val Pro Arg Ala Ile Ser Gly Ser Gly Ser Pro
                2000                2005                2010

Phe Ser Arg Thr Glu Ser Gly Pro Gly Asp Ala Thr Leu Ser Thr
                2015                2020                2025

Ile Ala Glu Ser Leu Pro Ser Ser Thr Pro Val Pro Phe Ser Ser
                2030                2035                2040

Ser Thr Phe Thr Thr Thr Asp Ser Ser Thr Ile Pro Ala Leu His
                2045                2050                2055

Glu Ile Thr Ser Ser Ser Ala Thr Pro Tyr Arg Val Asp Thr Ser
                2060                2065                2070

Leu Gly Thr Glu Ser Ser Thr Thr Glu Gly Arg Leu Val Met Val
                2075                2080                2085

Ser Thr Leu Asp Thr Ser Ser Gln Pro Gly Arg Thr Ser Ser Ser
                2090                2095                2100

Pro Ile Leu Asp Thr Arg Met Thr Glu Ser Val Glu Leu Gly Thr
                2105                2110                2115

Val Thr Ser Ala Tyr Gln Val Pro Ser Leu Ser Thr Arg Leu Thr
                2120                2125                2130

Arg Thr Asp Gly Ile Met Glu His Ile Thr Lys Ile Pro Asn Glu
                2135                2140                2145

Ala Ala His Arg Gly Thr Ile Arg Pro Val Lys Gly Pro Gln Thr
                2150                2155                2160

Ser Thr Ser Pro Ala Ser Pro Lys Gly Leu His Thr Gly Gly Thr
                2165                2170                2175

Lys Arg Met Glu Thr Thr Thr Thr Ala Leu Lys Thr Thr Thr Thr
                2180                2185                2190

Ala Leu Lys Thr Thr Ser Arg Ala Thr Leu Thr Thr Ser Val Tyr
                2195                2200                2205

Thr Pro Thr Leu Gly Thr Leu Thr Pro Leu Asn Ala Ser Met Gln
                2210                2215                2220

Met Ala Ser Thr Ile Pro Thr Glu Met Met Ile Thr Thr Pro Tyr
                2225                2230                2235
```

-continued

Val Phe Pro Asp Val Pro Glu Thr Thr Ser Ser Leu Ala Thr Ser
2240 2245 2250

Leu Gly Ala Glu Thr Ser Thr Ala Leu Pro Arg Thr Thr Pro Ser
2255 2260 2265

Val Phe Asn Arg Glu Ser Glu Thr Thr Ala Ser Leu Val Ser Arg
2270 2275 2280

Ser Gly Ala Glu Arg Ser Pro Val Ile Gln Thr Leu Asp Val Ser
2285 2290 2295

Ser Ser Glu Pro Asp Thr Thr Ala Ser Trp Val Ile His Pro Ala
2300 2305 2310

Glu Thr Ile Pro Thr Val Ser Lys Thr Thr Pro Asn Phe Phe His
2315 2320 2325

Ser Glu Leu Asp Thr Val Ser Ser Thr Ala Thr Ser His Gly Ala
2330 2335 2340

Asp Val Ser Ser Ala Ile Pro Thr Asn Ile Ser Pro Ser Glu Leu
2345 2350 2355

Asp Ala Leu Thr Pro Leu Val Thr Ile Ser Gly Thr Asp Thr Ser
2360 2365 2370

Thr Thr Phe Pro Thr Leu Thr Lys Ser Pro His Glu Thr Glu Thr
2375 2380 2385

Arg Thr Thr Trp Leu Thr His Pro Ala Glu Thr Ser Ser Thr Ile
2390 2395 2400

Pro Arg Thr Ile Pro Asn Phe Ser His His Glu Ser Asp Ala Thr
2405 2410 2415

Pro Ser Ile Ala Thr Ser Pro Gly Ala Glu Thr Ser Ser Ala Ile
2420 2425 2430

Pro Ile Met Thr Val Ser Pro Gly Ala Glu Asp Leu Val Thr Ser
2435 2440 2445

Gln Val Thr Ser Ser Gly Thr Asp Arg Asn Met Thr Ile Pro Thr
2450 2455 2460

Leu Thr Leu Ser Pro Gly Glu Pro Lys Thr Ile Ala Ser Leu Val
2465 2470 2475

Thr His Pro Glu Ala Gln Thr Ser Ser Ala Ile Pro Thr Ser Thr
2480 2485 2490

Ile Ser Pro Ala Val Ser Arg Leu Val Thr Ser Met Val Thr Ser
2495 2500 2505

Leu Ala Ala Lys Thr Ser Thr Thr Asn Arg Ala Leu Thr Asn Ser
2510 2515 2520

Pro Gly Glu Pro Ala Thr Thr Val Ser Leu Val Thr His Ser Ala
2525 2530 2535

Gln Thr Ser Pro Thr Val Pro Trp Thr Thr Ser Ile Phe Phe His
2540 2545 2550

Ser Lys Ser Asp Thr Thr Pro Ser Met Thr Thr Ser His Gly Ala
2555 2560 2565

Glu Ser Ser Ser Ala Val Pro Thr Pro Thr Val Ser Thr Glu Val
2570 2575 2580

Pro Gly Val Val Thr Pro Leu Val Thr Ser Ser Arg Ala Val Ile
2585 2590 2595

Ser Thr Thr Ile Pro Ile Leu Thr Leu Ser Pro Gly Glu Pro Glu
2600 2605 2610

Thr Thr Pro Ser Met Ala Thr Ser His Gly Glu Glu Ala Ser Ser
2615 2620 2625

Ala Ile Pro Thr Pro Thr Val Ser Pro Gly Val Pro Gly Val Val
2630 2635 2640

-continued

Thr Ser Leu Val Thr Ser Ser Arg Ala Val Thr Ser Thr Thr Ile
2645 2650 2655

Pro Ile Leu Thr Phe Ser Leu Gly Glu Pro Glu Thr Thr Pro Ser
2660 2665 2670

Met Ala Thr Ser His Gly Thr Glu Ala Gly Ser Ala Val Pro Thr
2675 2680 2685

Val Leu Pro Glu Val Pro Gly Met Val Thr Ser Leu Val Ala Ser
2690 2695 2700

Ser Arg Ala Val Thr Ser Thr Thr Leu Pro Thr Leu Thr Leu Ser
2705 2710 2715

Pro Gly Glu Pro Glu Thr Thr Pro Ser Met Ala Thr Ser His Gly
2720 2725 2730

Ala Glu Ala Ser Ser Thr Val Pro Thr Val Ser Pro Glu Val Pro
2735 2740 2745

Gly Val Val Thr Ser Leu Val Thr Ser Ser Ser Gly Val Asn Ser
2750 2755 2760

Thr Ser Ile Pro Thr Leu Ile Leu Ser Pro Gly Glu Leu Glu Thr
2765 2770 2775

Thr Pro Ser Met Ala Thr Ser His Gly Ala Glu Ala Ser Ser Ala
2780 2785 2790

Val Pro Thr Pro Thr Val Ser Pro Gly Val Ser Gly Val Val Thr
2795 2800 2805

Pro Leu Val Thr Ser Ser Arg Ala Val Thr Ser Thr Thr Ile Pro
2810 2815 2820

Ile Leu Thr Leu Ser Ser Ser Glu Pro Glu Thr Thr Pro Ser Met
2825 2830 2835

Ala Thr Ser His Gly Val Glu Ala Ser Ser Ala Val Leu Thr Val
2840 2845 2850

Ser Pro Glu Val Pro Gly Met Val Thr Phe Leu Val Thr Ser Ser
2855 2860 2865

Arg Ala Val Thr Ser Thr Thr Ile Pro Thr Leu Thr Ile Ser Ser
2870 2875 2880

Asp Glu Pro Glu Thr Thr Thr Ser Leu Val Thr His Ser Glu Ala
2885 2890 2895

Lys Met Ile Ser Ala Ile Pro Thr Leu Gly Val Ser Pro Thr Val
2900 2905 2910

Gln Gly Leu Val Thr Ser Leu Val Thr Ser Ser Gly Ser Glu Thr
2915 2920 2925

Ser Ala Phe Ser Asn Leu Thr Val Ala Ser Ser Gln Pro Glu Thr
2930 2935 2940

Ile Asp Ser Trp Val Ala His Pro Gly Thr Glu Ala Ser Ser Val
2945 2950 2955

Val Pro Thr Leu Thr Val Ser Thr Gly Glu Pro Phe Thr Asn Ile
2960 2965 2970

Ser Leu Val Thr His Pro Ala Glu Ser Ser Ser Thr Leu Pro Arg
2975 2980 2985

Thr Thr Ser Arg Phe Ser His Ser Glu Leu Asp Thr Met Pro Ser
2990 2995 3000

Thr Val Thr Ser Pro Glu Ala Glu Ser Ser Ser Ala Ile Ser Thr
3005 3010 3015

Thr Ile Ser Pro Gly Ile Pro Gly Val Leu Thr Ser Leu Val Thr
3020 3025 3030

Ser Ser Gly Arg Asp Ile Ser Ala Thr Phe Pro Thr Val Pro Glu

-continued 3035 3040 3045

Ser Pro His Glu Ser Glu Ala Thr Ala Ser Trp Val Thr His Pro
3050 3055 3060

Ala Val Thr Ser Thr Thr Val Pro Arg Thr Thr Pro Asn Tyr Ser
3065 3070 3075

His Ser Glu Pro Asp Thr Thr Pro Ser Ile Ala Thr Ser Pro Gly
3080 3085 3090

Ala Glu Ala Thr Ser Asp Phe Pro Thr Ile Thr Val Ser Pro Asp
3095 3100 3105

Val Pro Asp Met Val Thr Ser Gln Val Thr Ser Ser Gly Thr Asp
3110 3115 3120

Thr Ser Ile Thr Ile Pro Thr Leu Thr Leu Ser Ser Gly Glu Pro
3125 3130 3135

Glu Thr Thr Thr Ser Phe Ile Thr Tyr Ser Glu Thr His Thr Ser
3140 3145 3150

Ser Ala Ile Pro Thr Leu Pro Val Ser Pro Asp Ala Ser Lys Met
3155 3160 3165

Leu Thr Ser Leu Val Ile Ser Ser Gly Thr Asp Ser Thr Thr Thr
3170 3175 3180

Phe Pro Thr Leu Thr Glu Thr Pro Tyr Glu Pro Glu Thr Thr Ala
3185 3190 3195

Ile Gln Leu Ile His Pro Ala Glu Thr Asn Thr Met Val Pro Arg
3200 3205 3210

Thr Thr Pro Lys Phe Ser His Ser Lys Ser Asp Thr Thr Leu Pro
3215 3220 3225

Val Ala Ile Thr Ser Pro Gly Pro Glu Ala Ser Ser Ala Val Ser
3230 3235 3240

Thr Thr Thr Ile Ser Pro Asp Met Ser Asp Leu Val Thr Ser Leu
3245 3250 3255

Val Pro Ser Ser Gly Thr Asp Thr Ser Thr Thr Phe Pro Thr Leu
3260 3265 3270

Ser Glu Thr Pro Tyr Glu Pro Glu Thr Thr Ala Thr Trp Leu Thr
3275 3280 3285

His Pro Ala Glu Thr Ser Thr Thr Val Ser Gly Thr Ile Pro Asn
3290 3295 3300

Phe Ser His Arg Gly Ser Asp Thr Ala Pro Ser Met Val Thr Ser
3305 3310 3315

Pro Gly Val Asp Thr Arg Ser Gly Val Pro Thr Thr Thr Ile Pro
3320 3325 3330

Pro Ser Ile Pro Gly Val Val Thr Ser Gln Val Thr Ser Ser Ala
3335 3340 3345

Thr Asp Thr Ser Thr Ala Ile Pro Thr Leu Thr Pro Ser Pro Gly
3350 3355 3360

Glu Pro Glu Thr Thr Ala Ser Ser Ala Thr His Pro Gly Thr Gln
3365 3370 3375

Thr Gly Phe Thr Val Pro Ile Arg Thr Val Pro Ser Ser Glu Pro
3380 3385 3390

Asp Thr Met Ala Ser Trp Val Thr His Pro Pro Gln Thr Ser Thr
3395 3400 3405

Pro Val Ser Arg Thr Thr Ser Ser Phe Ser His Ser Ser Pro Asp
3410 3415 3420

Ala Thr Pro Val Met Ala Thr Ser Pro Arg Thr Glu Ala Ser Ser
3425 3430 3435

-continued

```
Ala Val Leu Thr Thr Ile Ser Pro Gly Ala Pro Glu Met Val Thr
                3440                3445                3450

Ser Gln Ile Thr Ser Ser Gly Ala Ala Thr Ser Thr Thr Val Pro
                3455                3460                3465

Thr Leu Thr His Ser Pro Gly Met Pro Glu Thr Thr Ala Leu Leu
                3470                3475                3480

Ser Thr His Pro Arg Thr Glu Thr Ser Lys Thr Phe Pro Ala Ser
                3485                3490                3495

Thr Val Phe Pro Gln Val Ser Glu Thr Thr Ala Ser Leu Thr Ile
                3500                3505                3510

Arg Pro Gly Ala Glu Thr Ser Thr Ala Leu Pro Thr Gln Thr Thr
                3515                3520                3525

Ser Ser Leu Phe Thr Leu Leu Val Thr Gly Thr Ser Arg Val Asp
                3530                3535                3540

Leu Ser Pro Thr Ala Ser Pro Gly Val Ser Ala Lys Thr Ala Pro
                3545                3550                3555

Leu Ser Thr His Pro Gly Thr Glu Thr Ser Thr Met Ile Pro Thr
                3560                3565                3570

Ser Thr Leu Ser Leu Gly Leu Leu Glu Thr Thr Gly Leu Leu Ala
                3575                3580                3585

Thr Ser Ser Ser Ala Glu Thr Ser Thr Ser Thr Leu Thr Leu Thr
                3590                3595                3600

Val Ser Pro Ala Val Ser Gly Leu Ser Ser Ala Ser Ile Thr Thr
                3605                3610                3615

Asp Lys Pro Gln Thr Val Thr Ser Trp Asn Thr Glu Thr Ser Pro
                3620                3625                3630

Ser Val Thr Ser Val Gly Pro Pro Glu Phe Ser Arg Thr Val Thr
                3635                3640                3645

Gly Thr Thr Met Thr Leu Ile Pro Ser Glu Met Pro Thr Pro Pro
                3650                3655                3660

Lys Thr Ser His Gly Glu Gly Val Ser Pro Thr Thr Ile Leu Arg
                3665                3670                3675

Thr Thr Met Val Glu Ala Thr Asn Leu Ala Thr Thr Gly Ser Ser
                3680                3685                3690

Pro Thr Val Ala Lys Thr Thr Thr Thr Phe Asn Thr Leu Ala Gly
                3695                3700                3705

Ser Leu Phe Thr Pro Leu Thr Thr Pro Gly Met Ser Thr Leu Ala
                3710                3715                3720

Ser Glu Ser Val Thr Ser Arg Thr Ser Tyr Asn His Arg Ser Trp
                3725                3730                3735

Ile Ser Thr Thr Ser Ser Tyr Asn Arg Arg Tyr Trp Thr Pro Ala
                3740                3745                3750

Thr Ser Thr Pro Val Thr Ser Thr Phe Ser Pro Gly Ile Ser Thr
                3755                3760                3765

Ser Ser Ile Pro Ser Ser Thr Ala Ala Thr Val Pro Phe Met Val
                3770                3775                3780

Pro Phe Thr Leu Asn Phe Thr Ile Thr Asn Leu Gln Tyr Glu Glu
                3785                3790                3795

Asp Met Arg His Pro Gly Ser Arg Lys Phe Asn Ala Thr Glu Arg
                3800                3805                3810

Glu Leu Gln Gly Leu Leu Lys Pro Leu Phe Arg Asn Ser Ser Leu
                3815                3820                3825

Glu Tyr Leu Tyr Ser Gly Cys Arg Leu Ala Ser Leu Arg Pro Glu
                3830                3835                3840
```

-continued

```
Lys Asp Ser Ser Ala Thr Ala Val Asp Ala Ile Cys Thr His Arg
                3845                3850                3855

Pro Asp Pro Glu Asp Leu Gly Leu Asp Arg Glu Arg Leu Tyr Trp
                3860                3865                3870

Glu Leu Ser Asn Leu Thr Asn Gly Ile Gln Glu Leu Gly Pro Tyr
                3875                3880                3885

Thr Leu Asp Arg Asn Ser Leu Tyr Val Asn Gly Phe Thr His Arg
                3890                3895                3900

Ser Ser Met Pro Thr Thr Ser Thr Pro Gly Thr Ser Thr Val Asp
                3905                3910                3915

Val Gly Thr Ser Gly Thr Pro Ser Ser Ser Pro Ser Pro Thr Thr
                3920                3925                3930

Ala Gly Pro Leu Leu Met Pro Phe Thr Leu Asn Phe Thr Ile Thr
                3935                3940                3945

Asn Leu Gln Tyr Glu Glu Asp Met Arg Arg Thr Gly Ser Arg Lys
                3950                3955                3960

Phe Asn Thr Met Glu Ser Val Leu Gln Gly Leu Leu Lys Pro Leu
                3965                3970                3975

Phe Lys Asn Thr Ser Val Gly Pro Leu Tyr Ser Gly Cys Arg Leu
                3980                3985                3990

Thr Leu Leu Arg Pro Glu Lys Asp Gly Ala Ala Thr Gly Val Asp
                3995                4000                4005

Ala Ile Cys Thr His Arg Leu Asp Pro Lys Ser Pro Gly Leu Asn
                4010                4015                4020

Arg Glu Gln Leu Tyr Trp Glu Leu Ser Lys Leu Thr Asn Asp Ile
                4025                4030                4035

Glu Glu Leu Gly Pro Tyr Thr Leu Asp Arg Asn Ser Leu Tyr Val
                4040                4045                4050

Asn Gly Phe Thr His Gln Ser Ser Val Ser Thr Thr Ser Thr Pro
                4055                4060                4065

Gly Thr Ser Thr Val Asp Leu Arg Thr Ser Gly Thr Pro Ser Ser
                4070                4075                4080

Leu Ser Ser Pro Thr Ile Met Ala Ala Gly Pro Leu Leu Val Pro
                4085                4090                4095

Phe Thr Leu Asn Phe Thr Ile Thr Asn Leu Gln Tyr Gly Glu Asp
                4100                4105                4110

Met Gly His Pro Gly Ser Arg Lys Phe Asn Thr Thr Glu Arg Val
                4115                4120                4125

Leu Gln Gly Leu Leu Gly Pro Ile Phe Lys Asn Thr Ser Val Gly
                4130                4135                4140

Pro Leu Tyr Ser Gly Cys Arg Leu Thr Ser Leu Arg Ser Glu Lys
                4145                4150                4155

Asp Gly Ala Ala Thr Gly Val Asp Ala Ile Cys Ile His His Leu
                4160                4165                4170

Asp Pro Lys Ser Pro Gly Leu Asn Arg Glu Arg Leu Tyr Trp Glu
                4175                4180                4185

Leu Ser Gln Leu Thr Asn Gly Ile Lys Glu Leu Gly Pro Tyr Thr
                4190                4195                4200

Leu Asp Arg Asn Ser Leu Tyr Val Asn Gly Phe Thr His Arg Thr
                4205                4210                4215

Ser Val Pro Thr Thr Ser Thr Pro Gly Thr Ser Thr Val Asp Leu
                4220                4225                4230

Gly Thr Ser Gly Thr Pro Phe Ser Leu Pro Ser Pro Ala Thr Ala
```

-continued

```
                4235                4240                4245

Gly Pro Leu Leu Val Leu Phe Thr Leu Asn Phe Thr Ile Thr Asn
                4250                4255                4260

Leu Lys Tyr Glu Glu Asp Met His Arg Pro Gly Ser Arg Lys Phe
                4265                4270                4275

Asn Thr Thr Glu Arg Val Leu Gln Thr Leu Val Gly Pro Met Phe
                4280                4285                4290

Lys Asn Thr Ser Val Gly Leu Leu Tyr Ser Gly Cys Arg Leu Thr
                4295                4300                4305

Leu Leu Arg Ser Glu Lys Asp Gly Ala Ala Thr Gly Val Asp Ala
                4310                4315                4320

Ile Cys Thr His Arg Leu Asp Pro Lys Ser Pro Gly Val Asp Arg
                4325                4330                4335

Glu Gln Leu Tyr Trp Glu Leu Ser Gln Leu Thr Asn Gly Ile Lys
                4340                4345                4350

Glu Leu Gly Pro Tyr Thr Leu Asp Arg Asn Ser Leu Tyr Val Asn
                4355                4360                4365

Gly Phe Thr His Trp Ile Pro Val Pro Thr Ser Ser Thr Pro Gly
                4370                4375                4380

Thr Ser Thr Val Asp Leu Gly Ser Gly Thr Pro Ser Ser Leu Pro
                4385                4390                4395

Ser Pro Thr Ser Ala Thr Ala Gly Pro Leu Leu Val Pro Phe Thr
                4400                4405                4410

Leu Asn Phe Thr Ile Thr Asn Leu Lys Tyr Glu Glu Asp Met His
                4415                4420                4425

Cys Pro Gly Ser Arg Lys Phe Asn Thr Thr Glu Arg Val Leu Gln
                4430                4435                4440

Ser Leu Leu Gly Pro Met Phe Lys Asn Thr Ser Val Gly Pro Leu
                4445                4450                4455

Tyr Ser Gly Cys Arg Leu Thr Leu Leu Arg Ser Glu Lys Asp Gly
                4460                4465                4470

Ala Ala Thr Gly Val Asp Ala Ile Cys Thr His Arg Leu Asp Pro
                4475                4480                4485

Lys Ser Pro Gly Val Asp Arg Glu Gln Leu Tyr Trp Glu Leu Ser
                4490                4495                4500

Gln Leu Thr Asn Gly Ile Lys Glu Leu Gly Pro Tyr Thr Leu Asp
                4505                4510                4515

Arg Asn Ser Leu Tyr Val Asn Gly Phe Thr His Gln Thr Ser Ala
                4520                4525                4530

Pro Asn Thr Ser Thr Pro Gly Thr Ser Thr Val Asp Leu Gly Thr
                4535                4540                4545

Ser Gly Thr Pro Ser Ser Leu Pro Ser Pro Thr Ser Ala Gly Pro
                4550                4555                4560

Leu Leu Val Pro Phe Thr Leu Asn Phe Thr Ile Thr Asn Leu Gln
                4565                4570                4575

Tyr Glu Glu Asp Met His His Pro Gly Ser Arg Lys Phe Asn Thr
                4580                4585                4590

Thr Glu Arg Val Leu Gln Gly Leu Leu Gly Pro Met Phe Lys Asn
                4595                4600                4605

Thr Ser Val Gly Leu Leu Tyr Ser Gly Cys Arg Leu Thr Leu Leu
                4610                4615                4620

Arg Pro Glu Lys Asn Gly Ala Ala Thr Gly Met Asp Ala Ile Cys
                4625                4630                4635
```

-continued

Ser His Arg Leu Asp Pro Lys Ser Pro Gly Leu Asn Arg Glu Gln
4640 4645 4650

Leu Tyr Trp Glu Leu Ser Gln Leu Thr His Gly Ile Lys Glu Leu
4655 4660 4665

Gly Pro Tyr Thr Leu Asp Arg Asn Ser Leu Tyr Val Asn Gly Phe
4670 4675 4680

Thr His Arg Ser Ser Val Ala Pro Thr Ser Thr Pro Gly Thr Ser
4685 4690 4695

Thr Val Asp Leu Gly Thr Ser Gly Thr Pro Ser Ser Leu Pro Ser
4700 4705 4710

Pro Thr Thr Ala Val Pro Leu Leu Val Pro Phe Thr Leu Asn Phe
4715 4720 4725

Thr Ile Thr Asn Leu Gln Tyr Gly Glu Asp Met Arg His Pro Gly
4730 4735 4740

Ser Arg Lys Phe Asn Thr Thr Glu Arg Val Leu Gln Gly Leu Leu
4745 4750 4755

Gly Pro Leu Phe Lys Asn Ser Ser Val Gly Pro Leu Tyr Ser Gly
4760 4765 4770

Cys Arg Leu Ile Ser Leu Arg Ser Glu Lys Asp Gly Ala Ala Thr
4775 4780 4785

Gly Val Asp Ala Ile Cys Thr His His Leu Asn Pro Gln Ser Pro
4790 4795 4800

Gly Leu Asp Arg Glu Gln Leu Tyr Trp Gln Leu Ser Gln Met Thr
4805 4810 4815

Asn Gly Ile Lys Glu Leu Gly Pro Tyr Thr Leu Asp Arg Asn Ser
4820 4825 4830

Leu Tyr Val Asn Gly Phe Thr His Arg Ser Ser Gly Leu Thr Thr
4835 4840 4845

Ser Thr Pro Trp Thr Ser Thr Val Asp Leu Gly Thr Ser Gly Thr
4850 4855 4860

Pro Ser Pro Val Pro Ser Pro Thr Thr Ala Gly Pro Leu Leu Val
4865 4870 4875

Pro Phe Thr Leu Asn Phe Thr Ile Thr Asn Leu Gln Tyr Glu Glu
4880 4885 4890

Asp Met His Arg Pro Gly Ser Arg Lys Phe Asn Ala Thr Glu Arg
4895 4900 4905

Val Leu Gln Gly Leu Leu Ser Pro Ile Phe Lys Asn Ser Ser Val
4910 4915 4920

Gly Pro Leu Tyr Ser Gly Cys Arg Leu Thr Ser Leu Arg Pro Glu
4925 4930 4935

Lys Asp Gly Ala Ala Thr Gly Met Asp Ala Val Cys Leu Tyr His
4940 4945 4950

Pro Asn Pro Lys Arg Pro Gly Leu Asp Arg Glu Gln Leu Tyr Trp
4955 4960 4965

Glu Leu Ser Gln Leu Thr His Asn Ile Thr Glu Leu Gly Pro Tyr
4970 4975 4980

Ser Leu Asp Arg Asp Ser Leu Tyr Val Asn Gly Phe Thr His Gln
4985 4990 4995

Asn Ser Val Pro Thr Thr Ser Thr Pro Gly Thr Ser Thr Val Tyr
5000 5005 5010

Trp Ala Thr Thr Gly Thr Pro Ser Ser Phe Pro Gly His Thr Glu
5015 5020 5025

Pro Gly Pro Leu Leu Ile Pro Phe Thr Phe Asn Phe Thr Ile Thr
5030 5035 5040

-continued

```
Asn Leu His Tyr Glu Glu Asn Met Gln His Pro Gly Ser Arg Lys
                5045                5050                5055

Phe Asn Thr Thr Glu Arg Val Leu Gln Gly Leu Leu Lys Pro Leu
                5060                5065                5070

Phe Lys Asn Thr Ser Val Gly Pro Leu Tyr Ser Gly Cys Arg Leu
                5075                5080                5085

Thr Leu Leu Arg Pro Glu Lys Gln Glu Ala Ala Thr Gly Val Asp
                5090                5095                5100

Thr Ile Cys Thr His Arg Val Asp Pro Ile Gly Pro Gly Leu Asp
                5105                5110                5115

Arg Glu Arg Leu Tyr Trp Glu Leu Ser Gln Leu Thr Asn Ser Ile
                5120                5125                5130

Thr Glu Leu Gly Pro Tyr Thr Leu Asp Arg Asp Ser Leu Tyr Val
                5135                5140                5145

Asn Gly Phe Asn Pro Trp Ser Ser Val Pro Thr Thr Ser Thr Pro
                5150                5155                5160

Gly Thr Ser Thr Val His Leu Ala Thr Ser Gly Thr Pro Ser Ser
                5165                5170                5175

Leu Pro Gly His Thr Ala Pro Val Pro Leu Leu Ile Pro Phe Thr
                5180                5185                5190

Leu Asn Phe Thr Ile Thr Asn Leu His Tyr Glu Glu Asn Met Gln
                5195                5200                5205

His Pro Gly Ser Arg Lys Phe Asn Thr Thr Glu Arg Val Leu Gln
                5210                5215                5220

Gly Leu Leu Lys Pro Leu Phe Lys Ser Thr Ser Val Gly Pro Leu
                5225                5230                5235

Tyr Ser Gly Cys Arg Leu Thr Leu Leu Arg Pro Glu Lys His Gly
                5240                5245                5250

Ala Ala Thr Gly Val Asp Ala Ile Cys Thr Leu Arg Leu Asp Pro
                5255                5260                5265

Thr Gly Pro Gly Leu Asp Arg Glu Arg Leu Tyr Trp Glu Leu Ser
                5270                5275                5280

Gln Leu Thr Asn Ser Val Thr Glu Leu Gly Pro Tyr Thr Leu Asp
                5285                5290                5295

Arg Asp Ser Leu Tyr Val Asn Gly Phe Thr His Arg Ser Ser Val
                5300                5305                5310

Pro Thr Thr Ser Ile Pro Gly Thr Ser Ala Val His Leu Glu Thr
                5315                5320                5325

Ser Gly Thr Pro Ala Ser Leu Pro Gly His Thr Ala Pro Gly Pro
                5330                5335                5340

Leu Leu Val Pro Phe Thr Leu Asn Phe Thr Ile Thr Asn Leu Gln
                5345                5350                5355

Tyr Glu Glu Asp Met Arg His Pro Gly Ser Arg Lys Phe Asn Thr
                5360                5365                5370

Thr Glu Arg Val Leu Gln Gly Leu Leu Lys Pro Leu Phe Lys Ser
                5375                5380                5385

Thr Ser Val Gly Pro Leu Tyr Ser Gly Cys Arg Leu Thr Leu Leu
                5390                5395                5400

Arg Pro Glu Lys Arg Gly Ala Ala Thr Gly Val Asp Thr Ile Cys
                5405                5410                5415

Thr His Arg Leu Asp Pro Leu Asn Pro Gly Leu Asp Arg Glu Gln
                5420                5425                5430

Leu Tyr Trp Glu Leu Ser Lys Leu Thr Arg Gly Ile Ile Glu Leu
```

-continued

```
                5435                5440                5445

Gly Pro Tyr Leu Leu Asp Arg Gly Ser Leu Tyr Val Asn Gly Phe
                5450                5455                5460

Thr His Arg Asn Phe Val Pro Ile Thr Ser Thr Pro Gly Thr Ser
                5465                5470                5475

Thr Val His Leu Gly Thr Ser Glu Thr Pro Ser Ser Leu Pro Arg
                5480                5485                5490

Pro Ile Val Pro Gly Pro Leu Leu Val Pro Phe Thr Leu Asn Phe
                5495                5500                5505

Thr Ile Thr Asn Leu Gln Tyr Glu Glu Ala Met Arg His Pro Gly
                5510                5515                5520

Ser Arg Lys Phe Asn Thr Thr Glu Arg Val Leu Gln Gly Leu Leu
                5525                5530                5535

Arg Pro Leu Phe Lys Asn Thr Ser Ile Gly Pro Leu Tyr Ser Ser
                5540                5545                5550

Cys Arg Leu Thr Leu Leu Arg Pro Glu Lys Asp Lys Ala Ala Thr
                5555                5560                5565

Arg Val Asp Ala Ile Cys Thr His His Pro Asp Pro Gln Ser Pro
                5570                5575                5580

Gly Leu Asn Arg Glu Gln Leu Tyr Trp Glu Leu Ser Gln Leu Thr
                5585                5590                5595

His Gly Ile Thr Glu Leu Gly Pro Tyr Thr Leu Asp Arg Asp Ser
                5600                5605                5610

Leu Tyr Val Asp Gly Phe Thr His Trp Ser Pro Ile Pro Thr Thr
                5615                5620                5625

Ser Thr Pro Gly Thr Ser Ile Val Asn Leu Gly Thr Ser Gly Ile
                5630                5635                5640

Pro Pro Ser Leu Pro Glu Thr Thr Ala Thr Gly Pro Leu Leu Val
                5645                5650                5655

Pro Phe Thr Leu Asn Phe Thr Ile Thr Asn Leu Gln Tyr Glu Glu
                5660                5665                5670

Asn Met Gly His Pro Gly Ser Arg Lys Phe Asn Ile Thr Glu Ser
                5675                5680                5685

Val Leu Gln Gly Leu Leu Lys Pro Leu Phe Lys Ser Thr Ser Val
                5690                5695                5700

Gly Pro Leu Tyr Ser Gly Cys Arg Leu Thr Leu Leu Arg Pro Glu
                5705                5710                5715

Lys Asp Gly Val Ala Thr Arg Val Asp Ala Ile Cys Thr His Arg
                5720                5725                5730

Pro Asp Pro Lys Ile Pro Gly Leu Asp Arg Gln Gln Leu Tyr Trp
                5735                5740                5745

Glu Leu Ser Gln Leu Thr His Ser Ile Thr Glu Leu Gly Pro Tyr
                5750                5755                5760

Thr Leu Asp Arg Asp Ser Leu Tyr Val Asn Gly Phe Thr Gln Arg
                5765                5770                5775

Ser Ser Val Pro Thr Thr Ser Thr Pro Gly Thr Phe Thr Val Gln
                5780                5785                5790

Pro Glu Thr Ser Glu Thr Pro Ser Ser Leu Pro Gly Pro Thr Ala
                5795                5800                5805

Thr Gly Pro Val Leu Leu Pro Phe Thr Leu Asn Phe Thr Ile Ile
                5810                5815                5820

Asn Leu Gln Tyr Glu Glu Asp Met His Arg Pro Gly Ser Arg Lys
                5825                5830                5835
```

```
Phe Asn Thr Thr Glu Arg Val Leu Gln Gly Leu Leu Met Pro Leu
                5840                5845                5850

Phe Lys Asn Thr Ser Val Ser Ser Leu Tyr Ser Gly Cys Arg Leu
                5855                5860                5865

Thr Leu Leu Arg Pro Glu Lys Asp Gly Ala Ala Thr Arg Val Asp
                5870                5875                5880

Ala Val Cys Thr His Arg Pro Asp Pro Lys Ser Pro Gly Leu Asp
                5885                5890                5895

Arg Glu Arg Leu Tyr Trp Lys Leu Ser Gln Leu Thr His Gly Ile
                5900                5905                5910

Thr Glu Leu Gly Pro Tyr Thr Leu Asp Arg His Ser Leu Tyr Val
                5915                5920                5925

Asn Gly Phe Thr His Gln Ser Ser Met Thr Thr Thr Arg Thr Pro
                5930                5935                5940

Asp Thr Ser Thr Met His Leu Ala Thr Ser Arg Thr Pro Ala Ser
                5945                5950                5955

Leu Ser Gly Pro Thr Thr Ala Ser Pro Leu Leu Val Leu Phe Thr
                5960                5965                5970

Ile Asn Phe Thr Ile Thr Asn Leu Arg Tyr Glu Glu Asn Met His
                5975                5980                5985

His Pro Gly Ser Arg Lys Phe Asn Thr Thr Glu Arg Val Leu Gln
                5990                5995                6000

Gly Leu Leu Arg Pro Val Phe Lys Asn Thr Ser Val Gly Pro Leu
                6005                6010                6015

Tyr Ser Gly Cys Arg Leu Thr Leu Leu Arg Pro Lys Lys Asp Gly
                6020                6025                6030

Ala Ala Thr Lys Val Asp Ala Ile Cys Thr Tyr Arg Pro Asp Pro
                6035                6040                6045

Lys Ser Pro Gly Leu Asp Arg Glu Gln Leu Tyr Trp Glu Leu Ser
                6050                6055                6060

Gln Leu Thr His Ser Ile Thr Glu Leu Gly Pro Tyr Thr Leu Asp
                6065                6070                6075

Arg Asp Ser Leu Tyr Val Asn Gly Phe Thr Gln Arg Ser Ser Val
                6080                6085                6090

Pro Thr Thr Ser Ile Pro Gly Thr Pro Thr Val Asp Leu Gly Thr
                6095                6100                6105

Ser Gly Thr Pro Val Ser Lys Pro Gly Pro Ser Ala Ala Ser Pro
                6110                6115                6120

Leu Leu Val Leu Phe Thr Leu Asn Phe Thr Ile Thr Asn Leu Arg
                6125                6130                6135

Tyr Glu Glu Asn Met Gln His Pro Gly Ser Arg Lys Phe Asn Thr
                6140                6145                6150

Thr Glu Arg Val Leu Gln Gly Leu Leu Arg Ser Leu Phe Lys Ser
                6155                6160                6165

Thr Ser Val Gly Pro Leu Tyr Ser Gly Cys Arg Leu Thr Leu Leu
                6170                6175                6180

Arg Pro Glu Lys Asp Gly Thr Ala Thr Gly Val Asp Ala Ile Cys
                6185                6190                6195

Thr His His Pro Asp Pro Lys Ser Pro Arg Leu Asp Arg Glu Gln
                6200                6205                6210

Leu Tyr Trp Glu Leu Ser Gln Leu Thr His Asn Ile Thr Glu Leu
                6215                6220                6225

Gly Pro Tyr Ala Leu Asp Asn Asp Ser Leu Phe Val Asn Gly Phe
                6230                6235                6240
```

-continued

```
Thr His Arg Ser Ser Val Ser Thr Thr Ser Thr Pro Gly Thr Pro
                6245                6250                6255

Thr Val Tyr Leu Gly Ala Ser Lys Thr Pro Ala Ser Ile Phe Gly
                6260                6265                6270

Pro Ser Ala Ala Ser His Leu Leu Ile Leu Phe Thr Leu Asn Phe
                6275                6280                6285

Thr Ile Thr Asn Leu Arg Tyr Glu Glu Asn Met Trp Pro Gly Ser
                6290                6295                6300

Arg Lys Phe Asn Thr Thr Glu Arg Val Leu Gln Gly Leu Leu Arg
                6305                6310                6315

Pro Leu Phe Lys Asn Thr Ser Val Gly Pro Leu Tyr Ser Gly Cys
                6320                6325                6330

Arg Leu Thr Leu Leu Arg Pro Glu Lys Asp Gly Glu Ala Thr Gly
                6335                6340                6345

Val Asp Ala Ile Cys Thr His Arg Pro Asp Pro Thr Gly Pro Gly
                6350                6355                6360

Leu Asp Arg Glu Gln Leu Tyr Leu Glu Leu Ser Gln Leu Thr His
                6365                6370                6375

Ser Ile Thr Glu Leu Gly Pro Tyr Thr Leu Asp Arg Asp Ser Leu
                6380                6385                6390

Tyr Val Asn Gly Phe Thr His Arg Ser Ser Val Pro Thr Thr Ser
                6395                6400                6405

Thr Gly Val Val Ser Glu Glu Pro Phe Thr Leu Asn Phe Thr Ile
                6410                6415                6420

Asn Asn Leu Arg Tyr Met Ala Asp Met Gly Gln Pro Gly Ser Leu
                6425                6430                6435

Lys Phe Asn Ile Thr Asp Asn Val Met Gln His Leu Leu Ser Pro
                6440                6445                6450

Leu Phe Gln Arg Ser Ser Leu Gly Ala Arg Tyr Thr Gly Cys Arg
                6455                6460                6465

Val Ile Ala Leu Arg Ser Val Lys Asn Gly Ala Glu Thr Arg Val
                6470                6475                6480

Asp Leu Leu Cys Thr Tyr Leu Gln Pro Leu Ser Gly Pro Gly Leu
                6485                6490                6495

Pro Ile Lys Gln Val Phe His Glu Leu Ser Gln Gln Thr His Gly
                6500                6505                6510

Ile Thr Arg Leu Gly Pro Tyr Ser Leu Asp Lys Asp Ser Leu Tyr
                6515                6520                6525

Leu Asn Gly Tyr Asn Glu Pro Gly Pro Asp Glu Pro Pro Thr Thr
                6530                6535                6540

Pro Lys Pro Ala Thr Thr Phe Leu Pro Pro Leu Ser Glu Ala Thr
                6545                6550                6555

Thr Ala Met Gly Tyr His Leu Lys Thr Leu Thr Leu Asn Phe Thr
                6560                6565                6570

Ile Ser Asn Leu Gln Tyr Ser Pro Asp Met Gly Lys Gly Ser Ala
                6575                6580                6585

Thr Phe Asn Ser Thr Glu Gly Val Leu Gln His Leu Leu Arg Pro
                6590                6595                6600

Leu Phe Gln Lys Ser Ser Met Gly Pro Phe Tyr Leu Gly Cys Gln
                6605                6610                6615

Leu Ile Ser Leu Arg Pro Glu Lys Asp Gly Ala Ala Thr Gly Val
                6620                6625                6630

Asp Thr Thr Cys Thr Tyr His Pro Asp Pro Val Gly Pro Gly Leu
```

-continued

```
                6635                6640                6645

Asp Ile Gln Gln Leu Tyr Trp Glu Leu Ser Gln Leu Thr His Gly
                6650                6655                6660

Val Thr Gln Leu Gly Phe Tyr Val Leu Asp Arg Asp Ser Leu Phe
                6665                6670                6675

Ile Asn Gly Tyr Ala Pro Gln Asn Leu Ser Ile Arg Gly Glu Tyr
                6680                6685                6690

Gln Ile Asn Phe His Ile Val Asn Trp Asn Leu Ser Asn Pro Asp
                6695                6700                6705

Pro Thr Ser Ser Glu Tyr Ile Thr Leu Leu Arg Asp Ile Gln Asp
                6710                6715                6720

Lys Val Thr Thr Leu Tyr Lys Gly Ser Gln Leu His Asp Thr Phe
                6725                6730                6735

Arg Phe Cys Leu Val Thr Asn Leu Thr Met Asp Ser Val Leu Val
                6740                6745                6750

Thr Val Lys Ala Leu Phe Ser Ser Asn Leu Asp Pro Ser Leu Val
                6755                6760                6765

Glu Gln Val Phe Leu Asp Lys Thr Leu Asn Ala Ser Phe His Trp
                6770                6775                6780

Leu Gly Ser Thr Tyr Gln Leu Val Asp Ile His Val Thr Glu Met
                6785                6790                6795

Glu Ser Ser Val Tyr Gln Pro Thr Ser Ser Ser Ser Thr Gln His
                6800                6805                6810

Phe Tyr Leu Asn Phe Thr Ile Thr Asn Leu Pro Tyr Ser Gln Asp
                6815                6820                6825

Lys Ala Gln Pro Gly Thr Thr Asn Tyr Gln Arg Asn Lys Arg Asn
                6830                6835                6840

Ile Glu Asp Ala Leu Asn Gln Leu Phe Arg Asn Ser Ser Ile Lys
                6845                6850                6855

Ser Tyr Phe Ser Asp Cys Gln Val Ser Thr Phe Arg Ser Val Pro
                6860                6865                6870

Asn Arg His His Thr Gly Val Asp Ser Leu Cys Asn Phe Ser Pro
                6875                6880                6885

Leu Ala Arg Arg Val Asp Arg Val Ala Ile Tyr Glu Glu Phe Leu
                6890                6895                6900

Arg Met Thr Arg Asn Gly Thr Gln Leu Gln Asn Phe Thr Leu Asp
                6905                6910                6915

Arg Ser Ser Val Leu Val Asp Gly Tyr Ser Pro Asn Arg Asn Glu
                6920                6925                6930

Pro Leu Thr Gly Asn Ser Asp Leu Pro Phe Trp Ala Val Ile Leu
                6935                6940                6945

Ile Gly Leu Ala Gly Leu Leu Gly Leu Ile Thr Cys Leu Ile Cys
                6950                6955                6960

Gly Val Leu Val Thr Thr Arg Arg Arg Lys Lys Glu Gly Glu Tyr
                6965                6970                6975

Asn Val Gln Gln Gln Cys Pro Gly Tyr Tyr Gln Ser His Leu Asp
                6980                6985                6990

Leu Glu Asp Leu Gln
                6995
```

<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val
1 5 10 15

Gly Asp Arg Val Thr Ile Thr Cys Arg Ala Ser Gln Ser Ile Ser
20 25 30

Asn Tyr Leu Ala Trp Tyr Gln Gln Lys Pro Gly Lys Ala Pro Lys
35 40 45

Leu Leu Ile Tyr Ala Ala Ser Ser Leu Glu Ser Gly Val Pro Ser
50 55 60

Arg Phe Ser Gly Ser Gly Ser Gly Thr Asp Phe Thr Leu Thr Ile
65 70 75

Ser Ser Leu Gln Pro Glu Asp Phe Ala Thr Tyr Tyr Cys Gln Gln
80 85 90

Tyr Asn Ser Leu Pro Trp Thr Phe Gly Gln Gly Thr Lys Val Glu
95 100 105

Ile Lys Arg

<210> SEQ ID NO 4
<211> LENGTH: 109
<212> TYPE: PRT
<213> ORGANISM: Homo sapiens

<400> SEQUENCE: 4

Asp Ile Val Leu Thr Gln Ser Pro Ala Ile Met Ser Ala Ser Leu
1 5 10 15

Gly Glu Arg Val Thr Met Thr Cys Thr Ala Ser Ser Ser Val Ser
20 25 30

Ser Ser Tyr Leu His Trp Tyr Gln Gln Lys Pro Gly Ser Ser Pro
35 40 45

Lys Leu Trp Ile Tyr Ser Thr Ser Asn Leu Ala Ser Gly Val Pro
50 55 60

Gly Arg Phe Ser Gly Ser Gly Ser Gly Thr Ser Tyr Ser Leu Thr
65 70 75

Ile Ser Ser Met Glu Ala Glu Asp Ala Ala Thr Tyr Tyr Cys His
80 85 90

Gln Tyr His Arg Ser Pro Tyr Thr Phe Gly Gly Gly Thr Lys Val
95 100 105

Glu Ile Lys Arg

<210> SEQ ID NO 5
<211> LENGTH: 109
<212> TYPE: PRT
<213> ORGANISM: Homo sapiens

<400> SEQUENCE: 5

Asp Ile Gln Met Thr Gln Ser Pro Ser Ser Leu Ser Ala Ser Val
1 5 10 15

Gly Asp Arg Val Thr Ile Thr Cys Thr Ala Ser Ser Ser Val Ser
20 25 30

Ser Ser Tyr Leu His Trp Tyr Gln Gln Lys Pro Gly Lys Ala Pro
35 40 45

Lys Leu Leu Ile Tyr Ser Thr Ser Asn Leu Ala Ser Gly Val Pro
50 55 60

Ser Arg Phe Ser Gly Ser Gly Ser Gly Thr Asp Phe Thr Leu Thr
65 70 75

Ile Ser Ser Leu Gln Pro Glu Asp Phe Ala Thr Tyr Tyr Cys His 80 85 90

Gln Tyr His Arg Ser Pro Tyr Thr Phe Gly Gln Gly Thr Lys Val
95 100 105

Glu Ile Lys Arg

<210> SEQ ID NO 6
<211> LENGTH: 113
<212> TYPE: PRT
<213> ORGANISM: Homo sapiens

<400> SEQUENCE: 6

Glu Val Gln Leu Val Glu Ser Gly Gly Gly Leu Val Gln Pro Gly
1 5 10 15

Gly Ser Leu Arg Leu Ser Cys Ala Ala Ser Gly Phe Thr Phe Ser
20 25 30

Ser Tyr Ala Met Ser Trp Val Arg Gln Ala Pro Gly Lys Gly Leu
35 40 45

Glu Trp Val Ser Val Ile Ser Gly Asp Gly Gly Ser Thr Tyr Tyr
50 55 60

Ala Asp Ser Val Lys Gly Arg Phe Thr Ile Ser Arg Asp Asn Ser
65 70 75

Lys Asn Thr Leu Tyr Leu Gln Met Asn Ser Leu Arg Ala Glu Asp
80 85 90

Thr Ala Val Tyr Tyr Cys Ala Arg Gly Phe Asp Tyr Trp Gly Gln
95 100 105

Gly Thr Leu Val Thr Val Ser Ser
110

<210> SEQ ID NO 7
<211> LENGTH: 120
<212> TYPE: PRT
<213> ORGANISM: Homo sapiens

<400> SEQUENCE: 7

Glu Val Gln Leu Gln Gln Ser Gly Ala Glu Leu Val Lys Pro Gly
1 5 10 15

Ala Ser Val Lys Leu Ser Cys Thr Ala Ser Gly Phe Asn Ile Lys
20 25 30

Asp Thr Tyr Met His Trp Val Lys Gln Arg Pro Glu Gln Gly Leu
35 40 45

Glu Trp Ile Gly Arg Val Asp Pro Ala Asn Gly Asn Thr Lys Tyr
50 55 60

Asp Pro Lys Phe Gln Gly Lys Ala Thr Leu Thr Ala Asp Thr Ser
65 70 75

Ser Asn Thr Ala Tyr Leu Gln Leu Ser Ser Leu Thr Ser Glu Asp
80 85 90

Thr Ala Val Tyr Phe Cys Val Arg Asp Tyr Tyr Gly His Thr Tyr
95 100 105

Gly Phe Ala Phe Cys Asp Gln Gly Thr Thr Leu Thr Val Ser Ala
110 115 120

<210> SEQ ID NO 8
<211> LENGTH: 120
<212> TYPE: PRT
<213> ORGANISM: Homo sapiens

<400> SEQUENCE: 8

Glu Val Gln Leu Val Glu Ser Gly Gly Gly Leu Val Gln Pro Gly

```
1               5                   10                  15

Gly Ser Leu Arg Leu Ser Cys Ala Ala Ser Gly Phe Asn Ile Lys
                20                  25                  30

Asp Thr Tyr Met His Trp Val Arg Gln Ala Pro Gly Lys Gly Leu
                35                  40                  45

Glu Trp Val Gly Arg Val Asp Pro Ala Asn Gly Asn Thr Lys Tyr
                50                  55                  60

Asp Pro Lys Phe Gln Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Val Arg Asp Tyr Tyr Gly His Thr Tyr
                95                  100                 105

Gly Phe Ala Phe Trp Gly Gln Gly Thr Leu Val Thr Val Ser Ser
                110                 115                 120


<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Ser Ser Phe Leu Ser Val Ser Leu
  1             5                   10                  15

Gly Gly Arg Val Thr Ile Thr Cys Lys Ala Ser Asp Leu Ile His
                20                  25                  30

Asn Trp Leu Ala Trp Tyr Gln Gln Lys Pro Gly Asn Ala Pro Arg
                35                  40                  45

Leu Leu Ile Ser Gly Ala Thr Ser Leu Glu Thr Gly Val Pro Ser
                50                  55                  60

Arg Phe Ser Gly Ser Gly Ser Gly Asn Asp Tyr Thr Leu Ser Ile
                65                  70                  75

Ala Ser Leu Gln Thr Glu Asp Ala Ala Thr Tyr Tyr Cys Gln Gln
                80                  85                  90

Tyr Trp Thr Thr Pro Phe Thr Phe Gly Ser Gly Thr Lys Leu Glu
                95                  100                 105

Ile Lys


<210> SEQ ID NO 10
<211> LENGTH: 108
<212> TYPE: PRT
<213> ORGANISM: Homo sapiens

<400> SEQUENCE: 10

Asp Ile Gln Met Thr Gln Ser Pro Ser Ser Leu Ser Ala Ser Val
  1             5                   10                  15

Gly Asp Arg Val Thr Ile Thr Cys Lys Ala Ser Asp Leu Ile His
                20                  25                  30

Asn Trp Leu Ala Trp Tyr Gln Gln Lys Pro Gly Lys Ala Pro Lys
                35                  40                  45

Leu Leu Ile Ser Gly Ala Thr Ser Leu Glu Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90
```

Tyr Trp Thr Thr Pro Phe Thr Phe Gly Gln Gly Thr Lys Val Glu
95 100 105

Ile Lys Arg

<210> SEQ ID NO 11
<211> LENGTH: 116
<212> TYPE: PRT
<213> ORGANISM: Homo sapiens

<400> SEQUENCE: 11

Asp Val Gln Leu Gln Glu Ser Gly Pro Gly Leu Val Asn Pro Ser
1 5 10 15

Gln Ser Leu Ser Leu Thr Cys Thr Val Thr Gly Tyr Ser Ile Thr
20 25 30

Asn Asp Tyr Ala Trp Asn Trp Ile Arg Gln Phe Pro Gly Asn Lys
35 40 45

Leu Glu Trp Met Gly Tyr Ile Asn Tyr Ser Gly Tyr Thr Thr Tyr
50 55 60

Asn Pro Ser Leu Lys Ser Arg Ile Ser Ile Thr Arg Asp Thr Ser
65 70 75

Lys Asn Gln Phe Phe Leu His Leu Asn Ser Val Thr Thr Glu Asp
80 85 90

Thr Ala Thr Tyr Tyr Cys Ala Arg Trp Asp Gly Gly Leu Thr Tyr
95 100 105

Trp Gly Gln Gly Thr Leu Val Thr Val Ser Ala
110 115

<210> SEQ ID NO 12
<211> LENGTH: 116
<212> TYPE: PRT
<213> ORGANISM: Homo sapiens

<400> SEQUENCE: 12

Glu Val Gln Leu Val Glu Ser Gly Gly Gly Leu Val Gln Pro Gly
1 5 10 15

Gly Ser Leu Arg Leu Ser Cys Ala Ala Ser Gly Tyr Ser Ile Thr
20 25 30

Asn Asp Tyr Ala Trp Asn Trp Val Arg Gln Ala Pro Gly Lys Gly
35 40 45

Leu Glu Trp Val Gly Tyr Ile Asn Tyr Ser Gly Tyr Thr Thr Tyr
50 55 60

Asn Pro Ser Leu Lys Ser Arg Phe Thr Ile Ser Arg Asp Asn Ser
65 70 75

Lys Asn Thr Leu Tyr Leu Gln Met Asn Ser Leu Arg Ala Glu Asp
80 85 90

Thr Ala Val Tyr Tyr Cys Ala Arg Trp Asp Gly Gly Leu Thr Tyr
95 100 105

Trp Gly Gln Gly Thr Leu Val Thr Val Ser Ser
110 115

<210> SEQ ID NO 13
<211> LENGTH: 116
<212> TYPE: PRT
<213> ORGANISM: Homo sapiens

<400> SEQUENCE: 13

Glu Val Gln Leu Val Glu Ser Gly Gly Gly Leu Val Gln Pro Gly
1 5 10 15

-continued

```
Gly Ser Leu Arg Leu Ser Cys Ala Ala Ser Gly Tyr Ser Ile Thr
                20                  25                  30

Asn Asp Tyr Ala Trp Asn Trp Val Arg Gln Ala Pro Gly Lys Gly
                35                  40                  45

Leu Glu Trp Val Gly Tyr Ile Asn Tyr Ser Gly Tyr Thr Thr Tyr
                50                  55                  60

Asn Pro Ser Leu Lys Ser Arg Phe Thr Ile Ser Arg Asp Asn Ser
                65                  70                  75

Lys Asn Thr Phe Tyr Leu Gln Met Asn Ser Leu Arg Ala Glu Asp
                80                  85                  90

Thr Ala Val Tyr Tyr Cys Ala Arg Trp Asp Gly Gly Leu Thr Tyr
                95                  100                 105

Trp Gly Gln Gly Thr Leu Val Thr Val Ser Ser
                110                 115


<210> SEQ ID NO 14
<211> LENGTH: 12
<212> TYPE: PRT
<213> ORGANISM: Homo sapiens

<400> SEQUENCE: 14

Thr Ala Ser Ser Ser Val Ser Ser Ser Tyr Leu His
  1               5                  10


<210> SEQ ID NO 15
<211> LENGTH: 12
<212> TYPE: PRT
<213> ORGANISM: Homo sapiens

<400> SEQUENCE: 15

Thr Gln Arg Thr Ser Val Lys Arg Ser Tyr Ile Ser
  1               5                  10


<210> SEQ ID NO 16
<211> LENGTH: 12
<212> TYPE: PRT
<213> ORGANISM: Homo sapiens

<400> SEQUENCE: 16

Thr Pro Arg Gly Arg Val Arg Ser Ser Tyr Leu Ser
  1               5                  10


<210> SEQ ID NO 17
<211> LENGTH: 12
<212> TYPE: PRT
<213> ORGANISM: Homo sapiens
<220> FEATURE:
<221> NAME/KEY: Unsure
<222> LOCATION: 4
<223> OTHER INFORMATION: Unknown amino acid

<400> SEQUENCE: 17

Pro Glu Cys Xaa Ser Leu Gly Thr Ile Tyr Leu His
  1               5                  10


<210> SEQ ID NO 18
<211> LENGTH: 12
<212> TYPE: PRT
<213> ORGANISM: Homo sapiens

<400> SEQUENCE: 18

Ser Ala Ser Ser Ser Val Asn Ser Thr Tyr Leu His
  1               5                  10
```

<210> SEQ ID NO 19
<211> LENGTH: 12
<212> TYPE: PRT
<213> ORGANISM: Homo sapiens

<400> SEQUENCE: 19

```
Thr Ala Ser Thr Ala Val Gly Ser Ser Tyr Leu His
  1               5                   10
```

<210> SEQ ID NO 20
<211> LENGTH: 11
<212> TYPE: PRT
<213> ORGANISM: Homo sapiens

<400> SEQUENCE: 20

```
Asn Ser Arg Ser Val Ser Thr Arg Tyr Leu His
  1               5                   10
```

<210> SEQ ID NO 21
<211> LENGTH: 12
<212> TYPE: PRT
<213> ORGANISM: Homo sapiens

<400> SEQUENCE: 21

```
Asn Thr Thr Arg Ser Val Ser Thr Gly Tyr Leu His
  1               5                   10
```

<210> SEQ ID NO 22
<211> LENGTH: 12
<212> TYPE: PRT
<213> ORGANISM: Homo sapiens

<400> SEQUENCE: 22

```
Thr Ala Ser Ser Arg Val Thr Ser Thr Tyr Leu His
  1               5                   10
```

<210> SEQ ID NO 23
<211> LENGTH: 12
<212> TYPE: PRT
<213> ORGANISM: Homo sapiens

<400> SEQUENCE: 23

```
Asn Thr Pro Thr Gly Val Asn Pro Val Tyr Leu His
  1               5                   10
```

<210> SEQ ID NO 24
<211> LENGTH: 12
<212> TYPE: PRT
<213> ORGANISM: Homo sapiens

<400> SEQUENCE: 24

```
Ala Ala Ser Ser Asp Val Ile Gly Ser Tyr Val His
  1               5                   10
```

<210> SEQ ID NO 25
<211> LENGTH: 12
<212> TYPE: PRT
<213> ORGANISM: Homo sapiens

<400> SEQUENCE: 25

```
Gly Leu Ser Thr Ser Val Asn Ser Ser Tyr Met His
  1               5                   10
```

<210> SEQ ID NO 26
<211> LENGTH: 12

<212> TYPE: PRT
<213> ORGANISM: Homo sapiens
<220> FEATURE:
<221> NAME/KEY: Unsure
<222> LOCATION: 10
<223> OTHER INFORMATION: Unknown amino acid

<400> SEQUENCE: 26

Asn Ala Lys Ser Gly Val Arg Ser Ser Xaa Val His
1 5 10

<210> SEQ ID NO 27
<211> LENGTH: 12
<212> TYPE: PRT
<213> ORGANISM: Homo sapiens

<400> SEQUENCE: 27

Asn Ser Asn Gly Ser Val Ser Ser Lys Tyr Ile His
1 5 10

<210> SEQ ID NO 28
<211> LENGTH: 12
<212> TYPE: PRT
<213> ORGANISM: Homo sapiens

<400> SEQUENCE: 28

Thr Pro Ser Arg Ile Val Ser Gly Ser Tyr Leu Ser
1 5 10

<210> SEQ ID NO 29
<211> LENGTH: 12
<212> TYPE: PRT
<213> ORGANISM: Homo sapiens

<400> SEQUENCE: 29

Asn Pro Ser Arg Arg Val Thr Gly His Tyr Val Ser
1 5 10

<210> SEQ ID NO 30
<211> LENGTH: 12
<212> TYPE: PRT
<213> ORGANISM: Homo sapiens

<400> SEQUENCE: 30

Thr Ser Ser Ser Ala Val Ser Gly Ser Tyr Val Ser
1 5 10

<210> SEQ ID NO 31
<211> LENGTH: 12
<212> TYPE: PRT
<213> ORGANISM: Homo sapiens

<400> SEQUENCE: 31

Thr Ser Thr Thr Ile Val Arg Gly Arg Tyr Val Ser
1 5 10

<210> SEQ ID NO 32
<211> LENGTH: 12
<212> TYPE: PRT
<213> ORGANISM: Homo sapiens

<400> SEQUENCE: 32

Thr Ala Ser Ser Thr Leu Ser Ser Asn Tyr Leu Thr
1 5 10

<210> SEQ ID NO 33

<211> LENGTH: 12
<212> TYPE: PRT
<213> ORGANISM: Homo sapiens

<400> SEQUENCE: 33

Thr Pro Thr Gly Ser Ile Ser Arg Arg Tyr Leu Ser
1 5 10

<210> SEQ ID NO 34
<211> LENGTH: 12
<212> TYPE: PRT
<213> ORGANISM: Homo sapiens

<400> SEQUENCE: 34

Thr Ala Gly Ser Lys Ala Asn Ser Ser Tyr Ile His
1 5 10

<210> SEQ ID NO 35
<211> LENGTH: 8
<212> TYPE: PRT
<213> ORGANISM: Homo sapiens

<400> SEQUENCE: 35

Tyr Ser Thr Ser Asn Leu Ala Ser
1 5

<210> SEQ ID NO 36
<211> LENGTH: 8
<212> TYPE: PRT
<213> ORGANISM: Homo sapiens

<400> SEQUENCE: 36

Tyr Ser Thr Ser His Phe Ala Ser
1 5

<210> SEQ ID NO 37
<211> LENGTH: 8
<212> TYPE: PRT
<213> ORGANISM: Homo sapiens

<400> SEQUENCE: 37

Tyr Ser Ala Ser Asn Val Pro Ser
1 5

<210> SEQ ID NO 38
<211> LENGTH: 8
<212> TYPE: PRT
<213> ORGANISM: Homo sapiens

<400> SEQUENCE: 38

Tyr Ser Thr Ile Asn Leu Ala Thr
1 5

<210> SEQ ID NO 39
<211> LENGTH: 8
<212> TYPE: PRT
<213> ORGANISM: Homo sapiens

<400> SEQUENCE: 39

Tyr Ser Thr Ser Lys Val Ala Asn
1 5

<210> SEQ ID NO 40
<211> LENGTH: 8
<212> TYPE: PRT
<213> ORGANISM: Homo sapiens

<400> SEQUENCE: 40

Tyr Ser Thr Thr Asn Leu Ala Ser
1 5

<210> SEQ ID NO 41
<211> LENGTH: 8
<212> TYPE: PRT
<213> ORGANISM: Homo sapiens

<400> SEQUENCE: 41

Tyr Ser Thr Asn His Leu Ala Ser
1 5

<210> SEQ ID NO 42
<211> LENGTH: 8
<212> TYPE: PRT
<213> ORGANISM: Homo sapiens

<400> SEQUENCE: 42

Tyr Ser Thr Asn Asn Leu Ala Ser
1 5

<210> SEQ ID NO 43
<211> LENGTH: 8
<212> TYPE: PRT
<213> ORGANISM: Homo sapiens

<400> SEQUENCE: 43

Tyr Ser Thr Ile His Pro Ala Ser
1 5

<210> SEQ ID NO 44
<211> LENGTH: 8
<212> TYPE: PRT
<213> ORGANISM: Homo sapiens

<400> SEQUENCE: 44

Tyr Ser Thr Ser His Leu Ser Tyr
1 5

<210> SEQ ID NO 45
<211> LENGTH: 8
<212> TYPE: PRT
<213> ORGANISM: Homo sapiens

<400> SEQUENCE: 45

Tyr Ser Thr Arg Thr Met Ala Ser
1 5

<210> SEQ ID NO 46
<211> LENGTH: 8
<212> TYPE: PRT
<213> ORGANISM: Homo sapiens
<220> FEATURE:
<221> NAME/KEY: Unsure
<222> LOCATION: 5
<223> OTHER INFORMATION: Unknown amino acid

<400> SEQUENCE: 46

Tyr Ser Thr Ser Xaa Leu Phe Ser
1 5

<210> SEQ ID NO 47
<211> LENGTH: 8
<212> TYPE: PRT

<213> ORGANISM: Homo sapiens

<400> SEQUENCE: 47

Tyr Asn Thr Ser Asn Arg Ala Ser
1 5

<210> SEQ ID NO 48
<211> LENGTH: 8
<212> TYPE: PRT
<213> ORGANISM: Rana catesbeiana

<400> SEQUENCE: 48

Tyr Gly Thr Ser His Leu Ala Ser
1 5

<210> SEQ ID NO 49
<211> LENGTH: 8
<212> TYPE: PRT
<213> ORGANISM: Homo sapiens

<400> SEQUENCE: 49

Tyr Gly Thr Gly Ser Pro Ala Ser
1 5

<210> SEQ ID NO 50
<211> LENGTH: 8
<212> TYPE: PRT
<213> ORGANISM: Homo sapiens

<400> SEQUENCE: 50

Tyr Ser Thr Asn Lys Leu Ala Arg
1 5

<210> SEQ ID NO 51
<211> LENGTH: 8
<212> TYPE: PRT
<213> ORGANISM: Homo sapiens

<400> SEQUENCE: 51

Tyr Ser Thr Ser Gln Leu Gly Arg
1 5

<210> SEQ ID NO 52
<211> LENGTH: 8
<212> TYPE: PRT
<213> ORGANISM: Homo sapiens

<400> SEQUENCE: 52

Tyr Ser Thr Ser Asn Val Pro Gln
1 5

<210> SEQ ID NO 53
<211> LENGTH: 8
<212> TYPE: PRT
<213> ORGANISM: Homo sapiens

<400> SEQUENCE: 53

Tyr Gly Thr Tyr Asn Leu Pro Ile
1 5

<210> SEQ ID NO 54
<211> LENGTH: 8
<212> TYPE: PRT
<213> ORGANISM: Homo sapiens

<400> SEQUENCE: 54

Tyr Gly Ser Asn Asn Arg Ala Tyr
  1               5

<210> SEQ ID NO 55
<211> LENGTH: 8
<212> TYPE: PRT
<213> ORGANISM: Homo sapiens
<220> FEATURE:
<221> NAME/KEY: Unsure
<222> LOCATION: 7
<223> OTHER INFORMATION: Unknown amino acid

<400> SEQUENCE: 55

Tyr Ser Ser Ser Asn Thr Xaa Ser
  1               5

<210> SEQ ID NO 56
<211> LENGTH: 8
<212> TYPE: PRT
<213> ORGANISM: Homo sapiens

<400> SEQUENCE: 56

Tyr Ser Ala Asn Lys Leu Ala Ser
  1               5

<210> SEQ ID NO 57
<211> LENGTH: 8
<212> TYPE: PRT
<213> ORGANISM: Homo sapiens

<400> SEQUENCE: 57

Tyr Ser Ala Thr Arg Arg Ala Ser
  1               5

<210> SEQ ID NO 58
<211> LENGTH: 8
<212> TYPE: PRT
<213> ORGANISM: Homo sapiens

<400> SEQUENCE: 58

Tyr Ser Ala Ser Asn Arg Ala Arg
  1               5

<210> SEQ ID NO 59
<211> LENGTH: 9
<212> TYPE: PRT
<213> ORGANISM: Homo sapiens

<400> SEQUENCE: 59

His Gln Tyr His Arg Ser Pro Tyr Thr
  1               5

<210> SEQ ID NO 60
<211> LENGTH: 9
<212> TYPE: PRT
<213> ORGANISM: Homo sapiens

<400> SEQUENCE: 60

His Gln Tyr His Arg Ser Pro Tyr Lys
  1               5

<210> SEQ ID NO 61
<211> LENGTH: 9
<212> TYPE: PRT
<213> ORGANISM: Homo sapiens

<400> SEQUENCE: 61

His Gln Tyr His Arg Thr Pro Tyr Lys
1 5

<210> SEQ ID NO 62
<211> LENGTH: 9
<212> TYPE: PRT
<213> ORGANISM: Homo sapiens

<400> SEQUENCE: 62

His Gln Tyr His Arg Ser Pro Tyr Gly
1 5

<210> SEQ ID NO 63
<211> LENGTH: 9
<212> TYPE: PRT
<213> ORGANISM: Homo sapiens

<400> SEQUENCE: 63

His Gln Tyr His Arg Ser Pro Tyr Asn
1 5

<210> SEQ ID NO 64
<211> LENGTH: 9
<212> TYPE: PRT
<213> ORGANISM: Homo sapiens

<400> SEQUENCE: 64

His Gln Tyr His Arg Ser Pro Tyr Ser
1 5

<210> SEQ ID NO 65
<211> LENGTH: 9
<212> TYPE: PRT
<213> ORGANISM: Homo sapiens

<400> SEQUENCE: 65

His Gln Tyr Tyr Arg Ser Pro Tyr Thr
1 5

<210> SEQ ID NO 66
<211> LENGTH: 9
<212> TYPE: PRT
<213> ORGANISM: Homo sapiens

<400> SEQUENCE: 66

His Gln Tyr Tyr Arg Thr Pro Tyr Ser
1 5

<210> SEQ ID NO 67
<211> LENGTH: 9
<212> TYPE: PRT
<213> ORGANISM: Homo sapiens

<400> SEQUENCE: 67

His Gln Tyr Gln Arg Ser Pro Tyr Thr
1 5

<210> SEQ ID NO 68
<211> LENGTH: 9
<212> TYPE: PRT
<213> ORGANISM: Homo sapiens

<400> SEQUENCE: 68

His Gln Tyr Gln Arg Ser Pro Tyr Arg

-continued

```
  1               5


<210> SEQ ID NO 69
<211> LENGTH: 9
<212> TYPE: PRT
<213> ORGANISM: Homo sapiens

<400> SEQUENCE: 69

His Gln Tyr Asn Arg Ser Pro Tyr Ala
  1               5


<210> SEQ ID NO 70
<211> LENGTH: 9
<212> TYPE: PRT
<213> ORGANISM: Homo sapiens

<400> SEQUENCE: 70

His Gln Tyr His Arg Thr Pro Tyr Thr
  1               5


<210> SEQ ID NO 71
<211> LENGTH: 9
<212> TYPE: PRT
<213> ORGANISM: Homo sapiens

<400> SEQUENCE: 71

His Gln Tyr His Arg Ser Pro Tyr Ile
  1               5


<210> SEQ ID NO 72
<211> LENGTH: 9
<212> TYPE: PRT
<213> ORGANISM: Homo sapiens

<400> SEQUENCE: 72

His Gln Tyr His Arg Arg Pro Tyr Arg
  1               5


<210> SEQ ID NO 73
<211> LENGTH: 9
<212> TYPE: PRT
<213> ORGANISM: Homo sapiens

<400> SEQUENCE: 73

His Gln Tyr His Arg Asn Pro Tyr Ile
  1               5


<210> SEQ ID NO 74
<211> LENGTH: 10
<212> TYPE: PRT
<213> ORGANISM: Homo sapiens

<400> SEQUENCE: 74

Gly Phe Asn Ile Lys Asp Thr Tyr Met His
  1               5                   10


<210> SEQ ID NO 75
<211> LENGTH: 10
<212> TYPE: PRT
<213> ORGANISM: Homo sapiens

<400> SEQUENCE: 75

Ala Phe Asn Ile Ala Asp Thr Tyr Ile His
  1               5                   10
```

<210> SEQ ID NO 76
<211> LENGTH: 10
<212> TYPE: PRT
<213> ORGANISM: Homo sapiens

<400> SEQUENCE: 76

Arg Phe Arg Ile Lys Asp Thr Tyr Val His
1 5 10

<210> SEQ ID NO 77
<211> LENGTH: 10
<212> TYPE: PRT
<213> ORGANISM: Homo sapiens

<400> SEQUENCE: 77

Arg Phe Asn Ile Lys Asp Thr Tyr Ile His
1 5 10

<210> SEQ ID NO 78
<211> LENGTH: 10
<212> TYPE: PRT
<213> ORGANISM: Homo sapiens

<400> SEQUENCE: 78

Ser Phe Gln Ile Asn Asp Thr Tyr Ile His
1 5 10

<210> SEQ ID NO 79
<211> LENGTH: 10
<212> TYPE: PRT
<213> ORGANISM: Homo sapiens

<400> SEQUENCE: 79

Ser Phe Gln Met Ser Asp Thr Tyr Val His
1 5 10

<210> SEQ ID NO 80
<211> LENGTH: 10
<212> TYPE: PRT
<213> ORGANISM: Homo sapiens

<400> SEQUENCE: 80

Asp Phe Asn Ile Lys Asp Thr Tyr Ile His
1 5 10

<210> SEQ ID NO 81
<211> LENGTH: 10
<212> TYPE: PRT
<213> ORGANISM: Homo sapiens

<400> SEQUENCE: 81

Gly Phe Asn Ile Ile Asp Thr Tyr Ile His
1 5 10

<210> SEQ ID NO 82
<211> LENGTH: 10
<212> TYPE: PRT
<213> ORGANISM: Homo sapiens

<400> SEQUENCE: 82

Gly Leu Gln Ile Val Asp Thr Tyr Ile His
1 5 10

<210> SEQ ID NO 83
<211> LENGTH: 10
<212> TYPE: PRT

<213> ORGANISM: Homo sapiens

<400> SEQUENCE: 83

Gly Phe Asn Ile Lys Asp Thr Tyr Leu His
1 5 10

<210> SEQ ID NO 84
<211> LENGTH: 10
<212> TYPE: PRT
<213> ORGANISM: Homo sapiens

<400> SEQUENCE: 84

Gly Phe Asn Ile Gln Asp Leu Tyr Leu His
1 5 10

<210> SEQ ID NO 85
<211> LENGTH: 10
<212> TYPE: PRT
<213> ORGANISM: Homo sapiens

<400> SEQUENCE: 85

Gly Phe Asn Ile Ile Asp Thr Tyr Met His
1 5 10

<210> SEQ ID NO 86
<211> LENGTH: 10
<212> TYPE: PRT
<213> ORGANISM: Homo sapiens

<400> SEQUENCE: 86

Gly Trp Lys Met Thr Asp Thr Tyr Met His
1 5 10

<210> SEQ ID NO 87
<211> LENGTH: 10
<212> TYPE: PRT
<213> ORGANISM: Homo sapiens

<400> SEQUENCE: 87

Glu Phe Lys Ile Lys Asp Thr Tyr Val His
1 5 10

<210> SEQ ID NO 88
<211> LENGTH: 10
<212> TYPE: PRT
<213> ORGANISM: Homo sapiens

<400> SEQUENCE: 88

Gly Phe Asn Ile Lys Asp Thr Tyr Val His
1 5 10

<210> SEQ ID NO 89
<211> LENGTH: 10
<212> TYPE: PRT
<213> ORGANISM: Homo sapiens

<400> SEQUENCE: 89

Gly Phe Tyr Ile Ser Asn Thr Tyr Ile His
1 5 10

<210> SEQ ID NO 90
<211> LENGTH: 10
<212> TYPE: PRT
<213> ORGANISM: Homo sapiens

<400> SEQUENCE: 90

Gly Phe Asn Ile Lys Asn Thr Tyr Leu His
1 5 10

<210> SEQ ID NO 91
<211> LENGTH: 10
<212> TYPE: PRT
<213> ORGANISM: Homo sapiens

<400> SEQUENCE: 91

Gly Phe Ser Ile Glu Asn Thr Tyr Met His
1 5 10

<210> SEQ ID NO 92
<211> LENGTH: 10
<212> TYPE: PRT
<213> ORGANISM: Homo sapiens

<400> SEQUENCE: 92

Gly Phe Asn Ile Lys Asn Thr Tyr Met His
1 5 10

<210> SEQ ID NO 93
<211> LENGTH: 10
<212> TYPE: PRT
<213> ORGANISM: Homo sapiens

<400> SEQUENCE: 93

Asp Phe Lys Ile Glu Asn Thr Tyr Val His
1 5 10

<210> SEQ ID NO 94
<211> LENGTH: 18
<212> TYPE: PRT
<213> ORGANISM: Homo sapiens

<400> SEQUENCE: 94

Gly Arg Val Asp Pro Ala Asn Gly Asn Thr Lys Tyr Asp Pro Lys
1 5 10 15

Phe Gln Gly

<210> SEQ ID NO 95
<211> LENGTH: 18
<212> TYPE: PRT
<213> ORGANISM: Homo sapiens

<400> SEQUENCE: 95

Gly Arg Val Asp Pro Ala Asn Gly Asn Thr Lys Ser Asp Pro Lys
1 5 10 15

Val Arg Gly

<210> SEQ ID NO 96
<211> LENGTH: 18
<212> TYPE: PRT
<213> ORGANISM: Homo sapiens

<400> SEQUENCE: 96

Gly Arg Val Asp Pro Ala Asn Gly Leu Thr Lys Tyr Asp Pro Lys
1 5 10 15

Phe Gln Gly

<210> SEQ ID NO 97
<211> LENGTH: 18
<212> TYPE: PRT

<213> ORGANISM: Homo sapiens

<400> SEQUENCE: 97

Gly Arg Val Asp Pro Ala Asn Gly Glu Ile Lys Ser His Pro Ile
1 5 10 15

Phe Gln Gly

<210> SEQ ID NO 98
<211> LENGTH: 18
<212> TYPE: PRT
<213> ORGANISM: Homo sapiens

<400> SEQUENCE: 98

Gly Arg Val Asp Pro Ala Asn Gly Asn Thr Lys Glu Asp Arg Gln
1 5 10 15

Phe Gln Gly

<210> SEQ ID NO 99
<211> LENGTH: 18
<212> TYPE: PRT
<213> ORGANISM: Homo sapiens

<400> SEQUENCE: 99

Gly Arg Val Asp Pro Glu Tyr Gly Asn Thr Lys Tyr Asp Pro Lys
1 5 10 15

Phe Gln Gly

<210> SEQ ID NO 100
<211> LENGTH: 18
<212> TYPE: PRT
<213> ORGANISM: Homo sapiens

<400> SEQUENCE: 100

Gly Arg Leu Asp Pro Ala Asn Gly Asn Thr Lys Tyr Asp Pro Lys
1 5 10 15

Phe Gln Gly

<210> SEQ ID NO 101
<211> LENGTH: 18
<212> TYPE: PRT
<213> ORGANISM: Homo sapiens

<400> SEQUENCE: 101

Gly Arg Val Asp Pro Ala Asn Gly Asp Thr Lys Tyr Asp Pro Lys
1 5 10 15

Phe Gln Gly

<210> SEQ ID NO 102
<211> LENGTH: 18
<212> TYPE: PRT
<213> ORGANISM: Homo sapiens

<400> SEQUENCE: 102

Gly Arg Val Asp Pro Ala Asn Gly Lys Thr Lys Tyr Asp Pro Lys
1 5 10 15

Phe Gln Gly

<210> SEQ ID NO 103
<211> LENGTH: 18
<212> TYPE: PRT
<213> ORGANISM: Homo sapiens

<400> SEQUENCE: 103

Gly Arg Val Asp Pro Ala Asn Gly Leu Thr Lys Tyr Asn Pro Lys
1 5 10 15

Phe Gln Gly

<210> SEQ ID NO 104
<211> LENGTH: 18
<212> TYPE: PRT
<213> ORGANISM: Homo sapiens

<400> SEQUENCE: 104

Gly Arg Val Asp Pro Ala Asn Gly Tyr Thr Lys Tyr Asn Pro Lys
1 5 10 15

Phe Gln Gly

<210> SEQ ID NO 105
<211> LENGTH: 18
<212> TYPE: PRT
<213> ORGANISM: Homo sapiens

<400> SEQUENCE: 105

Gly Arg Val Asp Pro Ala Asn Gly Tyr Thr Lys Tyr Asp Pro Lys
1 5 10 15

Phe Gln Gly

<210> SEQ ID NO 106
<211> LENGTH: 18
<212> TYPE: PRT
<213> ORGANISM: Homo sapiens

<400> SEQUENCE: 106

Gly Arg Val Asp Pro Ala Asn Gly Asn Tyr Lys Tyr Asp Pro Lys
1 5 10 15

Phe Gln Gly

<210> SEQ ID NO 107
<211> LENGTH: 18
<212> TYPE: PRT
<213> ORGANISM: Homo sapiens

<400> SEQUENCE: 107

Gly Arg Val Asp Pro Ala Asn Gly Asn Ser Lys Tyr Asp Pro Lys
1 5 10 15

Phe Gln Gly

<210> SEQ ID NO 108
<211> LENGTH: 18
<212> TYPE: PRT
<213> ORGANISM: Homo sapiens

<400> SEQUENCE: 108

Gly Arg Val Asp Pro Ala Asn Gly Asn Thr Lys Tyr Asp His Arg
1 5 10 15

Phe Gln Gly

<210> SEQ ID NO 109
<211> LENGTH: 18
<212> TYPE: PRT
<213> ORGANISM: Homo sapiens

<400> SEQUENCE: 109

Gly Arg Val Asp Pro Ala Asn Gly Asn Thr Lys Tyr Asp Pro Lys
1 5 10 15

Phe Arg Gly

<210> SEQ ID NO 110
<211> LENGTH: 18
<212> TYPE: PRT
<213> ORGANISM: Homo sapiens

<400> SEQUENCE: 110

Gly Arg Val Asp Pro Ser Asn Gly Asn Thr Lys Ser Asp Gly Lys
1 5 10 15

Phe Asn Gly

<210> SEQ ID NO 111
<211> LENGTH: 18
<212> TYPE: PRT
<213> ORGANISM: Homo sapiens

<400> SEQUENCE: 111

Gly Arg Val Asp Pro Val Asp Gly Lys Thr Lys Tyr Asn Pro Gln
1 5 10 15

Ile Gln Gly

<210> SEQ ID NO 112
<211> LENGTH: 18
<212> TYPE: PRT
<213> ORGANISM: Homo sapiens

<400> SEQUENCE: 112

Gly Arg Val Asp Pro Ala His Gly Asn Ile Lys Tyr Asp Pro Gln
1 5 10 15

Ile Met Gly

<210> SEQ ID NO 113
<211> LENGTH: 13
<212> TYPE: PRT
<213> ORGANISM: Homo sapiens

<400> SEQUENCE: 113

Val Arg Asp Tyr Tyr Gly His Thr Tyr Gly Phe Ala Phe
1 5 10

<210> SEQ ID NO 114
<211> LENGTH: 13
<212> TYPE: PRT
<213> ORGANISM: Homo sapiens

<400> SEQUENCE: 114

Val Arg Asp Tyr Tyr Gly His Thr Tyr Gly Phe Gln Pro
1 5 10

<210> SEQ ID NO 115
<211> LENGTH: 13
<212> TYPE: PRT
<213> ORGANISM: Homo sapiens

<400> SEQUENCE: 115

Ala Arg Asp Asn Tyr Gly His Thr Tyr Gly Phe Gly Phe
1 5 10

<210> SEQ ID NO 116
<211> LENGTH: 13

<212> TYPE: PRT
<213> ORGANISM: Homo sapiens

<400> SEQUENCE: 116

Val Arg Asp Thr Tyr Gly His Thr Tyr Gly Phe Ala Tyr
1 5 10

<210> SEQ ID NO 117
<211> LENGTH: 13
<212> TYPE: PRT
<213> ORGANISM: Homo sapiens

<400> SEQUENCE: 117

Val Arg Asp Tyr Tyr Gly His Thr Tyr Gly Phe Gly Tyr
1 5 10

<210> SEQ ID NO 118
<211> LENGTH: 13
<212> TYPE: PRT
<213> ORGANISM: Homo sapiens

<400> SEQUENCE: 118

Val Arg Asp Tyr Tyr Gly His Thr Tyr Gly Phe Gly Val
1 5 10

<210> SEQ ID NO 119
<211> LENGTH: 11
<212> TYPE: PRT
<213> ORGANISM: Homo sapiens

<400> SEQUENCE: 119

Lys Ala Ser Asp Leu Ile His Asn Trp Leu Ala
1 5 10

<210> SEQ ID NO 120
<211> LENGTH: 8
<212> TYPE: PRT
<213> ORGANISM: Homo sapiens

<400> SEQUENCE: 120

Ser Gly Ala Thr Ser Leu Glu Thr
1 5

<210> SEQ ID NO 121
<211> LENGTH: 8
<212> TYPE: PRT
<213> ORGANISM: Homo sapiens

<400> SEQUENCE: 121

Tyr Gly Ala Thr Ser Leu Glu Thr
1 5

<210> SEQ ID NO 122
<211> LENGTH: 9
<212> TYPE: PRT
<213> ORGANISM: Homo sapiens

<400> SEQUENCE: 122

Gln Gln Tyr Trp Thr Thr Pro Phe Thr
1 5

<210> SEQ ID NO 123
<211> LENGTH: 11
<212> TYPE: PRT
<213> ORGANISM: Homo sapiens

<400> SEQUENCE: 123

Gly Tyr Ser Ile Thr Asn Asp Tyr Ala Trp Asn
1 5 10

<210> SEQ ID NO 124
<211> LENGTH: 17
<212> TYPE: PRT
<213> ORGANISM: Homo sapiens

<400> SEQUENCE: 124

Gly Tyr Ile Asn Tyr Ser Gly Tyr Thr Thr Tyr Asn Pro Ser Leu
1 5 10 15

Lys Ser

<210> SEQ ID NO 125
<211> LENGTH: 17
<212> TYPE: PRT
<213> ORGANISM: Homo sapiens

<400> SEQUENCE: 125

Gly Tyr Ile Ser Tyr Ser Gly Tyr Thr Thr Tyr Asn Pro Ser Leu
1 5 10 15

Lys Ser

<210> SEQ ID NO 126
<211> LENGTH: 17
<212> TYPE: PRT
<213> ORGANISM: Homo sapiens

<400> SEQUENCE: 126

Gly Tyr Ile Asn Tyr Ala Gly Tyr Thr Thr Tyr Asn Pro Ser Leu
1 5 10 15

Lys Ser

<210> SEQ ID NO 127
<211> LENGTH: 17
<212> TYPE: PRT
<213> ORGANISM: Homo sapiens

<400> SEQUENCE: 127

Gly Tyr Ile Ser Tyr Ala Gly Tyr Thr Thr Tyr Asn Pro Ser Leu
1 5 10 15

Lys Ser

<210> SEQ ID NO 128
<211> LENGTH: 9
<212> TYPE: PRT
<213> ORGANISM: Homo sapiens

<400> SEQUENCE: 128

Ala Arg Trp Asp Gly Gly Leu Thr Tyr
1 5

<210> SEQ ID NO 129
<211> LENGTH: 9
<212> TYPE: PRT
<213> ORGANISM: Homo sapiens

<400> SEQUENCE: 129

Ala Arg Trp Ala Ala Gly Leu Thr Asn
1 5

<210> SEQ ID NO 130
<211> LENGTH: 9
<212> TYPE: PRT
<213> ORGANISM: Homo sapiens

<400> SEQUENCE: 130

Ala Arg Trp Asp Ala Gly Leu Ser Tyr
1 5

<210> SEQ ID NO 131
<211> LENGTH: 9
<212> TYPE: PRT
<213> ORGANISM: Homo sapiens

<400> SEQUENCE: 131

Ala Arg Trp Asp Ala Gly Leu Thr Tyr
1 5

<210> SEQ ID NO 132
<211> LENGTH: 9
<212> TYPE: PRT
<213> ORGANISM: Homo sapiens

<400> SEQUENCE: 132

Ala Arg Trp Glu Ala Gly Leu Asn His
1 5

<210> SEQ ID NO 133
<211> LENGTH: 9
<212> TYPE: PRT
<213> ORGANISM: Homo sapiens

<400> SEQUENCE: 133

Ala Arg Trp Glu Ala Gly Leu Asn Tyr
1 5

<210> SEQ ID NO 134
<211> LENGTH: 9
<212> TYPE: PRT
<213> ORGANISM: Homo sapiens

<400> SEQUENCE: 134

Ala Arg Trp Met Ala Gly Leu Ser Asp
1 5

<210> SEQ ID NO 135
<211> LENGTH: 9
<212> TYPE: PRT
<213> ORGANISM: Homo sapiens

<400> SEQUENCE: 135

Ala Arg Trp Ser Ala Gly Leu Asp His
1 5

<210> SEQ ID NO 136
<211> LENGTH: 9
<212> TYPE: PRT
<213> ORGANISM: Homo sapiens

<400> SEQUENCE: 136

Ala Arg Trp Thr Ala Gly Leu Asp Tyr
1 5

<210> SEQ ID NO 137
<211> LENGTH: 9
<212> TYPE: PRT

<213> ORGANISM: Homo sapiens

<400> SEQUENCE: 137

Ala Arg Trp Thr Ala Gly Leu Thr His
1 5

<210> SEQ ID NO 138
<211> LENGTH: 9
<212> TYPE: PRT
<213> ORGANISM: Homo sapiens

<400> SEQUENCE: 138

Ala Arg Trp Val Ala Gly Leu Thr Asn
1 5

<210> SEQ ID NO 139
<211> LENGTH: 9
<212> TYPE: PRT
<213> ORGANISM: Homo sapiens

<400> SEQUENCE: 139

Ala Arg Trp Ala Gly Gly Leu Glu Asn
1 5

<210> SEQ ID NO 140
<211> LENGTH: 9
<212> TYPE: PRT
<213> ORGANISM: Homo sapiens

<400> SEQUENCE: 140

Ala Arg Trp Asp Gly Gly Leu Ser Tyr
1 5

<210> SEQ ID NO 141
<211> LENGTH: 9
<212> TYPE: PRT
<213> ORGANISM: Homo sapiens

<400> SEQUENCE: 141

Ala Arg Trp Asp Arg Gly Leu Thr Tyr
1 5

<210> SEQ ID NO 142
<211> LENGTH: 9
<212> TYPE: PRT
<213> ORGANISM: Homo sapiens

<400> SEQUENCE: 142

Ala Arg Trp Ala Ser Gly Leu Ser His
1 5

<210> SEQ ID NO 143
<211> LENGTH: 9
<212> TYPE: PRT
<213> ORGANISM: Homo sapiens

<400> SEQUENCE: 143

Ala Arg Trp Ala Ser Gly Leu Ser Asn
1 5

<210> SEQ ID NO 144
<211> LENGTH: 9
<212> TYPE: PRT
<213> ORGANISM: Homo sapiens

<400> SEQUENCE: 144

Ala Arg Trp Ala Ser Gly Leu Ser Tyr
1 5

<210> SEQ ID NO 145
<211> LENGTH: 9
<212> TYPE: PRT
<213> ORGANISM: Homo sapiens

<400> SEQUENCE: 145

Ala Arg Trp Ala Ser Gly Leu Thr His
1 5

<210> SEQ ID NO 146
<211> LENGTH: 9
<212> TYPE: PRT
<213> ORGANISM: Homo sapiens

<400> SEQUENCE: 146

Ala Arg Trp Ala Ser Gly Leu Thr Asn
1 5

<210> SEQ ID NO 147
<211> LENGTH: 9
<212> TYPE: PRT
<213> ORGANISM: Homo sapiens

<400> SEQUENCE: 147

Ala Arg Trp Asp Ser Gly Leu Lys Tyr
1 5

<210> SEQ ID NO 148
<211> LENGTH: 9
<212> TYPE: PRT
<213> ORGANISM: Homo sapiens

<400> SEQUENCE: 148

Ala Arg Trp Asp Ser Gly Leu Asn Tyr
1 5

<210> SEQ ID NO 149
<211> LENGTH: 9
<212> TYPE: PRT
<213> ORGANISM: Homo sapiens

<400> SEQUENCE: 149

Ala Arg Trp Asp Ser Gly Leu Ser Ser
1 5

<210> SEQ ID NO 150
<211> LENGTH: 9
<212> TYPE: PRT
<213> ORGANISM: Homo sapiens

<400> SEQUENCE: 150

Ala Arg Trp Asp Ser Gly Leu Ser Val
1 5

<210> SEQ ID NO 151
<211> LENGTH: 9
<212> TYPE: PRT
<213> ORGANISM: Homo sapiens

<400> SEQUENCE: 151

Ala Arg Trp Asp Ser Gly Leu Ser Tyr
1 5

<210> SEQ ID NO 152
<211> LENGTH: 9
<212> TYPE: PRT
<213> ORGANISM: Homo sapiens

<400> SEQUENCE: 152

Ala Arg Trp Asp Ser Gly Leu Thr Tyr
1 5

<210> SEQ ID NO 153
<211> LENGTH: 9
<212> TYPE: PRT
<213> ORGANISM: Homo sapiens

<400> SEQUENCE: 153

Ala Arg Trp Glu Ser Gly Leu Ser His
1 5

<210> SEQ ID NO 154
<211> LENGTH: 9
<212> TYPE: PRT
<213> ORGANISM: Homo sapiens

<400> SEQUENCE: 154

Ala Arg Trp Glu Ser Gly Leu Ser Val
1 5

<210> SEQ ID NO 155
<211> LENGTH: 9
<212> TYPE: PRT
<213> ORGANISM: Homo sapiens

<400> SEQUENCE: 155

Ala Arg Trp Lys Ser Gly Leu Asp Ser
1 5

<210> SEQ ID NO 156
<211> LENGTH: 9
<212> TYPE: PRT
<213> ORGANISM: Homo sapiens

<400> SEQUENCE: 156

Ala Arg Trp Lys Ser Gly Leu Glu Tyr
1 5

<210> SEQ ID NO 157
<211> LENGTH: 9
<212> TYPE: PRT
<213> ORGANISM: Rana catesbeiana

<400> SEQUENCE: 157

Ala Arg Trp Leu Ser Gly Leu Asp Phe
1 5

<210> SEQ ID NO 158
<211> LENGTH: 9
<212> TYPE: PRT
<213> ORGANISM: Homo sapiens

<400> SEQUENCE: 158

Ala Arg Trp Leu Ser Gly Leu Asp Ser
1 5

<210> SEQ ID NO 159

<211> LENGTH: 9
<212> TYPE: PRT
<213> ORGANISM: Homo sapiens

<400> SEQUENCE: 159

Ala Arg Trp Leu Ser Gly Leu Glu Ser
1 5

<210> SEQ ID NO 160
<211> LENGTH: 9
<212> TYPE: PRT
<213> ORGANISM: Homo sapiens

<400> SEQUENCE: 160

Ala Arg Trp Leu Ser Gly Leu Ser Asp
1 5

<210> SEQ ID NO 161
<211> LENGTH: 9
<212> TYPE: PRT
<213> ORGANISM: Homo sapiens

<400> SEQUENCE: 161

Ala Arg Trp Arg Ser Gly Leu Glu His
1 5

<210> SEQ ID NO 162
<211> LENGTH: 9
<212> TYPE: PRT
<213> ORGANISM: Homo sapiens

<400> SEQUENCE: 162

Ala Arg Trp Ser Ser Gly Leu Asn Tyr
1 5

<210> SEQ ID NO 163
<211> LENGTH: 9
<212> TYPE: PRT
<213> ORGANISM: Homo sapiens

<400> SEQUENCE: 163

Ala Arg Trp Ser Ser Gly Leu Thr Tyr
1 5

<210> SEQ ID NO 164
<211> LENGTH: 9
<212> TYPE: PRT
<213> ORGANISM: Homo sapiens

<400> SEQUENCE: 164

Ala Arg Trp Thr Ser Gly Met Asp Ser
1 5

<210> SEQ ID NO 165
<211> LENGTH: 9
<212> TYPE: PRT
<213> ORGANISM: Homo sapiens

<400> SEQUENCE: 165

Ala Arg Trp Thr Ser Gly Leu Thr Tyr
1 5

<210> SEQ ID NO 166
<211> LENGTH: 9
<212> TYPE: PRT
<213> ORGANISM: Homo sapiens

<400> SEQUENCE: 166

Ala Arg Trp Asp Thr Gly Leu Thr Tyr
1 5

<210> SEQ ID NO 167
<211> LENGTH: 9
<212> TYPE: PRT
<213> ORGANISM: Homo sapiens

<400> SEQUENCE: 167

Ala Arg Trp Ala Ala Gly Leu Asp His
1 5

<210> SEQ ID NO 168
<211> LENGTH: 9
<212> TYPE: PRT
<213> ORGANISM: Homo sapiens

<400> SEQUENCE: 168

Ala Arg Trp Ala Ala Gly Leu Asp Ser
1 5

<210> SEQ ID NO 169
<211> LENGTH: 9
<212> TYPE: PRT
<213> ORGANISM: Homo sapiens

<400> SEQUENCE: 169

Ala Arg Trp Leu Ala Gly Leu Ser Asn
1 5

<210> SEQ ID NO 170
<211> LENGTH: 9
<212> TYPE: PRT
<213> ORGANISM: Homo sapiens

<400> SEQUENCE: 170

Ala Arg Trp Thr Ala Gly Leu Asp Gln
1 5

<210> SEQ ID NO 171
<211> LENGTH: 9
<212> TYPE: PRT
<213> ORGANISM: Homo sapiens

<400> SEQUENCE: 171

Ala Arg Trp Ala Ser Gly Leu Asp His
1 5

<210> SEQ ID NO 172
<211> LENGTH: 9
<212> TYPE: PRT
<213> ORGANISM: Homo sapiens

<400> SEQUENCE: 172

Ala Arg Trp Ala Ser Gly Leu Asp Asn
1 5

<210> SEQ ID NO 173
<211> LENGTH: 9
<212> TYPE: PRT
<213> ORGANISM: Homo sapiens

<400> SEQUENCE: 173

Ala Arg Trp Ala Ser Gly Leu Asp Ser
1 5

<210> SEQ ID NO 174
<211> LENGTH: 9
<212> TYPE: PRT
<213> ORGANISM: Homo sapiens

<400> SEQUENCE: 174

Ala Arg Trp Ala Ser Gly Leu Asp Tyr
1 5

<210> SEQ ID NO 175
<211> LENGTH: 9
<212> TYPE: PRT
<213> ORGANISM: Homo sapiens

<400> SEQUENCE: 175

Ala Arg Trp Lys Ser Gly Leu Asp Thr
1 5

<210> SEQ ID NO 176
<211> LENGTH: 9
<212> TYPE: PRT
<213> ORGANISM: Rana catesbeiana

<400> SEQUENCE: 176

Ala Arg Trp Lys Ser Gly Leu Gly Pro
1 5

<210> SEQ ID NO 177
<211> LENGTH: 9
<212> TYPE: PRT
<213> ORGANISM: Homo sapiens

<400> SEQUENCE: 177

Ala Arg Trp Met Ser Gly Leu Asp Ser
1 5

<210> SEQ ID NO 178
<211> LENGTH: 9
<212> TYPE: PRT
<213> ORGANISM: Homo sapiens

<400> SEQUENCE: 178

Ala Arg Trp Arg Ser Gly Leu Glu Ser
1 5

<210> SEQ ID NO 179
<211> LENGTH: 9
<212> TYPE: PRT
<213> ORGANISM: Homo sapiens

<400> SEQUENCE: 179

Ala Arg Trp Arg Ser Gly Leu Glu Tyr
1 5

<210> SEQ ID NO 180
<211> LENGTH: 9
<212> TYPE: PRT
<213> ORGANISM: Homo sapiens

<400> SEQUENCE: 180

Ala Arg Trp Thr Ser Gly Leu Asp Ser
1 5

<210> SEQ ID NO 181
<211> LENGTH: 9
<212> TYPE: PRT
<213> ORGANISM: Homo sapiens

<400> SEQUENCE: 181

```
Ala Arg Trp Thr Ser Gly Leu Asp Thr
  1               5
```

<210> SEQ ID NO 182
<211> LENGTH: 9
<212> TYPE: PRT
<213> ORGANISM: Homo sapiens

<400> SEQUENCE: 182

```
Ala Arg Trp Thr Ser Gly Leu Asp Val
  1               5
```

<210> SEQ ID NO 183
<211> LENGTH: 9
<212> TYPE: PRT
<213> ORGANISM: Homo sapiens

<400> SEQUENCE: 183

```
Ala Arg Trp Thr Ser Gly Leu Asp Tyr
  1               5
```

<210> SEQ ID NO 184
<211> LENGTH: 87
<212> TYPE: PRT
<213> ORGANISM: Homo sapiens

<400> SEQUENCE: 184

```
Gln Val Gln Leu Val Gln Ser Gly Ala Glu Val Lys Lys Pro Gly
  1               5                  10                  15

Ala Ser Val Lys Val Ser Cys Lys Ala Ser Gly Tyr Thr Phe Thr
                 20                  25                  30

Trp Val Arg Gln Ala Pro Gly Gln Gly Leu Glu Trp Met Gly Arg
                 35                  40                  45

Val Thr Ile Thr Ala Asp Thr Ser Thr Ser Thr Ala Tyr Met Glu
                 50                  55                  60

Leu Ser Ser Leu Arg Ser Glu Asp Thr Ala Val Tyr Tyr Cys Ala
                 65                  70                  75

Arg Trp Gly Gln Gly Thr Leu Val Thr Val Ser Ser
                 80                  85
```

<210> SEQ ID NO 185
<211> LENGTH: 81
<212> TYPE: PRT
<213> ORGANISM: Homo sapiens

<400> SEQUENCE: 185

```
Gln Val Gln Leu Val Gln Ser Gly Ala Glu Val Lys Lys Pro Gly
  1               5                  10                  15

Ala Ser Val Lys Val Ser Cys Lys Ala Ser Trp Val Arg Gln Ala
                 20                  25                  30

Pro Gly Gln Gly Leu Glu Trp Met Arg Val Thr Ile Thr Ala Asp
                 35                  40                  45

Thr Ser Thr Ser Thr Ala Tyr Met Glu Leu Ser Ser Leu Arg Ser
                 50                  55                  60

Glu Asp Thr Ala Val Tyr Tyr Cys Ala Arg Trp Gly Gln Gly Thr
```

```
                65                  70                  75

Leu Val Thr Val Ser Ser
                80


<210> SEQ ID NO 186
<211> LENGTH: 80
<212> TYPE: PRT
<213> ORGANISM: Homo sapiens

<400> SEQUENCE: 186

Gln Val Gln Leu Val Gln Ser Gly Ala Glu Val Lys Lys Pro Gly
  1               5                  10                  15

Ala Ser Val Lys Val Ser Cys Lys Ala Ser Trp Val Arg Gln Ala
                 20                  25                  30

Pro Gly Gln Gly Leu Glu Trp Met Arg Val Thr Ile Thr Ala Asp
                 35                  40                  45

Thr Ser Thr Ser Thr Ala Tyr Met Glu Leu Ser Ser Leu Arg Ser
                 50                  55                  60

Glu Asp Thr Ala Val Tyr Tyr Cys Ala Trp Gly Gln Gly Thr Leu
                 65                  70                  75

Val Thr Val Ser Ser
                 80


<210> SEQ ID NO 187
<211> LENGTH: 79
<212> TYPE: PRT
<213> ORGANISM: Homo sapiens

<400> SEQUENCE: 187

Gln Val Gln Leu Val Gln Ser Gly Ala Glu Val Lys Lys Pro Gly
  1               5                  10                  15

Ala Ser Val Lys Val Ser Cys Lys Ala Ser Trp Val Arg Gln Ala
                 20                  25                  30

Pro Gly Gln Gly Leu Glu Trp Met Arg Val Thr Ile Thr Ala Asp
                 35                  40                  45

Thr Ser Thr Ser Thr Ala Tyr Met Glu Leu Ser Ser Leu Arg Ser
                 50                  55                  60

Glu Asp Thr Ala Val Tyr Tyr Cys Trp Gly Gln Gly Thr Leu Val
                 65                  70                  75

Thr Val Ser Ser


<210> SEQ ID NO 188
<211> LENGTH: 87
<212> TYPE: PRT
<213> ORGANISM: Homo sapiens

<400> SEQUENCE: 188

Gln Val Gln Leu Gln Glu Ser Gly Pro Gly Leu Val Lys Pro Ser
  1               5                  10                  15

Gln Thr Leu Ser Leu Thr Cys Thr Val Ser Gly Gly Ser Val Ser
                 20                  25                  30

Trp Ile Arg Gln Pro Pro Gly Lys Gly Leu Glu Trp Ile Gly Arg
                 35                  40                  45

Val Thr Ile Ser Val Asp Thr Ser Lys Asn Gln Phe Ser Leu Lys
                 50                  55                  60

Leu Ser Ser Val Thr Ala Ala Asp Thr Ala Val Tyr Tyr Cys Ala
                 65                  70                  75

Arg Trp Gly Gln Gly Thr Leu Val Thr Val Ser Ser
```

80 85

<210> SEQ ID NO 189
<211> LENGTH: 81
<212> TYPE: PRT
<213> ORGANISM: Homo sapiens

<400> SEQUENCE: 189

Gln Val Gln Leu Gln Glu Ser Gly Pro Gly Leu Val Lys Pro Ser
1 5 10 15

Gln Thr Leu Ser Leu Thr Cys Thr Val Ser Trp Ile Arg Gln Pro
20 25 30

Pro Gly Lys Gly Leu Glu Trp Ile Arg Val Thr Ile Ser Val Asp
35 40 45

Thr Ser Lys Asn Gln Phe Ser Leu Lys Leu Ser Ser Val Thr Ala
50 55 60

Ala Asp Thr Ala Val Tyr Tyr Cys Ala Arg Trp Gly Gln Gly Thr
65 70 75

Leu Val Thr Val Ser Ser
80

<210> SEQ ID NO 190
<211> LENGTH: 80
<212> TYPE: PRT
<213> ORGANISM: Homo sapiens

<400> SEQUENCE: 190

Gln Val Gln Leu Gln Glu Ser Gly Pro Gly Leu Val Lys Pro Ser
1 5 10 15

Gln Thr Leu Ser Leu Thr Cys Thr Val Ser Trp Ile Arg Gln Pro
20 25 30

Pro Gly Lys Gly Leu Glu Trp Ile Arg Val Thr Ile Ser Val Asp
35 40 45

Thr Ser Lys Asn Gln Phe Ser Leu Lys Leu Ser Ser Val Thr Ala
50 55 60

Ala Asp Thr Ala Val Tyr Tyr Cys Ala Trp Gly Gln Gly Thr Leu
65 70 75

Val Thr Val Ser Ser
80

<210> SEQ ID NO 191
<211> LENGTH: 79
<212> TYPE: PRT
<213> ORGANISM: Homo sapiens

<400> SEQUENCE: 191

Gln Val Gln Leu Gln Glu Ser Gly Pro Gly Leu Val Lys Pro Ser
1 5 10 15

Gln Thr Leu Ser Leu Thr Cys Thr Val Ser Trp Ile Arg Gln Pro
20 25 30

Pro Gly Lys Gly Leu Glu Trp Ile Arg Val Thr Ile Ser Val Asp
35 40 45

Thr Ser Lys Asn Gln Phe Ser Leu Lys Leu Ser Ser Val Thr Ala
50 55 60

Ala Asp Thr Ala Val Tyr Tyr Cys Trp Gly Gln Gly Thr Leu Val
65 70 75

Thr Val Ser Ser

<210> SEQ ID NO 192
<211> LENGTH: 79
<212> TYPE: PRT
<213> ORGANISM: Homo sapiens

<400> SEQUENCE: 192

Glu Val Gln Leu Val Glu Ser Gly Gly Gly Leu Val Gln Pro Gly
1 5 10 15

Gly Ser Leu Arg Leu Ser Cys Ala Ala Ser Trp Val Arg Gln Ala
20 25 30

Pro Gly Lys Gly Leu Glu Trp Val Arg Phe Thr Ile Ser Arg Asp
35 40 45

Asn Ser Lys Asn Thr Leu Tyr Leu Gln Met Asn Ser Leu Arg Ala
50 55 60

Glu Asp Thr Ala Val Tyr Tyr Cys Trp Gly Gln Gly Thr Leu Val
65 70 75

Thr Val Ser Ser

<210> SEQ ID NO 193
<211> LENGTH: 79
<212> TYPE: PRT
<213> ORGANISM: Homo sapiens

<400> SEQUENCE: 193

Glu Val Gln Leu Val Glu Ser Gly Gly Gly Leu Val Gln Pro Gly
1 5 10 15

Gly Ser Leu Arg Leu Ser Cys Ala Ala Ser Trp Val Arg Gln Ala
20 25 30

Pro Gly Lys Gly Leu Glu Trp Val Arg Phe Thr Ile Ser Arg Asp
35 40 45

Asn Ser Lys Asn Thr Phe Tyr Leu Gln Met Asn Ser Leu Arg Ala
50 55 60

Glu Asp Thr Ala Val Tyr Tyr Cys Trp Gly Gln Gly Thr Leu Val
65 70 75

Thr Val Ser Ser

<210> SEQ ID NO 194
<211> LENGTH: 80
<212> TYPE: PRT
<213> ORGANISM: Homo sapiens

<400> SEQUENCE: 194

Asp Ile Gln Met Thr Gln Ser Pro Ser Ser Leu Ser Ala Ser Val
1 5 10 15

Gly Asp Arg Val Thr Ile Thr Cys Trp Tyr Gln Gln Lys Pro Gly
20 25 30

Lys Ala Pro Lys Leu Leu Ile Gly Val Pro Ser Arg Phe Ser Gly
35 40 45

Ser Gly Ser Gly Thr Asp Phe Thr Leu Thr Ile Ser Ser Leu Gln
50 55 60

Pro Glu Asp Phe Ala Thr Tyr Tyr Cys Phe Gly Gln Gly Thr Lys
65 70 75

Val Glu Ile Lys Arg
80

<210> SEQ ID NO 195
<211> LENGTH: 80
<212> TYPE: PRT
<213> ORGANISM: Homo sapiens

<400> SEQUENCE: 195

Asp Ile Val Met Thr Gln Ser Pro Leu Ser Leu Pro Val Thr Pro
1 5 10 15

Gly Glu Pro Ala Ser Ile Ser Cys Trp Tyr Leu Gln Lys Pro Gly
20 25 30

Gln Ser Pro Gln Leu Leu Ile Tyr Gly Val Pro Asp Arg Phe Ser
35 40 45

Gly Ser Gly Ser Gly Thr Asp Phe Thr Leu Lys Ile Ser Arg Val
50 55 60

Glu Ala Glu Asp Val Gly Val Tyr Tyr Cys Phe Gly Gln Gly Thr
65 70 75

Lys Val Glu Ile Lys
80

<210> SEQ ID NO 196
<211> LENGTH: 80
<212> TYPE: PRT
<213> ORGANISM: Homo sapiens

<400> SEQUENCE: 196

Glu Ile Val Leu Thr Gln Ser Pro Gly Thr Leu Ser Leu Ser Pro
1 5 10 15

Gly Glu Arg Ala Thr Leu Ser Cys Trp Tyr Gln Gln Lys Pro Gly
20 25 30

Gln Ala Pro Arg Leu Leu Ile Tyr Gly Ile Pro Asp Arg Phe Ser
35 40 45

Gly Ser Gly Ser Gly Thr Asp Phe Thr Leu Thr Ile Ser Arg Leu
50 55 60

Glu Pro Glu Asp Phe Ala Val Tyr Tyr Cys Phe Gly Gln Gly Thr
65 70 75

Lys Val Glu Ile Lys
80

<210> SEQ ID NO 197
<211> LENGTH: 80
<212> TYPE: PRT
<213> ORGANISM: Homo sapiens

<400> SEQUENCE: 197

Asp Ile Val Met Thr Gln Ser Pro Asp Ser Leu Ala Val Ser Leu
1 5 10 15

Gly Glu Arg Ala Thr Ile Asn Cys Trp Tyr Gln Gln Lys Pro Gly
20 25 30

Gln Pro Pro Lys Leu Leu Ile Tyr Gly Val Pro Asp Arg Phe Ser
35 40 45

Gly Ser Gly Ser Gly Thr Asp Phe Thr Leu Thr Ile Ser Ser Leu
50 55 60

Gln Ala Glu Asp Val Ala Val Tyr Tyr Cys Phe Gly Gln Gly Thr
65 70 75

Lys Val Glu Ile Lys
80

<210> SEQ ID NO 198
<211> LENGTH: 116
<212> TYPE: PRT
<213> ORGANISM: Homo sapiens

<400> SEQUENCE: 198

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Ala Ser Gly Leu Asp Tyr
                 95                 100                 105

Trp Gly Gln Gly Thr Leu Val Thr Val Ser Ser
                110                 115


<210> SEQ ID NO 199
<211> LENGTH: 116
<212> TYPE: PRT
<213> ORGANISM: Homo sapiens

<400> SEQUENCE: 199

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Trp Ala Ser Gly Leu Ser His
                 95                 100                 105

Trp Gly Gln Gly Thr Leu Val Thr Val Ser Ser
                110                 115


<210> SEQ ID NO 200
<211> LENGTH: 116
<212> TYPE: PRT
<213> ORGANISM: Homo sapiens

<400> SEQUENCE: 200

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75
```

```
Lys Asn Thr Phe Tyr Leu Gln Met Asn Ser Leu Arg Ala Glu Asp
                 80                  85                  90

Thr Ala Val Tyr Tyr Cys Ala Arg Trp Ala Ser Gly Leu Ser Tyr
                 95                 100                 105

Trp Gly Gln Gly Thr Leu Val Thr Val Ser Ser
                110                 115


<210> SEQ ID NO 201
<211> LENGTH: 116
<212> TYPE: PRT
<213> ORGANISM: Homo sapiens

<400> SEQUENCE: 201

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Thr Ser Gly Leu Asp Tyr
                 95                 100                 105

Trp Gly Gln Gly Thr Leu Val Thr Val Ser Ser
                110                 115


<210> SEQ ID NO 202
<211> LENGTH: 116
<212> TYPE: PRT
<213> ORGANISM: Homo sapiens

<400> SEQUENCE: 202

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Trp Asp Ala Gly Leu Thr Tyr
                 95                 100                 105

Trp Gly Gln Gly Thr Leu Val Thr Val Ser Ser
                110                 115


<210> SEQ ID NO 203
<211> LENGTH: 116
<212> TYPE: PRT
<213> ORGANISM: Homo sapiens

<400> SEQUENCE: 203
```

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Phe Tyr Leu Gln Met Asn Ser Leu Arg Ala Glu Asp
                 80                  85                  90

Thr Ala Val Tyr Tyr Cys Ala Arg Trp Asp Ser Gly Leu Thr Tyr
                 95                 100                 105

Trp Gly Gln Gly Thr Leu Val Thr Val Ser Ser
                110                 115


<210> SEQ ID NO 204
<211> LENGTH: 116
<212> TYPE: PRT
<213> ORGANISM: Homo sapiens

<400> SEQUENCE: 204

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Lys Ser Gly Leu Asp Ser
                 95                 100                 105

Trp Gly Gln Gly Thr Leu Val Thr Val Ser Ser
                110                 115


<210> SEQ ID NO 205
<211> LENGTH: 116
<212> TYPE: PRT
<213> ORGANISM: Homo sapiens

<400> SEQUENCE: 205

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75
```

```
Lys Asn Thr Leu Tyr Leu Gln Met Asn Ser Leu Arg Ala Glu Asp
                 80                  85                  90

Thr Ala Val Tyr Tyr Cys Ala Arg Trp Thr Ser Gly Leu Asp Ser
                 95                 100                 105

Trp Gly Gln Gly Thr Leu Val Thr Val Ser Ser
                110                 115


<210> SEQ ID NO 206
<211> LENGTH: 116
<212> TYPE: PRT
<213> ORGANISM: Homo sapiens

<400> SEQUENCE: 206

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Ser Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Ala Ser Gly Leu Asp Tyr
                 95                 100                 105

Trp Gly Gln Gly Thr Leu Val Thr Val Ser Ser
                110                 115


<210> SEQ ID NO 207
<211> LENGTH: 116
<212> TYPE: PRT
<213> ORGANISM: Homo sapiens

<400> SEQUENCE: 207

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ala Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Ala Ser Gly Leu Asp Tyr
                 95                 100                 105

Trp Gly Gln Gly Thr Leu Val Thr Val Ser Ser
                110                 115


<210> SEQ ID NO 208
<211> LENGTH: 116
<212> TYPE: PRT
<213> ORGANISM: Homo sapiens

<400> SEQUENCE: 208
```

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Ser Tyr Ser Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Thr Ser Gly Leu Asp Tyr
                 95                 100                 105

Trp Gly Gln Gly Thr Leu Val Thr Val Ser Ser
                110                 115


<210> SEQ ID NO 209
<211> LENGTH: 116
<212> TYPE: PRT
<213> ORGANISM: Homo sapiens

<400> SEQUENCE: 209

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Ser Ile Thr
                 20                  25                  30

Asn Asp Tyr Ala Trp Asn Trp Val Arg Gln Ala Pro Gly Lys Gly
                 35                  40                  45

Leu Glu Trp Val Gly Tyr Ile Asn Tyr Ala Gly Tyr Thr Thr Tyr
                 50                  55                  60

Asn Pro Ser Leu Lys Ser Arg Phe Thr Ile Ser Arg Asp Thr Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Trp Thr Ser Gly Leu Asp Tyr
                 95                 100                 105

Trp Gly Gln Gly Thr Leu Val Thr Val Ser Ser
                110                 115


<210> SEQ ID NO 210
<211> LENGTH: 108
<212> TYPE: PRT
<213> ORGANISM: Homo sapiens

<400> SEQUENCE: 210

Asp Ile Gln Met Thr Gln Ser Pro Ser Ser Leu Ser Ala Ser Val
  1               5                  10                  15

Gly Asp Arg Val Thr Ile Thr Cys Lys Ala Ser Asp Leu Ile His
                 20                  25                  30

Asn Trp Leu Ala Trp Tyr Gln Gln Lys Pro Gly Lys Ala Pro Lys
                 35                  40                  45

Leu Leu Ile Ser Gly Ala Thr Ser Leu Glu Thr Gly Val Pro Ser
                 50                  55                  60

Arg Phe Ser Gly Ser Gly Ser Gly Thr Asp Phe Thr Leu Thr Ile
                 65                  70                  75
```

```
Ser Ser Leu Gln Pro Glu Asp Phe Ala Thr Tyr Tyr Cys Gln Gln
            80                  85                  90

Tyr Trp Thr Thr Pro Phe Thr Phe Gly Gln Gly Thr Lys Val Glu
            95                 100                 105

Ile Lys Arg

<210> SEQ ID NO 211
<211> LENGTH: 108
<212> TYPE: PRT
<213> ORGANISM: Homo sapiens

<400> SEQUENCE: 211

Asp Ile Gln Met Thr Gln Ser Pro Ser Ser Leu Ser Ala Ser Val
 1               5                  10                  15

Gly Asp Arg Val Thr Ile Thr Cys Lys Ala Ser Asp Leu Ile His
            20                  25                  30

Asn Trp Leu Ala Trp Tyr Gln Gln Lys Pro Gly Lys Ala Pro Lys
            35                  40                  45

Leu Leu Ile Tyr Gly Ala Thr Ser Leu Glu Thr Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Trp Thr Thr Pro Phe Thr Phe Gly Gln Gly Thr Lys Val Glu
            95                 100                 105

Ile Lys Arg
```

COMPOSITIONS AND METHODS FOR THE DIAGNOSIS AND TREATMENT OF TUMOR

RELATED APPLICATIONS

This application is a non-provisional application filed under 37 C.F.R. §1.53(b)(1), claiming priority under 35 U.S.C. §119(e) to provisional applications Ser. Nos. 60/692,092, filed Jun. 20, 2005, and 60/793,951, filed Apr. 21, 2006, the contents of which are incorporated herein in their entirety by reference.

FIELD OF THE INVENTION

The present invention is directed to compositions of matter useful for the diagnosis and treatment of tumor in mammals and to methods of using those compositions of matter for the same.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

In attempts to discover effective cellular targets for cancer diagnosis and therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

Despite the above identified advances in mammalian cancer therapy, there is a great need for additional diagnostic and therapeutic agents capable of detecting the presence of tumor in a mammal and for effectively inhibiting neoplastic cell growth, respectively. Accordingly, it is an objective of the present invention to identify cell membrane-associated polypeptides that are more abundantly expressed on one or more type(s) of cancer cell(s) as compared to on normal cells or on other different cancer cells and to use those polypeptides, and their encoding nucleic acids, to produce compositions of matter useful in the therapeutic treatment and diagnostic detection of cancer in mammals.

SUMMARY OF THE INVENTION

A. Embodiments

In the present specification, Applicants describe for the first time the identification of cellular polypeptides (and their encoding nucleic acids or fragments thereof) which are expressed to a greater degree on the surface of one or more types of cancer cell(s) as compared to on the surface of one or more types of normal non-cancer cells. These polypeptides are herein referred to as Tumor-associated Antigenic Target polypeptides ("TAT" polypeptides) and are expected to serve as effective targets for cancer therapy and diagnosis in mammals.

Accordingly, in one embodiment of the present invention, the invention provides an isolated nucleic acid molecule having a nucleotide sequence that encodes a tumor-associated antigenic target polypeptide or fragment thereof (a "TAT" polypeptide).

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAT polypeptide having an amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAT polypeptide cDNA as disclosed herein, the coding sequence of a TAT polypeptide lacking the signal peptide as disclosed herein, the coding sequence of an extracellular domain of a transmembrane TAT polypeptide, with or without the signal peptide, as disclosed herein or the coding sequence of any other specifically defined fragment of the full-length TAT polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs deposited with the ATCC as disclosed herein, or (b) the complement of the DNA molecule of (a).

Another aspect of the invention provides an isolated nucleic acid molecule comprising a nucleotide sequence encoding a TAT polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAT polypeptides are contemplated.

In other aspects, the present invention is directed to isolated nucleic acid molecules which hybridize to (a) a nucleotide sequence encoding a TAT polypeptide having a full-length amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the nucleotide sequence of (a). In this regard, an embodiment of the present invention is directed to fragments of a full-length TAT polypeptide coding sequence, or the complement thereof, as disclosed herein, that may find use as, for example, hybridization probes useful as, for example, diagnostic probes, PCR primers, antisense oligonucleotide probes, or for encoding fragments of a full-length TAT polypeptide that may optionally encode a polypeptide comprising a binding site for an anti-TAT polypeptide antibody, a TAT binding oligopeptide or other small organic molecule that binds to a TAT polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. Moreover, such nucleic acid fragments are usually comprised of consecutive nucleotides derived from the full-length coding sequence of a TAT polypeptide or the complement thereof. It is noted that novel fragments of a TAT polypeptide-encoding nucleotide sequence, or the complement thereof, may be determined in a routine manner by aligning the TAT polypeptide-encoding nucleotide sequence with other known nucleotide sequences using any of a number of well known sequence alignment programs and determining which TAT polypeptide-encoding nucleotide sequence fragment(s), or the complement thereof, are novel. All of such novel fragments of TAT polypeptide-encoding nucleotide sequences, or the complement thereof, are contemplated herein. Also contemplated are the TAT polypeptide fragments encoded by these nucleotide molecule fragments, preferably those TAT polypeptide fragments that comprise a binding site for an anti-TAT antibody, a TAT binding oligopeptide or other small organic molecule that binds to a TAT polypeptide.

In another embodiment, the invention provides isolated TAT polypeptides encoded by any of the isolated nucleic acid sequences hereinabove identified.

In a certain aspect, the invention concerns an isolated TAT polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAT polypeptide having a full-length amino acid sequence as disclosed herein, a TAT polypeptide amino acid sequence lacking the signal peptide as disclosed herein, an extracellular domain of a transmembrane TAT polypeptide protein, with or without the signal peptide, as disclosed herein, an amino acid sequence encoded by any of the nucleic acid sequences disclosed herein or any other specifically defined fragment of a full-length TAT polypeptide amino acid sequence as disclosed herein.

In a further aspect, the invention concerns an isolated TAT polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to an amino acid sequence encoded by any of the human protein cDNAs deposited with the ATCC as disclosed herein.

In a yet further aspect, the invention concerns an isolated TAT polypeptide comprising an amino acid sequence that is encoded by a nucleotide sequence that hybridizes to the complement of a DNA molecule encoding (a) a TAT polypeptide having a full-length amino acid sequence as disclosed herein, (b) a TAT polypeptide amino acid sequence lacking the signal peptide as disclosed herein, (c) an extracellular domain of a transmembrane TAT polypeptide protein, with or without the signal peptide, as disclosed herein, (d) an amino acid sequence encoded by any of the nucleic acid sequences disclosed herein or (e) any other specifically defined fragment of a full-length TAT polypeptide amino acid sequence as disclosed herein.

In a specific aspect, the invention provides an isolated TAT polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

Another aspect of the invention provides an isolated TAT polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

In other embodiments of the present invention, the invention provides vectors comprising DNA encoding any of the herein described polypeptides. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAT polypeptides fused to a heterologous (non-TAT) polypeptide. Example of such chimeric molecules comprise any of the herein described TAT polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAT polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably inhibit the growth or proliferation of or induce the death of a cell to which they bind. For diagnostic purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("TAT binding oligopeptides") which bind, preferably specifically, to any of the above or below described TAT polypeptides. Optionally, the TAT binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding oligopeptides of the present invention may optionally be produced in CHO cells or bacterial cells and preferably inhibit the growth or proliferation of or induce the death of a cell to which they bind. For diagnostic purposes, the TAT binding oligopeptides of the present invention may be detectably labeled, attached to a solid support, or the like.

In other embodiments of the present invention, the invention provides vectors comprising DNA encoding any of the herein described TAT binding oligopeptides. Host cell comprising any such vector are also provided. By way of example, the host cells may be CHO cells, *E. coli* cells, or yeast cells. A process for producing any of the herein described TAT binding oligopeptides is further provided and comprises culturing host cells under conditions suitable for expression of the desired oligopeptide and recovering the desired oligopeptide from the cell culture.

In another embodiment, the invention provides small organic molecules ("TAT binding organic molecules") which bind, preferably specifically, to any of the above or below described TAT polypeptides. Optionally, the TAT binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding organic molecules of the present invention preferably inhibit the growth or proliferation of or induce the death of a cell to which they bind. For diagnostic purposes, the TAT binding organic molecules of the present invention may be detectably labeled, attached to a solid support, or the like.

In a still further embodiment, the invention concerns a composition of matter comprising a TAT polypeptide as described herein, a chimeric TAT polypeptide as described herein, an anti-TAT antibody as described herein, a TAT binding oligopeptide as described herein, or a TAT binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAT polypeptide as described herein, a chimeric TAT polypeptide as described herein, an anti-TAT antibody as described herein, a TAT binding oligopeptide as described herein, or a TAT binding organic molecule as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of a TAT polypeptide as described herein, a chimeric TAT polypeptide as described herein, an anti-TAT polypeptide antibody as described herein, a TAT binding oligopeptide as described herein, or a TAT binding organic molecule as described herein, for the preparation of a medicament useful in the treatment of a condition which is responsive to the TAT polypeptide, chimeric TAT polypeptide, anti-TAT polypeptide antibody, TAT binding oligopeptide, or TAT binding organic molecule.

Other embodiments of the present invention are directed to any isolated antibody comprising one or more of the HVR-L1, HVR-L2, HVR-L3, HVR-H1, HVR-H2, or HVR-H3 sequences disclosed herein, or any antibody that binds to the same epitope as any such antibody.

B. Additional Embodiments

Another embodiment of the present invention is directed to a method for inhibiting the growth of a cell that expresses a TAT polypeptide, wherein the method comprises contacting the cell with an antibody, an oligopeptide or a small organic molecule that binds to the TAT polypeptide, and wherein the binding of the antibody, oligopeptide or organic molecule to the TAT polypeptide causes inhibition of the growth of the cell expressing the TAT polypeptide. In preferred embodiments, the cell is a cancer cell and binding of the antibody, oligopeptide or organic molecule to the TAT polypeptide causes death of the cell expressing the TAT polypeptide. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a mammal having a cancerous tumor comprising cells that express a TAT polypeptide, wherein the method comprises administering to the mammal a therapeutically effective amount of an antibody, an oligopeptide or a small organic molecule that binds to the TAT polypeptide, thereby resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Yet another embodiment of the present invention is directed to a method of determining the presence of a TAT polypeptide in a sample suspected of containing the TAT polypeptide, wherein the method comprises exposing the sample to an antibody, oligopeptide or small organic molecule that binds to the TAT polypeptide and determining binding of the antibody, oligopeptide or organic molecule to the TAT polypeptide in the sample, wherein the presence of such binding is indicative of the presence of the TAT polypeptide in the sample. Optionally, the sample may contain cells (which may be cancer cells) suspected of expressing the TAT polypeptide. The antibody, TAT binding oligopeptide or TAT binding organic molecule employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding a TAT polypeptide (a) in a test sample of tissue cells obtained from said mammal, and (b) in a control sample of known normal non-cancerous cells of the same tissue origin or type, wherein a higher level of expression of the TAT polypeptide in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody, oligopeptide or small organic molecule that binds to a TAT polypeptide and (b) detecting the formation of a complex between the antibody, oligopeptide or small organic molecule and the TAT polypeptide in the test sample, wherein the formation of a complex is indicative of the presence of a tumor in the mammal. Optionally, the antibody, TAT binding oligopeptide or TAT binding organic molecule employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of a TAT polypeptide, the method comprising administering to a subject in need of such treatment an effective amount of an antagonist of a TAT polypeptide. Preferably, the cell proliferative disorder is cancer and the antagonist of the TAT polypeptide is an anti-TAT polypeptide antibody, TAT binding oligopeptide, TAT binding organic molecule or antisense oligonucleotide. Effective treatment or prevention of the cell proliferative disorder may be a result of direct killing or growth inhibition of cells that express a TAT polypeptide or by antagonizing the cell growth potentiating activity of a TAT polypeptide.

Yet another embodiment of the present invention is directed to a method of binding an antibody, oligopeptide or small organic molecule to a cell that expresses a TAT polypeptide, wherein the method comprises contacting a cell that expresses a TAT polypeptide with said antibody, oligopeptide or small organic molecule under conditions which are suitable for binding of the antibody, oligopeptide or small organic molecule to said TAT polypeptide and allowing binding therebetween. In preferred embodiments, the antibody is labeled with a molecule or compound that is useful for qualitatively and/or quantitatively determining the location and/or amount of binding of the antibody, oligopeptide or small organic molecule to the cell.

Other embodiments of the present invention are directed to the use of (a) a TAT polypeptide, (b) a nucleic acid encoding a TAT polypeptide or a vector or host cell comprising that nucleic acid, (c) an anti-TAT polypeptide antibody, (d) a TAT-binding oligopeptide, or (e) a TAT-binding small organic molecule in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a TAT polypeptide (wherein the TAT polypeptide may be expressed either by the cancer cell itself or a cell that produces polypeptide(s) that have a growth potentiating effect on cancer cells), wherein the method comprises contacting the TAT polypeptide with an antibody, an oligopeptide or a small organic molecule that binds to the TAT polypeptide, thereby antagonizing the growth-potentiating activity of the TAT polypeptide and, in turn, inhibiting the growth of the cancer cell. Preferably the growth of the cancer cell is completely inhibited. Even more preferably, binding of the antibody, oligopeptide or small organic molecule to the TAT polypeptide induces the death of the cancer cell. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a tumor in a mammal, wherein the growth of said tumor is at least in part dependent upon the growth potentiating effect(s) of a TAT polypeptide, wherein the method comprises administering to the mammal a therapeutically effective amount of an antibody, an oligopeptide or a small organic molecule that binds to the TAT polypeptide, thereby antagonizing the growth potentiating activity of said TAT polypeptide and resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

C. Further Additional Embodiments

In yet further embodiments, the invention is directed to the following:

An isolated nucleic acid having a nucleotide sequence that has at least 80% nucleic acid sequence identity to:

(a) a DNA molecule encoding the amino acid sequence shown as SEQ ID NO:2;

(b) a DNA molecule encoding the amino acid sequence shown as SEQ ID NO:2, lacking its associated signal peptide;

(c) a DNA molecule encoding an extracellular domain of the polypeptide shown as SEQ ID NO:2, with its associated signal peptide;

(d) a DNA molecule encoding an extracellular domain of the polypeptide shown as SEQ ID NO:2, lacking its associated signal peptide;

(e) the nucleotide sequence shown as SEQ ID NO: 1;

(f) the full-length coding sequence of the nucleotide sequence shown as SEQ ID NO: 1; or (g) the complement of (a), (b), (c), (d), (e) or (f).

An isolated nucleic acid having:

(a) a nucleotide sequence that encodes the amino acid sequence shown as SEQ ID NO:2;

(b) a nucleotide sequence that encodes the amino acid sequence shown as SEQ ID NO:2, lacking its associated signal peptide;

(c) a nucleotide sequence that encodes an extracellular domain of the polypeptide shown as SEQ ID NO:2, with its associated signal peptide;

(d) a nucleotide sequence that encodes an extracellular domain of the polypeptide shown as SEQ ID NO:2, lacking its associated signal peptide;

(e) the nucleotide sequence shown as SEQ ID NO: 1;

(f) the full-length coding region of the nucleotide sequence shown as SEQ ID NO: 1; or (g) the complement of (a), (b), (c), (d), (e) or (f).

An isolated nucleic acid that hybridizes to:

(a) a nucleic acid that encodes the amino acid sequence shown as SEQ ID NO:2;

(b) a nucleic acid that encodes the amino acid sequence shown as SEQ ID NO:2, lacking its associated signal peptide;

(c) a nucleic acid that encodes an extracellular domain of the polypeptide shown as SEQ ID NO:2, with its associated signal peptide;

(d) a nucleic acid that encodes an extracellular domain of the polypeptide shown as SEQ ID NO:2, lacking its associated signal peptide;

(e) the nucleotide sequence shown as SEQ ID NO: 1;

(f) the full-length coding region of the nucleotide sequence shown as SEQ ID NO: 1; or (g) the complement of (a), (b), (c), (d), (e) or (f).

In some embodiments, the hybridization occurs under stringent conditions. In some embodiments, the nucleic acid is at least about 5 nucleotides in length.

The invention also provides An expression vector comprising the forgoing nucleic acid molecules. In some embodiments of the expression vectors, the nucleic acid is operably linked to control sequences recognized by a host cell transformed with the vector.

The invention also provides host cells comprising such expression vectors. The host cell may be, for example, a CHO cell, an *E. coli* cell or a yeast cell.

The host cells may be used in a process for producing a polypeptide comprising culturing the host cell under conditions suitable for expression of said polypeptide and recovering said polypeptide from the cell culture.

The invention also provides an isolated polypeptide having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO: 1; or (f) a polypeptide encoded by the full-length coding region of the nucleotide sequence shown as SEQ ID NO: 1.

The invention further provides an isolated polypeptide having:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO: 1; or (f) an amino acid sequence encoded by the full-length coding region of the nucleotide sequence shown as SEQ ID NO:1.

The invention also provides chimeric polypeptide comprising the polypeptide as set forth in the preceeding two paragraphs fused to a heterologous polypeptide. Such heterologous polypeptide may be an epitope tag sequence or an Fc region of an immunoglobulin.

The invention further provides an isolated antibody that binds to a polypeptide having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO: 1; or (f) a polypeptide encoded by the full-length coding region of the nucleotide sequence shown as SEQ ID NO: 1.

The invention also provides an isolated antibody that binds to a polypeptide having:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO: 1; or (f) an amino acid sequence encoded by the full-length coding region of the nucleotide sequence shown as SEQ ID NO: 1.

An antibody as set forth in the preceeding two paragraphs may be a monoclonal antibody, an antibody fragment, a chimeric or a humanized antibody, conjugated to a growth inhibitory agent, or conjugated to a cytotoxic agent. The cytotoxic agent is selected from the group consisting of toxins, antibiotics, radioactive isotopes and nucleolytic enzymes. In some embodiments, for example, the cytotoxic agent is a toxin. In some embodiments, the toxin is selected from the group consisting of maytansinoid and calicheamicin. In some embodiments, the toxin is a maytansinoid. In some embodiments, the antibody is produced in bacteria. In some embodiments, the antibody is produced in CHO cells. Such an antibody can induce death of a cell to which it binds. In addition, the antibodies may be detectably labeled. The invention thus also provides isolated nucleic acid molecules having a nucleotide sequences that encode such antiboies, expression vectors comprising the nucleic acid molecules encoding the antibodies operably linked to control sequences recognized by a host cell transformed with the vector, and host cells comprising the expression vectors.

The host cell may be, for example, a CHO cell, an *E. coli* cell or a yeast cell.

The invention also provides a process for producing an antibody described above, which process comprises culturing a host cell described in the preceding paragraph under conditions suitable for expression of said antibody and recovering said antibody from the cell culture.

The invention further provides an isolated oligopeptide that binds to a polypeptide having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1.

The invention also provides an isolated oligopeptide that binds to a polypeptide having:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

These oligopeptides may be conjugated to a growth inhibitory agent, or a cytotoxic agent.

The cytotoxic agent may be selected from the group consisting of toxins, antibiotics, radioactive isotopes and nucleolytic enzymes. In some embodiments, the cytotoxic agent is a toxin. In some embodiments, the toxin is selected from the group consisting of maytansinoid and calicheamicin. In some embodiments, the toxin is a maytansinoid. In some embodiments, the oligopeptide induces death of a cell to which it binds. In some embodiments, the oligopeptide is detectably labeled.

The invention also provides a TAT binding organic molecule that binds to a polypeptide having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1.

In some embodiments, the organic molecule binds to a polypeptide having:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

In some embodiments, the organic molecule is conjugated to a growth inhibitory agent, or a cytotoxic agent.

The cytotoxic agent may be selected from the group consisting of toxins, antibiotics, radioactive isotopes and nucleolytic enzymes. In some embodiments, the cytotoxic agent is a toxin. In some embodiments, the toxin is selected from the group consisting of maytansinoid and calicheamicin. In some embodiments, the toxin is a maytansinoid. In some embodiments, the organic molecule induces death of a cell to which it binds.

In some embodiments, the organic molecule is detectably labeled.

The invention also provides a composition of matter comprising any forgoing polypeptide, chimeric polypeptide, antibody, oligopeptide, or TAT binding organic molecule, in combination with a carrier, such as a pharmaceutically acceptable carrier.

The invention also provides an article of manufacture comprising:

(a) a container; and (b) the composition of matter of the invention contained within said container.

The article of manufacture may further comprising a label affixed to said container, or a package insert included with said container, referring to the use of said composition of matter for the therapeutic treatment of or the diagnostic detection of a cancer.

The invention also provides a method of inhibiting the growth of a cell that expresses a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising contacting said cell with an antibody, oligopeptide or organic molecule that binds to said protein, the binding of said antibody, oligopeptide or organic molecule to said protein thereby causing an inhibition of growth of said cell.

In some embodiments of this method, the antibody may be a monoclonal antibody, an antibody fragment, a chimeric antibody or a humanized antibody.

In some embodiments of the method, the antibody, oligopeptide or organic molecule is conjugated to a growth inhibitory agent or a cytotoxic agent.

In some embodiments, the cytotoxic agent is selected from the group consisting of toxins, antibiotics, radioactive isotopes and nucleolytic enzymes. In some embodiments, the cytotoxic agent is a toxin.

In some embodiments, the toxin is selected from the group consisting of maytansinoid and calicheamicin. In some embodiments, the the toxin is a maytansinoid. In some embodiments, the antibody is produced in bacteria. In other embodiments, the antibody is produced in CHO cells.

In this method of the invention, the cell is a cancer cell, such as a cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell. In some embodiments, the cancer cell is further exposed to radiation treatment or a chemotherapeutic agent.

In this method the protein is more abundantly expressed by said cancer cell as compared to a normal cell of the same tissue origin. In some embodiments, the this method causes the death of said cell. In some embodiments of this method, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention further provides a method of therapeutically treating a mammal having a cancerous tumor comprising cells that express a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising administering to said mammal a therapeutically effective amount of an antibody, oligopeptide or organic molecule that binds to said protein, thereby effectively treating said mammal.

In some embodiments of this method, the antibody is a monoclonal antibody, an antibody fragment, a chimeric antibody or a humanized antibody. In some embodiments, the antibody, oligopeptide or organic molecule is conjugated to a growth inhibitory agent or a cytotoxic agent. In some embodiments, the cytotoxic agent is selected from the group consisting of toxins, antibiotics, radioactive isotopes and nucleolytic enzymes. In some embodiments, the cytotoxic agent is a toxin. In some embodiments, the toxin is selected from the group consisting of maytansinoid and calicheamicin. In some embodiments, the toxin is a maytansinoid. In some embodiments, the antibody is produced in bacteria. In some embodiments, the antibody is produced in CHO cells. In certain embodiments of this method, the tumor is further exposed to radiation treatment or a chemotherapeutic agent. The tumor may be a breast tumor, a colorectal tumor, a lung tumor, an ovarian tumor, a central nervous system tumor, a liver tumor, a bladder tumor, a pancreatic tumor, or a cervical tumor. In some embodiments, the protein is more abundantly expressed by the cancerous cells of said tumor as compared to a normal cell of the same tissue origin. In this method, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention further provides a method of determining the presence of a protein in a sample suspected of containing said protein, wherein said protein has at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising exposing said sample to an antibody, oligopeptide or organic molecule that binds to said protein and determining binding of said antibody, oligopeptide or organic molecule to said protein in said sample, wherein binding of the antibody, oligopeptide or organic molecule to said protein is indicative of the presence of said protein in said sample.

94. In some embodiments of this method of the invention, the sample comprises a cell suspected of expressing said protein. In some embodiments, the cell is a cancer cell. In some embodiments, the antibody, oligopeptide or organic molecule is detectably labeled. In some embodiments, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention also provides a method of diagnosing the presence of a tumor in a mammal, said method comprising determining the level of expression of a gene encoding a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, in a test sample of tissue cells obtained from said mammal and in a control sample of known normal cells of the same tissue origin, wherein a higher level of expression of said protein in the test sample, as compared to the control sample, is indicative of the presence of tumor in the mammal from which the test sample was obtained.

In this method, the step of determining the level of expression of a gene encoding said protein may comprise employing an oligonucleotide in an in situ hybridization or RT-PCR analysis or an antibody in an immunohistochemistry or Western blot analysis.

In this method, the protein may have:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention further provides a method of diagnosing the presence of a tumor in a mammal, comprising contacting a test sample of tissue cells obtained from said mammal with an antibody, oligopeptide or organic molecule that binds to a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, and detecting the formation of a complex between said antibody, oligopeptide or organic molecule and said protein in the test sample, wherein the formation of a complex is indicative of the presence of a tumor in said mammal.

In this method, the antibody, oligopeptide or organic molecule may be detectably labeled. In some embodiments, the test sample of tissue cells is obtained from an individual suspected of having a cancerous tumor. In some embodiments of this method, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention also provides a method for treating or preventing a cell proliferative disorder associated with increased expression or activity of a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising administering to a subject in need of such treatment an effective amount of an antagonist of said protein, thereby effectively treating or preventing said cell proliferative disorder. In some embodiments, the cell proliferative disorder is cancer. In some embodiments, the antagonist is an anti-TAT polypeptide antibody, TAT binding oligopeptide, TAT binding organic molecule or antisense oligonucleotide.

The invention also provides a method of binding an antibody, oligopeptide or organic molecule to a cell that expresses a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising contacting said cell with an antibody, oligopeptide or organic molecule that binds to said protein and allowing the binding of the antibody, oligopeptide or organic molecule to said protein to occur, thereby binding said antibody, oligopeptide or organic molecule to said cell. In some embodiments, the antibody is a monoclonal antibody. In some embodiments, the antibody is an antibody fragment. In some embodiments, the antibody is a chimeric or a humanized antibody. In some embodiments, the antibody, oligopeptide or organic molecule is conjugated to a growth inhibitory agent. In some embodiments, the antibody, oligopeptide or organic molecule is conjugated to a cytotoxic agent. In some embodiments, the cytotoxic agent is selected from the group consisting of toxins, antibiotics, radioactive isotopes and nucleolytic enzymes. In some embodiments, the the cytotoxic agent is a toxin. In some embodiments, the toxin is selected from the group consisting of maytansinoid and calicheamicin. In some embodiments, the toxin is a maytansinoid. In some embodiments, the antibody is produced in bacteria. In some embodiments, the antibody is produced in CHO cells. In some embodiments of this method, the cell is a cancer cell. In some embodiments, the cancer cell is further exposed to radiation treatment or a chemotherapeutic agent. In this method, the cancer cell may be selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell. In some embodiments, the protein is more abundantly expressed by said cancer cell as compared to a normal cell of the same tissue origin. In some embodiments, the method causes the death of said cell.

The invention also provides for the use of the foregoing nucleic acids of the invention in the preparation of a medicament for the therapeutic treatment or diagnostic detection of a cancer.

The invention also provides for the use of the foregoing nucleic acids of the invention in the preparation of a medicament for treating a tumor.

The invention also provides for the use of the foregoing nucleic acids of the invention in the preparation of a medicament for treatment or prevention of a cell proliferative disorder.

The invention also provides for the use of the foregoing expression vectors of the invention in the preparation of a medicament for the therapeutic treatment or diagnostic detection of a cancer.

The invention also provides for the use of the foregoing expression vectors of the invention in the preparation of medicament for treating a tumor.

The invention also provides for the use of the foregoing expression vectors of the invention in the preparation of a medicament for treatment or prevention of a cell proliferative disorder.

The invention also provides for the use of the foregoing host cells of the invention in the preparation of a medicament for the therapeutic treatment or diagnostic detection of a cancer.

The invention also provides for the use of the foregoing host cells of the invention in the preparation of a medicament for treating a tumor.

The invention also provides for the use of the foregoing host cells of the invention in the preparation of a medicament for treatment or prevention of a cell proliferative disorder.

The invention also provides for the use of the foregoing polypeptides of the invention in the preparation of a medicament for the therapeutic treatment or diagnostic detection of a cancer.

The invention also provides for the use of the foregoing polypeptides of the invention in the preparation of a medicament for treating a tumor.

The invention also provides for the use of the foregoing polypeptides of the invention in the preparation of a medicament for treatment or prevention of a cell proliferative disorder.

The invention also provides for the use of the foregoing antibodies of the invention in the preparation of a medicament for the therapeutic treatment or diagnostic detection of a cancer.

The invention also provides for the use of the foregoing antibodies of the invention in the preparation of a medicament for treating a tumor.

The invention also provides for the use of the foregoing antibodies of the invention in the preparation of a medicament for treatment or prevention of a cell proliferative disorder.

The invention also provides for the use of the foregoing oligopeptides of the invention in the preparation of a medicament for the therapeutic treatment or diagnostic detection of a cancer.

The invention also provides for the use of the foregoing oligopeptides of the invention in the preparation of a medicament for treating a tumor.

The invention also provides for the use of the foregoing oligopeptides of the invention in the preparation of a medicament for treatment or prevention of a cell proliferative disorder.

The invention also provides for the use of the foregoing TAT binding organic molecules of the invention in the preparation of a medicament for the therapeutic treatment or diagnostic detection of a cancer.

The invention also provides for the use of the foregoing TAT binding organic molecules of the invention in the preparation of a medicament for treating a tumor.

The invention also provides for the use of the foregoing TAT binding organic molecules of the invention in the preparation of a medicament for treatment or prevention of a cell proliferative disorder.

The invention also provides for the use of the foregoing compositions of matter of the invention in the preparation of a medicament for the therapeutic treatment or diagnostic detection of a cancer.

The invention also provides for the use of the foregoing compositions of matter of the invention in the preparation of a medicament for treating a tumor.

The invention also provides for the use of the foregoing compositions of matter of the invention in the preparation of a medicament for treatment or prevention of a cell proliferative disorder.

The invention also provides for the use of the foregoing articles of manufacture of the invention in the preparation of a medicament for the therapeutic treatment or diagnostic detection of a cancer.

The invention also provides for the use of the foregoing articles of manufacture of the invention in the preparation of a medicament for treating a tumor.

The invention also provides for the use of the foregoing articles of manufacture of the invention in the preparation of a medicament for treatment or prevention of a cell proliferative disorder.

The invention further provides a method for inhibiting the growth of a cell, wherein the growth of said cell is at least in part dependent upon a growth potentiating effect of a protein having at least 80% amino acid sequence identity to:

(a) the polypeptide shown as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising contacting said protein with an antibody, oligopeptide or organic molecule that binds to said protein, there by inhibiting the growth of said cell. In some embodiments, the cell is a cancer cell. In some embodiments, the protein is expressed by said cell. In some embodiments, the binding of said antibody, oligopeptide or organic molecule to said protein antagonizes a cell growth-potentiating activity of said protein. In some embodiments, the binding of said antibody, oligopeptide or organic molecule to said protein induces the death of said cell. In some embodiments, the antibody is a monoclonal antibody. In some embodiments, the antibody is an antibody fragment. In some embodiments, the said antibody is a chimeric or a humanized antibody. In some embodiments, the antibody, oligopeptide or organic molecule is conjugated to a growth inhibitory agent. In some embodiments, the antibody, oligopeptide or organic molecule is conjugated to a cytotoxic agent. In some embodiments, the cytotoxic agent is selected from the group consisting of toxins, antibiotics, radioactive isotopes and nucleolytic enzymes. In some embodiments, the the cytotoxic agent is a toxin. In some embodiments, the the toxin is selected from the group consisting of maytansinoid and calicheamicin. In some embodiments, the toxin is a maytansinoid. In some embodiments, the antibody is produced in bacteria. In some embodiments, the antibody is produced in CHO cells. In some embodiments, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention also provides a method of therapeutically treating a tumor in a mammal, wherein the growth of said tumor is at least in part dependent upon a growth potentiating effect of a protein having at least 80% amino acid sequence identity to:

(a) the polypeptide shown in as SEQ ID NO:2;

(b) the polypeptide shown as SEQ ID NO:2, lacking its associated signal peptide;

(c) an extracellular domain of the polypeptide shown as SEQ ID NO:2, with its associated signal peptide;

(d) an extracellular domain of the polypeptide shown as SEQ ID NO:2, lacking its associated signal peptide;

(e) a polypeptide encoded by the nucleotide sequence shown as SEQ ID NO:1; or (f) a polypeptide encoded by the full-length coding region of the nucleotide sequence shown as SEQ ID NO:1, said method comprising contacting said protein with an antibody, oligopeptide or organic molecule that binds to said protein, thereby effectively treating said tumor.

In some embodiments of this method, the protein is expressed by cells of said tumor. In some embodiments, the the binding of said antibody, oligopeptide or organic molecule to said protein antagonizes a cell growth-potentiating activity of said protein. In some embodiments, the antibody is a monoclonal antibody. In some embodiments, the antibody is an antibody fragment. In some embodiments, the antibody is a chimeric or a humanized antibody. In some embodiments, the antibody, oligopeptide or organic molecule is conjugated to a growth inhibitory agent. In some embodiments, the antibody, oligopeptide or organic molecule is conjugated to a cytotoxic agent. In some embodiments, the cytotoxic agent is selected from the group consisting of toxins, antibiotics, radioactive isotopes and nucleolytic enzymes. In some embodiments, the the cytotoxic agent is a toxin. In some embodiments, the toxin is selected from the group consisting of maytansinoid and calicheamicin. In some embodiments, the toxin is a maytansinoid. In some embodiments, the antibody is produced in bacteria. In some embodiments, the antibody is produced in CHO cells. In some embodiments, the protein has:

(a) the amino acid sequence shown as SEQ ID NO:2;

(b) the amino acid sequence shown as SEQ ID NO:2, lacking its associated signal peptide sequence;

(c) an amino acid sequence of an extracellular domain of the polypeptide shown as SEQ ID NO:2, with its associated signal peptide sequence;

(d) an amino acid sequence of an extracellular domain of the polypeptide shown as SEQ ID NO:2, lacking its associated signal peptide sequence;

(e) an amino acid sequence encoded by the nucleotide sequence shown as SEQ ID NO:1; or (f) an amino acid sequence encoded by the full-length coding region of the nucleotide sequence shown as SEQ ID NO:1.

The invention further provides an isolated antibody that binds to the same epitope bound by an antibody produced by any of the hybridoma cell lines shown in Table 11. In some embodiments, the antibody is a monoclonal antibody. In some embodiments, the antibody is an antibody fragment. In some embodiments, the antibody is a chimeric or a humanized antibody. In some embodiments, the antibody is conjugated to a growth inhibitory agent. In some embodiments, the antibody is conjugated to a cytotoxic agent. In some embodiments, the cytotoxic agent is selected from the group consisting of toxins, antibiotics, radioactive isotopes and nucleolytic enzymes. In some embodiments, the cytotoxic agent is a toxin. In some embodiments, the toxin is selected from the group consisting of maytansinoid and calicheamicin. In some embodiments, the toxin is a maytansinoid. In some embodiments, the antibody is produced in bacteria. In some embodiments, the antibody is produced in CHO cells. In some embodiments, the antibody induces death of a cell to which it binds. In some embodiments, the antibody is detectably labeled. In some embodiments, the antibody comprises at least one of the complementarity determining regions of any antibody produced by any of the hybridoma cell lines shown in Table 11.

The invention also provides a monoclonal antibody produced by any of the hybridoma cells shown in Table 11.

The invention also provides a hybridoma cell which produces a monoclonal antibody that binds to a TAT polypeptide.

The invention also provides a method of identifying an antibody that binds to an epitope bound by an antibody produced by any of the hybridoma cell lines shown in Table 11, said method comprising determining the ability of a first antibody to block binding of a second antibody produced by any of the hybridoma cell lines shown in Table 11 to a TAT polypeptide, wherein the ability of said first antibody to block the binding of said second antibody to said TAT polypeptide by at least 40% and at equal antibody concentrations is indicative of said first antibody being capable of binding to an epitope bound by said second antibody.

Yet further embodiments of the present invention will be evident to the skilled artisan upon a reading of the present specification.

BRIEF DESCRIPTION OF THE DRAWINGS

FIGS. 1A-E show a nucleotide sequence (SEQ ID NO:1) of a TAT10772 cDNA, wherein SEQ ID NO:1 is a clone designated herein as "DNA772".

FIGS. 2A-B show the amino acid sequence (SEQ ID NO:2) derived from the coding sequence of SEQ ID NO: 1 shown in FIG. 1.

FIG. 3 shows alignment of amino acid sequences of the variable light chains for the following: light chain human subgroup I consensus sequence (huKI; SEQ ID NO:3), murine 11D10 anti-TAT10772 antibody (mu11D10-L; SEQ ID NO:4), and 11D10 anti-TAT10772 grafted "humanized" antibody (11D10-graft; SEQ ID NO:5).

FIG. 4 shows alignment of amino acid sequences of the variable heavy chains for the following: heavy chain human subgroup III consensus sequence (hum III; SEQ ID NO:6), murine 11D10 anti-TAT10772 antibody (mu11D10-H; SEQ ID NO:7), and 11D10 anti-TAT10772 grafted "humanized" antibody (11D10-graft; SEQ ID NO:8).

FIG. 5 shows alignment of amino acid sequences of the variable light chains for the following: light chain human subgroup I consensus sequence (huKI; SEQ ID NO:3), murine 3A5 anti-TAT10772 antibody (mu3A5-L; SEQ ID NO:9), and 3A5 anti-TAT10772 grafted "humanized" antibody (3A5-graft; SEQ ID NO: 10).

FIG. 6 shows alignment of amino acid sequences of the variable heavy chains for the following: heavy chain human subgroup III consensus sequence (hum III; SEQ ID NO:6), murine 3A5 anti-TAT10772 antibody (mu3A5-H; SEQ ID NO:11), 3A5 anti-TAT10772 grafted "humanized" antibody "L variant" (3A5.L-graft; SEQ ID NO:12), and 3A5 anti-TAT10772 grafted "humanized" antibody "F variant" (3A5.F-graft; SEQ ID NO:13).

FIG. 7 shows various HVR-L1 sequences (SEQ ID NOS: 14-34) of selected affinity-matured 11D10-derived antibodies.

FIG. 8 shows various HVR-L2 sequences (SEQ ID NOS: 35-58) of selected affinity-matured 11D10-derived antibodies.

FIG. 9 shows various HVR-L3 sequences (SEQ ID NOS: 59-73) of selected affinity-matured 11D10-derived antibodies.

FIG. 10 shows various HVR-H1 sequences (SEQ ID NOS: 74-93) of selected affinity-matured 11D10-derived antibodies.

FIG. 11 shows various HVR-H2 sequences (SEQ ID NOS: 94-112) of selected affinity-matured 11D10-derived antibodies.

FIG. 12 shows various HVR-H3 sequences (SEQ ID NOS: 113-118) of selected affinity-matured 11D10-derived antibodies.

FIG. 13 shows an HVR-L1 sequence (SEQ ID NO: 119) of a selected affinity-matured 3A5-derived antibody.

FIG. 14 shows various HVR-L2 sequences (SEQ ID NOS: 120-121) of selected affinity-matured 3A5-derived antibodies.

FIG. 15 shows an HVR-L3 sequence (SEQ ID NO:122) of a selected affinity-matured 3A5-derived antibody.

FIG. 16 shows an HVR-H1 sequence (SEQ ID NO:123) of a selected affinity-matured 3A5-derived antibody.

FIG. 17 shows various HVR-H2 sequences (SEQ ID NOS: 124-127) of selected affinity-matured 3A5-derived antibodies.

FIGS. 18A-B show various HVR-H3 sequences (SEQ ID NOS:128-183) of selected affinity-matured 3A5-derived antibodies.

FIG. 19 shows exemplary acceptor human consensus framework sequences for use in practicing the instant invention with the sequence identifiers as follows: human VH subgroup I consensus framework minus Kabat CDRs (SEQ ID NO: 184), human VH subgroup I consensus framework minus extended hypervariable regions (SEQ ID NOS:185-187), human VH subgroup II consensus framework minus Kabat CDRs (SEQ ID NO: 188), human VH subgroup II consensus framework minus extended hypervariable regions (SEQ ID NOS:189-191), human VH subgroup III consensus framework minus Kabat CDRs “L-variant” (SEQ ID NO: 192), and human VH subgroup III consensus framework minus Kabat CDRs “F-variant” (SEQ ID NO: 193).

FIG. 20 shows exemplary acceptor human consensus framework sequences for use in practicing the instant invention with the sequence identifiers as follows: human VL kappa subgroup I consensus framework minus Kabat CDRs (SEQ ID NO: 194), human VL kappa subgroup II consensus framework minus Kabat CDRs (SEQ ID NO: 195), human VL kappa subgroup III consensus framework minus Kabat CDRs (SEQ ID NO: 196), and human VL kappa subgroup IV consensus framework minus Kabat CDRs (SEQ ID NO:1197).

FIGS. 21A-B shows the complete variable heavy chain sequences for the following antibodies: 3A5v1 (SEQ ID NO:198), 3A5v2 (SEQ ID NO:199), 3A5v3 (SEQ ID NO:200), 3A5v4 (SEQ ID NO:201), 3A5v5 (SEQ ID NO:202), 3A5v6 (SEQ ID NO:203), 3A5v7 (SEQ ID NO:204), 3A5v8 (SEQ ID NO:205), 3A5v1b.52 (SEQ ID NO:206), 3A5v1b.54 (SEQ ID NO:207), 3A5v4b.52 (SEQ ID NO:208), and 3A5v4b.54 (SEQ ID NO:209). All of these antibodies contain the huKI variable light chain amino acid sequence of SEQ ID NO:3.

FIG. 22 shows the complete variable light chain sequences (SEQ ID NOS:210-211) employed for certain anti-TAT10772 antibodies described herein.

DETAILED DESCRIPTION OF THE PREFERRED EMBODIMENTS

I. Definitions

Figure 23:
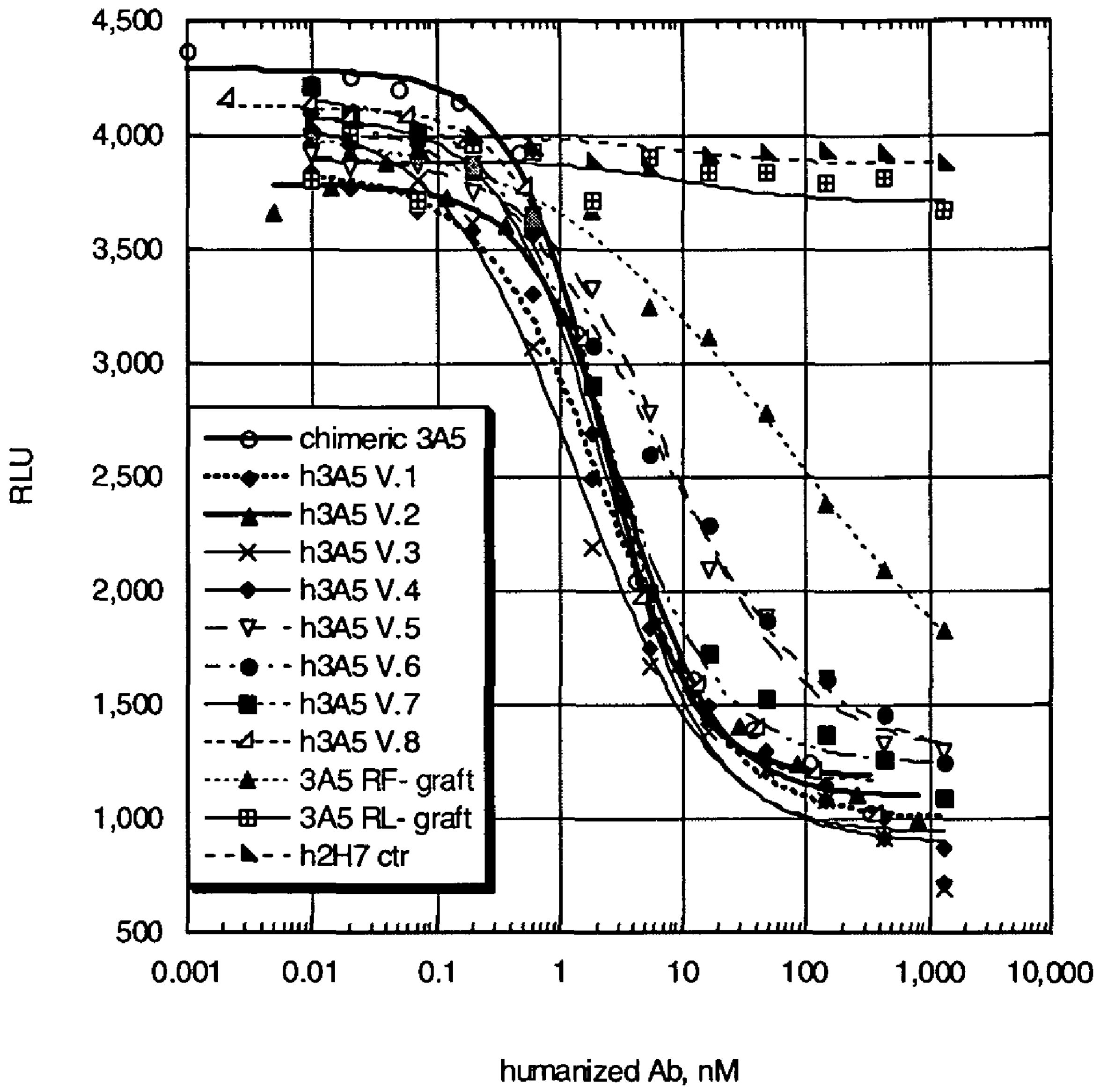
FIG. 23 shows the ability of various humanized 3A5 antibodies to inhibit the binding of ruthenium-labeled chimeric 3A5 to a biotinylated 5'-domain TAT10772 polypeptide target. “h2H7 ctr” is a negative control antibody that does not specifically bind to TAT10772.

The terms “TAT polypeptide” and “TAT” as used herein and when immediately followed by a numerical designation, refer to various polypeptides, wherein the complete designation (i.e.,TAT/number) refers to specific polypeptide sequences as described herein. The terms “TAT/number polypeptide” and “TAT/number” wherein the term “number” is provided as an actual numerical designation as used herein encompass native sequence polypeptides, polypeptide variants and fragments of native sequence polypeptides and polypeptide variants (which are further defined herein). The TAT polypeptides described herein may be isolated from a variety of sources, such as from human tissue types or from another source, or prepared by recombinant or synthetic methods. The term "TAT polypeptide" refers to each individual TAT/number polypeptide disclosed herein. All disclosures in this specification which refer to the "TAT polypeptide" refer to each of the polypeptides individually as well as jointly. For example, descriptions of the preparation of, purification of, derivation of, formation of antibodies to or against, formation of TAT binding oligopeptides to or against, formation of TAT binding organic molecules to or against, administration of, compositions containing, treatment of a disease with, etc., pertain to each polypeptide of the invention individually. The term "TAT polypeptide" also includes variants of the TAT/number polypeptides disclosed herein.

A "native sequence TAT polypeptide" comprises a polypeptide having the same amino acid sequence as the corresponding TAT polypeptide derived from nature. Such native sequence TAT polypeptides can be isolated from nature or can be produced by recombinant or synthetic means. The term "native sequence TAT polypeptide" specifically encompasses naturally-occurring truncated or secreted forms of the specific TAT polypeptide (e.g., an extracellular domain sequence), naturally-occurring variant forms (e.g., alternatively spliced forms) and naturally-occurring allelic variants of the polypeptide. In certain embodiments of the invention, the native sequence TAT polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" or "X" in the accompanying figures are any nucleic acid residue. However, while the TAT polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAT polypeptides.

The TAT polypeptide "extracellular domain" or "ECD" refers to a form of the TAT polypeptide which is essentially free of the transmembrane and cytoplasmic domains. Ordinarily, a TAT polypeptide ECD will have less than 1% of such transmembrane and/or cytoplasmic domains and preferably, will have less than 0.5% of such domains. It will be understood that any transmembrane domains identified for the TAT polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAT polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAT polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAT polypeptide variant" means a TAT polypeptide, preferably an active TAT polypeptide, as defined herein having at least about 80% amino acid sequence identity with a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Such TAT polypeptide variants include, for instance, TAT polypeptides wherein one or more amino acid residues are added, or deleted, at the N- or C-terminus of the full-length native amino acid sequence. Ordinarily, a TAT polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other specifically defined fragment of a full-length TAT polypeptide sequence as disclosed herein. Ordinarily, TAT variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAT variant polypeptides will have no more than one conservative amino acid substitution as compared to the native TAT polypeptide sequence, alternatively no more than 2, 3, 4, 5, 6, 7, 8, 9, or 10 conservative amino acid substitution as compared to the native TAT polypeptide sequence.

"Percent (%) amino acid sequence identity" with respect to the TAT polypeptide sequences identified herein is defined as the percentage of amino acid residues in a candidate sequence that are identical with the amino acid residues in the specific TAT polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "TAT", wherein "TAT" represents the amino acid sequence of a hypothetical TAT polypeptide of interest, "Comparison Protein" represents the amino acid sequence of a polypeptide against which the "TAT" polypeptide of interest is being compared, and "X, "Y" and "Z" each represent different hypothetical amino acid residues. Unless specifically stated otherwise, all % amino acid sequence identity values used herein are obtained as described in the immediately preceding paragraph using the ALIGN-2 computer program.

"TAT variant polynucleotide" or "TAT variant nucleic acid sequence" means a nucleic acid molecule which encodes a TAT polypeptide, preferably an active TAT polypeptide, as defined herein and which has at least about 80% nucleic acid sequence identity with a nucleotide acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Ordinarily, a TAT variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal sequence, as disclosed herein or any other fragment of a full-length TAT polypeptide sequence as disclosed herein. Variants do not encompass the native nucleotide sequence.

Ordinarily, TAT variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAT-encoding nucleic acid sequences identified herein is defined as the percentage of nucleotides in a candidate sequence that are identical with the nucleotides in the TAT nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "TAT-DNA", wherein "TAT-DNA" represents a hypothetical TAT-encoding nucleic acid sequence of interest, "Comparison DNA" represents the nucleotide sequence of a nucleic acid molecule against which the "TAT-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, TAT variant polynucleotides are nucleic acid molecules that encode a TAT polypeptide and which are capable of hybridizing, preferably under stringent hybridization and wash conditions, to nucleotide sequences encoding a full-length TAT polypeptide as disclosed herein. TAT variant polypeptides may be those that are encoded by a TAT variant polynucleotide.

The term "full-length coding region" when used in reference to a nucleic acid encoding a TAT polypeptide refers to the sequence of nucleotides which encode the full-length TAT polypeptide of the invention (which is often shown between start and stop codons, inclusive thereof, in the accompanying figures). The term "full-length coding region" when used in reference to an ATCC deposited nucleic acid refers to the TAT polypeptide-encoding portion of the cDNA that is inserted into the vector deposited with the ATCC (which is often shown between start and stop codons, inclusive thereof, in the accompanying figures).

"Isolated," when used to describe the various TAT polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAT polypeptide natural environment will not be present. Ordinarily, however, isolated polypeptide will be prepared by at least one purification step.

An "isolated" TAT polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular *Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAT polypeptide or anti-TAT antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAT polypeptide which retain a biological and/or an immunological activity of native or naturally-occurring TAT, wherein "biological" activity refers to a biological function (either inhibitory or stimulatory) caused by a native or naturally-occurring TAT other than the ability to induce the production of an antibody against an antigenic epitope possessed by a native or naturally-occurring TAT and an "immunological" activity refers to the ability to induce the production of an antibody against an antigenic epitope possessed by a native or naturally-occurring TAT.

The term "antagonist" is used in the broadest sense, and includes any molecule that partially or fully blocks, inhibits, or neutralizes a biological activity of a native TAT polypeptide disclosed herein. In a similar manner, the term "agonist" is used in the broadest sense and includes any molecule that mimics a biological activity of a native TAT polypeptide disclosed herein. Suitable agonist or antagonist molecules specifically include agonist or antagonist antibodies or antibody fragments, fragments or amino acid sequence variants of native TAT polypeptides, peptides, antisense oligonucleotides, small organic molecules, etc. Methods for identifying agonists or antagonists of a TAT polypeptide may comprise contacting a TAT polypeptide with a candidate agonist or antagonist molecule and measuring a detectable change in one or more biological activities normally associated with the TAT polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAT polypeptide-expressing cancer if, after receiving a therapeutic amount of an anti-TAT antibody, TAT binding oligopeptide or TAT binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAT antibody or TAT binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAT binding oligopeptide or TAT binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAT polypeptide, an antibody thereto or a TAT binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAT binding oligopeptide, TAT binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAT binding oligopeptide, TAT binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAT antibody, TAT polypeptide, TAT binding oligopeptide or TAT binding organic molecule is an amount capable of inhibiting the growth of a cell, especially tumor, e.g., cancer cell, either in vitro or in vivo. A "growth inhibitory amount" of an anti-TAT antibody, TAT polypeptide, TAT binding oligopeptide or TAT binding organic molecule for purposes of inhibiting neoplastic cell growth may be determined empirically and in a routine manner.

A "cytotoxic amount" of an anti-TAT antibody, TAT polypeptide, TAT binding oligopeptide or TAT binding organic molecule is an amount capable of causing the destruction of a cell, especially tumor, e.g., cancer cell, either in vitro or in vivo. A "cytotoxic amount" of an anti-TAT antibody, TAT polypeptide, TAT binding oligopeptide or TAT binding organic molecule for purposes of inhibiting neoplastic cell growth may be determined empirically and in a routine manner.

The term "antibody" is used in the broadest sense and specifically covers, for example, single anti-TAT monoclonal antibodies (including agonist, antagonist, and neutralizing antibodies), anti-TAT antibody compositions with polyepitopic specificity, polyclonal antibodies, single chain anti-TAT antibodies, and fragments of anti-TAT antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the $\alpha$ and $\gamma$ chains and four $C_H$ domains for $\mu$ and $\epsilon$ isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology,* 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$, and $\mu$, respectively. The $\gamma$ and $\alpha$ classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a $\beta$-sheet configuration, connected by three hypervariable regions, which form loops connecting, and in some cases forming part of, the $\beta$-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation 4 Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette. The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol 293:865-881. If the on-rate exceeds $10^6$ $M^{-1}S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

In one embodiment, an "on-rate" or "rate of association" or "association rate" or "$k_{on}$" according to this invention is determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol 293:865-881. However, if the on-rate exceeds 10 $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the invention and the other associated with a reference/comparator antibody) such that one of skill in the art would consider the difference between the two values to be of statistical significance within the context of the biological characteristic measured by said values (e.g., Kd values, HAMA response). The difference between said two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

Antibodies of the present invention may be able to compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The "contact" hypervariable regions are based on an analysis of the available complex crystal structures. The residues from each of these hypervariable regions are noted below. Unless otherwise denoted, Kabat numbering will be employed. Hypervariable region locations are generally as follows: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3).

Hypervariable regions may also comprise "extended hypervariable regions" as follows: amino acids 24-36 (L1), and amino acids 46-56 (L2) in the VL. The variable domain residues are numbered according to Kabat et al., supra for each of these definitions.

"Framework" or "FR" residues are those variable domain residues other than the hypervariable region residues as herein defined.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it bind. Preferred blocking antibodies or antagonist antibodies substantially or completely inhibit the biological activity of the antigen.

A "TAT binding oligopeptide" is an oligopeptide that binds, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAT binding organic molecule" is an organic molecule other than an oligopeptide or antibody as defined herein that binds, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAT polypeptide" or a "growth inhibitory" antibody, oligopeptide or other organic molecule is one which results in measurable growth inhibition of cancer cells expressing or overexpressing the appropriate TAT polypeptide. The TAT polypeptide may be a transmembrane polypeptide expressed on the surface of a cancer cell or may be a polypeptide that is produced and secreted by a cancer cell. Preferred growth inhibitory anti-TAT antibodies, oligopeptides or organic molecules inhibit growth of TAT-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAT antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAT polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAT polypeptide, preferably a cell that overexpresses a TAT polypeptide as compared to a normal cell of the same tissue type. The TAT polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAT-expressing cell" is a cell which expresses an endogenous or transfected TAT polypeptide either on the cell surface or in a secreted form. A "TAT-expressing cancer" is a cancer comprising cells that have a TAT polypeptide present on the cell surface or that produce and secrete a TAT polypeptide. A "TAT-expressing cancer" optionally produces sufficient levels of TAT polypeptide on the surface of cells thereof, such that an anti-TAT antibody, oligopeptide ot other organic molecule can bind thereto and have a therapeutic effect with respect to the cancer. In another embodiment, a "TAT-expressing cancer" optionally produces and secretes sufficient levels of TAT polypeptide, such that an anti-TAT antibody, oligopeptide ot other organic molecule antagonist can bind thereto and have a therapeutic effect with respect to the cancer. With regard to the latter, the antagonist may be an antisense oligonucleotide which reduces, inhibits or prevents production and secretion of the secreted TAT polypeptide by tumor cells. A cancer which "overexpresses" a TAT polypeptide is one which has significantly higher levels of TAT polypeptide at the cell surface thereof, or produces and secretes, compared to a noncancerous cell of the same tissue type. Such overexpression may be caused by gene amplification or by increased transcription or translation. TAT polypeptide overexpression may be determined in a diagnostic or prognostic assay by evaluating increased levels of the TAT protein present on the surface of a cell, or secreted by the cell (e.g., via an immunohistochemistry assay using anti-TAT antibodies prepared against an isolated TAT polypeptide which may be prepared using recombinant DNA technology from an isolated nucleic acid encoding the TAT polypeptide; FACS analysis, etc.). Alternatively, or additionally, one may measure levels of TAT polypeptide-encoding nucleic acid or mRNA in the cell, e.g., via fluorescent in situ hybridization using a nucleic acid based probe corresponding to a TAT-encoding nucleic acid or the complement thereof; (FISH; see WO98/45479 published October, 1998), Southern blotting, Northern blotting, or polymerase chain reaction (PCR) techniques, such as real time quantitative PCR(RT-PCR). One may also study TAT polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell, especially a TAT-expressing cancer cell, either in vitro or in vivo. Thus, the growth inhibitory agent may be one which significantly reduces the percentage of TAT-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon -α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

```
/*
 *
 * C-C increased from 12 to 15
 * Z is average of EQ
 * B is average of ND
 * match with stop is _M; stop-stop = 0; J (joker) match = 0
 */
#define    _M        -8        /* value of a match with a stop */
int        _day[26][26] = {
/*      A B C D E F G H I J K L M N O P Q R S T U V W X Y Z */
/* A */     { 2, 0,-2, 0, 0,-4, 1,-1,-1, 0,-1,-2,-1, 0,_M, 1, 0,-2, 1, 1, 0, 0,-6, 0,-3, 0},
/* B */     { 0, 3,-4, 3, 2,-5, 0, 1,-2, 0, 0,-3,-2, 2,_M,-1, 1, 0, 0, 0, 0,-2,-5, 0,-3, 1},
/* C */     {-2,-4,15,-5,-5,-4,-3,-3,-2, 0,-5,-6,-5,-4,_M,-3,-5,-4, 0,-2, 0,-2,-8, 0, 0,-5},
/* D */     { 0, 3,-5, 4, 3,-6, 1, 1,-2, 0, 0,-4,-3, 2,_M,-1, 2,-1, 0, 0, 0,-2,-7, 0,-4, 2},
/* E */     { 0, 2,-5, 3, 4,-5, 0, 1,-2, 0, 0,-3,-2, 1,_M,-1, 2,-1, 0, 0, 0,-2,-7, 0,-4, 3},
/* F */     {-4,-5,-4,-6,-5, 9,-5,-2, 1, 0,-5, 2, 0,-4,_M,-5,-5,-4,-3,-3, 0,-1, 0, 0, 7,-5},
/* G */     { 1, 0,-3, 1, 0,-5, 5,-2,-3, 0,-2,-4,-3, 0,_M,-1,-1,-3, 1, 0, 0,-1,-7, 0,-5, 0},
/* H */     {-1, 1,-3, 1, 1,-2,-2, 6,-2, 0, 0,-2,-2, 2,_M, 0, 3, 2,-1,-1, 0,-2,-3, 0, 0, 2},
/* I */     {-1,-2,-2,-2,-2, 1,-3,-2, 5, 0,-2, 2, 2,-2,_M,-2,-2,-2,-1, 0, 0, 4,-5, 0,-1,-2},
/* J */     { 0, 0, 0, 0, 0, 0, 0, 0, 0, 0, 0, 0, 0, 0,_M, 0, 0, 0, 0, 0, 0, 0, 0, 0, 0, 0},
/* K */     {-1, 0,-5, 0, 0,-5,-2, 0,-2, 0, 5,-3, 0, 1,_M,-1, 1, 3, 0, 0, 0,-2,-3, 0,-4, 0},
/* L */     {-2,-3,-6,-4,-3, 2,-4,-2, 2, 0,-3, 6, 4,-3,_M,-3,-2,-3,-3,-1, 0, 2,-2, 0,-1,-2},
/* M */     {-1,-2,-5,-3,-2, 0,-3,-2, 2, 0, 0, 4, 6,-2,_M,-2,-1, 0,-2,-1, 0, 2,-4, 0,-2,-1},
/* N */     { 0, 2,-4, 2, 1,-4, 0, 2,-2, 0, 1,-3,-2, 2,_M,-1, 1, 0, 1, 0, 0,-2,-4, 0,-2, 1},
/* O */     {_M,_M,_M,_M,_M,_M,_M,_M,_M,_M,_M,_M,_M,_M, 0,_M,_M,_M,_M,_M,_M,_M,_M,_M,_M,_M},
/* P */     { 1,-1,-3,-1,-1,-5,-1, 0,-2, 0,-1,-3,-2,-1,_M, 6, 0, 0, 1, 0, 0,-1,-6, 0,-5, 0},
/* Q */     { 0, 1,-5, 2, 2,-5,-1, 3,-2, 0, 1,-2,-1, 1,_M, 0, 4, 1,-1,-1, 0,-2,-5, 0,-4, 3},
/* R */     {-2, 0,-4,-1,-1,-4,-3, 2,-2, 0, 3,-3, 0, 0,_M, 0, 1, 6, 0,-1, 0,-2, 2, 0,-4, 0},
/* S */     { 1, 0, 0, 0, 0,-3, 1,-1,-1, 0, 0,-3,-2, 1,_M, 1,-1, 0, 2, 1, 0,-1,-2, 0,-3, 0},
/* T */     { 1, 0,-2, 0, 0,-3, 0,-1, 0, 0, 0,-1,-1, 0,_M, 0,-1,-1, 1, 3, 0, 0,-5, 0,-3, 0},
/* U */     { 0, 0, 0, 0, 0, 0, 0, 0, 0, 0, 0, 0, 0, 0,_M, 0, 0, 0, 0, 0, 0, 0, 0, 0, 0, 0},
/* V */     { 0,-2,-2,-2,-2,-1,-1,-2, 4, 0,-2, 2, 2,-2,_M,-1,-2,-2,-1, 0, 0, 4,-6, 0,-2,-2},
/* W */     {-6,-5,-8,-7,-7, 0,-7,-3,-5, 0,-3,-2,-4,-4,_M,-6,-5, 2,-2,-5, 0,-6,17, 0, 0,-6},
/* X */     { 0, 0, 0, 0, 0, 0, 0, 0, 0, 0, 0, 0, 0, 0,_M, 0, 0, 0, 0, 0, 0, 0, 0, 0, 0, 0},
/* Y */     {-3,-3, 0,-4,-4, 7,-5, 0,-1, 0,-4,-1,-2,-2,_M,-5,-4,-4,-3,-3, 0,-2, 0, 0,10,-4},
/* Z */     { 0, 1,-5, 2, 3,-5, 0, 2,-2, 0, 0,-2,-1, 1,_M, 0, 3, 0, 0, 0, 0,-2,-6, 0,-4, 4}
};
/*
 */
#include <stdio.h>
#include <ctype.h>
#define MAXJMP        16        /* max jumps in a diag */
#define MAXGAP        24        /* don't continue to penalize gaps larger than this */
#define JMPS          1024      /* max jmps in an path */
#define MX            4         /* save if there's at least MX-1 bases since last jmp */
#define DMAT          3         /* value of matching bases */
#define DMIS          0         /* penalty for mismatched bases */
#define DINS0         8         /* penalty for a gap */
#define DINS1         1         /* penalty per base */
#define PINS0         8         /* penalty for a gap */
#define PINS1         4         /* penalty per residue */
struct jmp {
        short             n[MAXJMP];      /* size of jmp (neg for dely) */
        unsigned short    x[MAXJMP];      /* base no. of jmp in seq x */
};                                        /* limits seq to 2^16 -1 */
struct diag {
        int               score;          /* score at last jmp */
        long              offset;         /* offset of prev block */
        short             ijmp;           /* current jmp index */
        struct jmp        jp;             /* list of jmps */
};
struct path {
        int     spc;                      /* number of leading spaces */
        short   n[JMPS];/* size of jmp (gap) */
        int     x[JMPS];/* loc of jmp (last elem before gap) */
};
char            *ofile;                   /* output file name */
char            *namex[2];                /* seq names: getseqs( ) */
char            *prog;                    /* prog name for err msgs */
char            *seqx[2];                 /* seqs: getseqs( ) */
int             dmax;                     /* best diag: nw( ) */
int             dmax0;                    /* final diag */
int             dna;                      /* set if dna: main( ) */
int             endgaps;                  /* set if penalizing end gaps */
int             gapx, gapy;               /* total gaps in seqs */
int             len0, len1;               /* seq lens */
int             ngapx, ngapy;             /* total size of gaps */
int             smax;                     /* max score: nw( ) */
int             *xbm;                     /* bitmap for matching */
long            offset;                   /* current offset in jmp file */
```

TABLE 1-continued

```
struct  diag    *dx;                    /* holds diagonals */
struct  path    pp[2];                  /* holds path for seqs */
char            *calloc( ), *malloc( ), *index( ), *strcpy( );
char            *getseq( ), *g_calloc( );
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"
static  _dbval[26] = {
        1,14,2,13,0,0,4,11,0,0,12,0,3,15,0,0,0,5,6,8,8,7,9,0,10,0
};
static  _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)                                                    main
        int     ac;
        char    *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;                    /* 1 to penalize endgaps */
        ofile = "align.out";            /* output file */
        nw( );          /* fill in the matrix, get the possible jmps */
        readjmps( );    /* get the actual jmps */
        print( );       /* print stats, alignment */
        cleanup(0);     /* unlink any tmp files */}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                           nw
{
        char            *px, *py;       /* seqs and ptrs */
        int             *ndely, *dely;  /* keep track of dely */
        int             ndelx, delx;    /* keep track of delx */
        int             *tmp;           /* for swapping row0, row1 */
        int             mis;            /* score for each type */
        int             ins0, ins1;     /* insertion penalties */
        register        id;             /* diagonal index */
        register        ij;             /* jmp index */
        register        *col0, *col1;   /* score for curr, last row */
        register        xx, yy;         /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
```

TABLE 1-continued

```
            for (col0[0] = dely[0] = -ins0, yy = 1; yy <= len1; yy++) {
                    col0[yy] = dely[yy] = col0[yy-1] - ins1;
                    ndely[yy] = yy;
            }
            col0[0] = 0;         /* Waterman Bull Math Biol 84 */
    }
    else
            for (yy = 1; yy <= len1; yy++)
                    dely[yy] = -ins0;
/* fill in match matrix
 */
for (px = seqx[0], xx = 1; xx <= len0; px++, xx++) {
            /* initialize first entry in col
             */
            if (endgaps) {
                    if (xx == 1)
                            col1[0] = delx = -(ins0+ins1);
                    else
                            col1[0] = delx = col0[0] - ins1;
                    ndelx = xx;
            }
            else {
                    col1[0] = 0;
                    delx = -ins0;
                    ndelx = 0;
            }
                                                                                ...nw
    for (py = seqx[1], yy = 1; yy <= len1; py++, yy++) {
            mis = col0[yy-1];
            if (dna)
                    mis += (xbm[*px-'A']&xbm[*py-'A'])? DMAT : DMIS;
            else
                    mis += __day[*px-'A'][*py-'A'];
            /* update penalty for del in x seq;
             * favor new del over ongong del
             * ignore MAXGAP if weighting endgaps
             */
            if (endgaps || ndely[yy] < MAXGAP) {
                    if (col0[yy] - ins0 >= dely[yy]) {
                            dely[yy] = col0[yy] - (ins0+ins1);
                            ndely[yy] = 1;
                    } else {
                            dely[yy] -= ins1;
                            ndely[yy]++;
                    }
            } else {
                    if (col0[yy] - (ins0+ins1) >= dely[yy]) {
                            dely[yy] = col0[yy] - (ins0+ins1);
                            ndely[yy] = 1;
                    } else
                            ndely[yy]++;
            }
            /* update penalty for del in y seq;
             * favor new del over ongong del
             */
            if (endgaps || ndelx < MAXGAP) {
                    if (col1[yy-1] - ins0 >= delx) {
                            delx = col1[yy-1] - (ins0+ins1);
                            ndelx = 1;
                    } else {
                            delx -= ins1;
                            ndelx++;
                    }
            } else {
                    if (col1[yy-1] - (ins0+ins1) >= delx) {
                            delx = col1[yy-1] - (ins0+ins1);
                            ndelx = 1;
                    } else
                            ndelx++;
            }
            /* pick the maximum score; we're favoring
             * mis over any del and delx over dely
             */
                                                                                ...nw
            id = xx - yy + len1 - 1;
            if (mis >= delx && mis >= dely[yy])
                    col1[yy] = mis;
            else if (delx >= dely[yy]) {
                    col1[yy] = delx;
                    ij = dx[id].ijmp;
```

TABLE 1-continued

```
				if (dx[id].jp.n[0] && (!dna || (ndelx >= MAXJMP
				&& xx > dx[id].jp.x[ij]+MX) || mis > dx[id].score+DINS0)) {
					dx[id].ijmp++;
					if (++ij >= MAXJMP) {
						writejmps(id);
						ij = dx[id].ijmp = 0;
						dx[id].offset = offset;
						offset += sizeof(struct jmp) + sizeof(offset);
					}
				}
				dx[id].jp.n[ij] = ndelx;
				dx[id].jp.x[ij] = xx;
				dx[id].score = delx;
			}
			else {
				col1[yy] = dely[yy];
				ij = dx[id].ijmp;
if (dx[id].jp.n[0] && (!dna || (ndely[yy] >= MAXJMP
				&& xx > dx[id].jp.x[ij]+MX) || mis > dx[id].score+DINS0)) {
					dx[id].ijmp++;
					if (++ij >= MAXJMP) {
						writejmps(id);
						ij = dx[id].ijmp = 0;
						dx[id].offset = offset;
						offset += sizeof(struct jmp) + sizeof(offset);
					}
				}
				dx[id].jp.n[ij] = −ndely[yy];
				dx[id].jp.x[ij] = xx;
				dx[id].score = dely[yy];
			}
			if (xx == len0 && yy < len1) {
				/* last col
				 */
				if (endgaps)
					col1[yy] −= ins0+ins1*(len1−yy);
				if (col1[yy] > smax) {
					smax = col1[yy];
					dmax = id;
				}
			}
		}
		if (endgaps && xx < len0)
			col1[yy−1] −= ins0+ins1*(len0−xx);
		if (col1[yy−1] > smax) {
			smax = col1[yy−1];
			dmax = id;
		}
		tmp = col0; col0 = col1; col1 = tmp;			}
(void) free((char *)ndely);
(void) free((char *)dely);
(void) free((char *)col0);
(void) free((char *)col1);				}
/*
 *
 * print( ) -- only routine visible outside this module
 *
 * static:
 * getmat( ) -- trace back best path, count matches: print( )
 * pr__align( ) -- print alignment of described in array p[ ]: print( )
 * dumpblock( ) -- dump a block of lines with numbers, stars: pr__align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC		3
#define P__LINE	256		/* maximum output line */
#define P__SPC	3		/* space between name or num and seq */
extern	__day[26][26];
int		olen;			/* set output line length */
FILE	*fx;			/* output file */
print( )													print
{
		int		lx, ly, firstgap, lastgap;		/* overlap */
		if ((fx = fopen(ofile, "w")) == 0) {
			fprintf(stderr,"%s: can't write %s\n", prog, ofile);
			cleanup(1);
		}
```

TABLE 1-continued

```
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 − 1) {              /* leading gap in x */
                pp[0].spc = firstgap = len1 − dmax − 1;
                ly −= pp[0].spc;
        }
        else if (dmax > len1 − 1) {         /* leading gap in y */
                pp[1].spc = firstgap = dmax − (len1 − 1);
                lx −= pp[1].spc;
        }
        if (dmax0 < len0 − 1) {             /* trailing gap in x */
                lastgap = len0 − dmax0 −1;
                lx −= lastgap;
        }
        else if (dmax0 > len0 − 1) {        /* trailing gap in y */
                lastgap = dmax0 − (len0 − 1);
                ly −= lastgap;
        }
        getmat(lx, ly, firstgap, lastgap);
        pr__align( );           }
/*
 * trace back the best path, count matches
 */
static
getmat(lx, ly, firstgap, lastgap)                                              getmat
        int         lx, ly;                     /* "core" (minus endgaps) */
        int         firstgap, lastgap;          /* leading trailing overlap */
{
        int                 nm, i0, i1, siz0, siz1;
        char                outx[32];
        double              pct;
        register            n0, n1;
        register char       *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0−−;
                }
                else if (siz1) {
                        p0++;
                        n0++;
                        siz1−−;
                }
                else {
                        if (xbm[*p0−'A']&xbm[*p1−'A'])
                                nm++;
                        if (n0++ == pp[0].x[i0])
                                siz0 = pp[0].n[i0++];
                        if (n1++ == pp[1].x[i1])
                                siz1 = pp[1].n[i]++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx); ...getmat
```

TABLE 1-continued

```
        if (gapx) {
                (void) sprintf(outx, " (%d %s%s)",
                        ngapx, (dna)? "base":"residue", (ngapx == 1)? "":"s");
                fprintf(fx,"%s", outx);
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
 * print alignment of described in struct path pp[ ]
 */
static
pr_align( )                                                             pr_align
{
        int             nn;     /* char count */
        int             more;
        register        i;
        for (i = 0, lmax = 0; i < 2; i++) {
                nn = stripname(namex[i]);
                if (nn > lmax)
                        lmax = nn;
                nc[i] = 1;
                ni[i] = 1;
                siz[i] = ij[i] = 0;
                ps[i] = seqx[i];
                po[i] = out[i];                 }
        for (nn = nm = 0, more = 1; more; ) {                           ...pr_align
                for (i = more = 0; i < 2; i++) {
                        /*
                         * do we have more of this sequence?
                         */
                        if (!*ps[i])
                                continue;
                        more++;
                        if (pp[i].spc) {        /* leading space */
                                *po[i]++ = ' ';
                                pp[i].spc--;
                        }
                        else if (siz[i]) {      /* in a gap */
                                *po[i]++ = '-';
                                siz[i]--;
                        }
                        else {                  /* we're putting a seq element
                                                 */
                                *po[i] = *ps[i];
                                if (islower(*ps[i]))
                                        *ps[i] = toupper(*ps[i]);
                                po[i]++;
                                ps[i]++;
                                /*
                                 * are we at next gap for this seq?
                                 */
```

TABLE 1-continued

```
				if (ni[i] == pp[i].x[ij[i]]) {
					/*
					 * we need to merge all gaps
					 * at this location
					 */
					siz[i] = pp[i].n[ij[i]++];
					while (ni[i] == pp[i].x[ij[i]])
						siz[i] += pp[i].n[ij[i]++];
				}
				ni[i]++;
			}
		}
		if (++nn == olen || !more && nn) {
			dumpblock( );
			for (i = 0; i < 2; i++)
				po[i] = out[i];
			nn = 0;
		}
	}
}
/*
 * dump a block of lines, including numbers, stars: pr_align( )
 */
static
dumpblock( )                                                    dumpblock
{
	register i;
	for (i = 0; i < 2; i++)
		*po[i]-- = '\0';
                                                                ...dumpblock
	(void) putc('\n', fx);
	for (i = 0; i < 2; i++) {
		if (*out[i] && (*out[i] != ' ' || *(po[i]) != ' ')) {
			if (i == 0)
				nums(i);
			if (i == 0 && *out[1])
				stars( );
			putline(i);
			if (i == 0 && *out[1])
				fprintf(fx, star);
			if (i == 1)
				nums(i);
		}
	}
}
/*
 * put out a number line: dumpblock( )
 */
static
nums(ix)                                                        nums
	int	ix;	/* index in out[ ] holding seq line */
{
	char		nline[P_LINE];
	register	i, j;
	register char	*pn, *px, *py;
	for (pn = nline, i = 0; i < lmax+P_SPC; i++, pn++)
		*pn = ' ';
	for (i = nc[ix], py = out[ix]; *py; py++, pn++) {
		if (*py == ' ' || *py == '-')
			*pn = ' ';
		else {
			if (i%10 == 0 || (i == 1 && nc[ix] != 1)) {
				j = (i < 0)? -i : i;
				for (px = pn; j; j /= 10, px--)
					*px = j%10 + '0';
				if (i < 0)
					*px = '-';
			}
			else
				*pn = ' ';
			i++;
		}
	}
	*pn = '\0';
	nc[ix] = i;
	for (pn = nline; *pn; pn++)
		(void) putc(*pn, fx);
	(void) putc('\n', fx);
}
/*
```

TABLE 1-continued

```
 * put out a line (name, [num], seq, [num]): dumpblock( )
 */
static
putline(ix)                                                                putline
        int     ix;                 {
                                                                         ..putline
        int             i;
        register char   *px;
        for (px = namex[ix], i = 0; *px && *px != ':'; px++, i++)
                (void) putc(*px, fx);
        for (; i < lmax+P_SPC; i++)
                (void) putc(' ', fx);
        /* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock( )
 */
static
stars( )                                                                   stars
{
        int             i;
        register char   *p0, *p1, cx, *px;
        if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';
        for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
/*
 * strip path or prefix from pn, return len: pr_align( )
 */
static
stripname(pn)                                                              stripname
        char    *pn;    /* file name (may be path) */
{
        register char   *px, *py;
        py = 0;
        for (px = pn; *px; px++)
                if (*px == '/')
                        py = px + 1;
        if (py)
                (void) strcpy(pn, py);
        return(strlen(pn));
}
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char    *jname = "/tmp/homgXXXXXX";             /* tmp file for jmps */
FILE    *fj;
int     cleanup( );                             /* cleanup tmp file */
```

TABLE 1-continued

```
long        lseek( );
/*
 * remove any tmp file if we blow
 */
cleanup(i)                                                              cleanup
            int         i;
{
            if (fj)
                        (void) unlink(jname);
            exit(i);
}
/*
 * read, return.ptr to seq, set dna, len, maxlen
 * skip lines starting with ';', '<', or '>'
 * seq in upper or lower case
 */
char        *
getseq(file, len)                                                       getseq
            char        *file;      /* file name */
            int         *len;       /* seq len */
{
            char                    line[1024], *pseq;
            register char           *px, *py;
            int                     natgc, tlen;
            FILE                    *fp;
            if ((fp = fopen(file,"r")) == 0) {
                        fprintf(stderr,"%s: can't read %s\n", prog, file);
                        exit(1);
            }
            tlen = natgc = 0;
            while (fgets(line, 1024, fp)) {
                        if (*line == ';' || *line == '<' || *line == '>')
                                    continue;
                        for (px = line; *px != '\n'; px++)
                                    if (isupper(*px) || islower(*px))
                                                tlen++;
            }
            if ((pseq = malloc((unsigned)(tlen+6))) == 0) {
                        fprintf(stderr,"%s: malloc( ) failed to get %d bytes for %s\n", prog, tlen+6, file);
                        exit(1);
            }
            pseq[0] = pseq[1] = pseq[2] = pseq[3] = '\0';
                                                                        ...getseq
            py = pseq + 4;
            *len = tlen;
            rewind(fp);
            while (fgets(line, 1024, fp)) {
                        if (*line == ';' || *line == '<' || *line == '>')
                                    continue;
                        for (px = line; *px != '\n'; px++) {
                                    if (isupper(*px))
                                                *py++ = *px;
                                    else if (islower(*px))
                                                *py++ = toupper(*px);
                                    if (index("ATGCU",*(py-1)))
                                                natgc++;
                        }
            }
            *py++ = '\0';
            *py = '\0';
            (void) fclose(fp);
            dna = natgc > (tlen/3);
            return(pseq+4);
}
char        *
g_calloc(msg, nx, sz)                                                   g_calloc
            char        *msg;                   /* program, calling routine */
            int         nx, sz;                 /* number and size of elements */
{
            char                    *px, *calloc( );
            if ((px = calloc((unsigned)nx, (unsigned)sz)) == 0) {
                        if (*msg) {
                                    fprintf(stderr, "%s: g_calloc( ) failed %s (n=%d, sz=%d)\n", prog, msg, nx, sz);
                                    exit(1);
                        }
            }
            return(px);
}
/*
 * get final jmps from dx[ ] or tmp file, set pp[ ], reset dmax: main( )
```

TABLE 1-continued

```
 */
readjmps( )                                                              readjmps
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                                                                      ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1;               }
                        else
                                break;          }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {          /* gap in second seq */
                                pp[1].n[i1] = -siz;
                                xx += siz;
                                /* id = xx - yy + len1 - 1                  */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {   /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
        /* reverse the order of jmps */
        for (j = 0, i0--; j < i0; j++, i0--) {
                i = pp[0].n[j]; pp[0].n[j] = pp[0].n[i0]; pp[0].n[i0] = i;
                i = pp[0].x[j]; pp[0].x[j] = pp[0].x[i0]; pp[0].x[i0] = i;
        }
        for (j = 0, i1--; j < i1; j++, i1--) {
                i = pp[1].n[j]; pp[1].n[j] = pp[1].n[i1]; pp[1].n[i1] = i;
                i = pp[1].x[j]; pp[1].x[j] = pp[1].x[i1]; pp[1].x[i1] = i;
        }
        if (fd >= 0)
                (void) close(fd);
        if (fj) {
                (void) unlink(jname);
                fj = 0;
                offset = 0;
        }                               }
/*
 * write a filled jmp struct offset of the prev one (if any): nw( )
 */
writejmps(ix)                                                           writejmps
        int     ix;
{
        char    *mktemp( );
```

TABLE 1-continued

```
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| TAT | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the TAT polypeptide) = 5 divided by 15 = 33.3%

TABLE 3

| | | |
|---|---|---|
| TAT | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the TAT polypeptide) = 5 divided by 10 = 50%

TABLE 4

| | | |
|---|---|---|
| TAT-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 6 divided by 14 = 42.9%

TABLE 5

| | | |
|---|---|---|
| TAT-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 4 divided by 12 = 33.3%

II. Compositions and Methods of the Invention

A. Anti-TAT Antibodies

In one embodiment, the present invention provides anti-TAT antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.,* 133:3001 (1984); and Brodeur et al.,

*Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Pluckthun, *Immunol. Revs.* 130: 151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352: 624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-TAT antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAT protein as described herein. Other such antibodies may combine a TAT binding site with a binding site for another protein. Alternatively, an anti-TAT arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAT-expressing cell. Bispecific antibodies may also be used to localize cytotoxic agents to cells which express TAT. These antibodies possess a TAT-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-Fc-γRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain (s) comprise two or more variable domains. For instance, the polypeptide chain(s) may comprise VD1-$(X1)_n$-VD2-$(X2)_n$—Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-TAT antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866;

4,424,219; 4,450,254; 4,362,663; and 4,371,533, the disclosures of which are hereby expressly incorporated by reference.

Maytansinoid-antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAT Polypeptide Antibody-maytansinoid Conjugates (Immunoconjugates)

Anti-TAT antibody-maytansinoid conjugates are prepared by chemically linking an anti-TAT antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0425235B1, Chari et al., *Cancer Research* 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (i.e., MMAE and MMAF), disclosed in "Senter et al, Proceedings of the American Association for Cancer Research, Volume 45, Abstract Number 623, presented Mar. 28, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J. Chem. Soc. Perkin Trans.* 15:859-863; and Doronina (2003) *Nat Biotechnol* 21(7):778-784.

Calicheamicin

Another immunoconjugate of interest comprises an anti-TAT antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAT antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAT antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-11, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Alternatively, a fusion protein comprising the anti-TAT antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAT antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. TAT Binding Oligopeptides

TAT binding oligopeptides of the present invention are oligopeptides that bind, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., Cancer Research, 58(15): 3209-3214 (1998); Jiang et al., Infection & Immunity, 65(11): 4770-4777 (1997); Ren et al., Gene, 195(2):303-311 (1997); Ren, Protein Sci., 5: 1833 (1996); Efimov et al., Virus Genes, 10: 173 (1995)) and T7 phage display systems (Smith and Scott, Methods in Enzymology, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAT Binding Organic Molecules

TAT binding organic molecules are organic molecules other than oligopeptides or antibodies as defined herein that bind, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAT binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAT Antibodies, TAT Binding Oligopeptides and TAT Binding Organic Molecules With the Desired Properties Techniques for generating antibodies, oligopeptides and organic molecules that bind to TAT polypeptides have been described above. One may further select antibodies, oligopeptides or other organic molecules with certain biological characteristics, as desired.

The growth inhibitory effects of an anti-TAT antibody, oligopeptide or other organic molecule of the invention may be assessed by methods known in the art, e.g., using cells which express a TAT polypeptide either endogenously or following transfection with the TAT gene. For example, appropriate tumor cell lines and TAT-transfected cells may treated with an anti-TAT monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-TAT antibody, TAT binding oligopeptide or TAT binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a TAT polypeptide. Preferably, the anti-TAT antibody, TAT binding oligopeptide or TAT binding organic molecule will inhibit cell proliferation of a TAT-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1-10 days after exposure of the tumor cells to the antibody. The antibody is growth inhibitory in vivo if administration of the anti-TAT antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an anti-TAT antibody, TAT binding oligopeptide or TAT binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAT polypeptide-expressing tumor cells are incubated with medium alone or medium containing the appropriate anti-TAT antibody (e.g, at about 10 μg/ml), TAT binding oligopeptide or TAT binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-TAT antibodies, TAT binding oligopeptides or TAT binding organic molecules that induce statistically significant levels of cell death as determined by PI uptake may be selected as cell death-inducing anti-TAT antibodies, TAT binding oligopeptides or TAT binding organic molecules.

To screen for antibodies, oligopeptides or other organic molecules which bind to an epitope on a TAT polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-TAT antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAT polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-TAT antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Full-Length TAT Polypeptides

The present invention also provides newly identified and isolated nucleotide sequences encoding polypeptides referred to in the present application as TAT polypeptides. In particular, cDNAs (partial and full-length) encoding various TAT polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAT polypeptides and encoding nucleic acids described herein, in some cases, Applicants have identified what is believed to be the reading frame best identifiable with the sequence information available at the time.

G. Anti-TAT Antibody and TAT Polypeptide Variants

In addition to the anti-TAT antibodies and full-length native sequence TAT polypeptides described herein, it is contemplated that anti-TAT antibody and TAT polypeptide variants can be prepared. Anti-TAT antibody and TAT polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-TAT antibody or TAT polypeptide, such as changing the number or position of glycosylation sites or altering the membrane anchoring characteristics.

Variations in the anti-TAT antibodies and TAT polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAT antibody or TAT polypeptide. Guidance in determining which amino acid residue may be inserted, substituted or deleted without adversely affecting the desired activity may be found by comparing the sequence of the anti-TAT antibody or TAT polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAT antibody and TAT polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAT antibody or TAT polypeptide.

Anti-TAT antibody and TAT polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAT antibody and TAT polypeptide fragments share at least one biological and/or immunological activity with the native anti-TAT antibody or TAT polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser, Ala | Ser |
| Gln (Q) | Asn; Glu | Asn |
| Glu (E) | Asp, Gln | Asp |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-TAT antibody or TAT polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the anti-TAT antibody or TAT polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

Any cysteine residue not involved in maintaining the proper conformation of the anti-TAT antibody or TAT polypeptide also may be substituted, generally with serine, to improve the oxidative stability of the molecule and prevent aberrant crosslinking. Conversely, cysteine bond(s) may be added to the anti-TAT antibody or TAT polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAT polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAT antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAT antibody.

H. Modifications of Anti-TAT Antibodies and TAT Polypeptides

Covalent modifications of anti-TAT antibodies and TAT polypeptides are included within the scope of this invention. One type of covalent modification includes reacting targeted amino acid residues of an anti-TAT antibody or TAT polypeptide with an organic derivatizing agent that is capable of reacting with selected side chains or the N- or C-terminal residues of the anti-TAT antibody or TAT polypeptide. Derivatization with bifunctional agents is useful, for instance, for crosslinking anti-TAT antibody or TAT polypeptide to a water-insoluble support matrix or surface for use in the method for purifying anti-TAT antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the anti-TAT antibody or TAT polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAT antibody or TAT polypeptide (either by removing the underlying glycosylation site or by deleting the glycosylation by chemical and/or enzymatic means), and/or adding one or more glycosylation sites that are not present in the native sequence anti-TAT antibody or TAT polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-TAT antibody or TAT polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-TAT antibody or TAT polypeptide (for O-linked glycosylation sites). The anti-TAT antibody or TAT polypeptide amino acid sequence may optionally be altered through changes at the DNA level, particularly by mutating the DNA encoding the anti-TAT antibody or TAT polypeptide at preselected bases such that codons are generated that will translate into the desired amino acids.

Another means of increasing the number of carbohydrate moieties on the anti-TAT antibody or TAT polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem*., pp. 259-306 (1981).

Removal of carbohydrate moieties present on the anti-TAT antibody or TAT polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of anti-TAT antibody or TAT polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-TAT antibody or TAT polypeptide of the present invention may also be modified in a way to form chimeric molecules comprising an anti-TAT antibody or TAT polypeptide fused to another, heterologous polypeptide or amino acid sequence.

In one embodiment, such a chimeric molecule comprises a fusion of the anti-TAT antibody or TAT polypeptide with a tag polypeptide which provides an epitope to which an anti-tag antibody can selectively bind. The epitope tag is generally placed at the amino- or carboxyl-terminus of the anti-TAT antibody or TAT polypeptide. The presence of such epitope-tagged forms of the anti-TAT antibody or TAT polypeptide can be detected using an antibody against the tag polypeptide. Also, provision of the epitope tag enables the anti-TAT antibody or TAT polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the anti-TAT antibody or TAT polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAT antibody or TAT polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

I. Preparation of Anti-TAT Antibodies and TAT Polypeptides

The description below relates primarily to production of anti-TAT antibodies and TAT polypeptides by culturing cells transformed or transfected with a vector containing anti-TAT antibody- and TAT polypeptide-encoding nucleic acid. It is, of course, contemplated that alternative methods, which are well known in the art, may be employed to prepare anti-TAT antibodies and TAT polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.,* 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAT antibody or TAT polypeptide may be chemically synthesized separately and combined using chemical or enzymatic methods to produce the desired anti-TAT antibody or TAT polypeptide.

1. Isolation of DNA Encoding Anti-TAT Antibody or TAT Polypeptide

DNA encoding anti-TAT antibody or TAT polypeptide may be obtained from a cDNA library prepared from tissue believed to possess the anti-TAT antibody or TAT polypeptide mRNA and to express it at a detectable level. Accordingly, human anti-TAT antibody or TAT polypeptide DNA can be conveniently obtained from a cDNA library prepared from human tissue. The anti-TAT antibody- or TAT polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-TAT antibody or TAT polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAT antibody or TAT polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT $kan^r$; *E. coli* W3110 strain 37D6, which has the complete genotype tonA ptr3 phoA E15 (argF-lac) 169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TAT antibody- or TAT polypeptide-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244, 234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs*, 269 (1982).

Suitable host cells for the expression of glycosylated anti-TAT antibody or TAT polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-TAT antibody or TAT polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAT antibody or TAT polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAT may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAT antibody- or TAT polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-TAT antibody- or TAT polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the anti-TAT antibody- or TAT polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding anti-TAT antibody or TAT polypeptide.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAT antibody or TAT polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAT antibody or TAT polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAT antibody or TAT polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAT antibody or TAT polypeptide.

Still other methods, vectors, and host cells suitable for adaptation to the synthesis of anti-TAT antibody or TAT polypeptide in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the anti-TAT antibody or TAT polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102: 255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAT polypeptide or against a synthetic peptide based on the DNA sequences provided herein or against exogenous sequence fused to TAT DNA and encoding a specific antibody epitope.

6. Purification of Anti-TAT Antibody and TAT Polypeptide

Forms of anti-TAT antibody and TAT polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAT antibody and TAT polypeptide can be disrupted by various physical or chemical means, such as freeze-thaw cycling, sonication, mechanical disruption, or cell lysing agents.

It may be desired to purify anti-TAT antibody and TAT polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAT antibody and TAT polypeptide. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular anti-TAT antibody or TAT polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$ or $\gamma 4$ heavy chains (Lindmark et al., *J. Immunol. Meth.* 62:1-13 (1983)). Protein G is recommended for all mouse isotypes and for human $\gamma 3$ (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAT antibodies, TAT binding oligopeptides, TAT binding organic molecules and/or TAT polypeptides used in accordance with the present invention are prepared for storage by mixing the antibody, polypeptide, oligopeptide or organic molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAT antibody, TAT binding oligopeptide, or TAT binding organic molecule, it may be desirable to include in the one formulation, an additional antibody, e.g., a second anti-TAT antibody which binds a different epitope on the TAT polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Diagnosis and Treatment with Anti-TAT Antibodies, TAT Binding Oligopeptides and TAT Binding Organic Molecules To determine TAT expression in the cancer, various diagnostic assays are available. In one embodiment, TAT polypeptide overexpression may be analyzed by immunohistochemistry (IHC). Parrafin embedded tissue sections from a tumor biopsy may be subjected to the IHC assay and accorded a TAT protein staining intensity criteria as follows:

Score 0— no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAT polypeptide expression may be characterized as not overexpressing TAT, whereas those tumors with 2+ or 3+ scores may be characterized as overexpressing TAT.

Alternatively, or additionally, FISH assays such as the INFORM® (sold by Ventana, Arizona) or PATHVISION® (Vysis, Illinois) may be carried out on formalin-fixed, paraffin-embedded tumor tissue to determine the extent (if any) of TAT overexpression in the tumor.

TAT overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAT antibodies, oligopeptides and organic molecules of the invention have various non-therapeutic applications. The anti-TAT antibodies, oligopeptides and organic molecules of the present invention can be useful for diagnosis and staging of TAT polypeptide-expressing cancers (e.g., in radioimaging). The antibodies, oligopeptides and organic molecules are also useful for purification or immunoprecipitation of TAT polypeptide from cells, for detection and quantitation of TAT polypeptide in vitro, e.g., in an ELISA or a Western blot, to kill and eliminate TAT-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAT antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAT antibodies, oligopeptides and organic molecules of the invention are useful to alleviate TAT-expressing cancers upon initial diagnosis of the disease or during relapse. For therapeutic applications, the anti-TAT antibody, oligopeptide or organic molecule can be used alone, or in combination therapy with, e.g., hormones, antiangiogens, or radiolabelled compounds, or with surgery, cryotherapy, and/or radiotherapy. Anti-TAT antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAT antibody, oligopeptide or organic molecule in conjunction with treatment with the one or more of the preceding chemotherapeutic agents. In particular, combination therapy with palictaxel and modified derivatives (see, e.g., EP0600517) is contemplated. The anti-TAT antibody, oligopeptide or organic molecule will be administered with a therapeutically effective dose of the chemotherapeutic agent. In another embodiment, the anti-TAT antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAT antibody, oligopeptide or organic molecule conjugated with a cytotoxic agent is administered to the patient. Preferably, the immunoconjugate bound to the TAT protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAT antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-TAT antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAT antibody or antibodies, oligopeptides or organic molecules, with administration of an antibody directed against another tumor antigen associated with the particular cancer.

In another embodiment, the therapeutic treatment methods of the present invention involves the combined administration of an anti-TAT antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAT antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAT antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 μg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAT antibody. However, other dosage regimens may be useful. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The anti-TAT antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAT antibodies of the invention are also contemplated, specifically including the in vivo tumor targeting and any cell proliferation inhibition or cytotoxic characteristics.

Methods of producing the above antibodies are described in detail herein.

The present anti-TAT antibodies, oligopeptides and organic molecules are useful for treating a TAT-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding. The antibody, oligopeptide or organic molecule is able to bind to at least a portion of the cancer cells that express TAT polypeptide in the mammal. In a preferred embodiment, the antibody, oligopeptide or organic molecule is effective to destroy or kill TAT-expressing tumor cells or inhibit the growth of such tumor cells, in vitro or in vivo, upon binding to TAT polypeptide on the cell. Such an antibody includes a naked anti-TAT antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAT antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAT antibody, oligopeptide or organic molecule of the invention, and a carrier. For the purposes of treating cancer, compositions can be administered to the patient in need of such treatment, wherein the composition can comprise one or more anti-TAT antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAT antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAT antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAT polypeptide-expressing cancer or alleviating one or more symptoms of the cancer in a mammal, comprising administering a therapeutically effective amount of an anti-TAT antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAT polypeptide-expressing cell.

The invention also provides kits and articles of manufacture comprising at least one anti-TAT antibody, oligopeptide or organic molecule. Kits containing anti-TAT antibodies, oligopeptides or organic molecules find use, e.g., for TAT cell killing assays, for purification or immunoprecipitation of TAT polypeptide from cells. For example, for isolation and purification of TAT, the kit can contain an anti-TAT antibody, oligopeptide or organic molecule coupled to beads (e.g., sepharose beads). Kits can be provided which contain the antibodies, oligopeptides or organic molecules for detection and quantitation of TAT in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAT expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAT antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAT-expressing cell killing assays, for purification or immunoprecipitation of TAT polypeptide from cells. For isolation and purification of TAT polypeptide, the kit can contain an anti-TAT antibody, oligopeptide or organic molecule coupled to beads (e.g., sepharose beads). Kits can be provided which contain the antibodies, oligopeptides or organic molecules for detection and quantitation of TAT polypeptide in vitro, e.g., in an ELISA or a Western blot. As with the article of manufacture, the kit comprises a container and a label or package insert on or associated with the container. The container holds a composition comprising at least one anti-TAT antibody, oligopeptide or organic molecule of the invention. Additional containers may be included that contain, e.g., diluents and buffers, control antibodies. The label or package insert may provide a description of the composition as well as instructions for the intended in vitro or diagnostic use.

M. Uses for TAT Polypeptides and TAT-Polypeptide Encoding Nucleic Acids

Nucleotide sequences (or their complement) encoding TAT polypeptides have various applications in the art of molecular biology, including uses as hybridization probes, in chromosome and gene mapping and in the generation of anti-sense RNA and DNA probes. TAT-encoding nucleic acid will also be useful for the preparation of TAT polypeptides by the recombinant techniques described herein, wherein those TAT polypeptides may find use, for example, in the preparation of anti-TAT antibodies as described herein.

The full-length native sequence TAT gene, or portions thereof, may be used as hybridization probes for a cDNA library to isolate the full-length TAT cDNA or to isolate still other cDNAs (for instance, those encoding naturally-occurring variants of TAT or TAT from other species) which have a desired sequence identity to the native TAT sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAT. By way of example, a screening method will comprise isolating the coding region of the TAT gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TAT gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAT-encoding nucleic acids include antisense or sense oligonucleotides comprising a singe-stranded nucleic acid sequence (either RNA or DNA) capable of binding to target TAT mRNA (sense) or TAT DNA (antisense) sequences. Antisense or sense oligonucleotides, according to the present invention, comprise a fragment of the coding region of TAT DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAT proteins, wherein those TAT proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAT proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to C, alkenyl and alkynyl. Particularly preferred are $O[(CH_2)_nO]_mCH_3$, $O(CH_2)_nOCH_3$, $O(CH_2)_nNR_2$, $O(CH_2)_nCH_3$, $O(CH_2)_nONH_2$, and $O(CH_2)_nON[(CH_2)_nCH_3)]_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy ($2'-O—CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., $2'-O—CH_2—O—CH_2—N(CH_2)$.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne $(—CH_2—)_n$ group bridging the 2' oxygen atom and the 4' carbon atom wherein n is 1 or 2. LNAs and preparation thereof are described in WO 98/39352 and WO 99/14226.

Other preferred modifications include 2'-methoxy ($2'-O—CH_3$), 2'-aminopropoxy ($2'-OCH_2CH_2CH_2$ $NH_2$), 2'-allyl ($2'-CH_2—CH═CH_2$), 2'-O-allyl ($2'-O—CH_2—CH═CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C≡C—CH_3$ or $—CH_2—C≡CH$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCTSA, DCTSB and DCTSC (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAT coding sequences.

Nucleotide sequences encoding a TAT can also be used to construct hybridization probes for mapping the gene which encodes that TAT and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAT encode a protein which binds to another protein (example, where the TAT is a receptor), the TAT can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAT can be used to isolate correlative ligand(s). Screening assays can be designed to find lead compounds that mimic the biological activity of a native TAT or a receptor for TAT. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode TAT or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAT can be used to clone genomic DNA encoding TAT in accordance with established techniques and the genomic sequences used to generate transgenic animals that contain cells which express DNA encoding TAT. Methods for generating transgenic animals, particularly animals such as mice or rats, have become conventional in the art and are described, for example, in U.S. Pat. Nos. 4,736,866 and 4,870,009. Typically, particular cells would be targeted for TAT transgene incorporation with tissue-specific enhancers. Transgenic animals that include a copy of a transgene encoding TAT introduced into the germ line of the animal at an embryonic stage can be used to examine the effect of increased expression of DNA encoding TAT. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAT can be used to construct a TAT "knock out" animal which has a defective or altered gene encoding TAT as a result of homologous recombination between the endogenous gene encoding TAT and altered genomic DNA encoding TAT introduced into an embryonic stem cell of the animal. For example, cDNA encoding TAT can be used to clone genomic DNA encoding TAT in accordance with established techniques. A portion of the genomic DNA encoding TAT can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAT polypeptide.

Nucleic acid encoding the TAT polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the TAT polypeptides or fragments thereof described herein are useful for chromosome identification. In this regard, there exists an ongoing need to identify new chromosome markers, since relatively few chromosome marking reagents, based upon actual sequence data are presently available. Each TAT nucleic acid molecule of the present invention can be used as a chromosome marker.

The TAT polypeptides and nucleic acid molecules of the present invention may also be used diagnostically for tissue typing, wherein the TAT polypeptides of the present invention may be differentially expressed in one tissue as compared to another, preferably in a diseased tissue as compared to a normal tissue of the same tissue type. TAT nucleic acid molecules will find use for generating probes for PCR, Northern analysis, Southern analysis and Western analysis.

This invention encompasses methods of screening compounds to identify those that mimic the TAT polypeptide (agonists) or prevent the effect of the TAT polypeptide (antagonists). Screening assays for antagonist drug candidates are designed to identify compounds that bind or complex with the TAT polypeptides encoded by the genes identified herein, or otherwise interfere with the interaction of the encoded polypeptides with other cellular proteins, including e.g., inhibiting the expression of TAT polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAT polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAT polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAT polypeptide and drying. Alternatively, an immobilized antibody, e.g., a monoclonal antibody, specific for the TAT polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAT polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GALA, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAT polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAT polypeptide may be added to a cell along with the compound to be screened for a particular activity and the ability of the compound to inhibit the activity of interest in the presence of the TAT polypeptide indicates that the compound is an antagonist to the TAT polypeptide. Alternatively, antagonists may be detected by combining the TAT polypeptide and a potential antagonist with membrane-bound TAT polypeptide receptors or recombinant receptors under appropriate conditions for a competitive inhibition assay. The TAT polypeptide can be labeled, such as by radioactivity, such that the number of TAT polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the TAT polypeptide and a cDNA library created from this RNA is divided into pools and used to transfect COS cells or other cells that are not responsive to the TAT polypeptide. Transfected cells that are grown on glass slides are exposed to labeled TAT polypeptide. The TAT polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAT polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAT polypeptide in the presence of the candidate compound. The ability of the compound to enhance or block this interaction could then be measured.

More specific examples of potential antagonists include an oligonucleotide that binds to the fusions of immunoglobulin with TAT polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAT polypeptide that recognizes the receptor but imparts no effect, thereby competitively inhibiting the action of the TAT polypeptide.

Another potential TAT polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAT polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the TAT polypeptide. The antisense RNA oligonucleotide hybridizes to the mRNA in vivo and blocks translation of the mRNA molecule into the TAT polypeptide (antisense—Okano, *Neurochem.,* 56:560 (1991); *Oligodeoxynucleotides*

*as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the TAT polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAT polypeptide, thereby blocking the normal biological activity of the TAT polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAT polypeptide-encoding nucleic acid can be used herein for recombinantly producing TAT polypeptide using techniques well known in the art and as described herein. In turn, the produced TAT polypeptides can be employed for generating anti-TAT antibodies using techniques well known in the art and as described herein.

Antibodies specifically binding a TAT polypeptide identified herein, as well as other molecules identified by the screening assays disclosed hereinbefore, can be administered for the treatment of various disorders, including cancer, in the form of pharmaceutical compositions.

If the TAT polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al, *Proc. Natl. Acad. Sci. USA,* 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly and detectably upregulated in a particular human tumor tissue(s) of interest as compared to other human tumor(s) and/or normal human tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following molecule(s) exhibit a tissue expression profile showing high tissue expression and significant and reproducibly detectable upregulation of expression in a specific human tumor or tumors as compared to other human tumor(s) and/or normal human tissues and optionally relatively low expression in normal essential and/or normal proliferating human tissues.

Using the expression analysis described above, it was determined that mRNA encoding the TAT10772 polypeptide is significantly, reproducibly and detectably overexpressed in certain types of human cancerous ovarian, breast and pancreatic tumors as compared to the corresponding normal human ovarian, breast and pancreatic tissues, respectively.

A. Ovary

In a first experiment, expression of TAT10772 was analyzed in a group of 89 independent normal human ovarian tissue samples. The results of these analyses demonstrated that the level of TAT10772 mRNA expression in all of the normal human ovarian tissue samples analyzed was remarkably consistent and fell within a very tight distribution, with no normal human ovarian tissue sample evidencing greater than a 6-fold increase in TAT10772 expression as compared to the mean level of TAT10772 expression for the group of samples as a whole.

For purposes of quantitative comparison, a variety of independent and different types of cancerous human ovarian tissue samples were also analyzed for TAT10772 expression. The results obtained from these analyses demonstrated that the level of expression of TAT10772 in the cancerous samples was quite variable, with a significant number of the cancerous samples showing an at least 6-fold (to as high as an about 580-fold) increase in TAT10772 expression when compared to the mean level of TAT10772 expression for the group of normal ovarian tissue samples analyzed. More specifically, detectable and reproducible TAT10772 overexpression was observed for the following ovarian cancer types as compared to normal ovarian (wherein the numbers shown in parentheses for each cancer type represent the number of independent samples that exhibited at least a 6-fold increase in TAT10772 expression when compared to the mean level of TAT10772 expression for the group of normal ovarian tissue samples analyzed/the total number of independent tumor samples analyzed): endometrioid adenocarcinoma (13/17), serous cystadenocarcinoma, including papillary (52/57), and clear cell adenocarcinoma (7/10). Additional experiments were conducted which confirmed these results.

B. Breast

In another experiment, expression of TAT10772 was analyzed in a group of 22 independent normal human breast tissue samples. The results of these analyses demonstrated that the level of TAT10772 mRNA expression in all of the normal human breast tissue samples analyzed was remarkably consistent and fell within a very tight distribution, with no normal human breast tissue sample evidencing greater than a 2-fold increase in TAT10772 expression as compared to the mean level of TAT10772 expression for the group of samples as a whole.

For purposes of quantitative comparison, 209 independent human HER-2 negative infiltrating ductal carcinomas of the breast tissue samples were also analyzed for TAT10772 expression. The results obtained from these analyses demonstrated that the level of expression of TAT10772 in the cancerous samples was quite variable, with 76 of the 209 samples tested showing at least a 2-fold (to as high as an about 15-fold) increase in TAT10772 expression when compared to the mean level of TAT10772 expression for the group of normal breast tissue samples analyzed.

C. Pancreas

In another experiment, expression of TAT10772 was analyzed in a group of 51 independent normal human pancreas tissue samples. The results of these analyses demonstrated that the level of TAT10772 mRNA expression in all of the normal human pancreas tissue samples analyzed was remarkably consistent and fell within a very tight distribution, with no normal human pancreas tissue sample evidencing greater than a 2-fold increase in TAT10772 expression as compared to the mean level of TAT10772 expression for the group of samples as a whole.

For purposes of quantitative comparison, 65 independent human pancreatic adenocarcinoma tissue samples were also analyzed for TAT10772 expression. The results obtained from these analyses demonstrated that the level of expression of TAT10772 in the cancerous samples was quite variable, with 33 of the 65 samples tested showing at least a 2-fold (to as high as an about 21-fold) increase in TAT10772 expression when compared to the mean level of TAT10772 expression for the group of normal pancreas tissue samples analyzed.

Given the above, the TAT10772 polypeptide, and the nucleic acid encoding that polypeptide, are excellent targets which can be exploited for quantitatively and qualitatively determining the expression level of the TAT10772 polypeptide, and the mRNA encoding it, in various mammalian tissue samples, thereby allowing one to make quantitative and qualitative comparisons therebetween. Therefore, the TAT10772 polypeptide, and the nucleic acid encoding that polypeptide, are molecules whose unique expression profile can be exploited for the diagnosis of certain types of cancerous tumors in mammals as described above. Moreover, as this analysis demonstrates that the TAT10772 polypeptide is significantly, reproducibly and detectably overexpressed in certain human tumors as compared to their corresponding normal human tissues, the TAT10772 polypeptide serves as an excellent target that can be exploited for the therapeutic treatment of such tumors in mammals.

Example 2

Microarray Analysis to Detect Upregulation of TAT Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for TAT polypeptide expression. Additionally, cancerous human tumor tissue from any of a variety of different human tumors was obtained and compared to a “universal” epithelial control sample which was prepared by pooling non-cancerous human tissues of epithelial origin, including liver, kidney, and lung. mRNA isolated from the pooled epithelial tissues represents a mixture of expressed gene products from various different epithelial tissues, thereby providing an excellent negative control against which to quantitatively compare gene expression levels in tumors of epithelial origin. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described TAT polypeptide-encoding nucleic acid sequences were used in the creation of the microarray and RNA from various tumor tissues were used for the hybridization thereto. A value based upon the normalized ratio:experimental ratio was designated as a "cutoff ratio". Only values that were above this cutoff ratio were determined to be significant. Significance of ratios were estimated from the amount of noise or scatter associated with each experiment, but typically, a ratio cutoff of 1.8 fold-2 fold or greater was used to identify candidate genes relatively overexpressed in tumor samples compared to the corresponding normal tissue and/or the pooled normal epithelial universal control. Ratios for genes identified in this way as being relatively overexpressed in tumor samples varied from 2 fold to 40 fold, or even greater. By comparison, in a control experiment in which the same RNA was labeled in each color and hybridized against itself, for virtually all genes with signals above background, the observed ratio is significantly less than 1.8 fold. This indicates that experimental noise above a ratio of 1.8 fold is extremely low, and that an observed fold change of 1.8 fold or greater is significant and is expected to represent a real, detectably and reproducible difference in expression between the samples analyzed and compared.

The results of these experiments demonstrated that mRNA encoding the TAT10772 polypeptide is significantly overexpressed (i.e., at least 2-fold) in 8 of 10 independent human ovarian tumor samples tested when compared to both normal human ovarian tissue and the pooled epithelial control sample. These data also demonstrate that the observed overexpression is significant, detectable and reproducible across multiple human ovarian tumor samples when compared to both normal counterpart human ovarian samples as well as the pooled human epithelial control sample. As described above, these data demonstrate that the TAT10772 polypeptide of the present invention, and the encoding nucleic acid, are useful not only as diagnostic markers for the presence of human ovarian tumors, but also serve as potential therapeutic targets for the treatment of those tumors in humans.

Example 3

Quantitative Analysis of TAT mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative and quantitative interpretation of the data. This assay is well known and routinely used in the art to quantitatively identify gene expression differences between two different human tissue samples, see, e.g., Higuchi et al., *Biotechnology* 10:413-417 (1992); Livak et al., *PCR Methods Appl.,* 4:357-362 (1995); Heid et al., *Genome Res.* 6:986-994 (1996); Pennica et al., *Proc. Natl. Acad. Sci. USA* 95(25):14717-14722 (1998); Pitti et al., *Nature* 396 (6712):699-703 (1998) and Bieche et al., *Int. J. Cancer* 78:661-666 (1998).

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested. Frequently, tumor sample(s) are directly compared to "matched" normal sample(s) of the same tissue type, meaning that the tumor and normal sample(s) are obtained from the same individual.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively and quantitatively measure the relative fold increase in mRNA expression between two or more different tissues. In this regard, it is well accepted in the art that this assay is sufficiently technically sensitive to reproducibly detect an at least 2-fold increase in mRNA expression in a human tumor sample relative to a normal control.

Using this technique, it was determined that mRNA encoding the TAT10772 polypeptide is significantly and reproducibly overexpressed (i.e., at least 2-fold) in 9 of 10 independent human ovarian tumor samples when compared to both normal human ovarian samples from different human tissue donors as well as various "matched" normal human ovarian tumor samples derived from the same human tissue donor as from which the tumor sample(s) was derived. As described above, therefore, these data demonstrate that the TAT10772 polypeptide of the present invention, and the encoding nucleic acid, are useful not only as diagnostic markers for the presence of human ovarian tumors, but also serve as potential therapeutic targets for the treatment of those tumors in humans.

Example 4

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer 1.0 µl DTT (100 mM)

2.0 µl NTP mix (2.5 mM: 10µ; each of 10 mM GTP, CTP & ATP+10 µl $H_2O$)

1.0 µl UTP (50 µM)

1.0 µl Rnasin 1.0 µl DNA template (1 µg)

1.0 µl $H_2O$ 1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µL of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ $H_2O$). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-embedded Sections

The slides were deparaffinized, placed in SQ $H_2O$, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization $1.0\times10^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, VF=4L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

With regard to expression of TAT10772 in normal human tissues, strong expression is observed in bronchial mucosa and submucous glands. However, all other normal human tissues tested are negative for TAT10772 expression. In contrast, strong TAT10772 expression is observed in 13 of 15 human ovarian tumors (adenocarcinoma and surface epithelial tumors) tested. Additionally, strong TAT10772 expression is also observed in 8 of 9 human uterine adenocarcinomas.

Example 5

Preparation of Antibodies that Bind TAT10772

This example illustrates preparation of monoclonal antibodies which can specifically bind TAT10772.

Techniques for producing the monoclonal antibodies are known in the art and are described, for instance, in Goding, supra. Immunogens that may be employed include purified TAT, fusion proteins containing TAT, and cells expressing recombinant TAT on the cell surface. Selection of the immunogen can be made by the skilled artisan without undue experimentation.

Mice, such as Balb/c, are immunized with the TAT immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAT antibodies.

After a suitable antibody titer has been detected, the animals "positive" for antibodies can be injected with a final intravenous injection of TAT. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against TAT. Determination of "positive" hybridoma cells secreting the desired monoclonal antibodies against TAT is within the skill in the art.

The positive hybridoma cells can be injected intraperitoneally into syngeneic Balb/c mice to produce ascites containing the anti-TAT monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Using the above described technique, 11 separate and distinct hybridoma cell lines have been generated, each of which produce monoclonal antibodies that bind to the TAT10772 polypeptide. These 11 hybridoma cell lines are herein referred to as 16F7.1.15 (producing monoclonal antibody 16F7), 17A8.1.3 (producing monoclonal antibody 17A8), 9F3.1.3 (producing monoclonal antibody 9F3), 16E12.2.15 (producing monoclonal antibody 16E12), 16A7.1.3 (producing monoclonal antibody 16A7), 10G11.1.1 (producing monoclonal antibody 10G11), 5B10 (producing monoclonal antibody 5B10), 11D10.1.14 (producing monoclonal antibody 11D11), 5F6.1.24 (producing monoclonal antibody 5F6), 7G6.2.6 (producing monoclonal antibody 7G6), and 3A5.3 (producing monoclonal antibody 3A5.3). The monoclonal antibodies produced by these 11 hybridoma lines have been shown to bind to the TAT10772 polypeptide using well-known and routinely employed techniques such as Western blot, ELISA analysis, FACS sorting analysis of cells expressing the TAT10772 polypeptide and/or immunohistochemistry analysis. Of the 11 hybridoma lines that produce functional anti-TAT10772 monoclonal antibodies, two (hybridoma clones 11D10.1.14 and 3A5.3) have been deposited under the terms of the Budapest Treaty with the American Tissue Type Collection, Manassas, Va. as described in further detail below.

Example 6

Competitive Binding Analyses and Epitope Mapping

The TAT10772 epitopes bound by the monoclonal antibodies described were determined by standard competitive binding analysis (Fendly et al., *Cancer Research* 50:1550-1558 (1990)). Cross-blocking studies were done on antibodies by direct fluorescence on intact PC3 cells engineered to express TAT10772 using the PANDEX™Screen Machine to quantitate fluorescence. Each monoclonal antibody was conjugated with fluorescein isothiocyanate (FITC), using established procedures (Wofsy et al., *Selected Methods in Cellular Immunology*, p. 287, Mishel and Schiigi (eds.) San Francisco: W.J. Freeman Co. (1980)). Confluent monolayers of TAT10772-expressing PC3 cells were trypsinized, washed once, and resuspended at $1.75\times10^6$ cell/ml in cold PBS containing 0.5% bovine serum albumin (BSA) and 0.1% $NaN_3$. A final concentration of 1% latex particles (IDC, Portland, Oreg.) was added to reduce clogging of the PANDEX™ plate membranes. Cells in suspension, 20111, and 20 µl of purified monoclonal antibodies (100 µg/ml to 0.1 µg/ml) were added to the PANDEX™ plate wells and incubated on ice for 30 minutes. A predetermined dilution of FITC-labeled monoclonal antibodies in 20 µl was added to each well, incubated for 30 minutes, washed, and the fluorescence was quantitated by the PANDEX™ Screen Machine. Monoclonal antibodies were considered to share an epitope if each blocked binding of the other by 40% or greater in comparison to an irrelevant monoclonal antibody control and at the same antibody concentration. In this experiment, monoclonal antibodies 16F7, 17A8, 9F3, 16E12, 16A7, 10G11, 5B10, 11D10, 5F6, 7G6, and 3A5 were assigned TAT10772 epitopes B, B, B, B, B, B, A, B, B, C, and D, respectively. Using this assay, one of ordinary skill in the art can identify other monoclonal antibodies that bind to the same epitope as those described above.

Deletion analysis was also conducted to identify the approximate location in the polypeptide sequence shown as SEQ ID NO:2 of the above described antigenic epitopes. These analyses demonstrated that TAT10772 antigenic epitope A is found between amino acids 6471-6560 of SEQ ID NO:2, TAT10772 antigenic epitope B is found between amino acids 6389-6470 of SEQ ID NO:2, TAT10772 antigenic epitope C is found between amino acids 6663-6806 of SEQ ID NO:2, and TAT10772 antigenic epitope D is found between amino acids 3765-6397 of SEQ ID NO:2 (which comprises approximately seventeen 150 amino acid mucin-like repeat sequences and, therefore, most likely comprises multiple similar antigenic epitope sites). Polypeptides comprising any of these specifically identified antigenic epitope sites (and nucleic acid molecules encoding those polypeptides) are encompassed within the present invention.

In a separate experiment, it was demonstrated that the binding of monoclonal antibody to 3A5 to OVCAR-3, OVCA-432 and SK-OV-3 cells as determined by standard flow cytometry analyses parallels the expression level of TAT10772 mRNA expressed in each of these three specific cell lines as determined by standard quantitative PCR analyses. More specifically, as determined by standard quantitative PCR analysis, OVCAR-3, OVCA-432 and SK-OV-3 cells express a high, moderate and low level of TAT10772 mRNA, respectively. When monoclonal antibody 3A5 was employed in standard flow cytometry analyses to quantitate the ability of 3A5 to bind to these cells, it was observed that 3A5 binding quantitatively parallels the relative amount of TAT10772 mRNA present in those cell lines. These data suggest that the amount of TAT10772 mRNA in any particular cell type is quantitatively determinative of the amount of TAT10772 polypeptide expressed by that cell type and, in turn, is determinative of the ability of any specific anti-TAT10772 antibody to bind to that cell type.

Example 7

Immunohistochemistry Analysis

Antibodies against TAT10772 were prepared as described above and immunohistochemistry analysis was performed using the monoclonal antibodies 3A5 and 11D10 as follows. Tissue sections were first fixed for 5 minutes in acetone/ethanol (frozen or paraffin-embedded). The sections were then washed in PBS and then blocked with avidin and biotin (Vector kit) for 10 minutes each followed by a wash in PBS. The sections were then blocked with 10% serum for 20 minutes and then blotted to remove the excess. A primary antibody was then added to the sections at a concentration of 10 μg/ml for 1 hour and then the sections were washed in PBS. A biotinylated secondary antibody (anti-primary antibody) was then added to the sections for 30 minutes and then the sections were washed with PBS. The sections were then exposed to the reagents of the Vector ABC kit for 30 minutes and then the sections were washed in PBS. The sections were then exposed to Diaminobenzidine (Pierce) for 5 minutes and then washed in PBS. The sections were then counterstained with Mayers hematoxylin, covered with a coverslip and visualized. Immunohistochemistry analysis can also be performed as described in Sambrook et al., *Molecular Cloning: A Laboratory Manual*, New York: Cold Spring Harbor Press, 1989 and Ausubel et al., *Current Protocols of Molecular Biology*, Unit 3.16, John Wiley and Sons (1997).

The results from these analyses demonstrate that monoclonal antibody 11D10 does not detectably bind to any of the following normal human tissues: aorta, brain, colon, liver, kidney, small intestine, stomach, lung (both alveolar and bronchial tissue), testis, spleen thyroid, ovarian, uterine, urothelium and placenta. However, 6 of 13 independent human ovarian adenocarcinoma samples and 1 of 7 independent human endometrial adenocarcinoma samples show strong binding to antibody 11D10. Moreover, in a separate experiment, antibody 11D10 binds strongly to 1 of 9 human mucinous adenocarcinoma tumor samples, 13 of 22 human endometrioid adenocarcinoma tumor samples, 17 of 26 human serous cystadenocarcinoma tumor samples and 3 of 8 human clear cell tumor samples.

Moreover, the results from these analyses demonstrate that monoclonal antibody 3A5, like monoclonal antibody 11D10, does not detectably bind to any of the above listed normal human tissues. However, antibody 3A5 binds strongly to 2 of 2 independent human ovarian adenocarcinomas (membranous staining), 16 of 20 human endometrioid adenocarcinoma tumor samples, 24 of 25 human serous cystadenocarcinoma tumor samples and 5 of 10 human clear cell tumor samples.

Example 8

Monoclonal Antibody 3A5 is Internalized Upon Binding to TAT10772 Polypeptide on Cells This experiment demonstrates that monoclonal antibody 3A5 becomes internalized into cells to which it binds TAT10772 polypeptide on the cell surface. Specifically, OVCAR-3 cells were incubated for 18 hours with monoclonal antibody 3A5 and fluorescent dextran and then cell-associated 3A5 was quantitatively detected with a fluorescein-labeled anti-3A5 antibody. These analyses demonstrated that antibody 3A5 colocalizes with dextran, indicating trafficking of the 3A5 antibody into subcellular components of the incubated cells, including the lysosomal compartments of these cells.

Example 9

Humanization of Murine Monoclonal Antibodies

This example demonstrates the applicability of the method of CDR-repair for humanization of murine antibodies 11D10 and 3A5 directed against TAT10772.

Three forms of TAT10772 were used during the humanization process. The human TAT10772 shed antigen, CA125, encompasses of the entire shed antigen and was purchased from US Biological C0050-10. The TAT10772-stalk consists of the last, most C-terminal mucin domain and the following C-terminal sequence leading to the predicted transmembrane region (amino acids 6282-6979 of SEQ ID NO:2). 5-domain TAT10772 (amino acids 4471-5171 of SEQ ID NO:2) is a recombinant portion of the extracellular domain encoding 5 mucin domains plus the C-terminal sequence leading to the predicted transmembrane region. The MUC16-stalk and the 5-mucin domain were expressed in CHO cells and purified by conventional means.

Residue numbers are according to Kabat (Kabat et al., Sequences of proteins of immunological interest, 5th Ed., Public Health Service, National Institutes of Health, Bethesda, Md. (1991)). Single letter amino acid abbreviations are used. DNA degeneracies are represented using the IUB code (N=A1C/G1T, D=A/G/T, V=A/C/G, B=C/G/T, H=A/C/T, K=G/T, M=A/C, R=A/G, S=G/C, W=A/T, Y=C/T).

Cloning of Murine 11D10 and 3A5 Variable Domains and Generation of Chimeric 11D10 and 3A5 Antibodies Total RNA was extracted from hybridoma cells producing 11D10 or 3A5 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. Amplified VL and VH were cloned into mammalian expression vectors. The polynucleotide sequence of the inserts was determined using routine sequencing methods. The 11D10 VL (mu11D10-L) and VH (mu11D10-H) amino acid sequences are shown in FIGS. 3 and 4, respectively (SEQ ID NOS:4 and 7, respectively); the 3A5 VL (mu3A5-L) and VH (mu3A5-H) amino acid sequences are shown in FIGS. 5 and 6, respectively (SEQ ID NOS:9 and 11, respectively). HVR regions according to Kabat numbering are shown in bold font in FIGS. 3-6.

Direct Hypervariable Region Grafts onto the Acceptor Human Consensus Framework

The phagemid used for this work is a monovalent Fab-g3 display vector and consists of 2 open reading frames under control of the phoA promoter. The first open reading frame consists of the stII signal sequence fused to the VL and CH1 domains of the acceptor light chain and the second consists of the stII signal sequence fused to the VH and CH1 domains of the acceptor heavy chain followed by the minor phage coat protein P3.

The VL and VH domains from the murine 11D10 and 3A5 antibodies were aligned with the human VL kappa I (huKI; SEQ ID NO:3) and human VH subgroup III (huIII; SEQ ID NO:6) consensus sequences. To make the HVR grafts, hypervariable regions from the murine antibodies were grafted into the huKI and huIII acceptor frameworks. For 3A5, two acceptor VH frameworks were tested (designated herein as 3A5.L and 3A5.F, respectively) differing only at amino acid position 78 (see FIGS. 6A-B).

Hypervariable regions from murine 11D10 and 3A5 antibodies were engineered into the acceptor human consensus framework to generate the direct HVR-grafts, 11D10-graft, 3A5.L-graft and 3A5.F-graft. In the VL domain the following regions were grafted to the human consensus acceptor: positions 24-34 (HVR-L1), 49-56 (HVR-L2) and 89-97 (HVR-L3). In the VH domain, positions 26-35A (HVR-H1), 49-65

(HVR-H2) and 93-102 (HVR-H3) were grafted (FIGS. 3 through 6). MacCallum et al. (MacCallum et al. J. Mol. Biol. 262: 732-745 (1996)) have analyzed antibody and antigen complex crystal structures and found position 49 of the light chain and positions 49, 93 and 94 of the heavy chain are part of the contact region thus it seems reasonable to include these positions in the definition of HVR-L2, HVR-H2 and HVR-H3 when humanizing antibodies.

The direct-graft variants were generated by Kunkel mutagenesis using a separate oligonucleotide for each hypervariable region. Correct clones were assessed by DNA sequencing.

Randomization of the Hypervariable Regions

For each grafted antibody, sequence diversity was introduced separately into each hypervariable region using a soft randomization strategy (SR libraries) that maintains a bias towards the murine hypervariable region sequence. This was accomplished using a poisoned oligonucleotide synthesis strategy first described by Gallop et al., J. Med. Chem. 37:1233-1251 (1994). For a given position within a hypervariable region to be mutated, the codon encoding the wild-type amino acid is poisoned with a 70-10-10-10 mixture of nucleotides resulting in an average 50 percent mutation rate at each position.

Soft randomized oligonucleotides were patterned after the murine hypervariable region sequences and encompassed the same regions defined by the direct hypervariable region grafts. The amino acid position at the beginning of H2 (position 49) in the VH domain, was limited in sequence diversity to A, G, S or T by using the codon RGC.

In addition to the soft randomization libraries outlined above, each position in each hypervariable region of 3A5.L-graft and 3A5.F-graft was fully randomized to all possible 20 amino acids using oligonucleotides encoding NNS. This was accomplished in 2 types of libraries. In the first, multiple libraries were made each consisting of 20 members having a single position located within one of the hypervariable regions of 3A5 fully randomized. To cover each position in the hypervariable regions, 63 libraries of this type were generated and combined into a pooled "single position library" (SP library) encompassing single mutations located throughout each hypervariable position. The second library introduced all 20 amino acids into all positions (FR library) within a single hypervariable region at the same time. For both of these library types there were 6 libraries each encompassing a separate hypervariable region of the 3A5.L-graft or 3A5.F-graft.

To avoid reselecting the wild type CDR grafted sequence, a stop codon (TAA) was introduced in the middle of each HVR by Kunkel mutagenesis resulting in 6 different templates for each graft (11D10-graft, 3A5.L-graft and 3A5.F-graft) each with a stop codon introduced into a different HVR. When generating the SR, FR and SP libraries, randomized oligonucleotides were used to introduce diversity as well as to repair the stop codon in the corresponding template. For 3A5 libraries, a mixture of 3A5.L and 3A5.F templates was used during the construction of each library. All 3 types of libraries were generated for humanization of 3A5, while only the SR library was generated for humanization of 11D10.

Generation of Phage Libraries

Randomized oligonucleotide pools designed to introduce diversity into each hypervariable region as outlined above, were phosphorylated separately in 20 μl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C.

To generate the SR and FR libraries each phosphorylated oligonucleotide pool directed to introduce diversity into a single HVR was combined with 20 μg of Kunkel template containing the corresponding stop codon. The reaction was performed in 50 mM Tris pH 7.5, 10 mM $MgCl_2$ in a final volume of 500 μl resulting in a oligonucleotide to template ratio of 3. The mixture was annealed at 90° C. for 4 min, 50° C. for 5 min and then cooled on ice. The annealed template (250 μl) was then filled in by adding 1 μl 100 mM ATP, 10 μl 25 mM dNTPs (25 mM each of dATP, dCTP, dGTP and dTTP), 15 μl 100 mM DTT, 25 μl 10× TM buffer (0.5 M Tris pH 7.5, 0.1 M $MgCl_2$), 2400 U T4 ligase, and 30 U T7 polymerase for 3 hours at room temperature. The filled in product was then cleaned-up and electroporated into SS320 cells and propagated in the presence of M13/KO7 helper phage as described by Sidhu et al., Methods in Enzymology 328:333-363 (2000). Library sizes ranged from 1-2×$10^9$ independent clones. Random clones from the initial libraries were sequenced to assess library quality.

Multiple (63) standard Kunkel mutagenesis reactions were performed in a 96-well PCR plate to generate the 3A5 SP libraries. From the phosphorylated oligonucleotides reactions (above), 2 μl was added to 300 ng Kunkel template containing the corresponding stop codon in 50 mM Tris pH 7.5, 10 mM $MgCl_2$ in a final volume of 10 μl. The mixture was annealed at 90° C. for 2 min, 50° C. for 5 min and then cooled on ice. The annealed template was then filled in by adding 0.5 μl 10 mM ATP, 0.5 μl 10 mM dNTPs (10 mM each of dATP, dCTP, dGTP and dTTP), 1 μl 100 mM DTT, 1 μl 10× TM buffer (0.5 M Tris pH 7.5, 0.1 M $MgCl_2$), 80 U T4 ligase, and 4 U T7 polymerase in a total volume of 20 μl for 2 h at room temperature. These filled in and ligated products were then each transformed into XL1-blue cells, grown in 0.5 ml of 2YT containing 5 μg/ml of tetracycline and M13/KO7 helper phage (MOI 10) for 2 hr at 37° C. and then pooled and transferred to 500 ml 2YT containing 50 μg/ml carbenacillin and grown 16 h at 37° C.

Phage Selection

For the phage selections outlined below, TAT10772-stalk (2 μg/ml), CA125 (17 μg/ml), 5-domain TAT10772 (2 μg/ml) or neutravidin (2 μg/ml) were immobilized in PBS on on MaxiSorp microtiter plates (Nunc) overnight at 4° C. Plates were blocked for at least 1 h using Casein Blocker (Pierce). Phage were harvested from the culture supernatant and suspended in PBS containing 1% BSA and 0.05% Tween 20 (PBSBT). Following phage selection, as outlined below, microtiter wells were washed extensively with PBS containing 0.05% Tween 20 (PBST) and bound phage were eluted by incubating the wells with 100 mM HCl for 30 min. Phage were neutralized with 1 M Tris, pH 8 and amplified using XL1-Blue cells and M13/KO7 helper phage and grown overnight at 37° C. in 2YT, 50 μg/ml carbenacillin. The titers of phage eluted from a target containing well were compared to titers of phage recovered from a non-target containing well to assess enrichment.

The solution sorting method has been described (Fuh et al. J. Mol. Biol. (2004)) and enables the selection of faster on-rates through a control of biotinylated target concentration and slower off-rates resulting from competition with unlabeled target. TAT10772-stalk and 5-domain TAT10772 were biotinylated using Sulfo-NHS-LC-biotin (Pierce).

The TAT10772-stalk was used as a phage target for the humanization of 11D10. The TAT10772-stalk was immobilized directly on MaxiSorp microtiter plates (Nunc) at 2 ug/ml in PBS for the first round of phage selection. Successive rounds of selection used a soluble selection method (Fuh et al. J. Mol. Biol. (2004)). Biotinylated-TAT10772-stalk was first incubated with the phage library for 1 hr, followed by a 5' min capture of the bound phage on a neutravidin-coated plate. Excess unlabeled TAT10772-stalk (greater than 100 nM) was added prior to the capture step for increasing lengths of time to increase selection stringency. The following table summarizes the conditions that were used for solution-panning the 11D10 libraries.

| Selection Round | [Biotinylated TAT10772-stalk] | Incubation with excess TAT10772-stalk |
|---|---|---|
| 2 | 10 nM | 20 min at 25° C. |
| 3 | 10 nM | 6.5 hr at 25° C. |
| 4 | 10 nM | 88.5 hr at 25° C. |
| 5 | 1 nM | 48 hr at 25° C., then 52 hr at 37° C. |

CA125 and 5-domain TAT10772 were used as a phage targets for the humanization of 3A5. Libraries were sorted individually for the first round of selection against immobilized 5-domain TAT10772 (2 μg/ml in PBS) or CA125 (17 μg/ml in PBS) that was coated on Nunc MaxiSorp microtitre plates. Following amplification, the libraries were pooled according to their library type (FR/SR/SP) and whether they were panned against CA125 or 5-domain TAT10772 and sorted for an additional 2 rounds against their respective immobilized targets. Three successive rounds of selection were performed by continued panning against the immobilized targets or by selection against soluble biotinylated 5-domain TAT10772 using a solution sorting strategy (Fuh et al. J. Mol. Biol. (2004)). For the solution sorting method, phage libraries were incubated with 1 nM biotinylated 5-domain TAT10772 for 1 hr followed by the addition of an excess of unlabeled 5-domain TAT10772 (greater than 100 nM) for up to 22 hrs to increase selection stringency. Phage bound to the biotinylated 5-domain TAT10772 were captured briefly (5 min) using a neutravidin-coated plate.

TAT10772-stalk Phage ELISA

MaxiSorp microtiter plates were coated with TAT10772-stalk at 2 μg/ml in PBS over night and then blocked with Casein Blocker. Phage from culture supernatants were incubated with serially diluted TAT10772-stalk in PBST containing 1% BSA in a tissue culture microtiter plate for 1 h after which 80 μl of the mixture was transferred to the target coated wells for 15 min to capture unbound phage. The plate was washed with PBST and HRP conjugated anti-M13 (Amersham Pharmacia Biotech) was added (1:5000 in PBSBT) for 40 min. The plate was washed with PBST and developed by adding Tetramethylbenzidine substrate (Kirkegaard and Perry Laboratories, Gaithersburg, Md.). The absorbance at 450 nm was plotted as a function of target concentration in solution to determine an IC50. This was used as an affinity estimate for the Fab clone displayed on the surface of the phage.

Fab and IgG Production and Affinity Determination

To express Fab protein for affinity measurements, a stop codon was introduced between the heavy chain and g3 in the phage display vector. Clones were transformed into *E. coli* 34B8 cells and grown in Complete C.R.A.P. media at 30° C. (Presta et al. Cancer Res. 57: 4593-4599 (1997)). Cells were harvested by centrifugation, suspended in PBS, 100 uM PMSF, 100 uM benzamidine, 2.5 mM EDTA and broken open using a microfluidizer. Fab was purified with Protein G affinity chromatography.

Affinity determinations were performed by surface plasmon resonance using a BIAcore™-2000. Either ~500 RU of 5-domain TAT10772 or ~300 RU IgG was immobilized in 10 mM Sodium Acetate pH 4.8 on a CM5 sensor chip and serial 2-fold dilutions of the corresponding binding partner (1-100 mM) in PBST were injected at a flow rate of 20 μl/min. Each sample was analyzed with 5-minute association and 10-minute dissociation. After each injection the chip was regenerated using 10 mM Glycine pH 1.5. Binding response was corrected by subtracting the RU from a blank flow cell. A 1:1 Languir model of simultaneous fitting of $k_{on}$ and $k_{off}$ was used for kinetics analysis.

Humanization of 11D10

The human acceptor framework used for humanization of 11D10 consists of the consensus human kappa I VL domain and a variant of the human subgroup III consensus VH domain. The VL and VH domains of murine 11D10 were each aligned with the human kappa I and subgroup III domains; each complementarity determining region (CDR) was identified and grafted into the human acceptor framework to generate an HVR graft that could be displayed as an Fab on phage (FIGS. 3 and 4). When phage displaying the 11D10 HVR graft were tested for binding to immobilized CA125, phage binding was observed. When the 11D10 HVR graft sequence was expressed as a Fab, Biacore analysis also evidenced binding to CA125.

A SR library was generated for 11D10 in which each HVR was soft randomized individually. The 6 SR libraries were each panned separately against immobilized TAT10772-stalk for 5 rounds of selection. Enrichment was observed beginning after round 3 and following round 5, clones were picked for DNA sequence analysis. Sequence changes targeting each of the HVRs were observed. Clones were screened using the anti-TAT10772 phage ELISA. Select clones were expressed as Fab for further analysis by Biacore. Several clones were reformatted as IgG for Scatchard analysis. FACS analysis using OVCAR-3 cells demonstrated that all 11D10 humanized antibodies tested were capable of effectively FACS sorting said cells. From these results it is clear that there are multiple sequence changes that can repair the affinity of 11D10 grafted onto a human framework and that this antibody can be humanized by CDR-repair to generate affinities that meet or exceed that of the initial murine antibody.

Humanization of 3A5

Two human acceptor frameworks, 3A5.L and 3A5.F, were used for humanization of 3A5 and are based on the consensus human kappa I VL domain and the human subgroup III consensus VH domain. The VL and VH domains of murine 3A5 were each aligned with the human kappa I and subgroup III domains; each complementarity determining region (CDR) was identified and grafted into the human acceptor framework to generate an HVR graft that could be displayed as an Fab on phage (FIGS. 5 and 6). When phage displaying the 3A5 HVR grafts were tested for binding to immobilized CA125, phage binding was observed for both. When expressed as a Fab, Biacore analysis also evidenced binding for both to 5-domain TAT10772.

SR, FR and SP libraries were generated in which diversity was introduced separately into each HVR of the 3A5 HVR graft. Libraries were panned against CA125 and 5-domain TAT10772 using both solid phase and solution sorting strategies. The solution sorting method allows high affinity clones to be selected through manipulation of the biotinylated target concentration and phage capture time while the addition of unlabeled target can be used to eliminate clones with faster off rates (Fuh et al. J. Mol. Biol. 340, 1073-1093 (2004)). Enrichment was observed after the second round in all libraries. FACS analysis using OVCAR-3 cells demonstrated that all 3A5 humanized antibodies tested were capable of effectively FACS sorting said cells.

Following round 5, clones were picked for DNA sequence analysis from each library and revealed sequence changes targeted at HVR-H3 suggesting that the redesign of this CDR was important to the restoration of antigen binding.

Sequence Analysis of Humanized Clones

The amino acid sequences for all light chain and heavy chain HVR regions of all of the humanized clones were obtained. For humanized 11D10 antibodies, the obtained HVR sequences are shown in FIGS. 7-12. For humanized 3A5 antibodies, the obtained HVR sequences are shown in FIGS. 13-18. FIGS. 19 and 20 show exemplary acceptor human consensus framework sequences for variable heavy and variable light chains, respectively. The present invention encompasses antibodies comprising at least one of the disclosed acceptor human consensus framework sequences in combination with at least one of the HVR sequences disclosed.

Binding Analyses for Selected Humanized 3A5 Antibody Clones

Several humanized 3A5 clones were selected to be expressed as IgG and characterized for binding to TAT10772 by Biacore, a competitive binding ELISA, and OVCAR-3 cell binding analyses. Results from the standard ELISA analyses are shown in Table 7 below. Results from the standard Biacore analyses measuring binding to 5'-domain TAT10772 to immobilized 3A5 variant IgG antibodies are shown in Table 8 below. Note that all antibodies tested were IgG and contained the variable light chain sequence shown herein as SEQ ID NO:211. A back mutation of S49Y in VL was found to have no affect on binding and was incorporated into the final humanized variants as tyrosine is more commonly found at this position. The variable heavy chain sequence of the antibody is referred to in Tables 7 and 8. As shown in Tables 7 and 8, several clones met or exceeded the monomeric affinity of the chimeric antibody as summarized.

TABLE 7

| 3A5 Antibody Version (VH Chain Sequence) | ELISA Kd (nM) CA125 | 5'-Domain TAT10772 | OVCAR-3 Cells |
|---|---|---|---|
| 3A5 chimera (mu3A5-H; SEQ ID NO: 11) | 0.3 | 2.3 | 0.3 |
| 3A5.L-graft (SEQ ID NO: 12) | | | 7.1 |
| 3A5.F-graft (SEQ ID NO: 13) | 51.4 | 90.3 | 0.6 |
| 3A5v1 (SEQ ID NO: 198) | 0.6 | 3.0 | 0.5 |
| 3A5v2 (SEQ ID NO: 199) | 0.8 | 3.7 | 0.7 |
| 3A5v3 (SEQ ID NO: 200) | 0.5 | 1.6 | 0.2 |
| 3A5v4 (SEQ ID NO: 201) | 0.3 | 2.4 | 0.8 |
| 3A5v5 (SEQ ID NO: 202) | 8.2 | 10.2 | 0.6 |
| 3A5v6 (SEQ ID NO: 203) | 4.4 | 5.7 | 0.6 |
| 3A5v7 (SEQ ID NO: 204) | 1.2 | 3.3 | 0.8 |
| 3A5v8 (SEQ ID NO: 205) | 0.4 | 2.6 | 0.5 |

TABLE 8

| 3A5 Antibody Version (VH Chain Sequence) | ka (1/Ms) | Kd (1/s) | Kd (nM) |
|---|---|---|---|
| 3A5 chimera (mu3A5-H; SEQ ID NO: 11) | 4.48E+04 | 1.21E−04 | 2.7 |
| 3A5.F-graft (SEQ ID NO: 13) | 2.85E+04 | 2.92E−04 | 10 |
| 3A5v1 (SEQ ID NO: 198) | 3.69E+04 | 1.78E−04 | 4.8 |
| 3A5v2 (SEQ ID NO: 199) | 3.34E+04 | 1.21E−04 | 3.6 |
| 3A5v3 (SEQ ID NO: 200) | 3.62E+04 | 1.30E−04 | 3.6 |
| 3A5v8 (SEQ ID NO: 205) | 5.51E+04 | 1.27E−04 | 2.3 |

Figure 24:
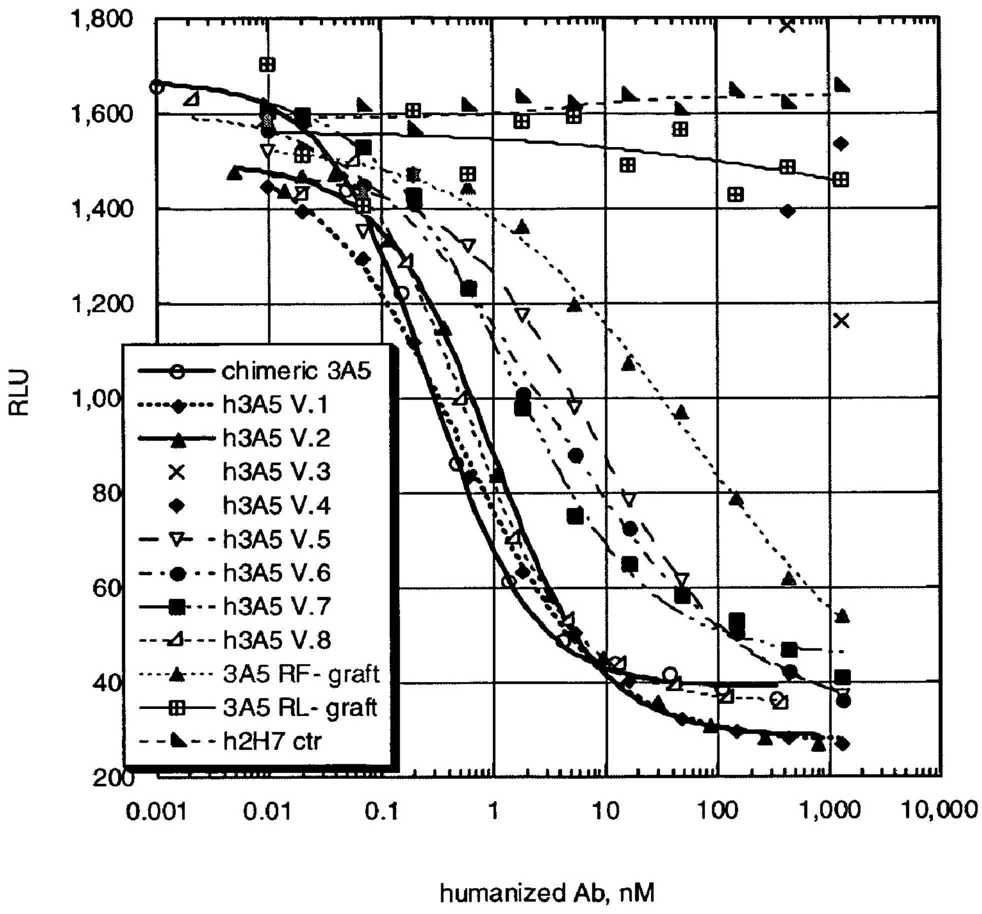
FIG. 24 shows the ability of various humanized 3A5 antibodies to inhibit the binding of ruthenium-labeled chimeric 3A5 to a biotinylated CA125 polypeptide. “h2H7 ctr” is a negative control antibody that does not specifically bind to TAT10772.
Figure 25:
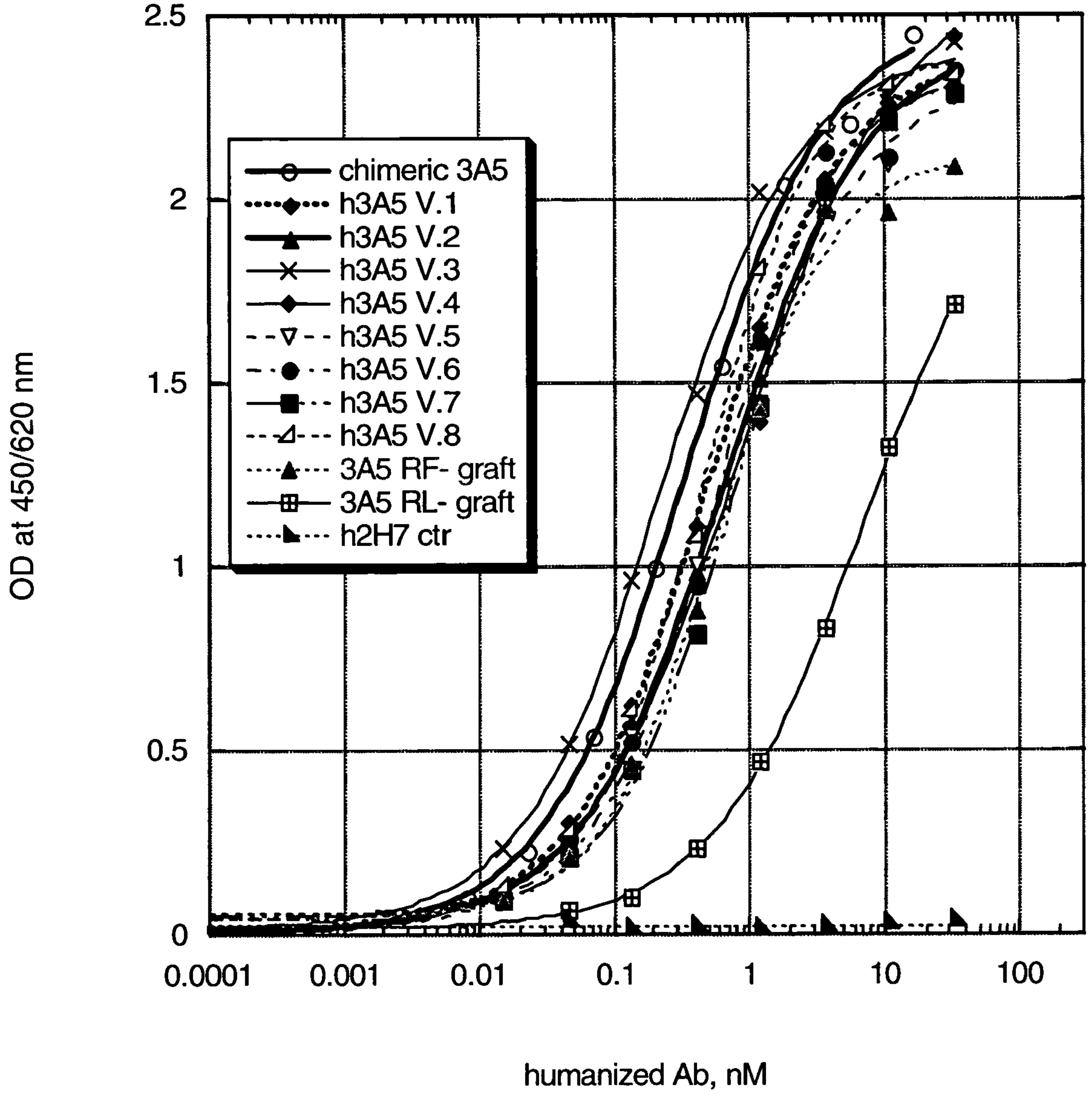
FIG. 25 shows the results from an ELISA analysis using various humanized 3A5 antibodies to measure binding to OVCAR-3 cells. “h2H7 ctr” is a negative control antibody that does not specifically bind to TAT10772.
Figure 26:
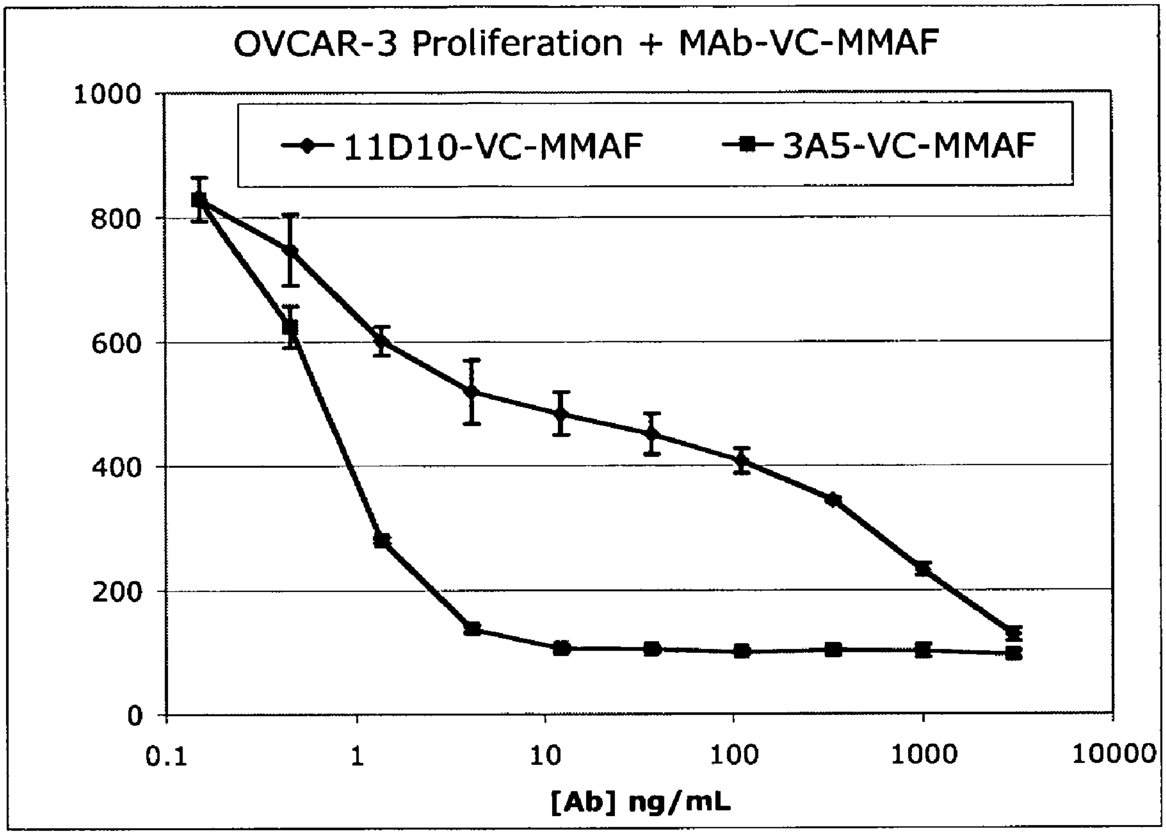
FIG. 26 shows in vitro proliferation of OVCAR-3 cells (which endogenously express TAT10772 polypeptide) following treatment with chimeric 11D10-vc-MMAF or chimeric 3A5-vc-MMAF antibodies.
Figure 27:
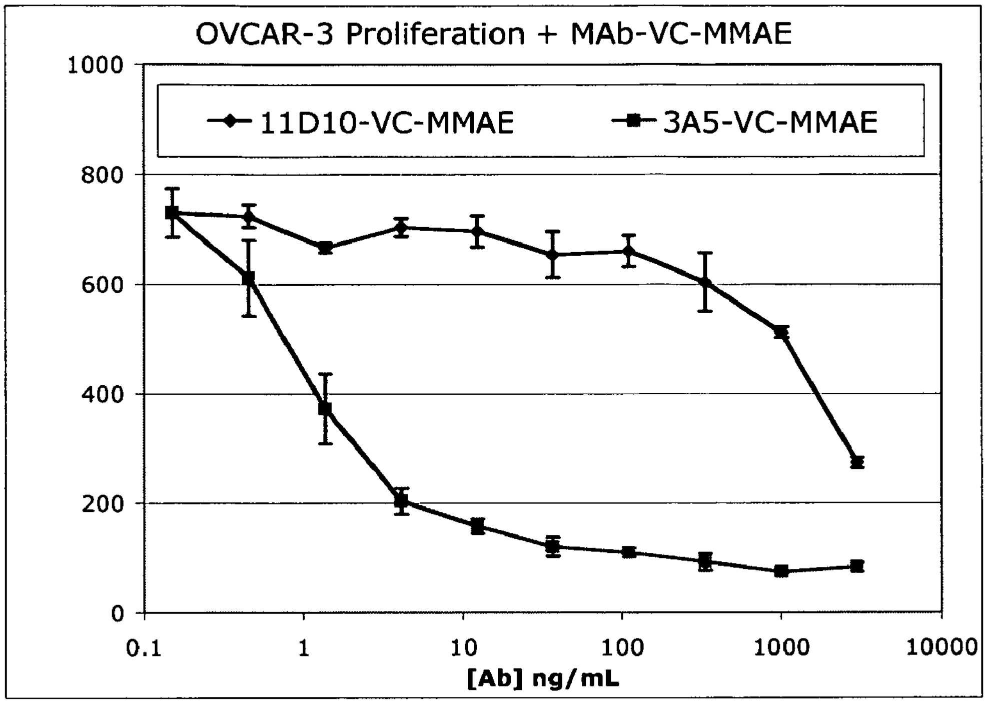
FIG. 27 shows in vitro proliferation of OVCAR-3 cells (which endogenously express TAT10772 polypeptide) following treatment with chimeric 11D10-vc-MMAE or chimeric 3A5-vc-MMAE antibodies.
Figure 28:
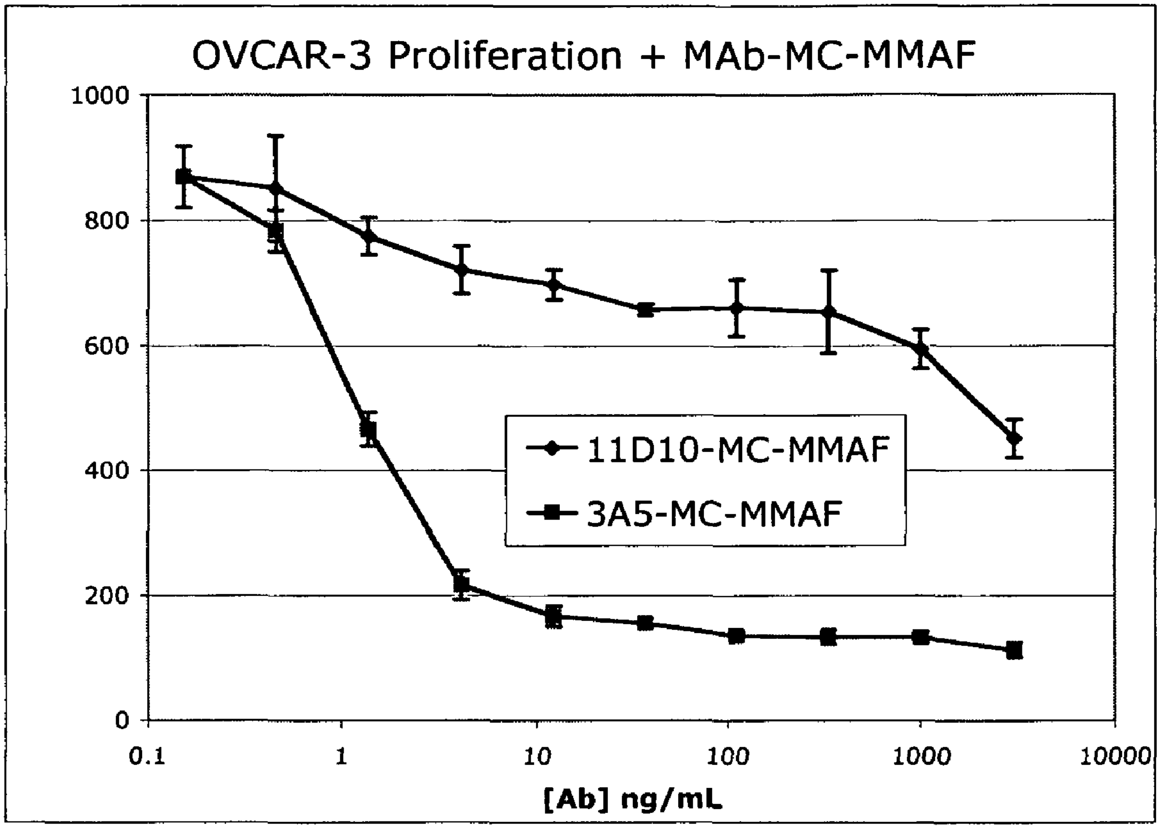
FIG. 28 shows in vitro proliferation of OVCAR-3 cells (which endogenously express TAT10772 polypeptide) following treatment with chimeric 11D10-MC-MMAF or chimeric 3A5-MC-MMAF antibodies.
Figure 29:
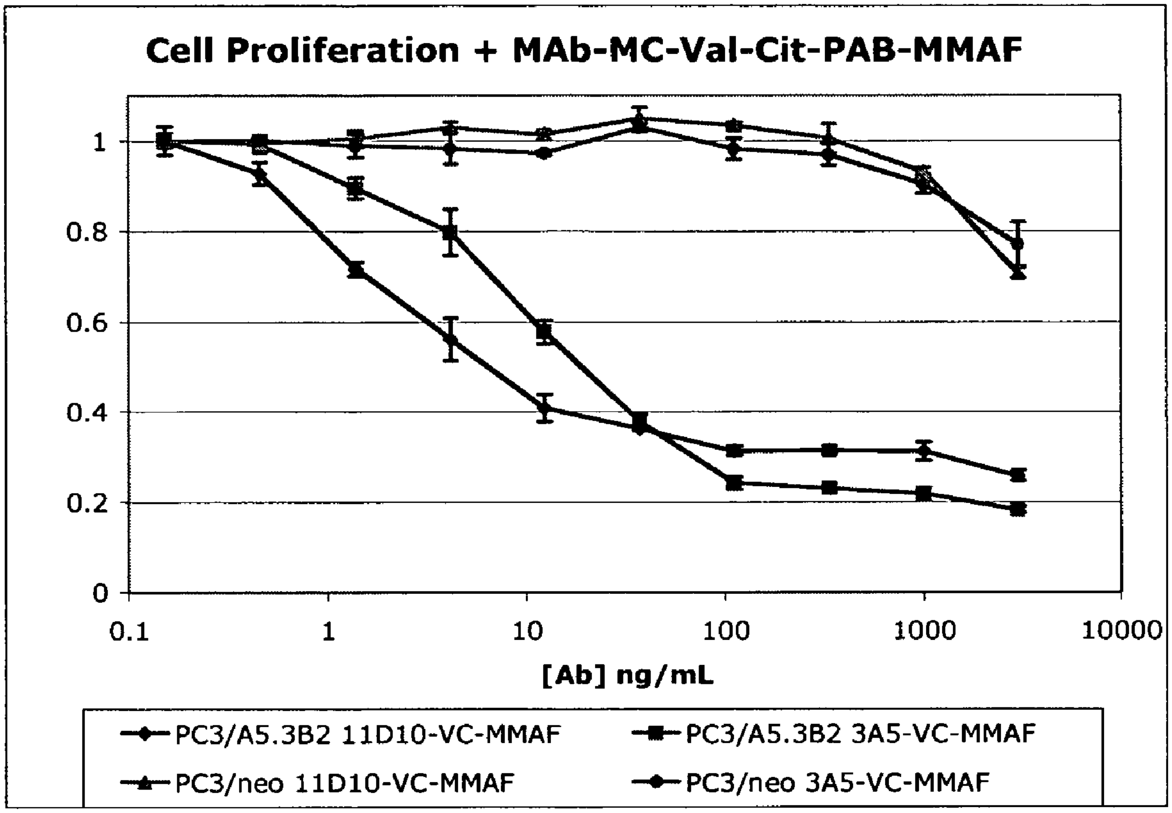
FIG. 29 shows in vitro proliferation of PC3 cells transfected with a vector allowing those cells to express TAT10772 polypeptide (PC3/A5.3B2) or PC3 cells which do not express TAT10772 polypeptide (PC3/neo) following treatment with chimeric 11D10-vc-MMAF or chimeric 3A5-vc-MMAF antibodies.
Figure 30:
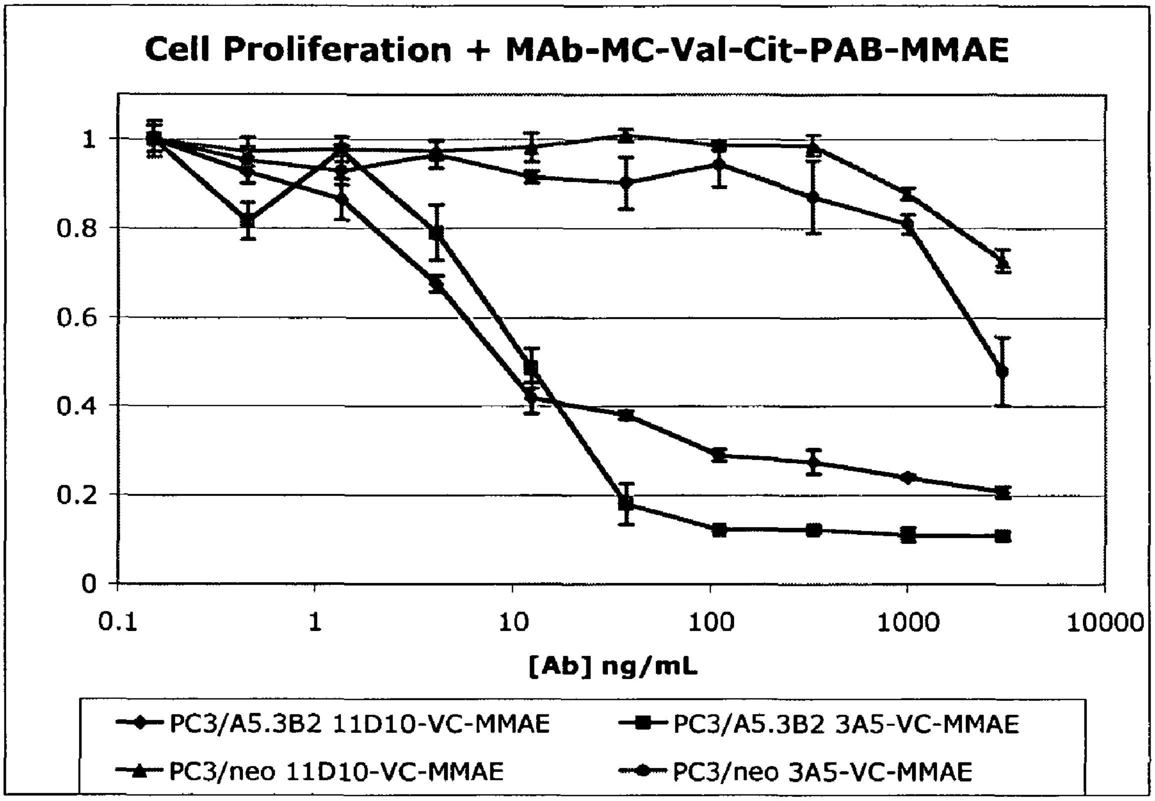
FIG. 30 shows in vitro proliferation of PC3 cells transfected with a vector allowing those cells to express TAT10772 polypeptide (PC3/A5.3B2) or PC3 cells which do not express TAT10772 polypeptide (PC3/neo) following treatment with chimeric 11D10-vc-PAB-MMAE or chimeric 3A5-vc-PAB-MMAE antibodies.
Figure 31:
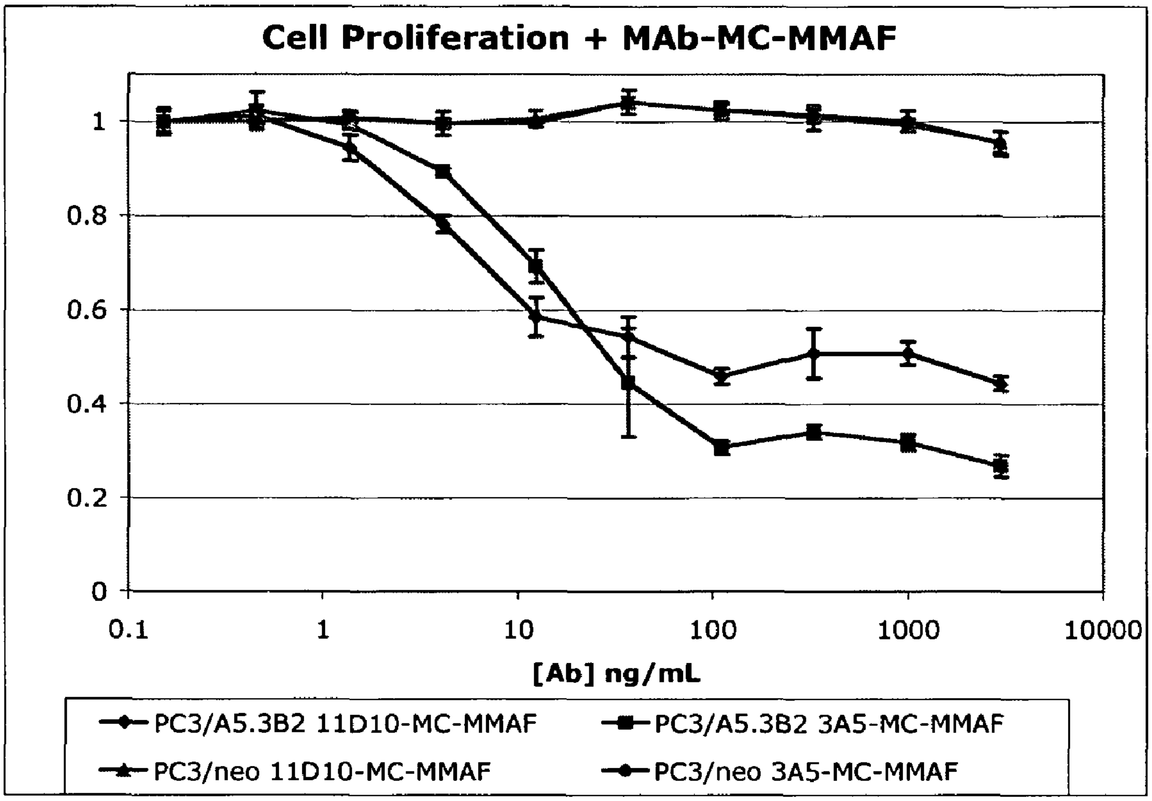
FIG. 31 shows in vitro proliferation of PC3 cells transfected with a vector allowing those cells to express TAT10772 polypeptide (PC3/A5.3B2) or PC3 cells which do not express TAT10772 polypeptide (PC3/neo) following treatment with chimeric 11D10-MC-MMAF or chimeric 3A5-MC-MMAf antibodies.
Figure 32:
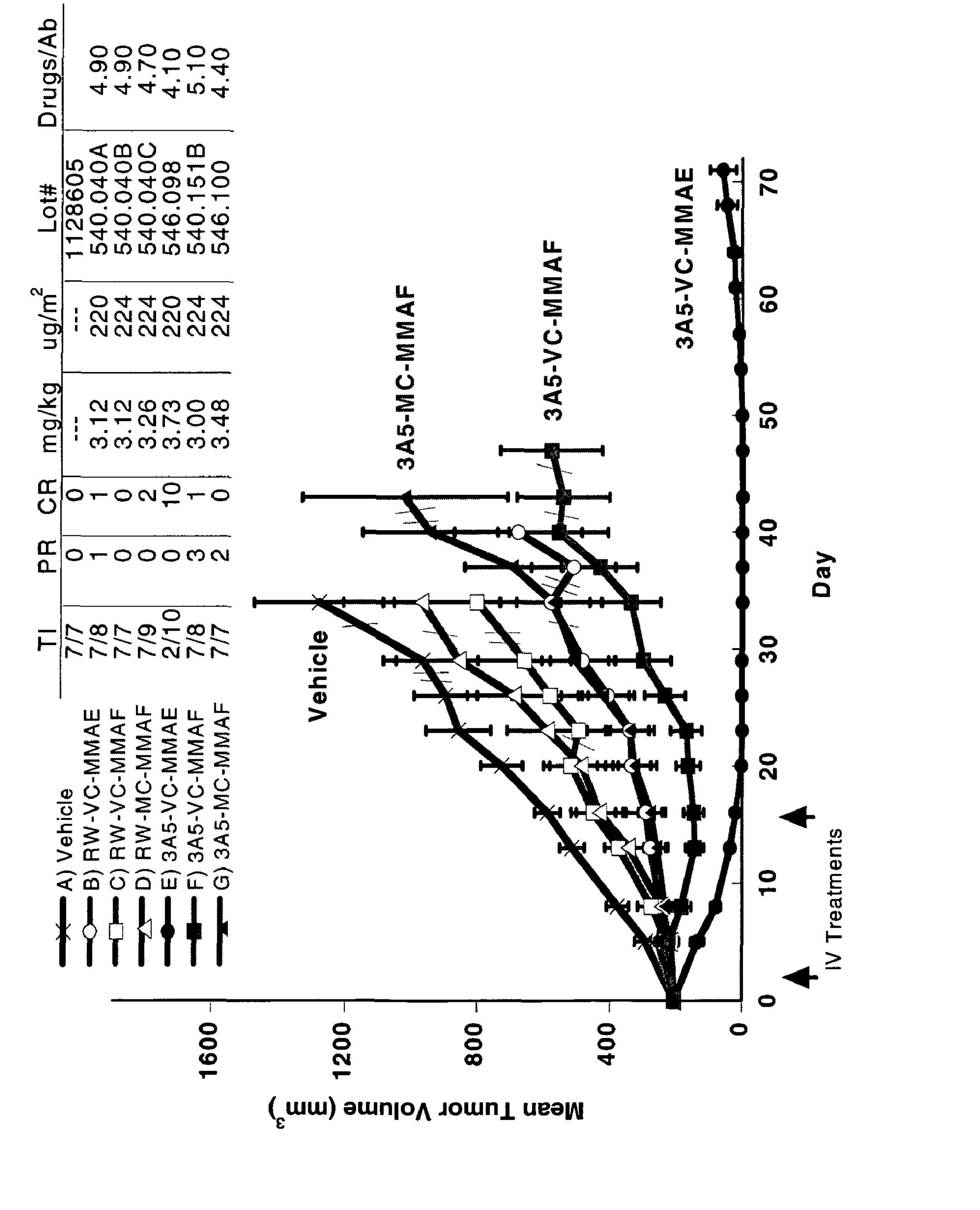
FIG. 32 shows in vivo mean tumor volume measurements (subcutaneous injection model) in PC3/A5.3B2-derived tumors following treatment with various toxin-conjugated chimeric 3A5 antibodies, control antibodies or vehicle alone.
Figure 33:
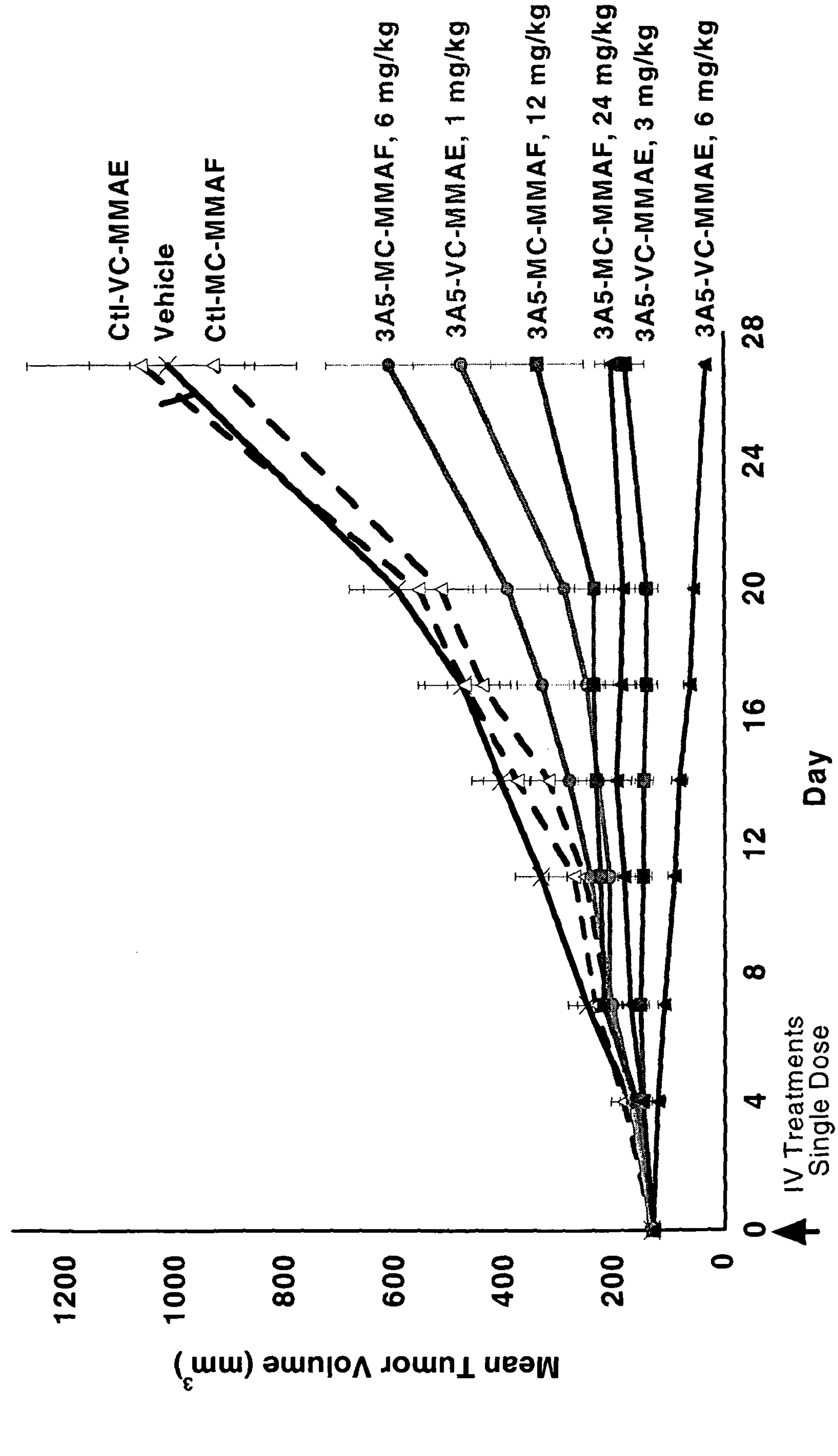
FIG. 33 shows in vivo mean tumor volume measurements (mammary fat pad transplant SCID beige mouse model) in OVCAR-3-derived tumors following treatment with various toxin-conjugated chimeric 3A5 antibodies, control antibodies or vehicle alone.
Figure 34:
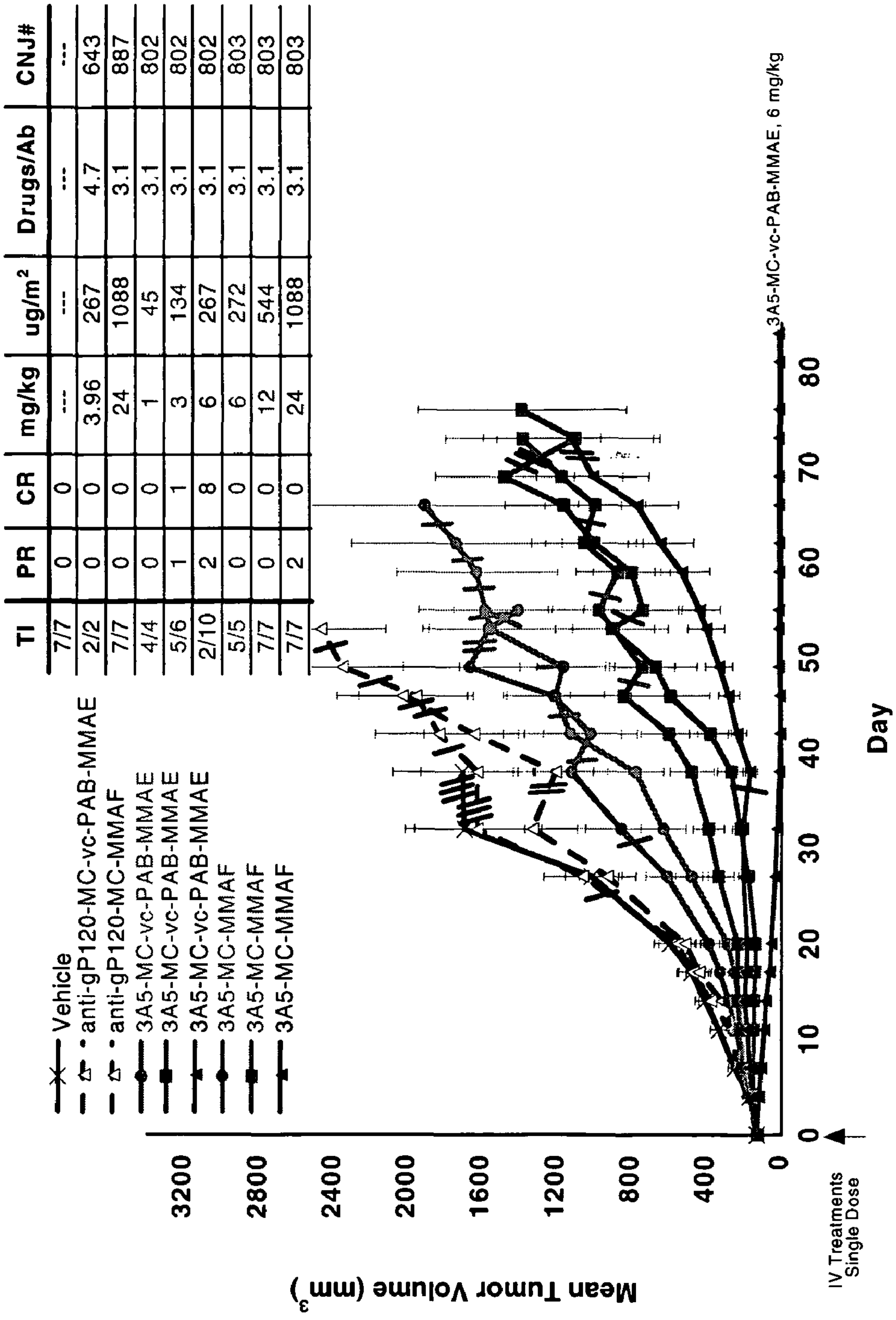
FIG. 34 shows in vivo mean tumor volume measurements (mammary fat pad transplant SCID beige mouse model) in OVCAR-3-derived tumors following treatment with various toxin-conjugated chimeric 3A5 antibodies, control antibodies or vehicle alone.
Figure 35:
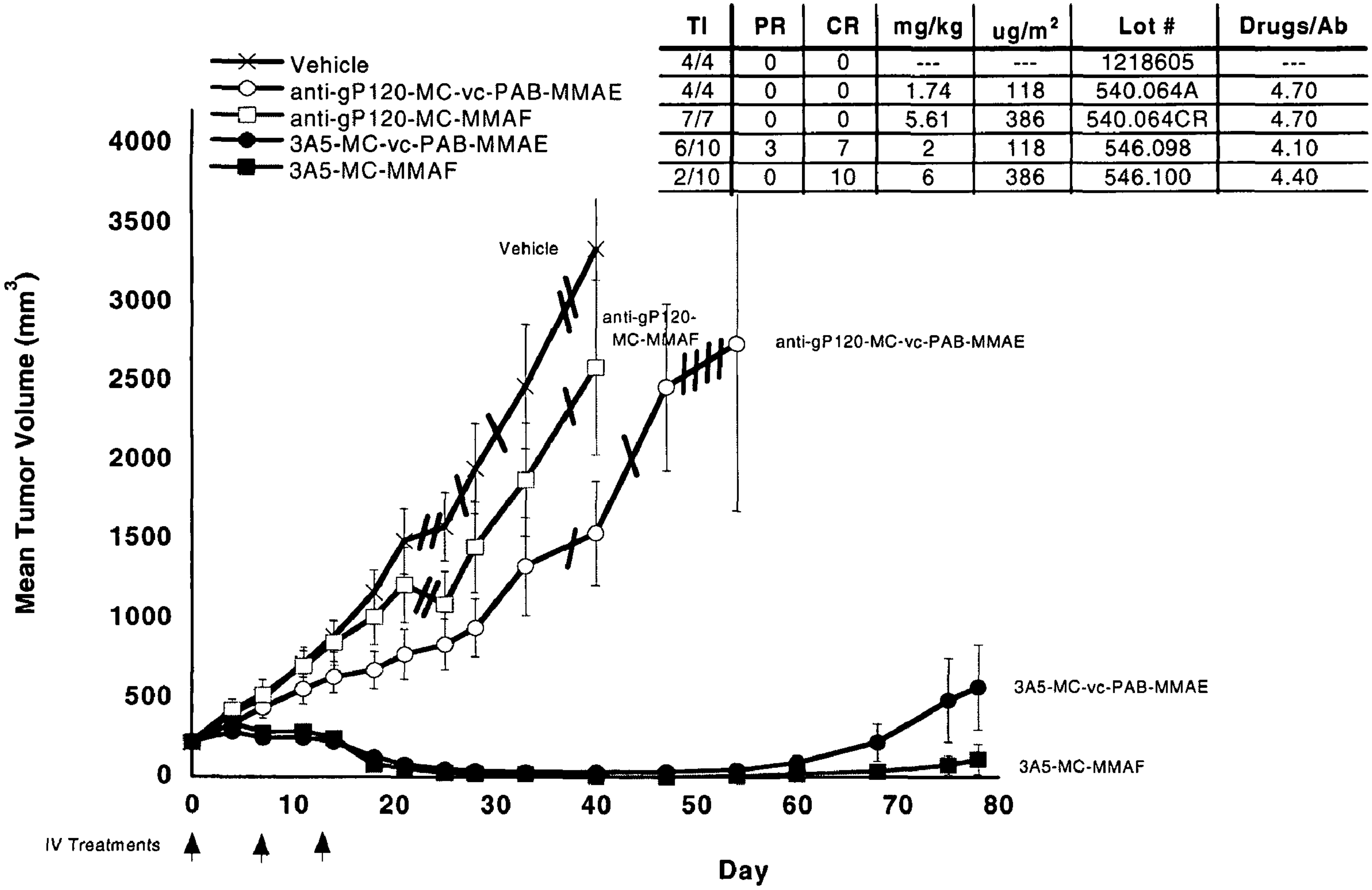
FIG. 35 shows in vivo mean tumor volume measurements (mammary fat pad transplant SCID beige mouse model) in OVCAR-3-derived tumors following treatment with various toxin-conjugated chimeric 3A5 antibodies, control antibodies or vehicle alone.

Several humanized 3A5 antibodies were also tested in competitive binding ELISA (measuring binding to immobilized 5'-domain TAT10772 and CA125) and OVCAR-3 cell binding analyses, wherein the results of these analyses are shown in FIGS. 23-25. As shown in FIGS. 23-25, all humanized 3A5 antibodies tested are capable of strongly binding to the TAT10772 target polypeptide and effectively competing for binding at antigenic sites on that target polypeptide.

Removal of a Potential Glycosylation Site in CDR-H2 of Humanized 3A5 Variants

To avoid potential manufacturing issues, a potential glycosylation site in CDR-H2 of the humanized 3A5 variants was eliminated using phage selection methods to identify suitable sequence changes. Separately both N52 and S54 were fully randomized using the codon NNS to allow all possible amino acid substitutions. These small 20-member phage libraries were selected for binding to 5'-domain TAT10772. Although both N52 and S54 were found, other substitutions were frequently observed at both positions with the changes N52S and S54A being the most abundant. Certain data from standard scatchard analyses are shown in Table 9 below, where the antibodies are expressed as IgGs having a variable light chain sequence shown herein as SEQ ID NO:211 and the variable heavy chain sequence shown in Table 9. When either of the described changes were incorporated into the humanized variants 3A5.v1 or 3A5.v4 (see SEQ ID NOS:206-209), they did not affect binding affinity for TAT10772.

TABLE 9

| 3A5 Antibody Version (VH Chain Sequence) | Kd (nM) |
|---|---|
| 3A5 chimera (mu3A5-H; SEQ ID NO: 11) | 0.57 ± 0.3 |
| 3A5v1b 52 (SEQ ID NO: 206) | 0.47 ± 0.1 |
| 3A5v1b 54 (SEQ ID NO: 207) | 0.37 ± 0.4 |
| 3A5v4b 52 (SEQ ID NO: 208) | 0.46 ± 0.5 |

Example 10

Preparation of Toxin-Conjugated Antibodies that Bind TAT10772

The use of antibody-drug conjugates (ADC), i.e. immunoconjugates, for the local delivery of cytotoxic or cytostatic agents, i.e. drugs to kill or inhibit tumor cells in the treatment of cancer (Payne (2003) *Cancer Cell* 3:207-212; Syrigos and Epenetos (1999) *Anticancer Research* 19:605-614; Niculescu-Duvaz and Springer (1997) *Adv. Drug Del. Rev.* 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) *Lancet* (Mar. 15, 1986) pp. 603-05; Thorpe, (1985) "Antibody Carriers Of Cytotoxic Agents In Cancer Therapy: A Review," in Monoclonal Antibodies '84: Biological And Clinical Applications, Pinchera et al. (eds.), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al., (1986) *Cancer Immunol. Immunother.,* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al. (2000) *J. of the*

*Nat. Cancer Inst.* 92(19):1573-1581; Mandler et al. (2000) *Bioorganic & Med. Chem. Letters* 10:1025-1028; Mandler et al. (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al. (1998) *Cancer Res.* 58:2928; Hinman et al. (1993) *Cancer Res.* 53:3336-3342).

In the antibody drug conjugates (ADC) of the invention, an antibody (Ab) is conjugated to one or more drug moieties (D), e.g. about 1 to about 20 drug moieties per antibody, through a linker (L). The ADC having the formula:

$$Ab\text{-}(L\text{-}D)_p$$

may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC⇆), and N-Succinimidyl (4-iodo-acetyl) aminobenzoate ("SIAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, hydroxyl, hydrazide, oxime, hydrazine, thiosemicarbazone, hydrazine carboxylate, and arylhydrazide groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Specific techniques for producing antibody-drug conjugates by linking toxins to purified antibodies are well known and routinely employed in the art. For example, conjugation of a purified monoclonal antibody to the toxin DM1 may be accomplished as follows. Purified antibody is derivatized with N-succinimidyl-4-(2-pyridylthio)pentanoate to introduce dithiopyridyl groups. Antibody (376.0 mg, 8 mg/mL) in 44.7 ml of 50 mM potassium phosphate buffer (pH 6.5) containing NaCl (50 mM) and EDTA (1 mM) is treated with SPP (5.3 molar equivalents in 2.3 ml ethanol). After incubation for 90 minutes under argon at ambient temperature, the reaction mixture is gel filtered through a Sephadex G25 column equilibrated with 35 mM sodium citrate, 154 mM NaCl and 2 mM EDTA. Antibody containing fractions are then pooled and assayed. Antibody-SPP-Py (337.0 mg with releasable 2-thiopyridine groups) is diluted with the above 35 mM sodium citrate buffer, pH 6.5, to a final concentration of 2.5 mg/ml. DM1 (1.7 equivalents, 16.1 mols) in 3.0 mM dimethylacetamide (DMA, 3% v/v in the final reaction mixture) is then added to the antibody solution. The reaction is allowed to proceed at ambient temperature under argon for 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate is 5.0 ml/min and 65 fractions (20.0 ml each) are collected. Fractions are pooled and assayed, wherein the number of DM1 drug molecules linked per antibody molecule (p') is determined by measuring the absorbance at 252 nm and 280 nm.

For illustrative purposes, conjugation of a purified monoclonal antibody to the toxin DM1 may also be accomplished as follows. Purified antibody is derivatized with (Succinimidyl 4-(N-maleimidomethyl) cyclohexane-1-carboxylate (SMCC, Pierce Biotechnology, Inc) to introduce the SMCC linker. The antibody is treated at 20 mg/ml in 50 mM potassium phosphate/50 mM sodium chloride/2 mM EDTA, pH 6.5 with 7.5 molar equivalents of SMCC (20 mM in DMSO, 6.7 mg/ml). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody containing fractions are pooled and assayed. Antibody-SMCC is then diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/antibody, 7.37 mg/ml) in dimethylacetamide. The reaction is stirred at ambient temperature under argon 16.5 hours. The conjugation reaction mixture is then filtered through a Sephadex G25 gel filtration column (1.5×4.9 cm) with 1×PBS at pH 6.5. The DM1/antibody ratio (p) is then measured by the absorbance at 252 nm and at 280 nm.

Moreover, a free cysteine on an antibody of choice may be modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing the antibody in phosphate buffered saline at a concentration of approximately 1.6 mg/ml (10 micromolar) and allowing it to react for 1 hour. Excess $BM(PEO)_4$ is removed by gel filtration in 30 mM citrate, pH 6 with 150 mM NaCl buffer. An approximate 10 fold molar excess DM1 is dissolved in dimethyl acetamide (DMA) and added to the antibody-BMPEO intermediate. Dimethyl formamide (DMF) may also be employed to dissolve the drug moiety reagent. The reaction mixture is allowed to react overnight before gel filtration or dialysis into PBS to remove unreacted drug. Gel filtration on S200 columns in PBS is used to remove high molecular weight aggregates and furnish purified antibody-BMPEO-DM1 conjugate.

Cytotoxic drugs have typically been conjugated to antibodies through the often numerous lysine residues of the antibody. Conjugation through thiol groups present, or engineered into, the antibody of interest has also been accomplished. For example, cysteine residues have been introduced into proteins by genetic engineering techniques to form covalent attachment sites for ligands (Better et al. (1994) *J. Biol. Chem.* 13:9644-9650; Bernhard et al. (1994) *Bioconjugate Chem.* 5:126-132; Greenwood et al. (1994) *Therapeutic Immunology* 1:247-255; Tu et al. (1999) *Proc. Natl. Acad. Sci. USA* 96:4862-4867; Kanno et al. (2000) *J. of Biotechnology,* 76:207-214; Chmura et al. (2001) *Proc. Nat. Acad. Sci. USA* 98(15):8480-8484; U.S. Pat. No. 6,248,564). Once a free cysteine residue exists in the antibody of interest, toxins can be linked to that site. As an example, the drug linker reagents, maleimidocaproyl-monomethyl auristatin E (MMAE), i.e. MC-MMAE, maleimidocaproyl-monomethyl auristatin F (MMAF), i.e. MC-MMAF, MC-val-cit-PAB-MMAE or MC-val-cit-PAB-MMAF, dissolved in DMSO, is diluted in acetonitrile and water at known concentration, and added to chilled cysteine-derivatized antibody in phosphate buffered saline (PBS). After about one hour, an excess of maleimide is added to quench the reaction and cap any unreacted antibody thiol groups. The reaction mixture is concentrated by centrifugal ultrafiltration and the toxin conjugated antibody is purified and desalted by elution through G25 resin in PBS, filtered through 0.2 m filters under sterile conditions, and frozen for storage.

Additionally, anti-TAT antibodies of the present invention may be conjugate to auristatin and dolostatin toxins (such as MMAE and MMAF) using the following technique. Antibody, dissolved in 500 mM sodium borate and 500 mM sodium chloride at pH 8.0 is treated with an excess of 10 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, (1) maleimidocaproyl-monomethyl auristatin E (MMAE), i.e. MC-MMAE, (2) MC-MMAF, (3) MC-val-cit-PAB-MMAE, or (4) MC-val-cit-PAB-MMAF dissolved in DMSO, is diluted in acetonitrile and water at known concentration, and added to the chilled reduced antibody in PBS. After about one hour, an excess of maleimide is added to quench the reaction and cap any unreacted antibody thiol groups. The reaction mixture is concentrated by centrifugal ultrafiltration and the conjugated antibody is purified and desalted by elution through G25 resin in PBS, filtered through 0.2 m filters under sterile conditions, and frozen for storage.

Example 11

In Vitro Tumor Cell Killing Assay

Mammalian cells expressing the TAT polypeptide of interest may be obtained using standard expression vector and cloning techniques. Alternatively, many tumor cell lines expressing TAT polypeptides of interest are publicly available, for example, through the ATCC and can be routinely identified using standard ELISA or FACS analysis. Anti-TAT polypeptide monoclonal antibodies (and toxin conjugated derivatives thereof) may then be employed in assays to determine the ability of the antibody to kill TAT polypeptide expressing cells in vitro.

For example, cells expressing the TAT polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. Cell viability is then measured using the CellTiter-Glo Luminescent Cell Viability Assay from Promega (Cat# G7571). Untreated cells serve as a negative control.

In a first experiment and with specific regard to the present invention, various concentrations of MMAF and MMAE conjugates of the chimeric 3A5 and chimeric 11D10 antibodies were tested for the ability to kill (1) the TAT10772 polypeptide-expressing cell line OVCAR-3, (2) a PC3-derived cell line engineered to stably express TAT10772 polypeptide on its cell surface (PC3/A5.3B2) and (3) a PC3 cell line that does not express TAT10772 polypeptide (PC3/neo). The chimeric 3A5 antibodies employed in these analyses contained the variable light chain amino acid sequence shown herein as SEQ ID NO:211 and the variable heavy chain amino acid sequence shown herein as SEQ ID NO: 11. The chimeric 11D10 antibodies employed in these analyses contained the variable light chain amino acid sequence shown herein as SEQ ID NO:4 and the variable heavy chain amino acid sequence shown herein as SEQ ID NO:7. Results from these experiments are shown in FIGS. 26-31 and demonstrated that each of the toxin conjugated antibodies caused significant levels of cell death in the OVCAR-3 and PC3/A5.3B2 cells (i.e., cells that express TAT10772 polypeptide on the cell surface), whereas no significant cell killing was observed for any of the antibodies in the PC3/neo cells (which do not express TAT10772 polypeptide on the cell surface). These data demonstrate the tested antibodies are capable of binding to the TAT10772 polypeptide on the surface of cells expressing that polypeptide and causing the death of those cells in vitro.

Example 12

In Vivo Tumor Cell Killing Assay

Intraperitoneal Tumor Model

To test the efficacy of the chimeric 11D10 and 3A5 anti-TAT10772 polypeptide antibodies in vivo, $2\times10^7$ OVCAR-3/luc cells per 110 SCID mouse were injected into the peritoneal cavity and allowed to grow for 20 days post-injection. At day 20 post-injection, the mice were segregated into 9 different groups of from 9-10 mice per group and the tumor volume was determined in each mouse. At days 23, 30, 37 and 44 post-injection, mice were treated as follows:

Group A—vehicle alone
Group B—2.5 mg/kg chimeric 11D10-MC-vc-PAB-MMAE
Group C—2.5 mg/kg chimeric 11D10-MC-vc-PAB-MMAF
Group D—2.5 mg/kg chimeric 11D10-MC-MMAF
Group E—2.5 mg/kg chimeric 3A5-MC-vc-PAB-MMAE
Group F—2.5 mg/kg chimeric 3A5-MC-vc-PAB-MMAF
Group G—2.5 mg/kg chimeric 3A5-MC-MMAF
Group H—2.5 mg/kg anti-ragweed-MC-vc-PAB-MMAE
Group I—2.5 mg/kg anti-ragweed-MC-vc-PAB-MMAF Tumor volume was measured in each mouse on days 27, 34, 41, 48, 55 and 69 post-injection to determine the efficacy of each treatment in reducing tumor volume. Additionally, % animal survival was determined daily through 250 days post treatment.

The results of these in vivo analyses demonstrated that mice which were treated with vehicle alone (Group A) or with the non-TAT10772-specific anti-ragweed antibody (Groups H and I) showed no observable reduction in tumor volume subsequent to treatment. In fact, the tumors in these animals simply continue to increase in size over time. These results demonstrate that antibodies that are incapable of binding to TAT10772 polypeptide, even if toxin-conjugated, provide no specific (or even non-specific) therapeutic effect. In contrast, the majority of animals in Groups B-G evidenced a significant and reproducible reduction in tumor volume post-treatment, demonstrating that both chimeric 11D10 and 3A5 provide a specific in vivo therapeutic effect. In fact, many of the animals in Groups B-G evidenced complete tumor necrosis. These data clearly demonstrate that both chimeric antibodies 11D10 and 3A5 provide a specific, significant and reproducible in vivo therapeutic effect for the treatment of tumors that express the TAT10772 polypeptide.

With regard to percent survival, all of the animals in Groups A, H and I had perished by day 125 post implantation. At the same time point, however, 90% of the animals in Group B, 80% of the animals in Groups E and F, and 55% of the animals in Groups C, D and G remained alive evidencing that both chimeric antibodies 11D10 and 3A5 provide a specific, significant and reproducible in vivo therapeutic effect for the treatment of tumors that express the TAT10772 polypeptide. Results from a standard Cox proportional hazard model is shown in Table 10 below, where a separate hazard ratio (H.R.) for each of the eight non-vehicle subgroups was determined (the vehicle only Group A was arbitrarily assigned a hazard ratio of 1.0).

TABLE 10

| Group | log H.R. | S.E. of log H.R. | H.R. | 95% confidence interval for H.R. |
|---|---|---|---|---|
| B | −2.86 | 0.55 | 0.057 | (0.019, 0.168) |
| C | −2.22 | 0.52 | 0.108 | (0.039, 0.300) |
| D | −1.40 | 0.48 | 0.248 | (0.096, 0.635) |
| E | −4.51 | 0.71 | 0.011 | (0.0027, 0.044) |
| F | −5.21 | 0.87 | 0.006 | (0.001, 0.030) |
| G | −3.12 | 0.59 | 0.044 | (0.013, 0.140) |

Figure 36:
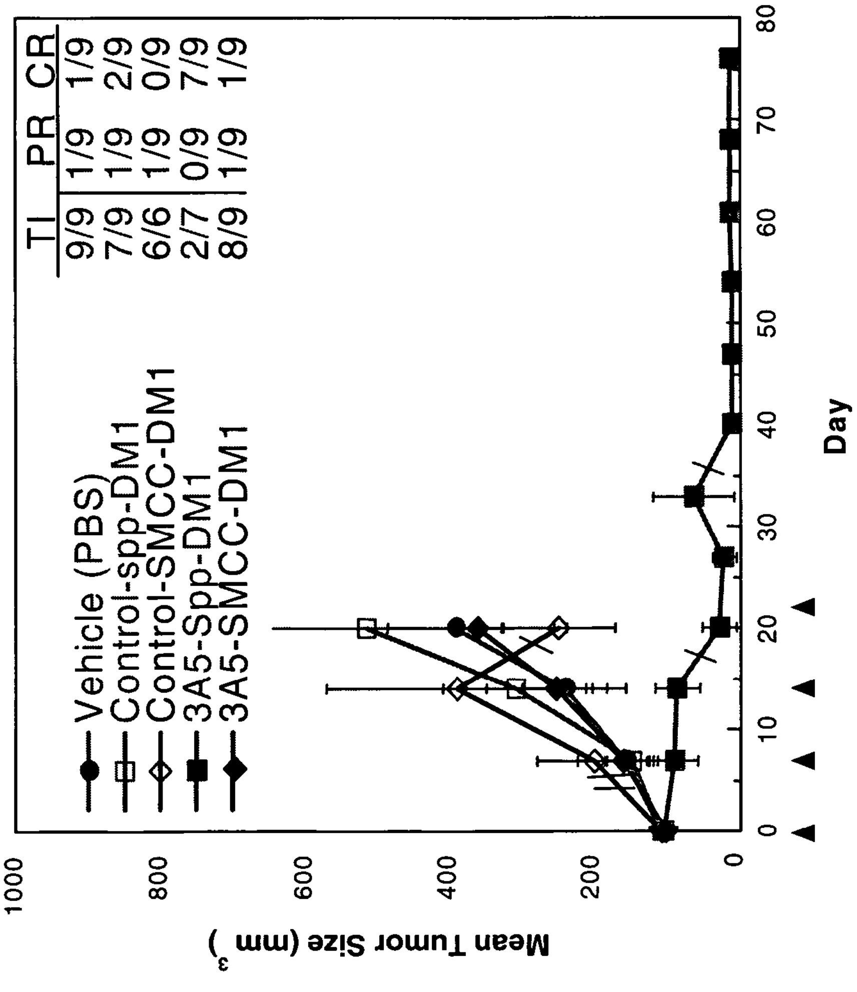
FIG. 36 shows in vivo mean tumor volume measurements (xenograft tumors in nude mice, 10 million cells per mouse) in PC3/A5.3B2-derived tumors following treatment with various toxin-conjugated chimeric 3A5 antibodies, control antibodies or vehicle alone.
Figure 37:
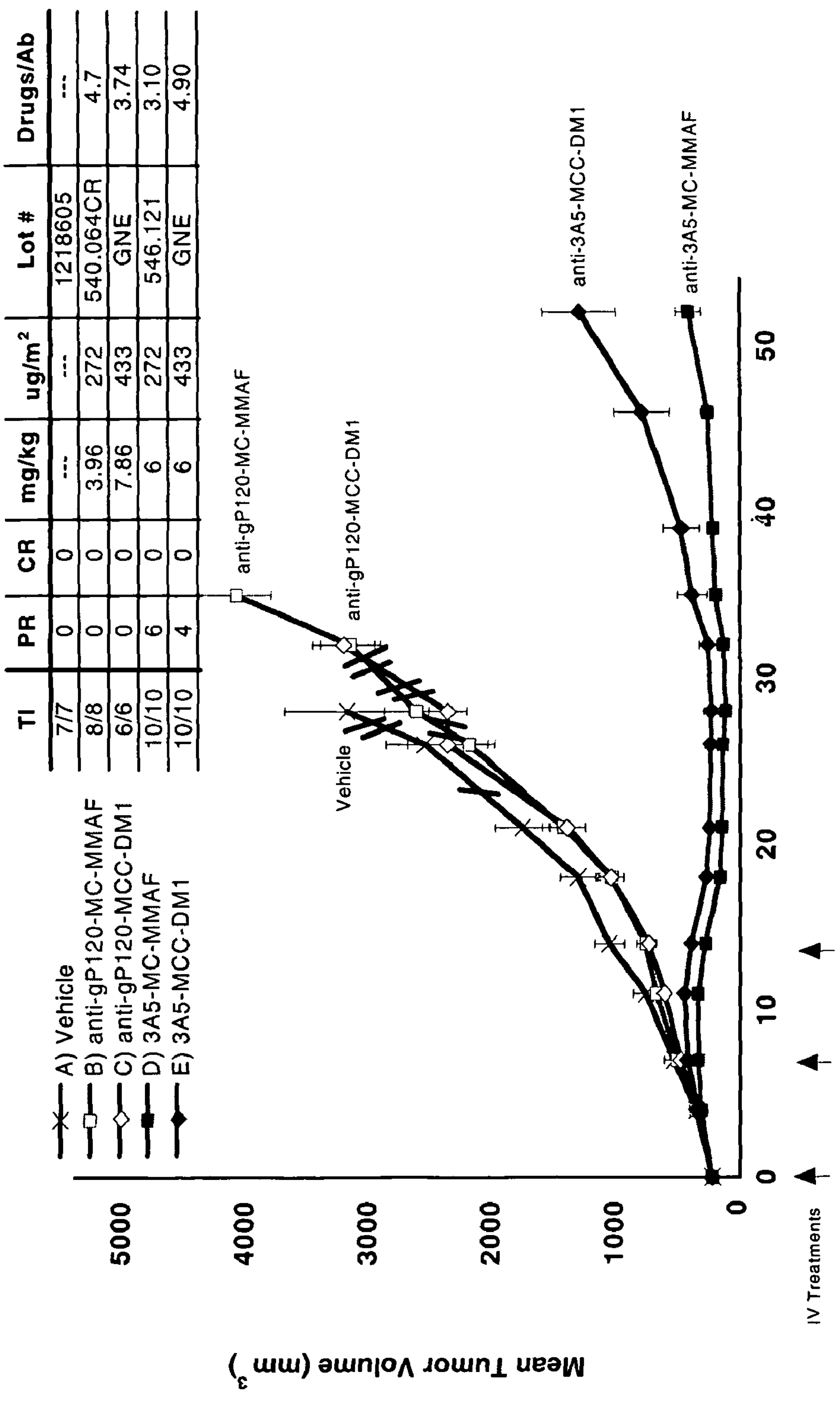
FIG. 37 shows in vivo mean tumor volume measurements (mammary fat pad transplant SCID beige mouse model) in OVCAR-3-derived tumors following treatment with various toxin-conjugated chimeric 3A5 antibodies, control antibodies or vehicle alone.

Subcutaneous Injection Model, Mammary Fat Pads Transplant Model, and Xenograft Transplant Models The results from additional in vivo experiments measuring the therapeutic efficacy of 3A5 chimeric antibodies are shown in FIGS. 32-37. More specifically, toxin-conjugated chimeric 3A5 antibodies were tested for their ability to decrease tumor size in vivo in a variety of different in vivo formats including, tumor formation by subcutaneous injection of PC3/C5.3B2 cells followed by various antibody treatments (FIG. 32), OVCAR-3 cell transplantation into the mammary fat pad of SCID beige mice followed by various antibody treatments (FIGS. 33-35 and 37), and xenograft transplantation of 10 million PC3/A5.3B2 cells per nude mouse followed by various antibody treatments (FIG. 36). The results of these experiments show that the various anti-TAT10772 antibodies tested are effective in the therapeutic treatment of TAT10772-expressing tumors in vivo.

Example 13

Use of TAT as a Hybridization Probe

The following method describes use of a nucleotide sequence encoding TAT as a hybridization probe for, i.e., diagnosis of the presence of a tumor in a mammal.

DNA comprising the coding sequence of full-length or mature TAT as disclosed herein can also be employed as a probe to screen for homologous DNAs (such as those encoding naturally-occurring variants of TAT) in human tissue cDNA libraries or human tissue genomic libraries.

Hybridization and washing of filters containing either library DNAs is performed under the following high stringency conditions. Hybridization of radiolabeled TAT-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence TAT can then be identified using standard techniques known in the art.

Example 14

Expression of TAT in *E. coli*

This example illustrates preparation of an unglycosylated form of TAT by recombinant expression in *E. coli.*

The DNA sequence encoding TAT is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TAT coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TAT protein can then be purified using a metal chelating column under conditions that allow tight binding of the protein.

TAT may be expressed in *E. coli* in a poly-His tagged form, using the following procedure. The DNA encoding TAT is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate-$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TAT polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Certain of the TAT polypeptides disclosed herein have been successfully expressed and purified using this technique(s).

Example 15

Expression of TAT in Mammalian Cells

This example illustrates preparation of a potentially glycosylated form of TAT by recombinant expression in mammalian cells.

The vector, pRK5 (see EP 307,247, published Mar. 15, 1989), is employed as the expression vector. Optionally, the TAT DNA is ligated into pRK5 with selected restriction enzymes to allow insertion of the TAT DNA using ligation methods such as described in Sambrook et al., supra. The resulting vector is called pRK5-TAT.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-TAT DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of TAT polypeptide. The cultures containing transfected cells may undergo further incubation (in serum free medium) and the medium is tested in selected bioassays.

In an alternative technique, TAT may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-TAT DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed TAT can then be concentrated and purified by any selected method, such as dialysis and/or column chromatography.

In another embodiment, TAT can be expressed in CHO cells. The pRK5-TAT can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of TAT polypeptide, the culture medium may be replaced with serum free medium. Preferably, the cultures are incubated for about 6 days, and then the conditioned medium is harvested. The medium containing the expressed TAT can then be concentrated and purified by any selected method.

Epitope-tagged TAT may also be expressed in host CHO cells. The TAT may be subcloned out of the pRK5 vector. The subclone insert can undergo PCR to fuse in frame with a selected epitope tag such as a poly-his tag into a Baculovirus expression vector. The poly-his tagged TAT insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TAT can then be concentrated and purified by any selected method, such as by $Ni^{2+}$-chelate affinity chromatography.

TAT may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT® (Quiagen), DOSPER® or FUGENE® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia)

which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Certain of the TAT polypeptides disclosed herein have been successfully expressed and purified using this technique(s).

Example 16

Expression of TAT in Yeast

The following method describes recombinant expression of TAT in yeast.

First, yeast expression vectors are constructed for intracellular production or secretion of TAT from the ADH2/GAPDH promoter. DNA encoding TAT and the promoter is inserted into suitable restriction enzyme sites in the selected plasmid to direct intracellular expression of TAT. For secretion, DNA encoding TAT can be cloned into the selected plasmid, together with DNA encoding the ADH2/GAPDH promoter, a native TAT signal peptide or other mammalian signal peptide, or, for example, a yeast alpha-factor or invertase secretory signal/leader sequence, and linker sequences (if needed) for expression of TAT.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TAT can subsequently be isolated and purified by removing the yeast cells from the fermentation medium by centrifugation and then concentrating the medium using selected cartridge filters. The concentrate containing TAT may further be purified using selected column chromatography resins.

Certain of the TAT polypeptides disclosed herein have been successfully expressed and purified using this technique(s).

Example 17

Expression of TAT in Baculovirus-Infected Insect Cells

The following method describes recombinant expression of TAT in Baculovirus-infected insect cells.

The sequence coding for TAT is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding TAT or the desired portion of the coding sequence of TAT such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD® virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged TAT can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TAT are pooled and dialyzed against loading buffer.

Alternatively, purification of the IgG tagged (or Fc tagged) TAT can be performed using known chromatography techniques, including for instance, Protein A or protein G column chromatography.

Certain of the TAT polypeptides disclosed herein have been successfully expressed and purified using this technique(s).

Example 18

Purification of TAT Polypeptides Using Specific Antibodies

Native or recombinant TAT polypeptides may be purified by a variety of standard techniques in the art of protein purification. For example, pro-TAT polypeptide, mature TAT polypeptide, or pre-TAT polypeptide is purified by immunoaffinity chromatography using antibodies specific for the TAT polypeptide of interest. In general, an immunoaffinity column is constructed by covalently coupling the anti-TAT polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TAT polypeptide by preparing a fraction from cells containing TAT polypeptide in a soluble form. This preparation is derived by solubilization of the whole cell or of a subcellular fraction obtained via differential centrifugation by the addition of detergent or by other methods well known in the art. Alternatively, soluble TAT polypeptide containing a signal sequence may be secreted in useful quantity into the medium in which the cells are grown.

A soluble TAT polypeptide-containing preparation is passed over the immunoaffinity column, and the column is washed under conditions that allow the preferential absorbance of TAT polypeptide (e.g., high ionic strength buffers in the presence of detergent). Then, the column is eluted under conditions that disrupt antibody/TAT polypeptide binding (e.g., a low pH buffer such as approximately pH 2-3, or a high concentration of a chaotrope such as urea or thiocyanate ion), and TAT polypeptide is collected.

Deposit of Material

The following materials have been deposited with the American Type Culture Collection, 10801 University Blvd., Manassas, Va. 20110-2209, USA (ATCC):

TABLE 11

| Material | ATCC Dep. No. | Deposit Date |
|---|---|---|
| Hybridoma cell line 3A5.3 | PTA-6695 | May 4, 2005 |
| Hybridoma cell line 11D10.1.14 | PTA-6696 | May 4, 2005 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A monoclonal antibody produced by the hybridoma cell 3A5.3 that binds to a TAT10772 polypeptide.

2. An isolated antibody that specifically binds a TAT10772 polypeptide, said antibody comprising three light chain hypervariable regions (HVR-L1, HVR-L2 and HVR-L3) and three heavy chain hypervariable regions (HVR-H1, HVR-H2 and HVR-H3) wherein:
   (a) HVR-L1 comprises the amino acid sequence of SEQ ID NO:119;
   (b) HVR-L2 comprises the amino acid sequence of any one of SEQ ID NOS:120-121;
   (c) HVR-L3 comprises the amino acid sequence of SEQ ID NO:122;
   (d) HVR-H1 comprises the amino acid sequence of SEQ ID NO:123;
   (e) HVR-H2 comprises the amino acid sequence of any one of SEQ ID NOS:124-127; and
   (f) HVR-H3 comprises the amino acid sequence of any one of SEQ ID NOS:128-183.

3. An antibody drug conjugate comprising an antibody covalently attached by a linker to one or more toxin drug moieties, the compound having the formula:

Ab-(L-D)p or a pharmaceutically acceptable salt or solvate thereof, wherein:
   Ab is an antibody according to claim 1 or 2;
   L is a linker;
   D is a toxin drug moiety; and
   p is 1 to about 20.

4. The antibody drug conjugate of claim 3 wherein Ab is a humanized 3A5.3 antibody.

5. The antibody drug conjugate of claim 3 wherein D is a maytansinoid.

6. The antibody drug conjugate of claim 5 wherein the maytansinoid is DM1.

7. The antibody drug conjugate of claim 3 wherein D is an auristatin.

8. The antibody drug conjugate of claim 7 wherein the auristatin is MMAE or MMAF.

9. The antibody drug conjugate of claim 3 wherein L is MC-val-cit-PAB or MC.

10. The antibody drug conjugate of claim 3 wherein L is SMCC, SPP, or BMPEO.

11. The antibody drug conjugate of claim 3 selected from the formula: Ab-MC-val-cit-PAB-MMAE, Ab-MC-val-cit-PAB-MMAF, Ab-MC-MMAE, Ab-MC-MMAF, Ab-SPP-DM1, and Ab-SMCC-DM1.

12. The antibody drug conjugate compound of claim 3 wherein the antibody is attached to the linker through a cysteine thiol of the antibody.

13. A pharmaceutical formulation comprising the antibody drug conjugate of claim 3, and a pharmaceutically acceptable diluent, carrier or excipient.

14. The pharmaceutical formulation of claim 13 further comprising a therapeutically effective amount of a chemotherapeutic agent selected from letrozole, oxaliplatin, doxetaxel, 5-FU, leucovorin, lapatinib, and gemcitabine.

15. An article of manufacture comprising
   an antibody-drug conjugate compound of claim 3;
   a container; and a package insert or label indicating that the compound can be used to treat cancer characterized by the overexpression of a TAT10772 polypeptide.

16. The article of manufacture of claim 15 wherein the cancer is prostate cancer, cancer of the urinary tract, pancreatic cancer, lung cancer, breast cancer, colon cancer or ovarian cancer.

17. The antibody of claim 2 which is an antibody fragment.

18. The antibody of claim 2 which is a chimeric or a humanized antibody.

19. The antibody of claim 2 which is conjugated to a growth inhibitory agent.

20. The antibody of claim 2 which is conjugated to a cytotoxic agent.

21. The antibody of claim 20, wherein the cytotoxic agent is selected from the group consisting of toxins, antibiotics, radioactive isotopes and nucleolytic enzymes.

22. The antibody of claim 20, wherein the cytotoxic agent is a toxin.

23. The antibody of claim 22, wherein the toxin is selected from the group consisting of maytansinoid and calicheamicin.

24. The antibody of claim 22, wherein the toxin is a maytansinoid.

25. The antibody of claim 2 which is produced in bacteria.

26. The antibody of claim 2 which is produced in CHO cells.

27. The antibody of claim 2 which induces death of a cell to which it binds.

28. The antibody of claim 27, wherein said cell is an ovarian cancer cell.

29. The antibody of claim 2 which is detectably labeled.

30. The antibody of claim 2 that comprises the VH sequence shown as SEQ ID NO:208.

* * * * *